United States Patent
Avery et al.

(10) Patent No.: US 9,107,415 B2
(45) Date of Patent: Aug. 18, 2015

(54) 2-(SUBSTITUTED-PHENYL)-CYCLO-PENTANE-1,3-DIONE COMPOUNDS, AND DERIVATIVES THEREOF

(71) Applicants: Syngenta Limited, Guilford Surrey (GB); Syngenta Participations AG, Basel (CH)

(72) Inventors: Alaric James Avery, Bracknell Berkshire (GB); Mangala Mahadev Phadte, Bracknell Berkshire (GB); James Nicholas Scutt, Bracknell Berkshire (GB); John Benjamin Taylor, Bracknell Berkshire (GB); Russell Colin Viner, Bracknell Berkshire (GB); Jeffrey Steven Wailes, Bracknell Berkshire (GB)

(73) Assignees: Syngenta Particpations AG, Basel (CH); Syngenta Limited, Guildford (GB)

( * ) Notice: Subject to any disclaimer, the term of this patent is extended or adjusted under 35 U.S.C. 154(b) by 0 days.

(21) Appl. No.: 14/361,409

(22) PCT Filed: Nov. 30, 2012

(86) PCT No.: PCT/EP2012/074172
§ 371 (c)(1),
(2) Date: May 29, 2014

(87) PCT Pub. No.: WO2013/079708
PCT Pub. Date: Jun. 6, 2013

(65) Prior Publication Data
US 2014/0323303 A1 Oct. 30, 2014

(30) Foreign Application Priority Data
Nov. 30, 2011 (IN) .......................... 3448/DEL/2011

(51) Int. Cl.
| | |
|---|---|
| *A01N 25/32* | (2006.01) |
| *A01N 43/90* | (2006.01) |
| *A01N 35/06* | (2006.01) |
| *A01N 43/14* | (2006.01) |
| *A01N 43/16* | (2006.01) |
| *A01N 43/56* | (2006.01) |
| *C07D 309/06* | (2006.01) |
| *C07D 215/227* | (2006.01) |
| *C07D 213/50* | (2006.01) |
| *C07C 49/683* | (2006.01) |
| *C07D 213/84* | (2006.01) |
| *C07D 213/85* | (2006.01) |
| *C07D 231/12* | (2006.01) |
| *C07D 493/08* | (2006.01) |
| *C07D 213/61* | (2006.01) |
| *A01N 43/12* | (2006.01) |
| *A01N 43/40* | (2006.01) |
| *A01N 43/84* | (2006.01) |

(52) U.S. Cl.
CPC ................ *A01N 43/90* (2013.01); *A01N 35/06* (2013.01); *A01N 43/12* (2013.01); *A01N 43/14* (2013.01); *A01N 43/16* (2013.01); *A01N 43/40* (2013.01); *A01N 43/56* (2013.01); *A01N 43/84* (2013.01); *C07C 49/683* (2013.01); *C07D 213/50* (2013.01); *C07D 213/61* (2013.01); *C07D 213/84* (2013.01); *C07D 213/85* (2013.01); *C07D 215/227* (2013.01); *C07D 231/12* (2013.01); *C07D 309/06* (2013.01); *C07D 493/08* (2013.01); *C07C 2101/08* (2013.01)

(58) Field of Classification Search
None
See application file for complete search history.

(56) References Cited

FOREIGN PATENT DOCUMENTS

| WO | 2009019005 | 2/2009 |
|---|---|---|
| WO | 2010000773 | 1/2010 |
| WO | WO 2010000773 A1 * | 1/2010 |
| WO | 2010069834 | 6/2010 |

OTHER PUBLICATIONS
International Search Report and Written Opinion dated Apr. 24, 2013 for International Patent Application No. PCT/EP074172.

* cited by examiner

*Primary Examiner* — Heidi Reese
(74) *Attorney, Agent, or Firm* — R. Kody Jones

(57) ABSTRACT

The present invention relates to a compound of formula (I): wherein: X is methyl or chlorine; $R^1$ is methyl or chlorine; $R^2$ is hydrogen, methyl, ethyl, n-propyl, cyclopropyl, vinyl, ethynyl, fluorine, chlorine, bromine, methoxy, ethoxy or fluoromethoxy; and G, $R^3$, $R^4$, $R^5$ and $R^6$ are as defined herein; wherein the compound of formula (I) is optionally present as an agrochemically acceptable salt thereof. These compounds are suitable for use as herbicides. The invention therefore also relates to a method of controlling weeds, especially grassy monocotyledonous weeds, in crops of useful plants, comprising applying a compound of formula (I), or a herbicidal composition comprising such a compound, to the plants or to the locus thereof.

26 Claims, No Drawings

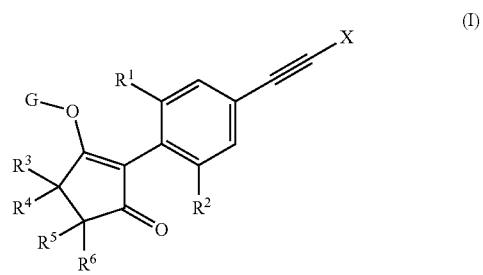

2-(SUBSTITUTED-PHENYL)-CYCLO-PENTANE-1,3-DIONE COMPOUNDS, AND DERIVATIVES THEREOF

RELATED APPLICATION INFORMATION

This application is a 371 of International Application No. PCT/EP2012/074172, filed 30 Nov. 2012, which claims priority to Indian Patent Application No. 3448/DEL/2011, filed 30 Nov. 2011, the contents of which are incorporated herein by reference herein.

The present invention relates to novel, herbicidally active cyclopentanedione compounds, specifically 2-(substituted-phenyl)-cyclopentane-1,3-dione compounds, and derivatives thereof (e.g. enol ketone tautomer and/or fused and/or spirocyclic bicyclic derivatives thereof), to processes for their preparation, to herbicidal compositions comprising those compounds, and to their use in controlling weeds such as grassy monocotyledonous weeds, especially in crops of useful plants, or in inhibiting undesired plant growth.

Cyclopentanedione compounds substituted by substituted-phenyl and having herbicidal activity are described, for example, in WO 2010/000773 A1, WO 2010/069834 A1, WO 2010/089210 A1, WO 2010/102848 A1 and WO 2011/007146 A1 (all Syngenta Limited et al.). For example, WO 2010/000773 A1 (Syngenta Limited) discloses 5-(heterocyclylalkyl)-3-hydroxy-2-phenylcyclopent-2-enone compounds and certain derivatives thereof as herbicides. Also, for example, WO 2010/069834 A1 (Syngenta Limited) discloses cyclopentane-1,3-diones having both heteroarylmethyl- and 2-(substituted-phenyl)- substituents on the cyclopentane ring, and derivatives thereof containing latentiating groups; these compounds are disclosed as having herbicidal properties. Fused bicyclic and oxygen-bridged cyclopentanedione derivatives, specifically 10-oxatricyclo-[5.2.1.0$^{2,6}$]decane-3,5-diones and derivatives, which are substituted by substituted-phenyl and which have herbicidal activity, are disclosed in WO 2009/019005 A2 (Syngenta Limited). Phenyl-substituted bicyclooctane-1,3-dione derivatives, and their use as pesticides and/or herbicides, are disclosed in WO 2010/040460 A2 (Bayer Cropscience AG).

Cyclopentane-1,3-dione compounds and derivatives (e.g. fused and/or spirocyclic bicyclic derivatives) thereof, which are substituted at the 2-position of the cyclopentane-1,3-dione by a phenyl which itself is substituted at the 4-position by (specifically) either prop-1-ynyl or chloroethynyl, and derivatives of the enol ketone tautomer of such cyclopentanediones, which have herbicidal activity and/or plant-growth-inhibiting properties, especially in the control of grassy monocotyledonous weeds and/or when used post-emergence, have now been found, which are encompassed by the present invention.

The specific Compounds A-1 to A-29 disclosed hereinafter, which are encompassed by the present invention, appear to have one or more of the following desirable properties as follows:

(a) Compounds A-2 to A-12, A-14, A-15, A-17 to A-21, and A-23 to A-29, and to a slightly lesser extent Compounds A-1, A-13, A-16, and A-22, have potent post-emergence herbicidal activity in the control of a number of grassy monocotyledonous weeds such as *Lolium, Alopecurus, Echinochloa* and/or *Avena*, and often also *Setaria* (see e.g. Biological Examples 1, 2, 3 and 4 hereinafter).

(b) Many or most of Compounds A-2 to A-15 and A-17 to A-29 are selective grassy-weed-herbicides (graminicides), when used post-emergence on wheat and/or barley, and when safened on the wheat and/or barley appropriately by the safener cloquintocet-mexyl.

(c) Compounds A-6, A-8, A-14, A-20, A-23 and A-26 appear to have quite a low half-life within soil, i.e. quite a low soil persistence (see Biological Example 5 hereinafter), which may lead to certain environmental and/or regulatory advantages such as: the compound not persisting for too long in the environment after spraying on a field, and/or possibly a reduced potential to leach into and/or to negatively affect groundwater.

Therefore, in a first aspect of the present invention, there is provided a compound of formula (I):

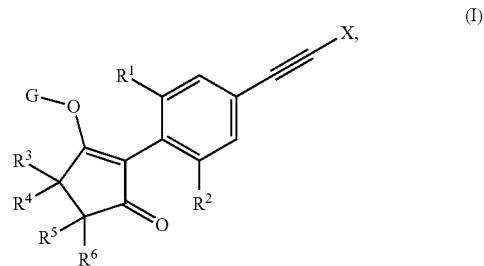

wherein:
X is methyl or chlorine;
$R^1$ is methyl or chlorine;
$R^2$ is hydrogen, methyl, ethyl, n-propyl, cyclopropyl, vinyl, ethynyl, fluorine, chlorine, bromine, methoxy, ethoxy or fluoromethoxy;
$R^3$, $R^4$ and $R^5$, independently of each other, are hydrogen, $C_1$-$C_5$alkyl (e.g. $C_1$-$C_4$alkyl, e.g. $C_1$-$C_2$alkyl), $C_2$-$C_4$ alkenyl (e.g. $C_2$-$C_3$alkenyl-$CH_2$—, e.g. ethenyl-$CH_2$—), $C_2$-$C_4$alkynyl (e.g. $C_2$-$C_3$alkynyl-$CH_2$—, e.g. ethynyl-$CH_2$—), $C_1$-$C_2$-fluoroalkyl or $C_1$-$C_3$alkoxy$C_1$-$C_3$alkyl; and
$R^6$ is: hydrogen; $C_1$-$C_5$alkyl (in particular $C_1$-$C_4$alkyl, e.g. $C_1$-$C_2$alkyl); $C_2$-$C_4$ alkenyl (in particular $C_2$-$C_3$alkenyl-$CH_2$—, e.g. ethenyl-$CH_2$—); $C_2$-$C_4$alkynyl (preferably $C_2$-$C_3$alkynyl-$CH_2$—, more preferably ethynyl-$CH_2$—); $R^{6AA}$—C≡C—$CH_2$—; $C_1$-$C_2$fluoroalkyl; $C_1$-$C_3$alkoxy$C_1$-$C_3$alkyl; $C_1$-$C_3$alkylthio$C_1$-$C_3$alkyl; $C_1$-$C_3$alkylsulfinyl$C_1$-$C_3$alkyl; $C_1$-$C_3$alkylsulfonyl$C_1$-$C_3$alkyl; $C_3$-$C_4$cycloalkyl (in particular cyclopropyl); or an unsubstituted 4, 5 or 6 (in particular 4 or 5) membered monocyclic heterocyclyl having one ring heteroatom independently selected from oxygen, sulfur and nitrogen, and attached at a ring carbon atom within the heterocyclyl (preferably tetrahydrofuranyl such as tetrahydrofuran-3-yl, or tetrahydropyranyl such as tetrahydropyran-4-yl);

or $R^6$ is Q-$(CH_2)_m$—CH($R^7$)—, wherein m is 0 or 1 (preferably m is 0), and either $R^7$ is hydrogen or $R^7$ and $R^5$ together are a bond, and Q is an optionally substituted heterocyclyl as defined below;

or $R^6$ is Het-CH($R^8$)—, wherein either $R^8$ is hydrogen or $R^8$ and $R^5$ together are a bond, and Het is an optionally substituted heteroaryl as defined below;

or $R^6$ is $C_3$-$C_6$cycloalkyl$C_1$-$C_2$alkyl- (in particular $C_3$-$C_6$cycloalkylmethyl-); or is $C_4$-$C_6$cycloalkyl$C_1$-$C_2$alkyl- (in particular $C_4$-$C_6$cycloalkylmethyl-) substituted, at a cycloalkyl ring-carbon atom which is not the ring-carbon atom attached to the —$C_1$-$C_2$alkyl- moiety and which is not bonded directly to the ring-carbon atom attached to the —$C_1$-$C_2$alkyl- moiety, by one or two ring substituents which independently are: =N—O—$R^{10}$, oxo (=O), $C_1$-$C_4$alkoxy, $C_1$-$C_2$haloalkoxy, 2-($C_1$-$C_3$alkoxy)-ethoxy, $C_3$-$C_5$cycloalkyloxy, ($C_3$-$C_5$cycloalkyl)methoxy, $C_2$-$C_3$alkenyl-$CH_2$-oxy, $C_1$-$C_3$alkyl or $C_1$-$C_2$-fluoroalkyl; or benzyloxy in which the phenyl ring is optionally substituted by one or two substituents independently being methyl, methoxy, $C_1$fluoroalkoxy, fluorine or chlorine;

or $R^6$ is benzyl optionally substituted on its phenyl ring by one or two substituents which independently are: cyano, —C≡C—$R^{6A}$, —C($R^{6B}$)=C($R^{6C}$)($R^{6CC}$), —C(O)—$R^{6D}$, —S(O)$_2$—$R^{6E}$, —N($R^{6F}$)($R^{6G}$), $C_1$-$C_3$alkoxy (preferably $C_1$-$C_2$alkoxy such as methoxy), $C_1$-$C_2$fluoroalkoxy (preferably $C_1$fluoroalkoxy), cyclopropyloxy, $CH_2$=CH—$CH_2$—O—, HC≡C—$CH_2$—O—, halogen (preferably fluorine, chlorine or bromine), $C_1$-$C_2$alkyl (preferably methyl), or $C_1$fluoroalkyl (preferably trifluoromethyl);

or $R^3$ and $R^4$ taken together are —(CH$_2$)$_{n1}$— or —(CH$_2$)$_{n2}$—$X^1$—(CH$_2$)$_{n3}$— and $R^5$ and $R^6$ are as defined herein (e.g. hereinabove), or $R^5$ and $R^6$ taken together are —(CH$_2$)$_{n1}$— or —(CH$_2$)$_{n2}$—$X^1$—(CH$_2$)$_{n3}$— and $R^3$ and $R^4$ are as defined herein (e.g. hereinabove);

or $R^4$ and $R^6$ taken together
are —C($R^{11}$)($R^{12}$)—C($R^{13}$)($R^{14}$)—C($R^{15}$)($R^{16}$)—C($R^{17}$)($R^{18}$)—, —C($R^{11}$)($R^{12}$)—C($R^{13}$)=C($R^{15}$)C(R)—C($R^{17}$)($R^{18}$)—, or —CH($R^{19}$)—C($R^{20}$)($R^{21}$)—CH($R^{22}$)—;

wherein Q is a 4 to 7 membered monocyclic or an 8 to 11 membered fused bicyclic heterocyclyl, having one or two ring heteroatoms independently selected from oxygen, sulfur and nitrogen; and wherein the heterocyclyl Q is optionally substituted by 1 or 2 ring-carbon substituents independently being $C_1$-$C_3$alkyl (preferably $C_1$-$C_2$alkyl), $C_1$-$C_2$fluoroalkyl (preferably $C_1$fluoroalkyl), or oxo (=O), and/or is optionally substituted by one $C_1$-$C_4$alkyl, $C_1$-$C_2$fluoroalkyl, $C_1$-$C_4$alkoxy, $C_1$-$C_2$fluoroalkoxy, $R^9$—C(O)— or $C_1$-$C_2$alkyl-S(O)$_2$— substituent on a ring nitrogen if present, and/or is optionally substituted by one or two oxo (=O) substituents on a ring sulfur if present;

wherein Het is a heteroaryl, attached at a ring-carbon, which is optionally substituted by 1, 2 or 3 (preferably 1 or 2, more preferably 1) ring-carbon substituents independently being $C_1$-$C_3$alkyl (preferably $C_1$-$C_2$alkyl), $C_1$-$C_2$fluoroalkyl (preferably $C_1$fluoroalkyl), $C_1$-$C_3$alkyl-C(O)— (preferably $C_1$-$C_2$alkyl-C(O)— such as methyl-C(O)—), $C_1$-$C_2$fluoroalkyl-C(O)— (preferably $C_1$fluoroalkyl-C(O)—), —C(O)—N($R^{6H}$)($R^{6J}$), —S(O)$_2$—$R^{6E}$, —N($R^{6F}$)($R^{6G}$), hydroxy (including any oxo tautomer), $C_2$-$C_3$alkenyl (preferably ethenyl or prop-1-enyl), —C($R^{6BB}$)=C($R^{6C1}$)($R^{6C2}$), $C_2$-$C_3$alkynyl (preferably ethynyl or prop-1-ynyl), —C≡C—$R^{6AA}$, $C_1$-$C_3$alkoxy (preferably $C_1$-$C_2$alkoxy such as methoxy), $C_1$-$C_2$fluoroalkoxy (preferably $C_1$fluoroalkoxy), cyclopropyloxy, $CH_2$=CH—$CH_2$—O—, HC≡C—$CH_2$—O—, halogen (preferably fluorine or chlorine), cyano or nitro; provided that any non-fluorine halogen, alkoxy, fluoroalkoxy, cyclopropyloxy, $CH_2$=CH—$CH_2$—O— or HC≡C—$CH_2$—O— is not substituted at any ring-carbon bonded directly to a ring-nitrogen of the heteroaryl;

and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$— substituent;

wherein:
$R^{6A}$ is hydrogen, methyl, $C_1$fluoroalkyl (preferably trifluoromethyl), fluorine, chlorine or bromine;

$R^{6AA}$ is $C_1$fluoroalkyl (preferably trifluoromethyl), fluorine, chlorine or bromine;

$R^{6B}$, $R^{6C}$ and $R^{6CC}$ independently are hydrogen, methyl, $C_1$fluoroalkyl (preferably trifluoromethyl), fluorine or chlorine; provided that $R^{6B}$, $R^{6C}$ and $R^{6CC}$ in total contain no more than one carbon atom, and $R^{6B}$, $R^{6C}$ and $R^{6CC}$ in total comprise no more than one chlorine; and $R^{6BB}$, $R^{6C1}$ and $R^{6C2}$ independently are hydrogen, methyl, $C_1$fluoroalkyl (preferably trifluoromethyl), fluorine or chlorine; provided that $R^{6BB}$, $R^{6C1}$ and $R^{6C2}$ in total contain no more than one carbon atom, and $R^{6BB}$, $R^{6C1}$ and $R^{6C2}$ in total comprise no more than one chlorine; and provided that —C($R^{6BB}$)=C($R^{6C1}$)($R^{6C2}$) is not $C_2$-$C_3$alkenyl; and $R^{6D}$ and $R^{6E}$ independently are $C_1$-$C_3$alkyl (preferably $C_1$-$C_2$alkyl such as methyl), $C_1$fluoroalkyl (preferably trifluoromethyl), or —N($R^{6H}$)($R^{6J}$);

$R^{6F}$ is —C(O)—$C_1$-$C_2$alkyl (preferably —C(O)-methyl), —C(O)—$C_1$fluoroalkyl (preferably —C(O)-trifluoromethyl), —S(O)$_2$—$C_1$-$C_2$alkyl (preferably —S(O)$_2$-methyl), —S(O)$_2$—$C_1$fluoroalkyl (preferably —S(O)$_2$-trifluoromethyl), $C_1$-$C_2$alkyl (preferably methyl), or $C_1$fluoroalkyl (preferably trifluoromethyl);

$R^{6G}$ and $R^{6J}$ independently are hydrogen, methyl or $C_1$fluoroalkyl (preferably trifluoromethyl); and $R^{6H}$ is hydrogen, $C_1$-$C_2$alkyl (preferably methyl), or $C_1$fluoroalkyl (preferably trifluoromethyl);

and wherein $R^9$ is $C_1$-$C_4$alkyl (e.g. methyl, ethyl, n-propyl, isopropyl or n-butyl), $C_2$-$C_4$alkenyl attached at a carbon atom partaking in the C=C double bond (e.g. Me$_2$C=CH—), $C_1$-$C_2$fluoroalkyl (e.g. CF$_3$ or CHF$_2$CF$_2$—), $C_1$-$C_2$alkoxymethyl- (e.g. methoxymethyl-), $C_1$-$C_3$alkoxy (e.g. methoxy), cyclopropyl, furanyl (e.g. furan-2-yl or furan-3-yl), morpholin-4-yl, isoxazol-3-yl, 5-methyl-isoxazol-3-yl, pyrazol-5-yl, 3-methylpyrazol-5-yl, 1-methylpyrazol-5-yl, 1,3-dimethylpyrazol-5-yl; or phenyl or phenyl substituted by 1 or 2 substituents independently being methyl, ethyl, $C_1$fluoroalkyl, methoxy, $C_1$fluoroalkoxy, fluorine or chlorine;

wherein $R^{10}$ and $R^{23}$ are independently hydrogen, $C_1$-$C_4$alkyl (e.g. methyl), $C_1$-$C_2$fluoroalkyl, 2-($C_1$-$C_3$alkoxy)-ethyl, $C_3$-$C_5$cycloalkyl or ($C_3$-$C_5$cycloalkyl)methyl;

wherein $X^1$ is O, S, S(O), S(O)$_2$, NH, N($C_1$-$C_3$alkyl), N($C_1$-$C_3$alkoxy), C(H)($C_1$-$C_2$alkyl), C($C_1$-$C_2$alkyl)$_2$, C(H)($C_1$-$C_3$alkoxy) or C(Me)($C_1$-$C_2$alkoxy); and n1 is 2, 3, 4 or 5 (e.g. 3, 4 or 5); and n2 and n3 are independently 1, 2 or 3 provided that n2+n3 is 2, 3 or 4;

wherein:
$R^{11}$ and $R^{18}$ are both hydrogen, or $R^{11}$ and $R^{18}$ are taken together and form an —O— or —$C_1$-$C_2$alkylene- bridge; and $R^{12}$ and $R^{17}$ are independently hydrogen, $C_1$-$C_3$alkyl or $C_1$-$C_2$alkoxy$C_1$-$C_2$alkyl;

$R^{13}$, $R^{14}$ and $R^{15}$ are independently hydrogen, $C_1$-$C_3$alkyl or $C_1$-$C_2$alkoxy$C_1$-$C_2$alkyl, provided that one, two or all of $R^{13}$, $R^{14}$ and $R^{15}$ are hydrogen; and $R^{16}$ is hydrogen; $C_1$-$C_3$alkyl; $C_1$-$C_2$alkoxy$C_1$-$C_2$alkyl; phenyl optionally substituted by 1, 2 or 3 (in particular 1 or 2) of, independently, methyl, $C_1$fluoroalkyl, methoxy, $C_1$fluoroalkoxy, methylthio, fluorine, chlorine, cyano or nitro; or pyridinyl attached at a ring-carbon and optionally substituted by 1, 2 or 3 (in particular 1 or 2) ring-carbon substituents independently being methyl, $C_1$fluoroalkyl, methoxy, $C_1$fluoroalkoxy, hydroxy (including any oxo tautomer), fluorine, chlorine, cyano or nitro, provided that any chlorine, methoxy or $C_1$fluoroalkoxy is not substituted at any ring-carbon bonded directly to the ring-nitrogen of the pyridinyl;

and wherein:
$R^{19}$ and $R^{22}$ are independently hydrogen, $C_1$-$C_3$alkyl or $C_1$-$C_2$alkoxy$C_1$-$C_2$alkyl; and $R^{20}$ and $R^{21}$ are independently hydrogen, $C_1$-$C_3$alkyl or $C_1$-$C_2$alkoxy$C_1$-$C_2$alkyl;

or $R^{20}$ and $R^{21}$ taken together are oxo (=O), =N—O—$R^{23}$, or =CH$_2$;

or $R^{20}$ and $R^{21}$, together with the carbon atom to which they are attached, form a 5, 6 or 7 (in particular 5 or 6) membered saturated heterocyclyl, wherein the heterocyclyl has two ring heteroatoms independently being oxygen or sulfur and which are not directly bonded to each other, and wherein the heterocyclyl is optionally substituted by 1, 2 or 3 (e.g. 1 or 2) ring-carbon substituents independently being $C_1$-$C_2$alkyl (e.g. methyl);

and wherein:

G is hydrogen; an agriculturally acceptable metal, or an agriculturally acceptable sulfonium or ammonium group; or G is $C_1$-$C_8$alkyl, $C_2$-$C_8$fluoroalkyl, phenyl$C_1$-$C_8$alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano or nitro), heteroaryl$C_1$-$C_8$alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), $C_2$-$C_7$alkenyl-CH$_2$—, $C_2$-$C_7$alkenyl-CH(Me)- , $C_2$-$C_7$alkenyl-CMe$_2$-, $C_2$-$C_4$fluoroalkenyl-CH$_2$—, $C_2$-$C_7$alkynyl-CH$_2$—, —C(X$^a$)—R$^a$, —C(X$^b$)—X$^c$—R$^b$, —C(X$^d$)—N(R$^c$)—R$^d$, —SO$_2$—R$^e$, —P(X$^e$)(R$^f$)—R$^g$ or —CH$_2$—X$^f$—R$^h$;

wherein X$^a$, X$^b$, X$^c$, X$^d$, X$^e$ and X$^f$ are independently of each other oxygen or sulfur (in particular oxygen); and wherein R$^a$ is H, $C_1$-$C_{21}$alkyl, $C_2$-$C_{21}$alkenyl, $C_2$-$C_{18}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl ($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro;

R$^b$ is $C_1$-$C_{18}$alkyl, $C_3$-$C_{18}$alkenyl, $C_3$-$C_{18}$alkynyl, $C_2$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl ($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$-trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or by nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino or $C_3$-$C_7$cycloalkoxy;

or $R^c$ and $R^d$, together with the nitrogen to which they are bonded, to form an unsubstituted 4, 5, 6 or 7 (e.g. 5 or 6) membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$alkoxy, $C_1$-$C_{10}$fluoroalkoxy, $C_1$-$C_5$alkylamino or di($C_1$-$C_4$alkyl)amino;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$fluoroalkoxy, $C_1$-$C_5$alkylamino or di($C_1$-$C_4$alkyl)amino; or benzyloxy or phenoxy, wherein the benzyl and phenyl groups are in turn optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), phenoxy($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryloxy($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or phenyl-C(O)— or $C_1$-$C_6$alkyl-C(O)—;

wherein "heteroaryl" means an aromatic ring system containing at least one ring heteroatom and consisting either of a single ring or of two fused rings;

and wherein the compound of formula (I) is optionally present (e.g. where chemically possible) as an agrochemically acceptable salt thereof.

In the substituent definitions of the compounds of the formula I, each alkyl moiety either alone or as part of a larger group (such as alkoxy, alkylthio, alkoxycarbonyl, alkylcarbonyl, alkylaminocarbonyl, or dialkylaminocarbonyl, et al.) can be straight-chained or branched. Typically, the alkyl is, for example, methyl, ethyl, n-propyl, isopropyl, n-butyl, sec-butyl, isobutyl, tert-butyl, n-pentyl, neopentyl, or n-hexyl. The alkyl groups can e.g. be $C_1$-$C_6$alkyl groups (except where already defined more narrowly), but are preferably $C_1$-$C_4$alkyl or $C_1$-$C_3$alkyl groups (except where already defined more narrowly), and, more preferably, are $C_1$-$C_2$alkyl groups such as methyl.

Alkenyl and alkynyl moieties can be in the form of straight or branched chains, and the alkenyl moieties, where appropriate, can be of either the (E)- or (Z)-configuration. The alkenyl or alkynyl are typically $C_2$-$C_3$alkenyl or $C_2$-$C_3$alkynyl such as vinyl, allyl, ethynyl, propargyl or prop-1-ynyl. Alkenyl and alkynyl moieties can contain one or more double and/or triple bonds in any combination; but preferably contain only one double bond (for alkenyl) or only one triple bond (for alkynyl).

Halogen is fluorine, chlorine, bromine or iodine. Preferred halogens are fluorine, chlorine or bromine, more preferably fluorine or chlorine.

Fluoroalkyl groups are alkyl groups which are substituted with one or more (e.g. 1, 2, 3, 4 or 5; in particular 1, 2 or 3; e.g. 1 or 2) fluorine atoms. Fluoroalkyl is typically $C_1$-$C_3$fluoroalkyl or $C_1$-$C_2$fluoroalkyl (preferably $C_1$fluoroalkyl), such as $CF_3$, $CHF_2$, $CH_2F$, $CH_3CHF$—, $CF_3CH_2$—, $CHF_2CH_2$—, $CH_2FCH_2$—, $CHF_2CF_2$— or $(CH_3)_2CF$—. Fluoroalkoxy is typically $C_1$-$C_3$fluoroalkoxy or $C_1$-$C_2$fluoroalkoxy (preferably $C_1$fluoroalkoxy), such as $CF_3O$, $CHF_2O$, $CH_2FO$, $CH_3CHFO$—, $CF_3CH_2O$—, $CHF_2CH_2O$— or $CH_2FCH_2O$—.

In the context of the present specification the term "aryl" means phenyl or naphthyl. A preferred aryl group is phenyl.

The term "heteroaryl" as used herein means an aromatic ring system containing at least one ring heteroatom and consisting either of a single ring or of two fused rings. Preferably, single rings will contain 1, 2 or 3 ring heteroatoms and bicyclic systems 1, 2, 3 or 4 ring heteroatoms which will preferably be selected from nitrogen, oxygen and sulfur. Typically, a "heteroaryl" is furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl; optionally present, where chemically possible, as an agrochemically acceptable salt thereof.

The term "heterocyclyl" as used herein, except where explicitly stated otherwise, means a 4, 5, 6 or 7 (in particular 5, 6 or 7) membered monocyclic organic ring or a 8, 9, 10 or 11 (in particular 8, 9 or 10) membered fused bicyclic organic ring system, which is fully saturated, and which has one or two (preferably one) ring heteroatoms independently selected from oxygen, sulfur and nitrogen. Where the heterocyclyl has two ring heteroatoms, preferably, the two ring heteroatoms are separated by at least two ring carbon atoms. Preferably, the heterocyclyl is attached at a ring carbon atom within the heterocyclyl. In particular, the heterocyclyl can be tetrahydrofuranyl, tetrahydropyranyl, tetrahydrothiophenyl, 1,4-dioxanyl, 1,4-dithianyl, morpholinyl, thiomorpholinyl, pyrrolidinyl, piperidinyl or piperazinyl; more particularly tetrahydrofuranyl (e.g. tetrahydrofuran-2-yl or particularly tetrahydrofuran-3-yl), tetrahydropyranyl (e.g. tetrahydropyran-2-yl, tetrahydropyran-3-yl or particularly tetrahydropyran-4-yl), morpholinyl, pyrrolidinyl (e.g. pyrrolidin-2-yl or particularly pyrrolidin-3-yl), piperidinyl (e.g. piperidin-2-yl, piperidin-3-yl or particularly piperidin-4-yl) or piperazinyl. In a particular embodiment, the heterocyclyl, when optionally substituted, is optionally substituted by 1 or 2 (e.g. 1) ring-carbon substituents independently being $C_1$-$C_3$alkyl (e.g. $C_1$-$C_2$alkyl), $C_1$-$C_2$fluoroalkyl or oxo (=O), and/or is optionally substituted by one $C_1$-$C_3$alkyl (e.g. $C_1$-$C_2$alkyl), $C_1$-$C_2$fluoroalkyl or $C_1$-$C_3$alkoxy (e.g. $C_1$-$C_2$alkyl or $C_1$-$C_2$fluoroalkyl) substituent on a ring nitrogen if present, and/or is optionally substituted by one or two oxo (=O) substituents on a ring sulfur if present.

Preferably, a cycloalkyl is cyclopropyl, cyclobutyl, cyclopentyl or cyclohexyl. (Cycloalkyl)alkyl is preferably (cycloalkyl)methyl such as ($C_3$-$C_6$cycloalkyl)methyl in particular cyclopropylmethyl. Preferably, cycloalkenyl is cyclopentenyl or cyclohexenyl.

The invention relates also to the agriculturally acceptable salts which the compounds of formula I are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkyl-amines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-isopropylamine, di-n-butylamine, di-n-amylamine, di-isoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-isopropylamine, tri-n-butylamine, tri-isobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and di-isopropylamine.

Preferred quaternary ammonium bases suitable for salt formation correspond, for example, to the formula [N($R_a R_b R_c R_d$)]OH, wherein $R_a$, $R_b$, $R_c$ and $R_d$ are each independently of the others hydrogen, $C_1$-$C_4$alkyl. Further suitable tetraalkylammonium bases with other anions can be obtained, for example, by anion exchange reactions.

Preferred tertiary sulfonium bases suitable for salt formation correspond, for example, to the formula [S$R_e R_f R_g$]OH, wherein $R_e$, $R_f$ and $R_g$ are each independently of the others $C_1$-$C_4$ alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions.

It should be understood that in those compounds of formula I, where G is a metal, ammonium or sulfonium as mentioned above and as such represents a cation, the corresponding negative charge is largely delocalised across the O=C—C=C—O unit.

The compounds of formula (I) according to the invention also include hydrates which may be formed during the salt formation.

The groups G (where G is other than hydrogen or an agriculturally acceptable metal, sulfonium, or ammonium group) are generally selected to allow its removal by one or a combination of biochemical, chemical or physical processes to afford compounds of formula (I) where G is H, e.g. before, during or following (preferably during or following, more preferably following) application to the treated area or plants. Examples of these processes include enzymatic cleavage, chemical hydrolysis and/or photoloysis, especially enzymatic cleavage within a plant. Compounds bearing such groups G may in some cases offer certain advantages, such as improved penetration of the cuticula of the plants (e.g. weed plants) treated, increased tolerance of (i.e. less damage to) certain crops, improved compatibility or stability in formulated mixtures containing other herbicides and/or herbicide safeners, and/or reduced leaching in soils; in particular improved penetration of the cuticula of the plants (e.g. weed plants) treated.

The preferred, suitable and/or particular values of the substituents in or other features of the compound of formula (I), in particular G, X, $R^1$, $R^2$, $R^3$, $R^4$, $R^5$, $R^6$, $R^{6A}$, $R^{6AA}$, $R^{6B}$, $R^{6C}$, $R^{6CC}$, $R^{6C1}$, $R^{6C2}$, $R^{6D}$, $R^{6E}$, $R^{6F}$, $R^{6G}$, $R^{6H}$, $R^{6J}$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^a$, $R^b$, $R^c$, $R^d$, $R^e$, $R^f$, $R^g$, $R^h$, $X^a$, $X^b$, $X^c$, $X^d$, $X^e$, $X^f$, Q, Het, $X^1$, n1, n2 and/or n3, are set out below (and/or generally herein), and can be either taken alone or taken together with one or more of any other preferred, suitable and/or particular features in any combination(s) thereof.

Particularly preferably, in the compound of formula (I):
$R^6$ is not $R^{6AA}$—C≡C—$CH_2$—, and is not optionally substituted benzyl;

and Het is a heteroaryl, attached at a ring-carbon, which is optionally substituted by 1, 2 or 3 ring-carbon substituents independently being $C_1$-$C_3$alkyl, $C_1$-$C_2$fluoroalkyl, $C_1$-$C_3$alkyl-C(O)—, $C_1$-$C_2$fluoroalkyl-C(O)—, hydroxy (including any oxo tautomer), $C_2$-$C_3$alkenyl, $C_2$-$C_3$alkynyl, $C_1$-$C_3$alkoxy, $C_1$-$C_2$fluoroalkoxy, halogen, cyano or nitro; provided that any non-fluorine halogen, alkoxy or fluoroalkoxy is not substituted at any ring-carbon bonded directly to a ring-nitrogen of the heteroaryl;

and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$— substituent;

and $R^h$ is not phenyl-C(O)— or $C_1$-$C_6$alkyl-C(O)—.

Preferably, $R^h$ is not phenyl-C(O)— or $C_1$-$C_6$alkyl-C(O)—.

In one preferred embodiment, G is hydrogen; an agriculturally acceptable metal (e.g. an agriculturally acceptable alkali metal or alkaline earth metal), or an agriculturally acceptable sulfonium or ammonium group; or G is —C($X^a$)—$R^a$ or —C($X^b$)—$X^c$—$R^b$, wherein $X^a$, $R^a$, $X^b$, $X^c$ and $R^b$ are as defined herein.

In a particular embodiment, G is a group —C($X^a$)—$R^a$ or —C($X^b$)—$X^c$—$R^b$, wherein $X^a$, $R^a$, $X^b$, $X^c$ and $R^b$ are as defined herein.

Preferably, $X^a$, $X^b$, $X^c$, $X^d$, $X^e$ and/or $X^f$ are oxygen. More preferably, $X^a$, $X^b$, $X^c$, $X^d$, $X^e$ and $X^f$ are oxygen.

Preferably, $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-$C_4$alkynyl), $C_3$-$C_6$cycloalkyl or $C_1$-$C_4$alkoxy$C_1$-$C_4$alkyl.

Preferably, $R^b$ is $C_1$-$C_{10}$alkyl (e.g. $C_1$-$C_6$alkyl), $C_2$-$C_5$alkenyl-$CH_2$— (e.g. $C_2$-$C_3$alkenyl-$CH_2$—), $C_2$-$C_4$alkenyl-CH(Me)- (e.g. $C_2$-$C_3$alkenyl-CH(Me)-), $C_2$-$C_5$alkynyl-$CH_2$— (e.g. $C_2$-$C_3$alkynyl-$CH_2$—), $C_2$-$C_4$alkynyl-CH(Me)- (e.g. $C_2$-$C_3$alkynyl-CH(Me)-), $C_3$-$C_6$cycloalkyl or $C_1$-$C_4$alkoxy$C_1$-$C_4$alkyl.

When G is —C($X^a$)—$R^a$ or —C($X^b$)—$X^c$—$R^b$, then preferably $X^a$, $X^b$ and $X^c$ are oxygen, $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-$C_4$alkynyl), $C_3$-$C_6$cycloalkyl or $C_1$-$C_4$alkoxy$C_1$-$C_4$alkyl; and $R^b$ is $C_1$-$C_{10}$alkyl (e.g. $C_1$-$C_6$alkyl), $C_2$-$C_5$alkenyl-$CH_2$— (e.g. $C_2$-$C_3$alkenyl-$CH_2$—), $C_2$-$C_4$alkenyl-CH(Me)- (e.g. $C_2$-$C_3$alkenyl-CH(Me)-), $C_2$-$C_5$alkynyl-$CH_2$— (e.g. $C_2$-$C_3$alkynyl-$CH_2$—), $C_2$-$C_4$alkynyl-CH(Me)- (e.g. $C_2$-$C_3$alkynyl-CH(Me)-), $C_3$-$C_6$cycloalkyl or $C_1$-$C_4$alkoxy$C_1$-$C_4$alkyl.

In a preferable embodiment, G is hydrogen, or an agriculturally acceptable alkali metal or alkaline earth metal, or an agriculturally acceptable sulfonium or ammonium group. More preferably, G is hydrogen, or an agriculturally acceptable alkali metal or alkaline earth metal.

In a preferable embodiment, G is hydrogen, —C($X^a$)—$R^a$ or —C($X^b$)—$X^c$—$R^b$.

Most preferably G is hydrogen.

In one particular embodiment, X is chlorine.

However, in the present invention, most preferably, X is methyl.

In one particular embodiment, $R^1$ is chlorine.

However, in the present invention, most preferably, $R^1$ is methyl.

Therefore, most preferably, X is methyl, and $R^1$ is methyl.

In another preferable embodiment, X is chlorine, and $R^1$ is methyl.

In an alternative particular embodiment, X is methyl, and $R^1$ is chlorine.

In an alternative particular embodiment, X is chlorine, and $R^1$ is chlorine.

In the invention, $R^2$ is hydrogen, methyl, ethyl, n-propyl, cyclopropyl, vinyl, ethynyl, fluorine, chlorine, bromine, methoxy, ethoxy or fluoromethoxy.

Preferably, $R^2$ is hydrogen, methyl, ethyl, ethynyl, chlorine, methoxy or fluoromethoxy (e.g. monofluoromethoxy, difluoromethoxy or trifluoromethoxy).

More preferably, $R^2$ is hydrogen, methyl, ethynyl, chlorine or methoxy; and/or more preferably, $R^2$ is methyl, ethynyl, chlorine or methoxy.

Even more preferably, $R^2$ is hydrogen, methyl or chlorine; and/or even more preferably, $R^2$ is methyl or chlorine.

Yet more preferably, $R^2$ is hydrogen or methyl.

Most preferably, $R^2$ is methyl.

Therefore, most preferably, $R^1$ is methyl, $R^2$ is methyl, and X is methyl or chlorine (preferably methyl).

In an alternative highly preferable embodiment, $R^1$ is methyl, $R^2$ is hydrogen, and X is methyl or chlorine (preferably methyl).

In an alternative highly preferable embodiment, $R^1$ is methyl, $R^2$ is chlorine, and X is methyl or chlorine (preferably methyl).

In an alternative preferable embodiment, $R^1$ is methyl, $R^2$ is ethynyl, and X is methyl or chlorine (preferably methyl).

In an alternative preferable embodiment, $R^1$ is methyl, $R^2$ is methoxy, and X is methyl or chlorine (preferably methyl).

In an alternative highly preferable embodiment, $R^1$ is chlorine, $R^2$ is chlorine, and X is methyl or chlorine (preferably methyl).

In an alternative highly preferable embodiment, $R^1$ is chlorine, $R^2$ is hydrogen, and X is methyl or chlorine (preferably methyl).

Preferably, $R^3$, $R^4$ and/or $R^5$, independently of each other, are hydrogen, $C_1$-$C_4$alkyl (e.g. $C_1$-$C_2$alkyl), $C_2$-$C_3$alkenyl-$CH_2$— (e.g. ethenyl-$CH_2$—), $C_2$-$C_3$alkynyl-$CH_2$— (e.g. ethynyl-$CH_2$—), $C_1$-$C_2$fluoroalkyl (e.g. $C_1$fluoroalkyl) or $C_1$-$C_2$alkoxy$C_1$-$C_2$alkyl;

or $R^3$ and $R^4$ taken together are —$(CH_2)_{n1}$— or —$(CH_2)_{n2}$—$X^1$—$(CH_2)_{n3}$— and $R^5$ and $R^6$ are as defined herein, or $R^5$ and $R^6$ taken together are —$(CH_2)_{n1}$— or —$(CH_2)_{n2}$—$X^1$—$(CH_2)_{n3}$— and $R^3$ and
$R^4$ are as defined herein;

or $R^4$ and $R^6$ taken together
are —$C(R^{11})(R^{12})$—$C(R^{13})(R^{14})$—$C(R^{15})(R^{16})$—$C(R^{17})(R^{18})$—, —$C(R^{11})(R^{12})$—$C(R^{13})$=$C(R^{15})C(R)$—$C(R^{17})(R^{18})$—, or —$CH(R^{19})$—$C(R^{20})(R^{21})$—$CH(R^{22})$—.

More preferably, $R^3$, $R^4$ and/or $R^5$, independently of each other, are hydrogen or $C_1$-$C_2$alkyl (in particular hydrogen);

or $R^3$ and $R^4$ taken together are —$(CH_2)_{n1}$— or —$(CH_2)_{n2}$—$X^1$—$(CH_2)_{n3}$— and $R^5$ and $R^6$ are as defined herein, or $R^5$ and $R^6$ taken together are —$(CH_2)_{n1}$— or —$(CH_2)_{n2}$—$X^1$—$(CH_2)_{n3}$— and $R^3$ and $R^4$ are as defined herein;

or $R^4$ and $R^6$ taken together
are —$C(R^{11})(R^{12})$—$C(R^{13})(R^{14})$—$C(R^{15})(R^{16})$—$C(R^{17})(R^{18})$—, —$C(R^{11})(R^{12})$—$C(R^{13})$=$C(R^{15})C(R)$—$C(R^{17})(R^{18})$—, or —$CH(R^{19})$—$C(R^{20})(R^{21})$—$CH(R^{22})$—.

Still more preferably, $R^3$, $R^4$ and $R^5$ are hydrogen;

or $R^3$ and $R^5$ are hydrogen, and $R^4$ and $R^6$ taken together are —$C(R^{11})(R^{12})$—$C(R^{13})(R^{14})$—$C(R^{15})(R^{16})$—$C(R^{17})(R^{18})$—, —$C(R^{11})(R^{12})$—$C(R^{13})$=$C(R^{15})$—$C(R)$—$C(R^{17})(R^{18})$—, or —$CH(R^{19})$—$C(R^{20})(R^{21})$—$CH(R^{22})$—.

Yet more preferably, $R^3$, $R^4$ and $R^5$ are hydrogen;

or $R^3$ and $R^5$ are hydrogen, and $R^4$ and $R^6$ taken together
are —$C(R^{11})(R^{12})$—$C(R^{13})(R^{16})$—$C(R^{17})(R^8)$— or —$C(R^{11})(R^{12})$—$C(R^{13})$=$C(R)$—$C(R^{17})(R^{18})$—.

Most preferably, $R^3$, $R^4$ and $R^5$ are hydrogen.

When $R^6$ is optionally substituted benzyl, then, preferably, $R^6$ is benzyl optionally substituted on its phenyl ring by one or two substituents which independently are: cyano, —C≡C—$R^{6A}$, —$C(R^{6B})$=$C(R^{6C})(R^{6CC})$, —$C(O)$—$R^{6D}$, —$S(O)_2$—$R^{6E}$, $C_1$-$C_3$alkoxy (preferably $C_1$-$C_2$alkoxy such as methoxy), $C_1$-$C_2$fluoroalkoxy (preferably $C_1$fluoroalkoxy), halogen (preferably fluorine or chlorine), methyl or $C_1$fluoroalkyl.

When $R^6$ is optionally substituted benzyl, then, more preferably, $R^6$ is benzyl substituted on its phenyl ring by a first substituent being: cyano, —C≡C—$R^{6A}$, —$C(R^{6B})$=$C(R^{6C})(R^{6CC})$ or —$C(O)$—$R^{6D}$; and optionally substituted on its phenyl ring by a second independent substituent being: cyano, —C≡C—$R^{6A}$, —$C(R^{6B})$=$C(R^{6C})(R^{6CC})$, —$C(O)$—$R^{6D}$, —$S(O)_2$—$R^{6E}$, $C_1$-$C_2$alkoxy (preferably methoxy), $C_1$-$C_2$fluoroalkoxy (preferably $C_1$fluoroalkoxy), halogen (preferably fluorine or chlorine), or methyl; in which $R^{6D}$ and $R^{6E}$ independently are methyl or trifluoromethyl.

When $R^6$ is optionally substituted benzyl, then, even more preferably, $R^6$ is benzyl substituted on its phenyl ring by a first substituent being: cyano or —C≡C—$R^{6A}$; and optionally substituted on its phenyl ring by a second independent substituent being:

cyano, —C≡C—$R^{6A}$, —$C(R^{6B})$=$C(R^{6C})(R^{6CC})$, —$C(O)$—$R^{6D}$, —$S(O)_2$—$R^{6E}$, methoxy, $C_1$fluoroalkoxy, fluorine, chlorine, or methyl; in which $R^{6D}$ and $R^{6E}$ independently are methyl or trifluoromethyl.

When $R^6$ is optionally substituted benzyl, then, still more preferably, $R^6$ is benzyl substituted on its phenyl ring by one substituent being cyano or —C≡C—$R^{6A}$.

However, preferably, $R^6$ is not $R^{6AA}$—C≡C—$CH_2$—; and/or preferably $R^6$ is not optionally substituted benzyl.

Preferably, $R^6$ is: hydrogen; $C_1$-$C_4$alkyl (e.g. $C_1$-$C_2$alkyl); $C_2$-$C_3$alkenyl-$CH_2$— (e.g. ethenyl-$CH_2$—); $C_2$-$C_3$alkynyl-$CH_2$— (preferably ethynyl-$CH_2$—); $C_1$-$C_2$fluoroalkyl (e.g. $C_1$fluoroalkyl); $C_1$-$C_2$alkoxy$C_1$-$C_2$alkyl; $C_1$-$C_2$alkylthio$C_1$-$C_2$alkyl; $C_1$-$C_2$alkylsulfinyl$C_1$-$C_2$alkyl; $C_1$-$C_2$alkylsulfonyl$C_1$-$C_2$alkyl; cyclopropyl; or tetrahydrofuranyl (such as tetrahydrofuran-3-yl), or tetrahydropyranyl (such as tetrahydropyran-4-yl);

or $R^6$ is Q-CH($R^7$)— (in particular, $R^7$ can be hydrogen);

or $R^6$ is Het-CH($R^8$)— (in particular, $R^8$ can be hydrogen);

or $R^6$ is $C_3$-$C_6$cycloalkylmethyl- (e.g. cyclohexylmethyl-);

or is $C_4$-$C_6$cycloalkylmethyl- (e.g. cyclohexylmethyl-) substituted, at a cycloalkyl ring-carbon atom which is not the ring-carbon atom attached to the —$C_1$-$C_2$alkyl- moiety and which is not bonded directly to the ring-carbon atom attached to the —$C_1$-$C_2$alkyl- moiety, by one ring substituent being =N—O—$R^{10}$, oxo (=O), $C_1$-$C_3$alkoxy, $C_1$haloalkoxy, cyclopropyloxy, (cyclopropyl)methoxy or vinyl-$CH_2$-oxy, and optionally by a second ring substituent being $C_1$-$C_2$alkyl (e.g. methyl);

or $R^3$ and $R^4$ taken together are —$(CH_2)_{n1}$— or —$(CH_2)_{n2}$—$X^1$—$(CH_2)_{n3}$— and $R^5$ and $R^6$ are as defined herein, or $R^5$ and $R^6$ taken together are —$(CH_2)_{n1}$— or —$(CH_2)_{n2}$—$X^1$—$(CH_2)_{n3}$— and $R^3$ and
$R^4$ are as defined herein;

or $R^4$ and $R^6$ taken together
are —$C(R^{11})(R^{12})$—$C(R^{13})(R^{14})$—$C(R^{15})(R^{16})$—$C(R^{17})(R^{18})$—, —$C(R^{11})(R^{12})$—$C(R^{13})$=$C(R^{15})C(R)$—$C(R^{17})(R^{18})$—, or —$CH(R^{19})$—$C(R^{20})(R^{21})$—$CH(R^{22})$—.

More preferably, $R^6$ is: hydrogen; $C_1$-$C_4$alkyl (in particular $C_1$-$C_2$alkyl); $C_2$-$C_3$alkynyl-$CH_2$— (preferably ethynyl-$CH_2$—); or $C_1$-$C_2$alkoxy$C_1$-$C_2$alkyl (in particular methoxymethyl);

or $R^6$ is Q-CH($R^7$)— (in particular, $R^7$ can be hydrogen);

or $R^6$ is Het-CH($R^8$)— (in particular, $R^8$ can be hydrogen);

or $R^6$ is cyclohexylmethyl- substituted, at the 4-position of the cyclohexyl ring (calculated with respect to the ring-carbon atom attached to the -methyl- moiety), either by one ring substituent being =N—O—$R^{10}$; or by a first ring substituent being oxo (═O), $C_1$-$C_3$alkoxy, $C_1$haloalkoxy, cyclopropyloxy, (cyclopropyl)methoxy or vinyl-$CH_2$-oxy, and optionally by a second ring substituent being $C_1$-$C_2$alkyl (in particular methyl);

or $R^3$ and $R^4$ taken together are —$(CH_2)_{n1}$— or —$(CH_2)_{n2}$—$X^1$—$(CH_2)_{n3}$— and $R^5$ and $R^6$ are as defined herein, or $R^5$ and $R^6$ taken together are —$(CH_2)_{n1}$— or —$(CH_2)_{n2}$—$X^1$—$(CH_2)_{n3}$— and $R^3$ and $R^4$ are as defined herein;

or $R^4$ and $R^6$ taken together
are —$C(R^{11})(R^{12})$—$C(R^{13})(R^{14})$—$C(R^{15})(R^{16})$—$C(R^{17})(R^{18})$—, —$C(R^{11})(R^{12})$—$C(R^{13})$═$C(R^{15})$—$C(R)$—$C(R^{17})(R^{18})$—, or —$CH(R^{19})$—$C(R^{20})(R^{21})$—$CH(R^{22})$—.

Still more preferably, $R^6$ is: hydrogen; $C_1$-$C_4$alkyl (in particular $C_1$-$C_2$alkyl);

$C_2$-$C_3$alkynyl-$CH_2$— (preferably ethynyl-$CH_2$—); or $C_1$-$C_2$alkoxy$C_1$-$C_2$alkyl (in particular methoxymethyl);

or $R^6$ is Q-CH($R^7$)— (in particular, $R^7$ can be hydrogen);
or $R^6$ is Het-CH($R^8$)— (in particular, $R^8$ can be hydrogen);
or $R^4$ and $R^6$ taken together
are —$C(R^{11})(R^{12})$—$C(R^{13})(R^{14})$—$C(R^{15})(R^{16})$—$C(R^{17})(R^{18})$—, —$C(R^{11})(R^{12})$—$C(R^{13})$═$C(R^{15})C(R)$—$C(R^{17})(R^{18})$—, or —$CH(R^{19})$—$C(R^{20})(R^{21})$—$CH(R^{22})$—.

Still more preferably, $R^6$ is: $C_1$-$C_4$alkyl (in particular $C_1$-$C_2$alkyl); $C_2$-$C_3$alkynyl-$CH_2$— (preferably ethynyl-$CH_2$—); or $C_1$-$C_2$alkoxy$C_1$-$C_2$alkyl (in particular methoxymethyl);

or $R^6$ is Q-CH($R^7$)— (in particular, $R^7$ can be hydrogen);
or $R^6$ is Het-CH($R^8$)— (in particular, $R^8$ can be hydrogen);
or $R^4$ and $R^6$ taken together
are —$C(R^{11})(R^{12})$—$C(R^{13})(R^{14})$—$C(R^{15})(R^{16})$—$C(R^{17})(R^{18})$—, —$C(R^{11})(R^{12})$—$C(R^{13})$═$C(R^{15})$—$C(R^{17})(R^{18})$—, or —$CH(R^{19})$—$C(R^{20})(R^{21})$—$CH(R^{22})$—.

Still more preferably, $R^6$ is $C_2$-$C_3$alkynyl-$CH_2$— (preferably ethynyl-$CH_2$—);

or $R^6$ is Q-CH($R^7$)— (in particular, $R^7$ can be hydrogen);
or $R^6$ is Het-CH($R^8$)— (in particular, $R^8$ can be hydrogen);
or $R^4$ and $R^6$ taken together
are —$C(R^{11})(R^{12})$—$C(R^{13})(R^{14})$—$C(R^{15})(R^{16})$—$C(R^{17})(R^{18})$—, —$C(R^{11})(R^{12})$—$C(R^{13})$═$C(R^{15})$—$C(R^{17})(R^{18})$—, or —$CH(R^{19})$—$C(R^{20})(R^{21})$—$CH(R^{22})$—.

Yet more preferably, $R^6$ is Q-CH($R^7$)— (in particular, $R^7$ can be hydrogen);
or $R^6$ is Het-CH($R^8$)— (in particular, $R^8$ can be hydrogen);
or $R^4$ and $R^6$ taken together
are —$C(R^{11})(R^{12})$—$C(R^{13})(R^{14})C(R^{15})(R^{16})$—$C(R(R^{17})(R^{18})$— or —$C(R^{11})(R^{12})$—$C(R^{13})$═$C(R^{15})$—$C(R^{17})(R^{18})$—.

Further more preferably, $R^6$ is Q-CH($R^7$)— or Het-CH($R^8$)—. Preferably, $R^7$ and/or $R^8$ are hydrogen.

Most preferably, $R^6$ is Het-CH($R^8$)—. Preferably, $R^8$ is hydrogen.

Most preferably, in all aspects and/or embodiments of the invention, $R^8$ is hydrogen.

Most preferably, in all aspects and/or embodiments of the invention, $R^7$ is hydrogen.

Preferably, Q is a 4 to 7 (e.g. 4, 5 or 6, preferably 5 or 6) membered monocyclic heterocyclyl, having one or two (preferably one) ring heteroatoms independently selected from oxygen, sulfur and nitrogen; and wherein the heterocyclyl Q is optionally substituted by 1 or 2 ring-carbon substituents independently being $C_1$-$C_3$alkyl (in particular $C_1$-$C_2$alkyl), $C_1$-$C_2$fluoroalkyl (in particular $C_1$fluoroalkyl) or oxo (═O), and/or is optionally substituted by one $C_1$-$C_4$alkyl (in particular $C_1$-$C_3$alkyl or $C_1$-$C_2$alkyl), $C_1$-$C_2$fluoroalkyl (in particular $C_1$fluoroalkyl), $C_1$-$C_4$alkoxy (in particular $C_1$-$C_3$alkoxy or $C_1$-$C_2$alkoxy), $C_1$-$C_2$fluoroalkoxy (in particular $C_1$fluoroalkoxy), $R^9$—C(O)— or $C_1$-$C_2$alkyl-$S(O)_2$— substituent on a ring nitrogen if present, and/or is optionally substituted by one or two oxo (═O) substituents on a ring sulfur if present.

More preferably, Q is a 4 to 7 (e.g. 4, 5 or 6, preferably 5 or 6) membered monocyclic heterocyclyl, having one or two (preferably one) ring heteroatoms independently selected from oxygen, sulfur and nitrogen; and wherein the heterocyclyl Q is optionally substituted by one $C_1$-$C_4$alkyl (in particular $C_1$-$C_3$alkyl or $C_1$-$C_2$alkyl), $C_1$-$C_2$fluoroalkyl (in particular $C_1$fluoroalkyl), $C_1$-$C_4$alkoxy (in particular $C_1$-$C_3$alkoxy or $C_1$-$C_2$alkoxy), $C_1$-$C_2$fluoroalkoxy (in particular $C_1$fluoroalkoxy), $R^9$—C(O)— or $C_1$-$C_2$alkyl-$S(O)_2$— substituent on a ring nitrogen if present, and/or is optionally substituted by one or two oxo (═O) substituents on a ring sulfur if present.

Still more preferably, Q is a 4 to 7 (e.g. 4, 5 or 6, preferably 5 or 6) membered monocyclic heterocyclyl, having one ring heteroatom independently selected from oxygen, sulfur and nitrogen; and wherein the heterocyclyl Q is optionally substituted by one $R^9$—C(O)— or $C_1$-$C_2$alkyl-$S(O)_2$— (preferably $R^9$—C(O)—) substituent on a ring nitrogen if present, and/or is optionally substituted by one or two oxo (═O) substituents on a ring sulfur if present.

Most preferably, Q is a 4, 5 or 6 (preferably 5 or 6) membered monocyclic heterocyclyl, having one ring heteroatom independently selected from oxygen and nitrogen; and wherein the heterocyclyl Q is optionally substituted by one $R^9$—C(O)— or $C_1$-$C_2$alkyl-$S(O)_2$— (preferably $R^9$—C(O)—) substituent on a ring nitrogen if present.

It is particularly preferred that Q is attached at a ring carbon atom to the —$(CH_2)_m$—CH($R^7$)— or —CH($R^7$)— moiety.

It is particularly preferred that, in Q, the one or two (e.g. one) ring heteroatoms are not directly bonded to the ring atom (e.g. ring carbon atom) which is the position of attachment to the —$(CH_2)_m$—CH($R^7$)— or —CH($R^7$)— moiety.

In Q, preferably, when there are two ring heteroatoms, then they are separated by one or (preferably) two carbon atoms (i.e. they are not directly bonded to each other).

Preferably, $R^9$ is $C_1$-$C_4$alkyl (in particular methyl, ethyl, n-propyl, isopropyl or n-butyl, preferably methyl, ethyl, n-propyl or isopropyl), $C_1$-$C_2$fluoroalkyl (e.g. $CF_3$ or $CHF_2CF_2$—), $C_1$-$C_2$alkoxymethyl- (e.g. methoxymethyl-), or cyclopropyl.

More preferably, $R^9$ is $C_1$-$C_3$alkyl (preferably methyl or ethyl), $C_1$-$C_2$fluoroalkyl (e.g. $CF_3$ or $CHF_2CF_2$—), methoxymethyl-, or cyclopropyl.

Most preferably, $R^9$ is methyl, ethyl, $C_1$-$C_2$fluoroalkyl (e.g. $CF_3$ or $CHF_2CF_2$—) or methoxymethyl-; in particular methyl.

Preferably, Q is one of the following sub-formulae $Q_1$, $Q_2$, $Q_3$, $Q_4$, $Q_5$, $Q_6$, $Q_7$, $Q_{33}$, $Q_{34}$, $Q_{37}$, $Q_{38}$, $Q_{41}$, $Q_{42}$, $Q_{43}$, $Q_{44}$, $Q_{47}$, $Q_{87}$, $Q_{89}$, $Q_{90}$ or $Q_{107}$:

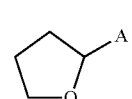

$Q_1$

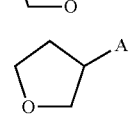

$Q_2$ wherein:
A is the position of attachment to the —(CH$_2$)$_m$—CH(R$^7$)— or —CH(R$^7$)— moiety; and
R$^9$ is as defined herein.

More preferably, Q is one of the sub-formulae Q$_1$, Q$_2$, Q$_4$, Q$_6$, Q$_7$, Q$_{33}$, Q$_{34}$, Q$_{41}$, Q$_{42}$, Q$_{43}$, Q$_{44}$, Q$_{87}$, Q$_{89}$ or Q$_{90}$. Even more preferably, Q is one of the sub-formulae Q$_2$, Q$_6$, Q$_7$, Q$_{33}$, Q$_{34}$, Q$_{41}$, Q$_{42}$, Q$_{43}$, Q$_{44}$, Q$_{87}$, Q$_{89}$ or Q$_{90}$.

Yet more preferably, Q is one of the sub-formulae Q$_2$, Q$_7$, Q$_{87}$ or Q$_{90}$. Further more preferably, Q is one of the sub-formulae Q$_2$, Q$_7$ or Q$_{90}$.

Most preferably, Q is sub-formula Q$_7$.

Preferably, R$^8$ is hydrogen.

Preferably, Het is a heteroaryl, attached at a ring-carbon, which is optionally substituted by 1, 2 or 3 (preferably 1 or 2, more preferably 1) ring-carbon substituents independently being C$_1$-C$_3$alkyl (preferably C$_1$-C$_2$alkyl), C$_1$-C$_2$fluoroalkyl (preferably C$_1$fluoroalkyl), C$_1$-C$_3$alkyl-C(O)— (preferably C$_1$alkyl-C(O)— which is methyl-C(O)—), C$_1$-C$_2$fluoroalkyl-C(O)— (preferably C$_1$fluoroalkyl-C(O)—), hydroxy (including any oxo tautomer), C$_2$-C$_3$alkenyl (preferably ethenyl or prop-1-enyl), C$_2$-C$_3$alkynyl (preferably ethynyl or prop-1-ynyl), C$_1$-C$_3$alkoxy (preferably C$_1$-C$_2$alkoxy, such as C$_1$-C$_2$alkoxy which is methoxy), C$_1$-C$_2$fluoroalkoxy (preferably C$_1$fluoroalkoxy), halogen (preferably fluorine or chlorine), cyano or nitro; provided that any non-fluorine halogen, alkoxy or fluoroalkoxy is not substituted at any ring-carbon bonded directly to a ring-nitrogen of the heteroaryl;

and/or, in the case of a 5-membered heteroaryl ring containing a ring-nitrogen atom not partaking in a C═N ring double bond, the heteroaryl is optionally substituted on the ring-nitrogen atom not partaking in a C═N ring double bond by one C$_1$-C$_3$alkyl, C$_1$-C$_2$fluoroalkyl, C$_1$-C$_3$alkyl-C(O)—, C$_1$-C$_2$fluoroalkyl-C(O)— or C$_1$-C$_2$alkyl-S(O)$_2$— substituent;

More preferably, Het is a heteroaryl (in particular monocyclic heteroaryl), attached at a ring-carbon, which is optionally substituted by 1, 2 or 3 (in particular 1 or 2, e.g. 1) ring-carbon substituents independently being C$_1$-C$_2$alkyl, C$_1$fluoroalkyl, C$_1$-C$_2$alkyl-C(O)—, C$_1$fluoroalkyl-C(O)—, hydroxy (including any oxo tautomer), ethynyl, prop-1-ynyl, C$_1$-C$_2$alkoxy, C$_1$fluoroalkoxy, fluorine, chlorine, bromine, cyano or nitro, provided that any chlorine, bromine, alkoxy or fluoroalkoxy is not substituted at any ring-carbon bonded directly to a ring-nitrogen of the heteroaryl;

and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$— substituent.

Even more preferably, Het is a heteroaryl (in particular monocyclic heteroaryl), attached at a ring-carbon, which is optionally substituted by 1 or 2 (in particular 1) ring-carbon substituents independently being $C_1$-$C_2$alkyl (in particular methyl), $C_1$fluoroalkyl (in particular $CF_3$), $C_1$-$C_2$alkyl-C(O)— (in particular Me-C(O)—), $C_1$fluoroalkyl-C(O)—, ethynyl, prop-1-ynyl, fluorine or cyano;

and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_2$alkyl (e.g. methyl), $C_1$fluoroalkyl, methyl-C(O)— or $C_1$fluoroalkyl-C(O)— substituent.

Still more preferably, Het is a heteroaryl (in particular monocyclic heteroaryl), attached at a ring-carbon, which is optionally substituted by 1 or 2 (in particular 1) ring-carbon substituents independently being $C_1$-$C_2$alkyl (in particular methyl), $C_1$fluoroalkyl (in particular $CF_3$), fluorine or cyano;

and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one methyl substituent.

Preferably, Het is an optionally substituted monocyclic heteroaryl, attached at a ring-carbon. Such as monocyclic heteroaryl can be 5-membered or 6-membered monocyclic heteroaryl.

More preferably, Het is an optionally substituted monocyclic heteroaryl, attached at a ring-carbon, which is:

pyridinyl (preferably pyridin-3-yl or most preferably pyridin-2-yl), pyrazolyl (preferably pyrazol-5-yl or pyrazol-4-yl, or most preferably pyrazol-3-yl), imidazolyl (preferably imidazol-2-yl), pyrazinyl, pyrimidinyl (preferably pyrimidin-4-yl), pyridazinyl (preferably pyridazin-3-yl), triazolyl (e.g. 1,2,3-triazolyl), tetrazol-5-yl, oxazolyl, thiazolyl, isoxazolyl, isothiazolyl or oxadiazolyl; optionally present (e.g. where chemically possible) as an agrochemically acceptable salt thereof (such as an agrochemically acceptable acid addition salt thereof).

Even more preferably, Het is an optionally substituted monocyclic heteroaryl, attached at a ring-carbon, which is:

pyridinyl (preferably pyridin-3-yl or most preferably pyridin-2-yl), pyrazolyl (preferably pyrazol-5-yl or pyrazol-4-yl, or most preferably pyrazol-3-yl), imidazolyl (preferably imidazol-2-yl), pyrazinyl, pyrimidinyl (preferably pyrimidin-4-yl), pyridazinyl (preferably pyridazin-3-yl), triazolyl (e.g. 1,2,3-triazolyl), or tetrazol-5-yl; optionally present (e.g. where chemically possible) as an agrochemically acceptable salt thereof (such as an agrochemically acceptable acid addition salt thereof).

Still more preferably, Het is an optionally substituted monocyclic heteroaryl, attached at a ring-carbon, which is:

pyridinyl (preferably pyridin-3-yl or most preferably pyridin-2-yl), pyrazolyl (preferably pyrazol-5-yl or pyrazol-4-yl, or most preferably pyrazol-3-yl), imidazolyl (preferably imidazol-2-yl), pyrazinyl, pyrimidinyl (preferably pyrimidin-4-yl), or pyridazinyl (preferably pyridazin-3-yl); optionally present (e.g. where chemically possible) as an agrochemically acceptable salt thereof (such as an agrochemically acceptable acid addition salt thereof).

Yet more preferably, Het is an optionally substituted monocyclic heteroaryl, attached at a ring-carbon, which is:

pyridin-3-yl, pyridin-2-yl, or pyrazolyl (preferably pyrazol-5-yl or pyrazol-4-yl, or most preferably pyrazol-3-yl); optionally present (e.g. where chemically possible) as an agrochemically acceptable salt thereof (such as an agrochemically acceptable acid addition salt thereof).

Most preferably, Het is an optionally substituted monocyclic heteroaryl, attached at a ring-carbon, which is: pyridin-2-yl or pyrazol-3-yl; optionally present (e.g. where chemically possible) as an agrochemically acceptable salt thereof (such as an agrochemically acceptable acid addition salt thereof).

It is particularly preferred that, in Het, any ring-carbon atom, which is directly bonded to the ring atom (ring-carbon atom) which is the point of attachment to the —CH(R$^8$)— moiety, is unsubstituted. Therefore, for example, preferably, when Het is an optionally substituted pyridin-2-yl (optionally present as an agrochemically acceptable salt thereof), then the ring-carbon atom at the 3-position of the ring (calculated with respect to the pyridine ring nitrogen atom) is unsubstituted.

It is particularly preferred that, Het is an optionally substituted 6-membered monocyclic heteroaryl, attached at a ring-carbon, and which, if substituted, is substituted by a substituent (e.g. as defined herein) at a ring-carbon which is at the 4-position with respect to (i.e. is diametrically opposite to) the heteroaryl ring-carbon which is the point of attachment to the —CH(R$^8$)— moiety. Therefore, for example, more preferably, when Het is an optionally substituted pyridin-2-yl (optionally present as an agrochemically acceptable salt thereof), then the ring-carbon atom at the 5-position of the ring (calculated with respect to the pyridine ring nitrogen atom) is substituted by a substituent (e.g. as defined herein); even more preferably in this embodiment, the ring-carbon atom at the 3-position of the ring (calculated with respect to the pyridine ring nitrogen atom) is unsubstituted.

Alternatively or additionally, in a particular embodiment, Het is an optionally substituted 6-membered monocyclic heteroaryl, attached at a ring-carbon, and which, if substituted, is substituted by a substituent (e.g. as defined herein) at a ring-carbon which is at a or the 3-position with respect to the heteroaryl ring-carbon which is the point of attachment to the —CH(R$^8$)— moiety. For example, more particularly, when Het is an optionally substituted pyridin-2-yl (optionally present as an agrochemically acceptable salt thereof), then the ring-carbon atom at the 6-position of the ring (calculated with respect to the pyridine ring nitrogen atom) is substituted by a substituent (e.g. as defined herein); even more particularly in this embodiment, the ring-carbon atom at the 3-position of the ring (calculated with respect to the pyridine ring nitrogen atom) is unsubstituted.

Preferably, Het is one of the heteroaryls defined in the relevant (e.g. left-hand-side) portion of compounds A-2, A-3, A-5, A-6, A-7, A-8, A-9, A-10, A-11, A-12, A-13, A-14, A-15 or A-19, as illustrated hereinbelow. Therefore, preferably, Het is one of the heteroaryls illustrated below:

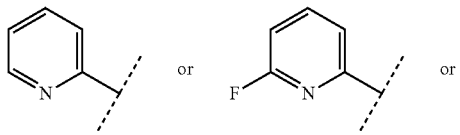

-continued

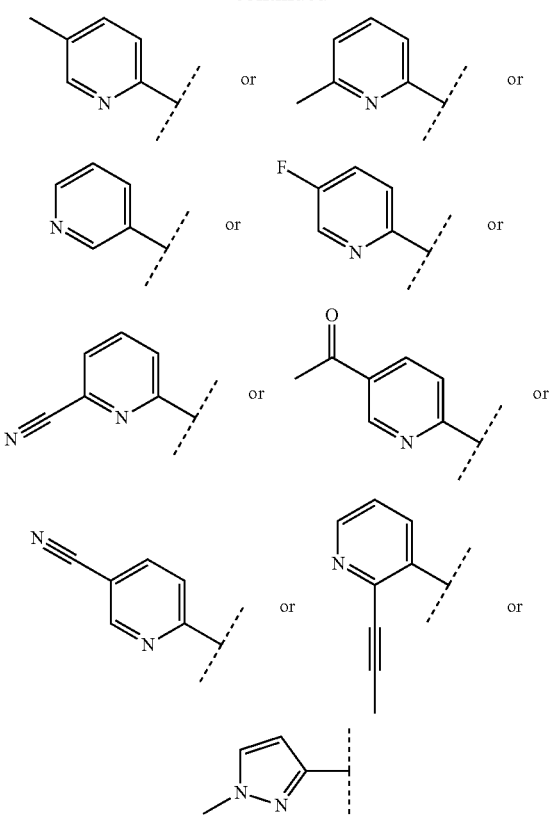

Alternatively, preferably, Het is one of the heteroaryls defined in the relevant (e.g. left-hand-side) portion of compounds A-23 or A-24, as illustrated hereinbelow. Therefore, alternatively, preferably, Het is one of the heteroaryls illustrated below:

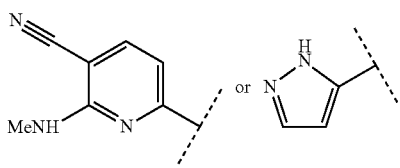

More preferably, Het is one of the heteroaryls defined in the relevant (e.g. left-hand-side) portion of compounds A-2, A-3, A-5, A-6, A-7, A-8, A-9, A-11, A-12 or A-14, as illustrated hereinbelow. Therefore, most preferably, Het is one of the heteroaryls illustrated below:

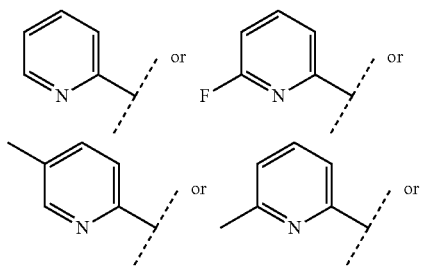

-continued

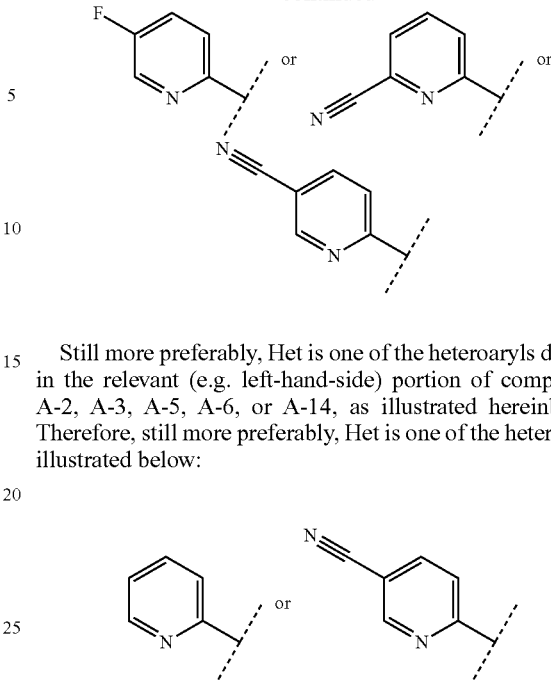

Still more preferably, Het is one of the heteroaryls defined in the relevant (e.g. left-hand-side) portion of compounds A-2, A-3, A-5, A-6, or A-14, as illustrated hereinbelow. Therefore, still more preferably, Het is one of the heteroaryls illustrated below:

Preferably, $R^{10}$ and/or $R^{23}$ are independently hydrogen, $C_1$-$C_2$alkyl (e.g. methyl) or $C_1$fluoroalkyl.

Preferably, $X^1$ is O, NH, N($C_1$-$C_3$alkyl) (e.g. NMe), N($C_1$-$C_3$alkoxy) (e.g. N(OMe)), C(H)($C_1$-$C_3$alkoxy) (e.g. C(H)(OMe)), or C(Me)($C_1$-$C_2$alkoxy) (e.g. C(Me)(OMe)). More preferably, $X^1$ is O or C(H)($C_1$-$C_3$alkoxy), such as O or C(H)(OMe).

Preferably, n1 is 3, 4 or 5, more preferably 4 or 5.

Preferably, n2 and n3 are independently 1, 2 or 3 (in particular 1 or 2) provided that n2+n3 is 3 or 4. More preferably, n2 and n3 are both 2.

Preferably,
$R^{11}$ and $R^{18}$ are both hydrogen, or $R^{11}$ and $R^{18}$ are taken together and form an —O— or —$C_1$-$C_2$alkylene- bridge; and
$R^{12}$ and $R^{17}$ are independently hydrogen, $C_1$-$C_3$alkyl (in particular methyl) or $C_1$-$C_2$alkoxy$C_1$-$C_2$alkyl (in particular methoxymethyl);
$R^{13}$, $R^{14}$ and $R^{15}$ are independently hydrogen or $C_1$-$C_3$alkyl (in particular methyl), provided that two or all (preferably all) of $R^{13}$, $R^{14}$ and $R^{15}$ are hydrogen; and
$R^{16}$ is hydrogen; $C_1$-$C_3$alkyl (in particular methyl); or $C_1$-$C_2$alkoxy$C_1$-$C_2$alkyl (in particular methoxymethyl).

Preferably, $R^{12}$ and $R^{17}$ are independently hydrogen, methyl or methoxymethyl.

Preferably, $R^{13}$, $R^{14}$ and $R^{15}$ are hydrogen.

Preferably, $R^{16}$ is hydrogen.

More preferably,
$R^{11}$ and $R^{18}$ are both hydrogen, or $R^{11}$ and $R^{18}$ are taken together and form an —O— or —$C_1$-$C_2$alkylene- bridge; and
$R^{12}$ and $R^{17}$ are independently hydrogen, methyl or methoxymethyl;
and $R^{13}$, $R^{14}$, $R^{15}$ and $R^{16}$ are hydrogen.

Still more preferably, when $R^4$ and $R^6$ taken together are —C($R^{11}$)($R^{12}$)—C($R^{13}$)($R^{14}$)C($R^{15}$)($R^{16}$)—C($R^{17}$)($R^{18}$)— or —C($R^{11}$)($R^{12}$)—C($R^{13}$)=C($R^{15}$)—C($R^{17}$)($R^{18}$)—, then $R^4$ and $R^6$ taken together are:

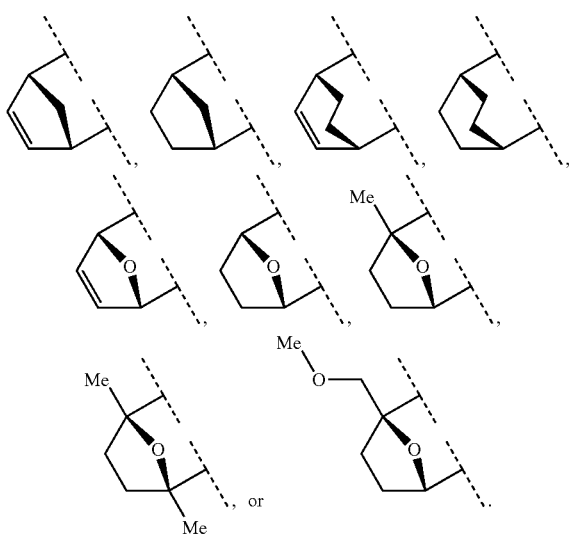

Preferably, when $R^4$ and $R^6$ taken together
are —C($R^{11}$)($R^{12}$)—C($R^{13}$)($R^{14}$)—C($R^{16}$)—C($R^{17}$)($R^{18}$)— or —C($R^{11}$)($R^{12}$)—C($R^{13}$)=C($R^{15}$)—C($R^{17}$)($R^{18}$)—, then the compound of formula (I) is a compound of formula (IA) or (IB):

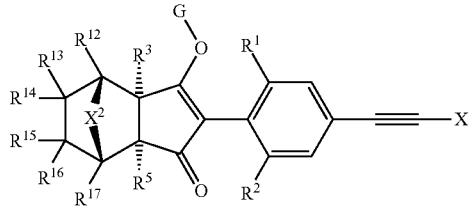

(IA)

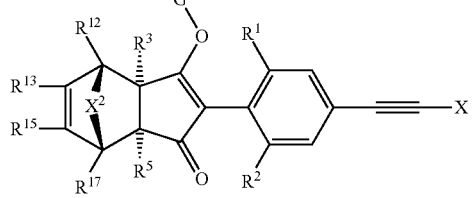

(IB)

wherein G, X, $R^1$, $R^2$, $R^3$, $R^5$, $R^{12}$, $R^{13}$, $R^{14}$, $R^{15}$, $R^{16}$ and $R^{17}$ are as defined herein, and wherein $X^2$ is —O— or —$C_1$-$C_2$alkylene-.

Preferably, $X^2$ is —O—.

Preferably, $R^{19}$ and/or $R^{22}$ are hydrogen.

Preferably, $R^{20}$ and $R^{21}$ taken together are oxo (=O), =N—O—$R^{23}$, or =$CH_2$;

or $R^{20}$ and $R^{21}$, together with the carbon atom to which they are attached, form a 5, 6 or 7 (in particular 5 or 6) membered saturated heterocyclyl, wherein the heterocyclyl has two ring heteroatoms independently being oxygen or sulfur and which are not directly bonded to each other, and wherein the heterocyclyl is optionally substituted by 1, 2 or 3 (in particular 1 or 2) ring-carbon substituents independently being $C_1$-$C_2$alkyl (e.g. methyl).

In a particularly preferable embodiment of the invention, the compound of formula (I) is a compound described in any of Tables 1 to 22, or Table 23, as described and/or illustrated herein, optionally present (e.g. where chemically possible) as an agrochemically acceptable salt thereof.

In a more particularly preferable embodiment of the invention, the compound of formula (I) is compound A-1, A-2, A-3, A-4, A-5, A-6, A-7, A-8, A-9, A-10, A-11, A-12, A-13, A-14, A-15, A-16, A-17, A-18 or A-19, as described and/or illustrated herein, optionally present (e.g. where chemically possible) as an agrochemically acceptable salt thereof.

In a yet more particularly preferable embodiment of the invention, the compound of formula (I) is compound A-2, A-3, A-4, A-5, A-6, A-7, A-8, A-9, A-10, A-11, A-12, A-14, A-15, A-17, A-18 or A-19 (or more preferably compound A-2, A-4, A-6, A-7, A-8, A-9, A-10, A-11, A-12, A-14, A-15, A-18 or A-19), as described and/or illustrated herein, optionally present (e.g. where chemically possible) as an agrochemically acceptable salt thereof.

In an alternative more particularly preferable embodiment of the invention, the compound of formula (I) is compound A-20, A-21, A-22, A-23, A-24, A-25, A-26, A-27, A-28, A-29, A-30, A-31, A-32, A-33, A-34, P-1, P-2, P-3, P-4, P-5, P-6, P-7, P-8, P-9, P-10, P-11, P-12, P-13, P-14, P-15, P-16, P-17, P-18, P-19, P-20, P-21, P-22 or P-23, as described and/or illustrated herein, optionally present (e.g. where chemically possible) as an agrochemically acceptable salt thereof.

In a yet more particularly preferable embodiment of the invention, the compound of formula (I) is compound A-2, A-4, A-6, A-7, A-8, A-9, A-10, A-11, A-12, A-14, A-15, A-18, A-19, A-20, A-23, A-24, A-26, A-27, A-28, A-29, A-30, A-31, A-32 or A-34, as described and/or illustrated herein, optionally present (e.g. where chemically possible) as an agrochemically acceptable salt thereof.

In all embodiments or aspects of the invention, it is strongly preferred that the compound of formula (I) is a compound of formula (IC):

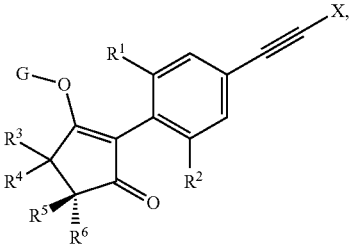

(IC)

wherein X, $R^1$, $R^2$, $R^3$, $R^4$, $R^5$, $R^6$ and G are as defined herein, and wherein 40% or more (in particular 45% or more) by molarity of the compound of formula (IC) has the indicated stereochemistry at the ring-carbon atom bonded to $R^5$ and $R^6$. For example, this broadest definition of formula (IC) includes compounds which are substantially racemic at the ring-carbon atom bonded to $R^5$ and $R^6$, and also includes compounds enriched with isomer(s) having the stereochemistry indicated at the ring-carbon atom bonded to $R^5$ and $R^6$.

More preferably, more than 50% (still more preferably more than 70% or more than 80%, most preferably more than 90% or more than 95%) by molarity of the compound of formula (IC) has the indicated stereochemistry at the ring-carbon atom bonded to $R^5$ and $R^6$. This more preferred definition of formula (IC) includes compounds enriched with isomer(s) having the stereochemistry indicated at the ring-carbon atom bonded to $R^5$ and $R^6$.

Based on the biological results shown herein (see Biological Examples 1 and 4, comparing the results for the chiral-column-separated enantiomers Compounds A-5 and A-6), it is believed that the compounds with the stereochemistry indicated in formula (IC) (e.g. Compound A-6) typically have more potent herbicidal activity against grassy weeds (e.g. when applied post-emergence to the weeds) than the compounds with the opposite stereochemistry (e.g. Compound A-5).

Depending on the nature of the substituents G, $R^1$, $R^2$, $R^3$, $R^4$, $R^5$ and $R^6$, compounds of formula (I) may exist in different isomeric forms. When G is hydrogen, for example, compounds of formula (I) may exist in different tautomeric forms, all of which are encompassed by the present invention:

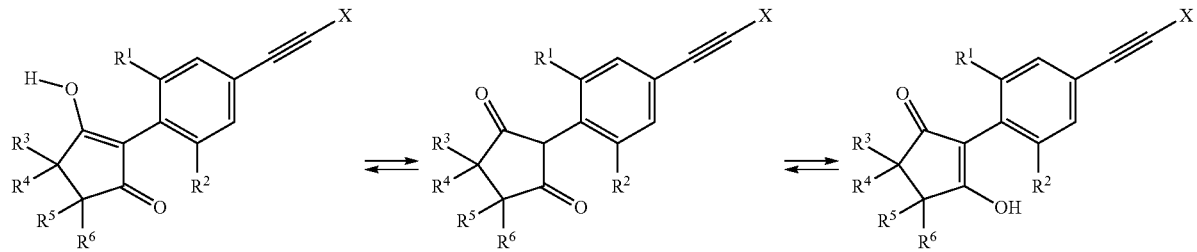

Also, when substituents contain double bonds, cis- and trans-isomers can exist. This invention covers all such isomers and tautomers and mixtures thereof in all proportions. These isomers, too, are within the scope of the claimed compounds of the formula I.

Processes for Preparation of Compounds, e.g. Compounds of Formula (I)

Processes for preparation of compounds, e.g. a compound of formula (I) (which optionally can be an agrochemically acceptable salt thereof), are now described, and form further aspects of the present invention.

A compound of formula I, wherein G is $C_1$-$C_8$alkyl, $C_2$-$C_8$fluoroalkyl, phenyl$C_1$-$C_8$alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano or nitro), heteroaryl$C_1$-$C_8$alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), $C_2$-$C_7$alkenyl-$CH_2$—, $C_2$-$C_7$alkenyl-CH(Me)—, $C_2$-$C_7$alkenyl-$CMe_2$-, $C_2$-$C_4$fluoroalkenyl-$CH_2$—, $C_2$-$C_7$alkynyl-$CH_2$—, —C($X^a$)—$R^a$, —C($X^b$)—$X^c$—$R^b$, —C($X^d$)—N($R^c$)—$R^d$, —$SO_2$—$R^e$, —P($X^e$)($R^f$)—$R^g$ or —$CH_2$—$X^f$—$R^h$, may be prepared by treating a compound of formula (A), which is a compound of formula I wherein G is H, with a reagent G-Z, wherein G-Z is an alkylating agent such as an alkyl halide (the definition of alkyl halides includes simple $C_1$-$C_8$ alkyl halides such as methyl iodide and ethyl iodide, substituted alkyl halides such as chloromethyl alkyl ethers, Cl—$CH_2$—$X^f$—$R^h$, wherein $X^f$ is oxygen, and chloromethyl alkyl sulfides Cl—$CH_2$—$X^f$—$R^h$, wherein $X^f$ is sulfur), a $C_1$-$C_8$alkyl sulfonate, or a di($C_1$-$C_8$alkyl)sulfate, or with a $C_3$-$C_8$alkenyl halide, or with a $C_3$-$C_8$alkynyl halide, or with an acylating agent such as a carboxylic acid, HO—C($X^a$)$R^a$, wherein $X^a$ is oxygen, an acid chloride, Cl—C($X^a$)$R^a$, wherein $X^a$ is oxygen, or acid anhydride, [$R^a$C($X^a$)]$_2$O, wherein $X^a$ is oxygen, or an isocyanate, $R^c$N=C=O, or a carbamoyl chloride, Cl—C($X^d$)—N($R^{cO}$)—$R^d$ (wherein $X^d$ is oxygen and with the proviso that neither $R^c$ or $R^d$ is hydrogen), or a thiocarbamoyl chloride Cl—($X^d$)—N($R^c$)—$R^d$ (wherein $X^d$ is sulfur and with the proviso that neither $R^c$ or $R^d$ is hydrogen) or a chloroformate, Cl—C($X^b$)—$X^c$—$R^b$, (wherein $X^b$ and $X^c$ are oxygen), or a chlorothioformate Cl—C($X^b$)—$X^c$—$R^b$ (wherein $X^b$ is oxygen and $X^c$ is sulfur), or a chlorodithioformate Cl—C($X^b$)—$X^c$—$R^b$, (wherein $X^b$ and $X^c$ are sulfur), or an isothiocyanate, $R^c$N=C=S, or by sequential treatment with carbon disulfide and an alkylating agent, or with a phosphorylating agent such as a phosphoryl chloride, Cl—P($X^e$)($R^f$)—$R^g$ or with a sulfonylating agent such as a sulfonyl chloride Cl—$SO_2$—$R^e$, preferably in the presence of at least one equivalent of base. Where substituents $R^3$ and $R^4$ are not equal to substituents $R^5$ and $R^6$, these reactions may produce, in addition to a compound of formula I, a second compound of formula (IA). This invention covers both a compound of formula I and a compound of formula (IA), together with mixtures of these compounds in any ratio.

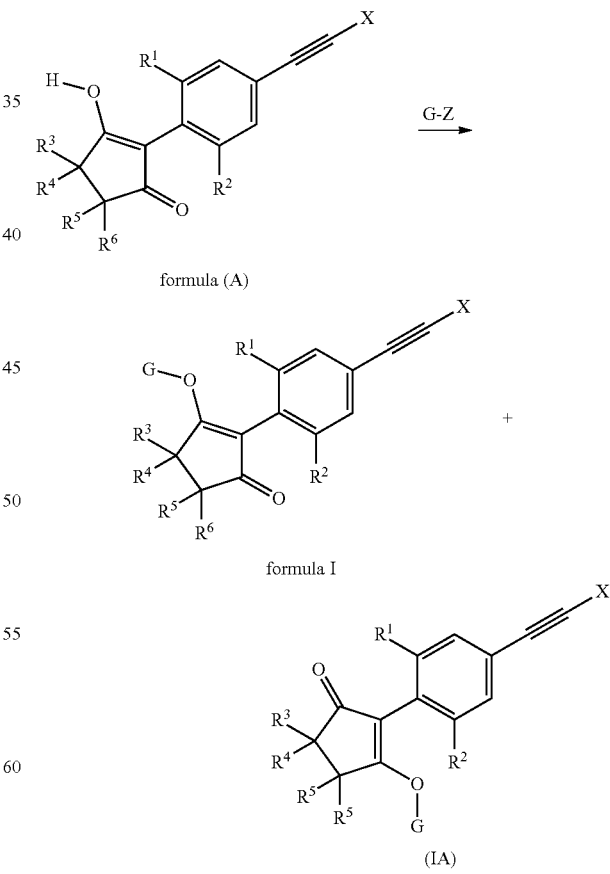

The O-alkylation of cyclic 1,3-diones is known; suitable methods are described, for example, by T. Wheeler, U.S. Pat.

No. 4,436,666. Alternative procedures have been reported by M. Pizzorno and S. Albonico, *Chem. Ind.* (*London*), (1972), 425-426; H. Born et al., *J. Chem. Soc.*, (1953), 1779-1782; M. G. Constantino et al., *Synth. Commun.*, (1992), 22 (19), 2859-2864; Y. Tian et al., *Synth. Commun.*, (1997), 27 (9), 1577-1582; S. Chandra Roy et al., *Chem. Letters*, (2006), 35 (1), 16-17; P. K. Zubaidha et al., *Tetrahedron Lett.*, (2004), 45, 7187-7188.

The O-acylation of cyclic 1,3-diones may be effected by procedures similar to those described, for example, by R. Haines, U.S. Pat. No. 4,175,135, and by T. Wheeler, U.S. Pat. Nos. 4,422,870, 4,659,372 and 4,436,666. Typically diones of formula (A) may be treated with an acylating agent preferably in the presence of at least one equivalent of a suitable base, and optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide; a suitable metal hydride is sodium hydride; and suitable organic bases include trialkylamines, such as trimethylamine and triethylamine, pyridines or other amine bases such as 1,4-diazobicyclo[2.2.2]-octane and 1,8-diazabicyclo [5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a known coupling agent such as 2-chloro-1-methylpyridinium iodide, N,N'-dicyclohexylcarbodiimide, 1-(3-dimethylaminopropyl)-3-ethylcarbodiimide and N,N'-carbodiimidazole, and optionally in the presence of a base such as triethylamine or pyridine in a suitable solvent such as tetrahydrofuran, dichloromethane or acetonitrile. Suitable procedures are described, for example, by W. Zhang and G. Pugh, *Tetrahedron Lett.*, (1999), 40 (43), 7595-7598; T. Isobe and T. Ishikawa, *J. Org. Chem.*, (1999), 64 (19), 6984-6988 and K. Nicolaou, T. Montagnon, G. Vassilikogiannakis, C. Mathison, *J. Am. Chem. Soc.*, (2005), 127 (24), 8872-8888.

Phosphorylation of cyclic 1,3-diones may be effected using a phosphoryl halide or thiophosphoryl halide and a base by procedures analogous to those described by L. Hodakowski, U.S. Pat. No. 4,409,153.

Sulfonylation of a compound of formula (A) may be achieved using an alkyl or aryl sulfonyl halide, preferably in the presence of at least one equivalent of base, for example by the procedure of C. Kowalski and K. Fields, *J. Org. Chem.*, (1981), 46, 197-201.

A compound of formula (A) may be prepared via the cyclisation of a compound of formula (B), preferably in the presence of an acid or base, and optionally in the presence of a suitable solvent, by analogous methods to those described by T. Wheeler, U.S. Pat. No. 4,209,532. The compounds of the formula (B) have been particularly designed as intermediates in the synthesis of the compounds of the formula I. Compounds of formula (B) wherein R is hydrogen or $C_1$-$C_4$alkyl, (especially methyl, ethyl and tert-butyl) may be cyclised under acidic conditions, preferably in the presence of a strong acid such as sulfuric acid, polyphosphoric acid or Eaton's reagent, optionally in the presence of a suitable solvent such as acetic acid, toluene or dichloromethane. A compound of formula (B) wherein R is alkyl (preferably methyl or ethyl) may also be cyclised under basic conditions in the presence of at least one equivalent of a strong base in a solvent such as tetrahydrofuran, toluene, dimethylsulfoxide or N,N-dimethylformamide. Suitable bases include potassium tert-butoxide, lithium diisopropylamide, sodium bis(trimethylsilyl)amide or sodium hydride. A compound of formula (B), wherein R is alkyl, may be produced from a compound of formula (B), wherein R is H, by esterification under known conditions (for example by treatment with an alcohol, R—OH, in the presence of an acid catalyst).

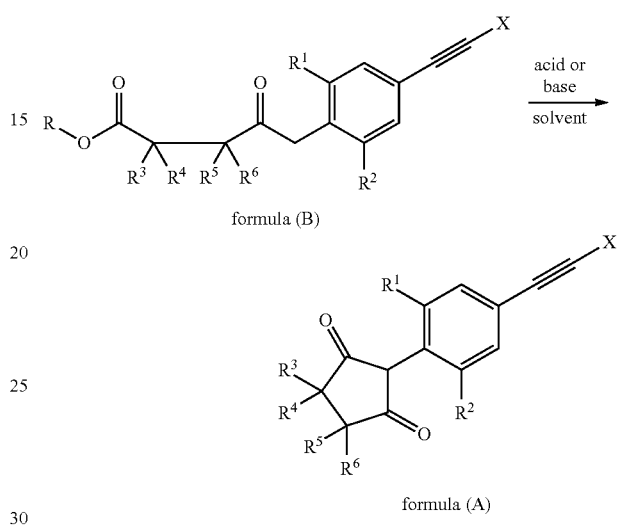

A compound of formula (B), wherein R is H may be prepared by hydrolysis of a compound of formula (C) wherein R is H or alkyl and R' is alkyl (preferably methyl or ethyl), followed by acidification of the reaction mixture to effect decarboxylation, by similar processes to those described by, for example, T. Wheeler, U.S. Pat. No. 4,209,532. Alternatively, a compound of formula (B), wherein R is alkyl or H may be prepared from a compound of formula (C), wherein R' is alkyl (preferably methyl), through a Krapcho decarboxylation procedure under known conditions using known reagents (see for example G. Quallich, P. Morrissey, *Synthesis*, (1993), (1), 51-53).

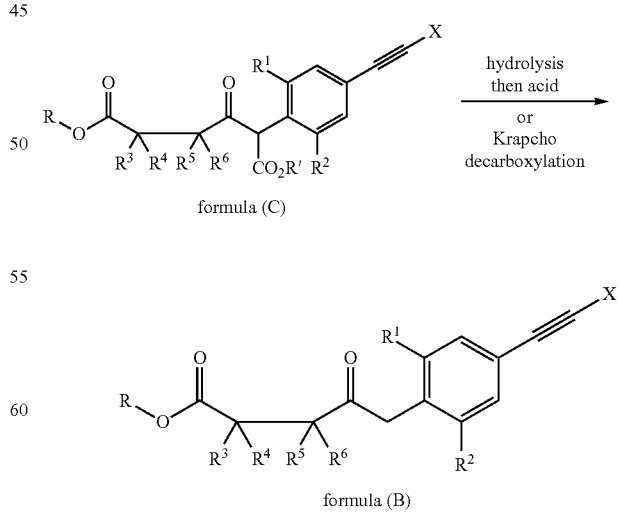

A compound of formula (C) wherein R is alkyl may be prepared by treating a compound of formula (D) with a suitable carboxylic acid chloride of formula (E) wherein R is alkyl under basic conditions. Suitable bases include potassium tert-butoxide, sodium bis(trimethyl-silyl)amide and lithium diisopropylamide and the reaction is preferably conducted in a suitable solvent (such as tetrahydrofuran or toluene) at a temperature between −78° C. and 30° C. Under similar conditions a compound of formula (C), wherein R is H, may be prepared from a suitable anhydride of formula (F).

Sanceau, WO 2008/124922; M. S. Viciu, S. P. Nolan, *Modern Arylation Methods* (2009), 183-220; R. Chinchilla, C. Najera, *Chemical Reviews* (2007), 107(3), 874-922; I. P. Beletskaya, G. V. Latyshev, A. V. Tsvetkov, N. V. Lukashev, *Tetrahedron Letters* (2003), 44(27), 5011-5013 and J. Mao, G. Xie, M. Wu, J. Guo, S. Ji, *Advanced Synthesis & Catalysis* (2008), 350 (16), 2477-2482).

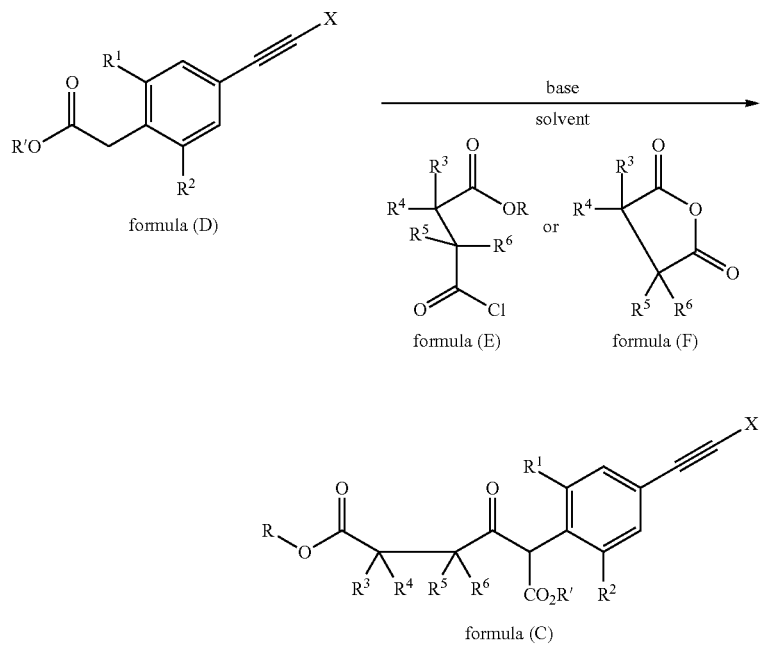

Compounds of formula (E) and formula (F) are known or can be prepared from known reagents using known methods.

Compounds of formula (D), wherein X is methyl and R' is $C_1$-$C_4$alkyl, can be prepared by reacting compounds of formula (G) with propyne in the presence of a suitable catalyst, optionally a suitable additive, optionally in a suitable solvent at a suitable temperature.

Suitable catalysts include transition metal salts or complexes of transition metal salts (for example palladium acetate, bis(triphenylphosphine) palladium(II) dichloride, tetrakis(triphenylphosphine)palladium(0), bis(triphenylphosphine) nickel(II) dichloride and tris(acetylacetonato) iron(III)), in an amount typically 0.001-25% with respect to a compound of formula (G). Suitable additives include copper salts (for example copper(I) iodide in an amount typically 0.001-50% with respect to a compound of formula (G)), and tetraalkyl ammonium salts. Suitable bases include diethylamine, triethylamine, piperidine and pyrrolidine, and suitable solvents include 1,4-dioxane, N,N-dimethylacetamide or N,N-dimethylformamide. Preferably the reaction is carried out using 0.05-10% bis(triphenylphosphine) palladium(II) dichloride (with respect to a compound of formula (G)), 0.05-10% triphenylphosphine (with respect to a compound of formula (G)), 0.05-25% copper(I) iodide (with respect to a compound of formula (G)), 5-200% tetrabutyl ammonium iodide (with respect to a compound of formula (G)), triethylamine and N,N-dimethylformamide at a temperature between 25° C. to 150° C. Such a reaction is an example of a Sonogashira coupling and similar reactions are known in the literature (see for example F. Labrie, S. Gauthier, J. Cloutier, J. Mailhot, S. Potvin, S. Dion, J-Y.

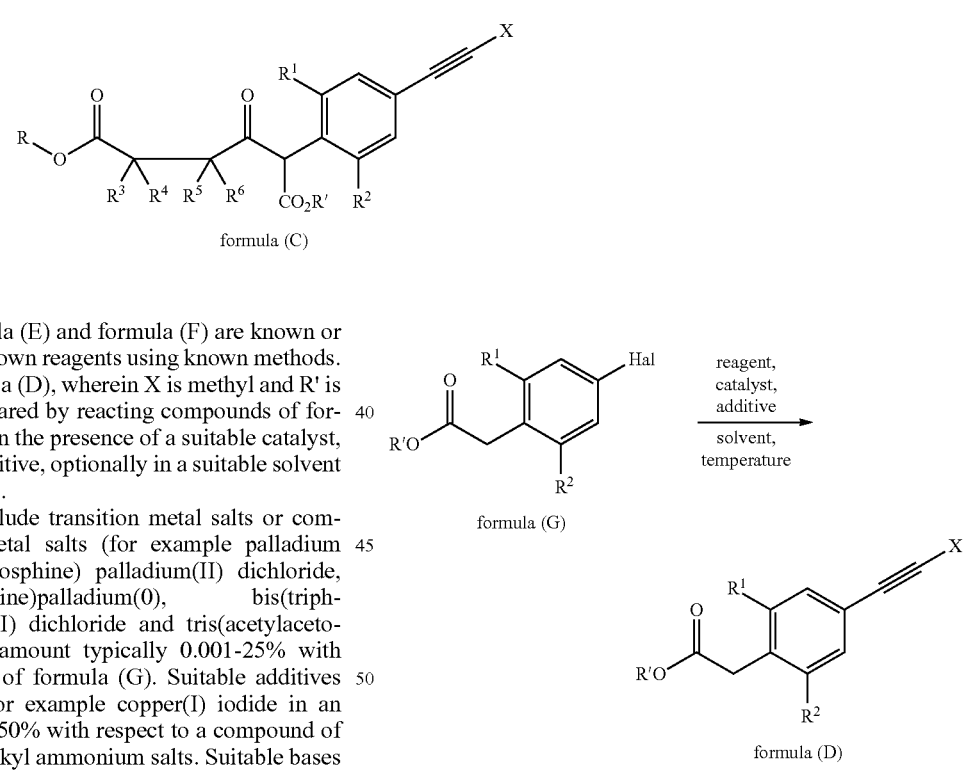

In an alternative approach a compound of formula (D) may be prepared from a compound of formula (G) by reaction with a propynyl transfer reagent such as 1-propynyllithium, 1-propynylmagnesium bromide, 1-propynylmagnesium chloride, 1-propynylmagnesium iodide, 1-propynylzinc chloride, 1-propynylzinc bromide, 1-propynylzinc iodide, tributylpropynylstannane, 1-propyne-1-boronic acid (or ester thereof), 2-butynoic acid or 1-(trimethylsilyl)propyne, with a transition metal catalyst system under suitable conditions (see for example P. Wessig, G. Mueller, C. Pick, A. Matthes, *Synthesis* (2007), (3), 464-477; J. H. Chaplin, G. S. Gill, D. W. Grobelny, B. L. Flynn, G. Kremmidiotis, WO07/087,684; A.

Akao, T. Tsuritani, S. Kii, K. Sato, N. Nonoyama, T. Mase, N. Yasuda, *Synlett* (2007), (1), 31-36. A. Coelho Coton, E. Sotelo Perez, F. Guitian Rivera, A. Gil Gonzalez, WO 2011/048247; C. H. Oh, S. H. Jung, *Tetrahedron Letters* (2000), 41 (44), 8513-8516; D. Zhao, C. Gao, X. Su, Y. He, J. You, Y. Xue, *Chemical Communications* (2010), 46 (47), 9049-9051; C. Yang, S. P. Nolan, *Organometallics* (2002), 21 (6), 1020-1022). In another set of preferred conditions a compound of formula (G) is reacted with 1-propynylmagnesium bromide in the presence of 0.05-10% bis(triphenylphosphine) palladium(II) dichloride (with respect to a compound of formula (G)), in tetrahydrofuran at a temperature between 25° C. and 100° C., as described by J. H. Chaplin, G. S. Gill, D. W. Grobelny, B. L. Flynn, G. Kremmidiotis, WO 07/087,684.

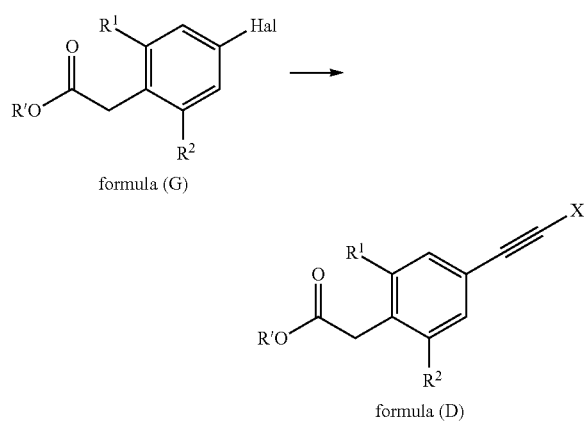

formula (G)

formula (D)

In yet another set of preferred conditions to prepare a compound of formula (D) in which X=methyl, a compound of formula (G) is reacted with 2-butynoic acid in the presence of bis(triphenylphosphine) palladium(II) dichloride (typically in an amount of 0.1 to 5 mole % with respect to the compound of formula (G)), in a suitable organic solvent such as dimethylsulfoxide, preferably at a temperature of from 25 to 125° C.; e.g. as described by J. Moon, M. Jang and S. Lee, *Journal of Organic Chemistry* (2009), page 1403 onwards. This is a decarboxylative coupling reaction.

Compounds of formula (G) are known, or can be prepared by known methods using known reagents.

Compounds of formula (D), wherein X is chlorine and R' is $C_1$-$C_4$alkyl, can be prepared from compounds of formula (H) or compounds of formula (I). In one approach a compound of formula (H) is first deprotonated with a base such as butyllithium, sodium hydride, lithium diisopropylamide or ethylmagnesium bromide, then reacted with a chlorine source such as N-chloro succinimide, chlorine or carbon tetrachloride. The specific chlorine source is selected to provide the required chloro-acetylene. Similar reactions and conditions are reported in the literature (see for example M. Tajbakhsh, S. Habibzadeh, *Letters in Organic Chemistry* (2007), 4 (7), 512-514; D. Sud, T. J. Wigglesworth, N. R. Branda, *Angewandte Chemie, International Edition* (2007), 46 (42), 8017-8019; M. A. P. Martins, D. J. Emmerich, C. M. P. Pereira, W. Cunico, M. Rossato, N. Zanatta, H. G. Bonacorso, *Tetrahedron Letters* (2004), 45 (25), 4935-4938; A. Poloukhtine, V. Rassadin, A. Kuzmin, V. V. Popik, *Journal of Organic Chemistry* (2010), 75 (17), 5953-5962; C. R. Hickenboth, J. D. Rule, J. S. Moore, *Tetrahedron* (2008), 64 (36), 8435-8448; F. H. M. Graichen, A. C. Warden, S. Kyi, M. S. O'Shea, *Australian Journal of Chemistry* (2010), 63 (4), 719-722; and M. L. Narayana, M. L. N. Rao, M. Periasamy, *Synthetic Communications* (1995), 25 (15), 2295-9).

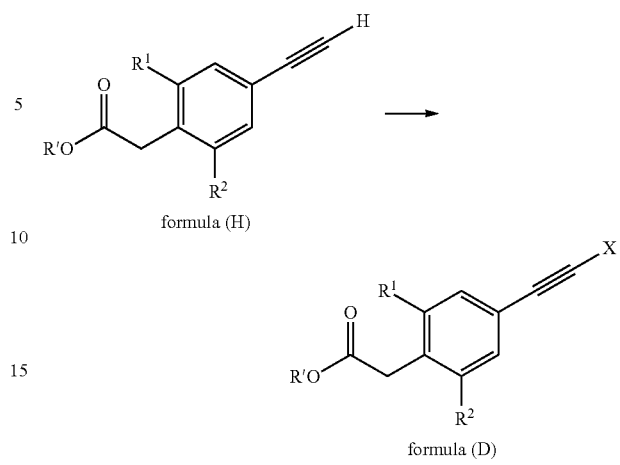

formula (H)

formula (D)

In another approach a compound of formula (D), wherein X is chlorine and R' is $C_1$-$C_4$alkyl, can be prepared from a compound of formula (H) by treatment with a mixture of reagents that are known to promote chlorination, such as potassium carbonate, tetrabutylammonium bromide and carbon tetrachloride (see for example T. Matsuda, S. Kadowaki, Y. Yamaguchi, M. Murakami, *Chemical Communications* (2008), (24), 2744-2746), pyridine and chlorine (see for example R. B. Gutsulyak, V. N. Britsuk, L. A. Kostrikina, Y. Serguchev, *Ukrainskii Khimicheskii Zhurnal* (1993), 59 (10), 1062-7), silver nitrate and N-chloro succinimide, N-chloro succinimide and hexamethylphosphoramide (see for example G. Pangon, J. L. Philippe, P. Cadiot, *Comptes Rendus des Seances de l'Academie des Sciences, Serie C: Sciences Chimiques* (1973), 277 (18), 879-81), and/or perchloric acid and acetic acid (see for example J. P. Montheard, M. Camps, M. Chatzopoulos, M. O. A. Yahia, R. Guilluy, D. Deruaz, *Journal of Chemical Research, Synopses* (1983), (9), 224-5). Conditions are selected to provide the required halo-acetylene. When X is chlorine, preferred conditions include reacting a compound of formula (H) with 1-5 equivalents of N-chloro succinimide and 0.05-50% silver acetate (with respect to a compound of formula (H)) in acetone at a temperature between 25° C. and 100° C.

Compounds of formula (I), wherein R' is $C_1$-$C_4$alkyl and R" is $C_1$-$C_4$alkyl, can also be directly converted to compounds of formula (D) by treatment with isocyanuric chloride or N-chloro succinimide and silver nitrate (see for example M. H. Vilhelmsen, A. S. Andersson, M B. Nielsen, *Synthesis* (2009), (9), 1469-1472).

A compound of formula (I), wherein R' is $C_1$-$C_4$alkyl and R" is $C_1$-$C_4$alkyl, can be prepared by reacting a compound of formula G with a trialkylsilylacetylene, under similar conditions described previously to convert a compound of formula (G) to a compound of formula (D) (wherein X is methyl).

A compound of formula (H) can either be prepared by deprotection of a compound of formula (I) under known conditions, or by reacting a compound of formula (G) with an ethynyl transfer reagent such as tributylstannylacetylene, lithium acetylide ethylenediamine complex, ethynylzinc bromide or ethynylmagnesium chloride in the presence of a suitable catalyst system, under conditions similar to those described previously (see for example C. Fischer, J. Methot, H. Zhou, A. J. Schell, B. Munoz, A. A. Rivkin, S. P. Ahearn, S. Chichetti, R. N. Maccoss, S. D. Kattar, M. Christopher, C. Li, A. Rosenau, W. C. Brown, WO 2010/071741; M. Behler, A. Eluntlaut, C. Ferman, A. Chapuf, CN 101195641; G. Wang, G. Zhu, E. Negishi, *Journal of Organometallic Chemistry* (2007), 692 (21), 4731-4736 and E. Negishi, M. Kotora, C. Xu, *Journal of Organic Chemistry* (1997), 62 (25), 8957-8960).

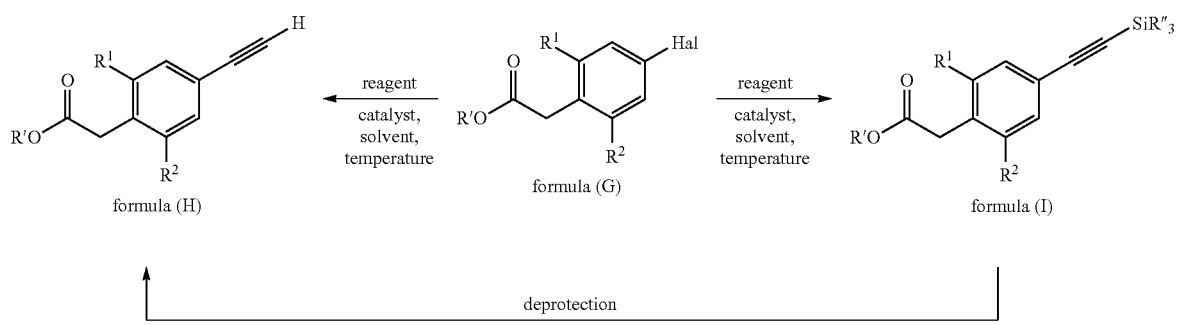

In a further approach, a compound of formula (D) (wherein X is chlorine) can either be prepared from a compound of formula (J) or a compound of formula (K), by treatment with a suitable base, in a suitable solvent, at a suitable temperature. A compound of formula (J) can be converted to a compound of formula (D) under conditions similar to those described in the literature, for example treatment using potassium tert-butoxide in tert-butanol at a temperature between 25° C. and 150° C., or lithium 2,2,6,6-tetramethylpiperidine in tetrahydrofuran at a temperature between −25° C. and 50° C. (see for example E. Bartmann, R. Hittich, H. Plach, U. Finkenzeller, U.S. Pat. No. 5,188,759 and *Indian Journal of Chemistry, Section B: Organic Chemistry Including Medicinal Chemistry,* 1978, vol. 16, 1051-1054). A compound of formula (K) can also be converted to a compound of formula (D) under conditions similar to those described in the literature, for example by treatment with cesium carbonate in N,N-dimethylformamide at a temperature between 25° C. and 150° C., sodium tert-butoxide in toluene at a temperature between 25° C. and 150° C., 1,8-diazabicyclo[5.4.0]undec-7-ene in dimethylsulfoxide at a temperature between 0° C. and 50° C. and potassium tert-butoxide in tetrahydrofuran at a temperature between −78° C. and 25° C. (see for example B. C. G. Soederberg, S. P. Gorugantula, C. R. Howerton, J. L. Petersen, S. W. Dantale, *Tetrahedron* (2009), 65 (36), 7357-7363; S-C. Lo, R. E. Harding, E. Brightman, P. L. Burn, I. D. W. Samuel, *Journal of Materials Chemistry* (2009). 19 (20), 3213-3227; S. Wang, T. Kohn, Z. Fu, X. Y. Jiao, S. Lai, M. Schmitt, *Tetrahedron Letters* (2008), 49 (51), 7284-7286 and M. L. G. Borst, R. E. Bulo, D. J. Gibney, Y. Alem, F. J. J. de Kanter, A. W. Ehlers, M. Schakel, M. Lutz, A. L. Spek, K. Lammertsma, *Journal of the American Chemical Society* (2005), 127 (48), 16985-16999). Compounds of formula (J) and (K) (wherein X is chlorine) can be prepared from known compounds using known methods and reagents.

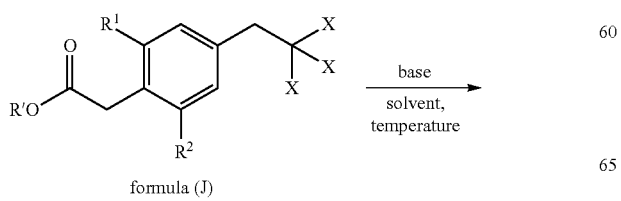

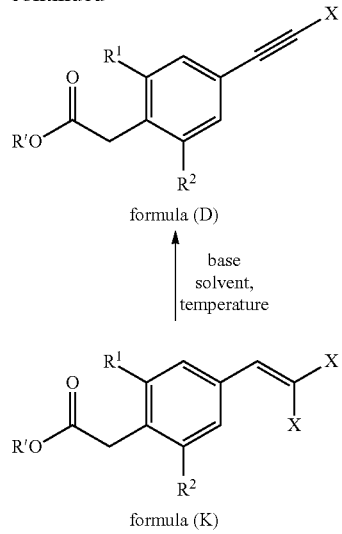

In a further approach a compound of formula (A), wherein X is methyl, can be prepared directly from a compound of formula (L), under similar conditions described previously to convert a compound of formula (G) to a compound of formula (D).

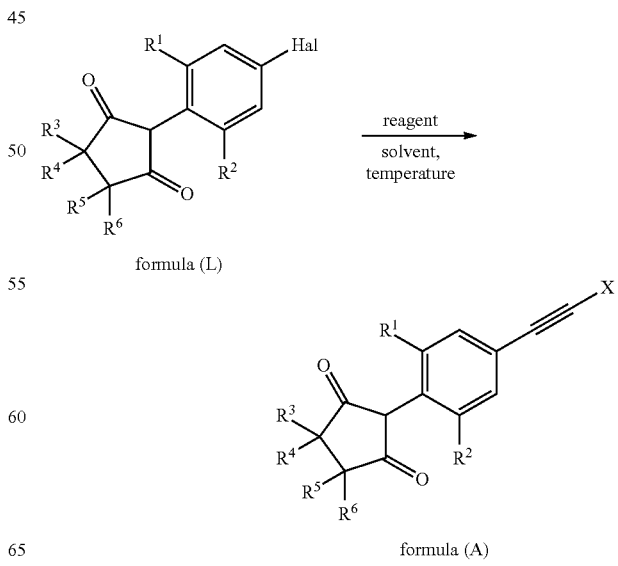

In a still further approach, a compound of formula (A1), wherein X is methyl and G is non-tertiary $C_1$-$C_4$alkyl such as methyl, can be prepared directly from a compound of formula (L1), under similar conditions described previously to convert a compound of formula (G) to a compound of formula (D).

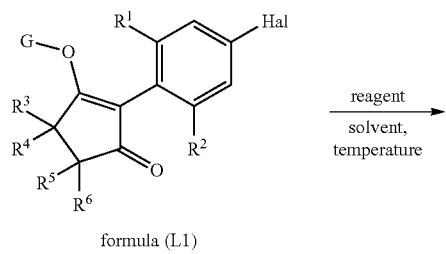

formula (L1)

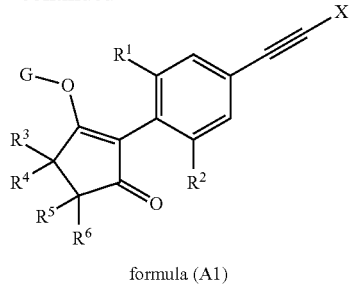

formula (A1)

The resulting compound of formula (A1) can then optionally be converted to a compound of formula (A), e.g. by a dealkylation/demethylation reaction, e.g. under known conditions.

A compound of formula (L) can be prepared from a compound of formula (G) using similar procedures to those outlined previously.

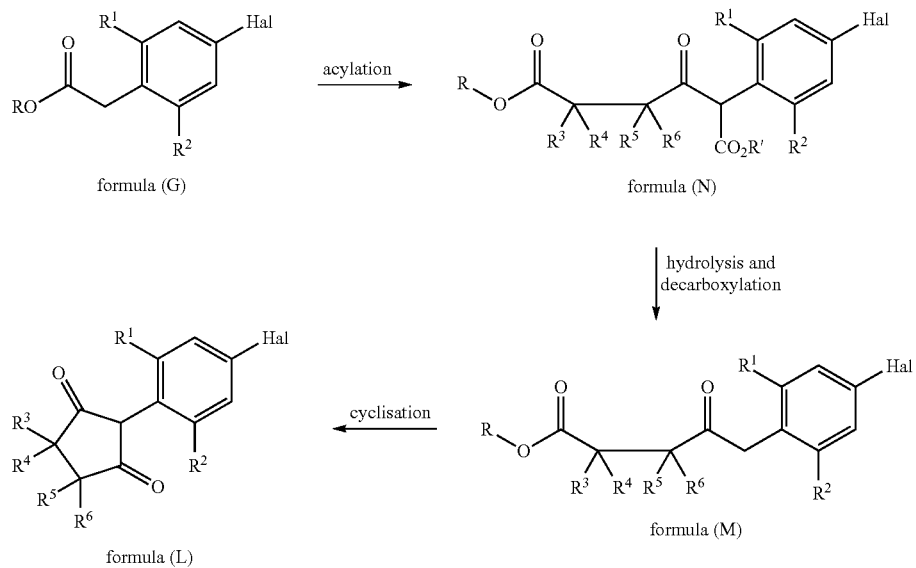

A compound of formula (A), wherein X is chlorine, can be prepared from a compound of formula (L), via either a compound of formula (O) or a compound of formula (P) (wherein R″ is $C_1$-$C_4$alkyl), under similar conditions to those described previously.

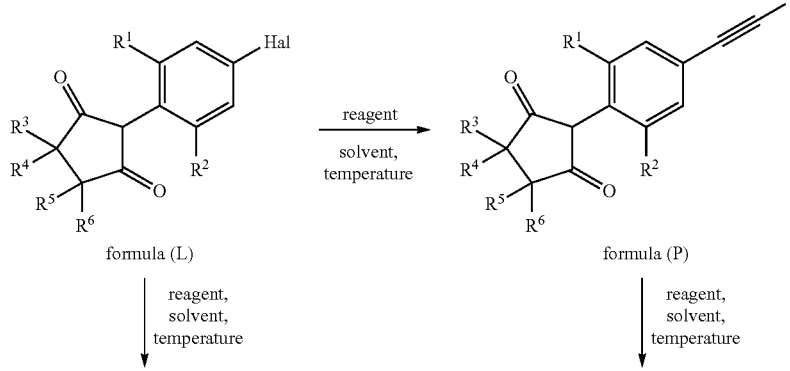

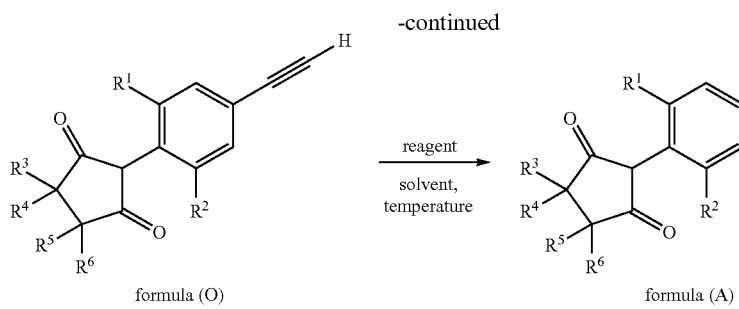

formula (O) → formula (A)

reagent, solvent, temperature

A compound of formula (A), wherein X is chlorine, can also be prepared from a compound of formula (O) under conditions similar to those described for converting a compound of formula (K) to a compound of formula (D).

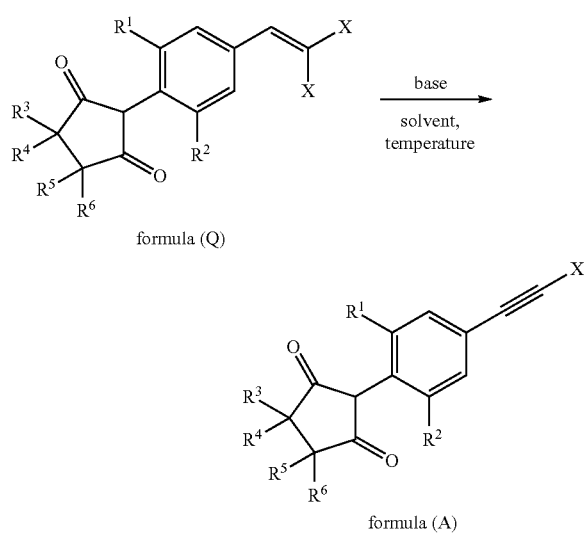

formula (Q) → formula (A)

base, solvent, temperature

A compound of formula (O), wherein X is chlorine may be prepared from an aldehyde of formula (R) by treatment with triphenylphosphine in the presence of carbon tetrachloride in a suitable solvent at a suitable temperature. Carbon tetrachloride is selected to provide the required dichloroalkene, and similar reactions are known in the literature (see for example A. Poloukhtine, V. V. Popik, *Journal of the American Chemical Society* (2007), 129 (40), 12062-12063; L. N. Michaelides, B. Darses, D. J. Dixon, *Organic Letters* (2011), 13 (4), 664-667 and F. Gavina, S. V. Luis, P. Ferrer, A. M. Costero, J. A. Marco, *Journal of Chemical Research, Synopses* (1986), (9), 330-1).

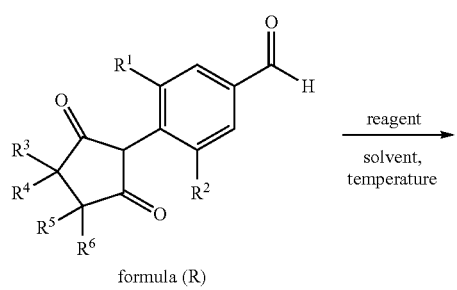

formula (R)

reagent, solvent, temperature

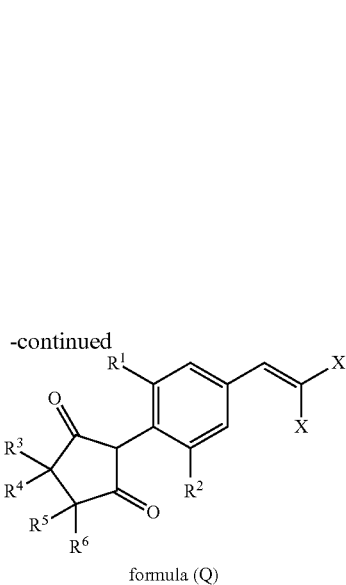

formula (Q)

A compound of formula (R) may be prepared by the formylation of a compound of formula (L) (wherein Hal is chlorine, bromine or iodine, preferably bromine or iodine). Suitable conditions for effecting the formylation of aryl halides are known, and include, for example, the treatment of an aryl halide with a suitable organometallic reagent (such as isopropyl magnesium chloride, n-butyllithium, sec-butyllithium or tert-butyllithium), or by treatment with a suitable alkali metal or alkali earth metal (such as lithium or magnesium) in a suitable solvent (such as diethyl ether, dimethoxyethane or tetrahydrofuran). The resulting arylmetal reagent is then reacted with a suitable formylating agent such as N,N-dimethylformamide or N-formylmorpholine. Alternatively a compound of formula (R) may be prepared from a compound of formula (L) (wherein Hal can also be a pseudohalogen such as triflate) by treatment with a carbonylating agent (such as carbon monoxide) in the presence of a suitable catalyst system, base, and reducing agent (see for example L. Ashfield and C. Barnard, *Org. Process Res. Dev.*, 11 (1), 39-43, 2007).

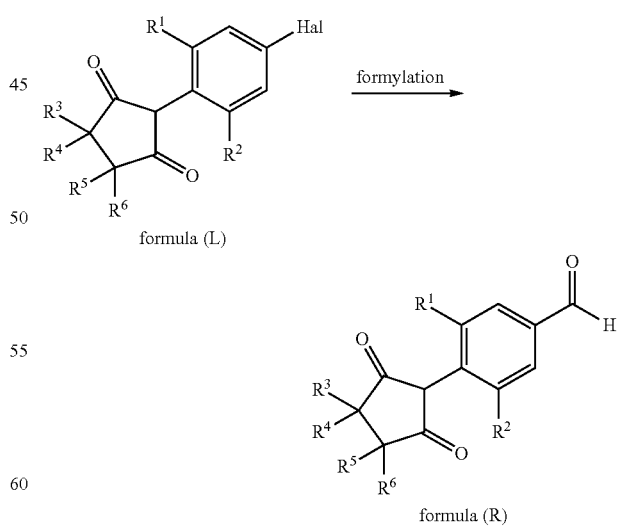

formula (L) → formula (R)

formylation

In an alternative approach a compound of formula I, wherein X is methyl and G is preferably methyl of ethyl, may be prepared from a boronic acid or boronic ester of formula (S) (as shown below) by treatment with either 1-bromo-1-propyne or 1-iodo-1-propyne in the presence of a suitable catalyst system, suitable base, suitable solvent at a suitable temperature. Similar reactions are known in the literature, and preferred conditions involve reacting a compound of formula (S) with 1-iodo-propyne in the presence of 0.005-25% palladium(II) chloride (with respect to a compound of formula (S)) and 1-10 equivalents potassium carbonate in a mixture of toluene, water and methanol at a temperature between 50° C.-150° C., as described by Y. Shi, X. Li, J. Liu, W. Jiang, L. Sun, *Tetrahedron Letters* (2010), 51 (28), 3626-3628. A compound of formula (T), wherein G is preferably methyl of ethyl and R" is $C_1$-$C_4$alkyl, may be prepared under similar conditions using either 1-bromo-2-(trimethylsilyl)acetylene or 1-iodo-2-(trimethylsilyl)acetylene as the coupling partner. Compounds of formula (A) and (P) may be prepared from compounds of formula I and (T) respectively, by hydrolysis of the enol ether.

In one approach a compound of formula (S) may be prepared from a compound of formula (L) (wherein Hal is preferably iodine or bromine) by treatment with a suitable base (such as sodium hydride, potassium hydride or isopropyl-magnesium chloride), in a suitable solvent (such as tetrahydrofuran or diethyl ether) followed by a metal-halogen exchange reaction (preferably by treatment with an alkyl-lithium reagent such as n-butyllithium, sec-butyllithium or tert-butyllithium, or an organomagnesium reagent such as isopropyl magnesium chloride) and subsequent treatment with a trialkylborate, B(OR")$_3$, (preferably trimethylborate) to give the corresponding boronate ester of formula (S).

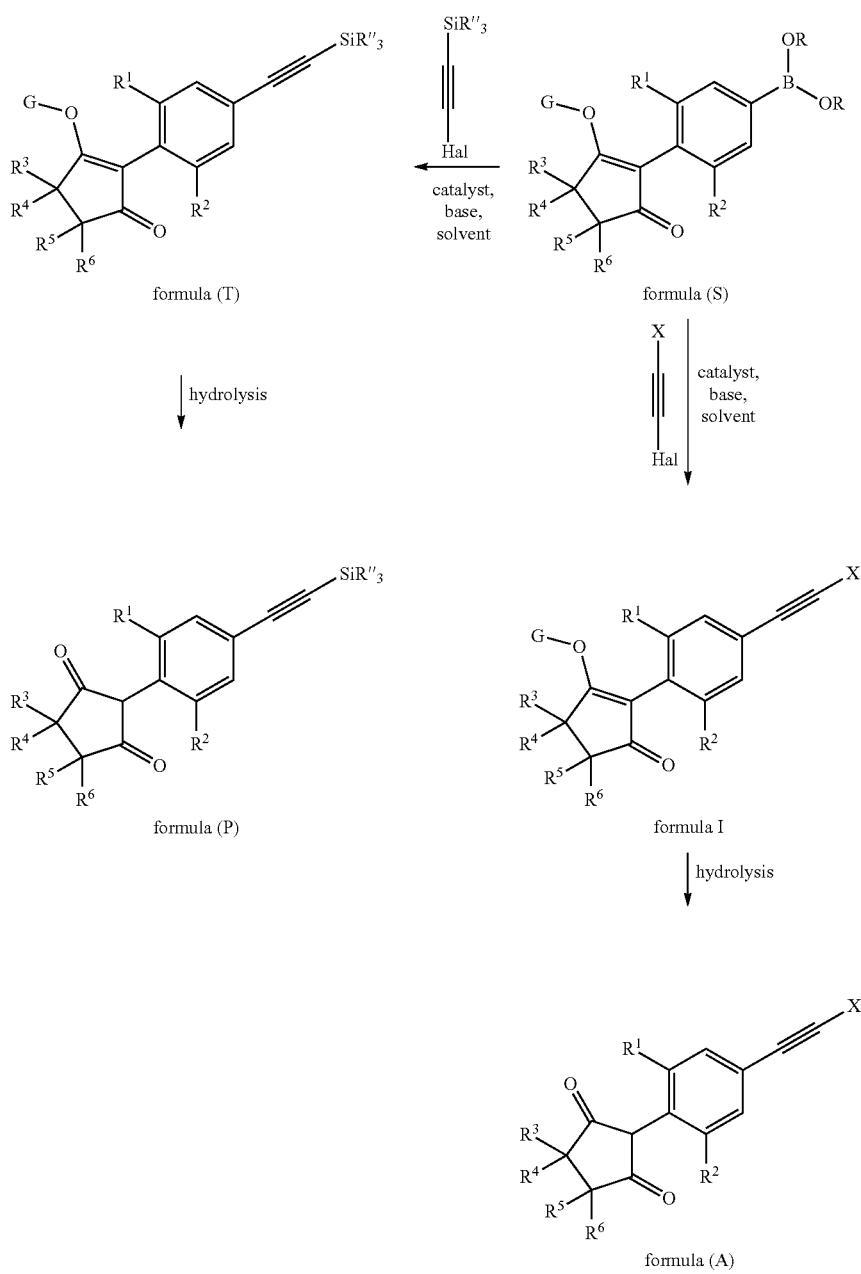

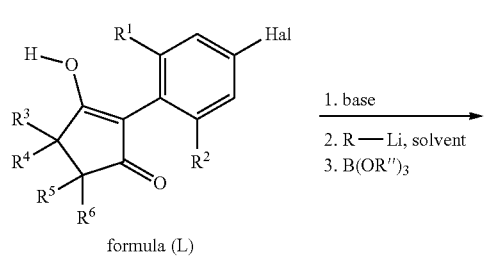

formula (L)

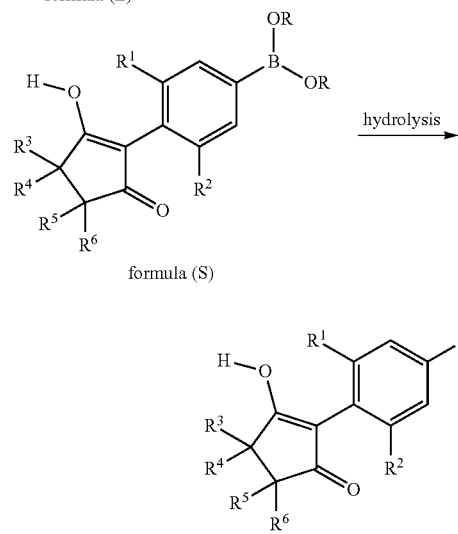

formula (S)

In an alternative approach a compound of formula (S) may be prepared from a compound of formula (U), wherein G is preferably methyl or ethyl, by C—H borylation with a suitable borylating agent, a suitable catalyst system, in a suitable solvent at a suitable temperature. Suitable catalysts include 1,5-cyclooctadiene)(methoxy)iridium(I) dimer in combination with 4,4'-di-tert-butyl-2,2'-dipyridyl, suitable borylating agents include bis(pinacolato)diboron or pinacol borane, and suitable solvents include hexane, octane, tetrahydrofuran and methyl tert-butyl ether. Similar examples are known in the literature (see for example J. F. Hartwig, *Chemical Society Reviews* (2011), 40 (4), 1992-2002 and T. Ishiyama, N. Miyaura, *Pure and Applied Chemistry* (2006), 78 (7), 1369-1375). Preferred conditions include treating a compound of formula (U) with 0.05-10% 1,5-cyclooctadiene)(methoxy)iridium(I) dimer (with respect to a compound of formula (U)), 0.05-10% 4,4'-di-tert-butyl-2,2'-dipyridyl (with respect to a compound of formula (U)), and 1-2 equivalents bis(pinacolato)diboron (with respect to a compound of formula (U)) in methyl tert-butyl ether at a temperature between 50° C.-150° C., optionally under microwave irradiation, as described by P. Harrisson, J. Morris, T. B. Marder, P. G. Steel, *Organic Letters* (2009), 11 (16), 3586-3589.

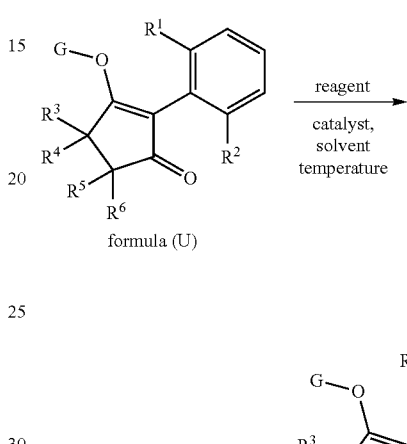

formula (U)

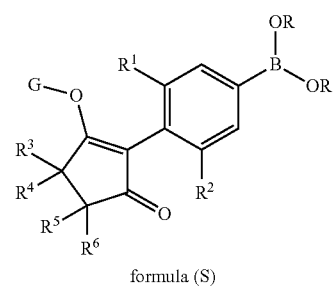

formula (S)

Compounds of formula (U) can be prepared from compounds of formula (W) using similar procedures described above, starting from compounds of formula (Y) which are known compounds.

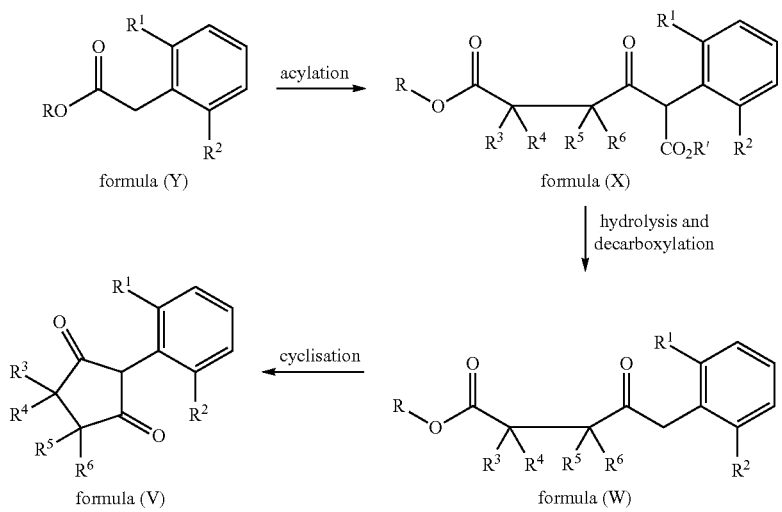

Additionally, a compound of formula (A), wherein X is methyl, may be prepared by the Pinacol rearrangement of a compound of formula (Z) or a compound of formula (AA), wherein X is methyl and R''' is $C_1$-$C_4$ alkyl (preferably methyl), under protic or Lewis acidic conditions (see, for example, Eberhardt, U. et. al., *Chem. Ber.* (1983), 116 (1), 119-35, and Wheeler, T. N. U.S. Pat. No. 4,283,348). Preferred conditions include reacting a compound of formula (Z) or (AA) with trifluoroacetic acid at room temperature.

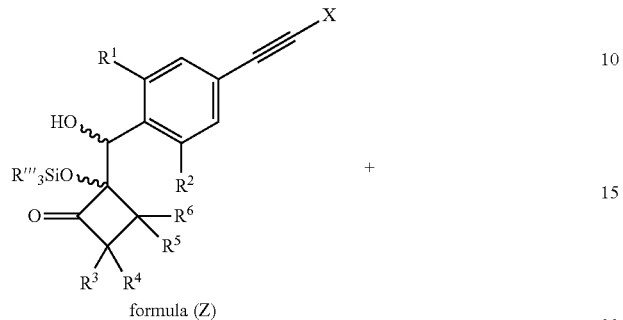

formula (Z)

+

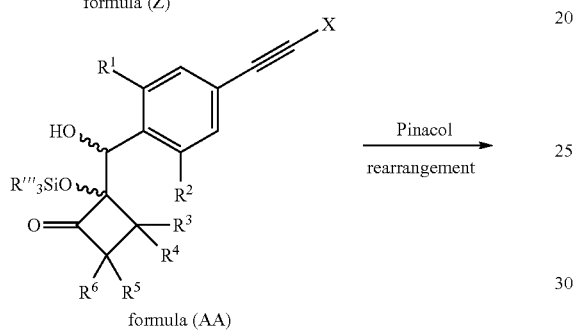

formula (AA)

Pinacol rearrangement

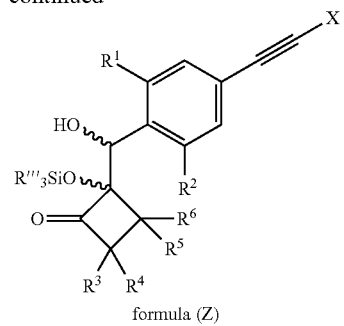

formula (Z)

+

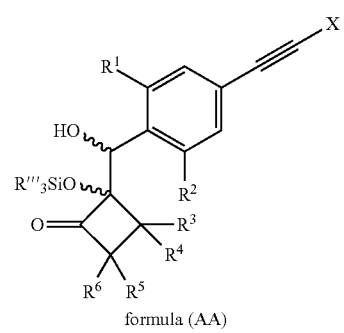

formula (AA)

Compounds of formula (AC), wherein R''' is $C_1$-$C_4$ alkyl (preferably methyl), may be prepared from compounds of formula (AD), where in R'''' is an alkyl group (preferably methyl), in the presence of chloro tri-$C_1$-$C_4$alkyl silyl and a metal (preferably sodium) in a suitable solvent (such as toluene or diethyl ether) at a temperature between 20° C. and 150° C. (see, for example, Blanchard, A. N. and Burnell, D. J., *Tetrahedron Lett.* (2001), 42 (29), 4779-4781 and Salaun, J. et al., *Tetrahedron* (1989), 45 (10), 3151-62).

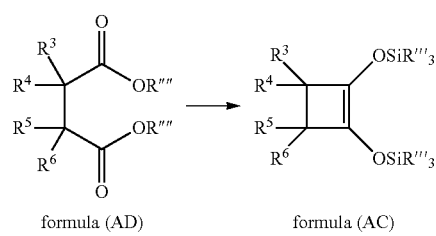

formula (AD)              formula (AC)

Compounds of formula (AD) are either known compounds or can be prepared from known reagents using known methods.

Similarly, compounds of formula (P) can also be prepared from compounds of formula (AC), wherein R''' is $C_1$-$C_4$alkyl (preferably methyl), and compounds of formula (AE), wherein R'' is $C_1$-$C_4$alkyl (preferably methyl), using similar procedures and conditions described previously. Compounds of formula (AE) are known or can be prepared from known reagents using known methods.

formula (A)

A compound of formula (Z) and a compound of formula (AA), wherein X is methyl and R''' is $C_1$-$C_4$ alkyl (preferably methyl), may be prepared by treating a compound of formula (AC) with a compound of formula (AB) in the presence of an acid (such as boron trifluoride, titanium chloride or magnesium iodide) optionally in a suitable solvent (such as dichloromethane) at a temperature between −80° C. and 30° C. (see, for example, Li, W.-D. Z. and Zhang, X.-X., *Org. Lett.* (2002), 4 (20), 3485-3488; Shimada, J. et al., *J. Am. Chem. Soc.* (1984), 106 (6), 1759-73; Eberhardt, U. et. al., *Chem. Ber.* (1983), 116 (1), 119-35 and Wheeler, T. N. U.S. Pat. No. 4,283,348). A compound of formula (AB), wherein X is methyl, is known or can be prepared from known reagents using known methods.

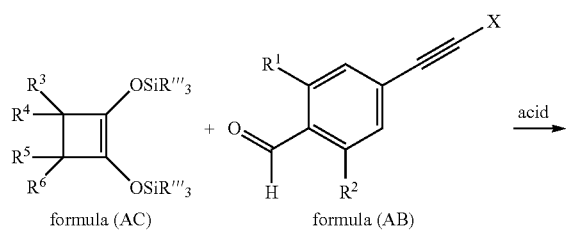

formula (AC)              formula (AB)

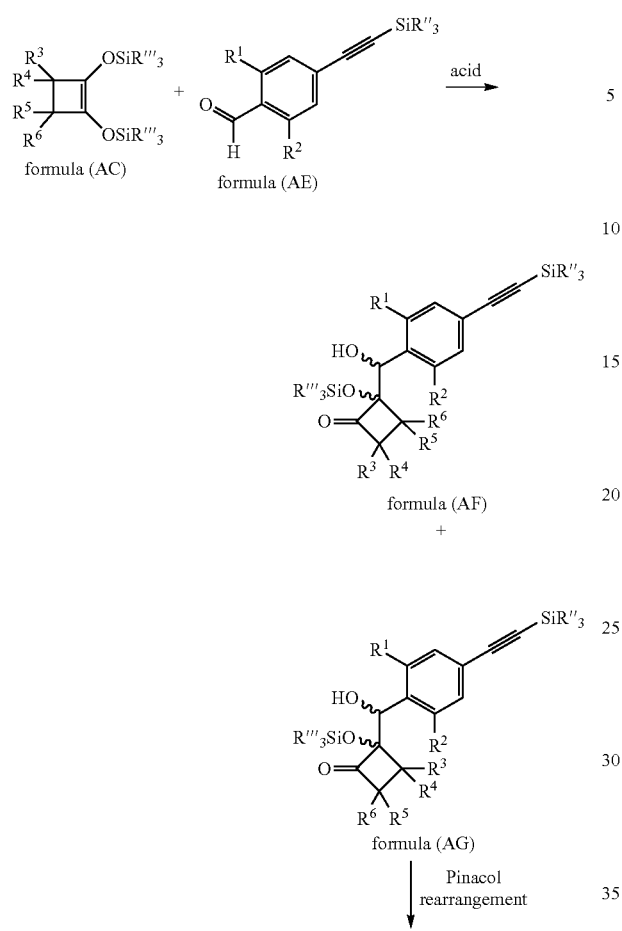

Similarly, compounds of formula (L) can also be prepared from compounds of formula (AC), wherein R''' is $C_1$-$C_4$alkyl (preferably methyl), and halogenated compounds of formula (AH), using similar procedures and conditions described previously. Compounds of formula (AH) are known or can be prepared from known reagents using known methods.

Additionally, compounds of formula (V) can also be prepared from compounds of formula (AC), wherein R''' is $C_1$-$C_4$alkyl (preferably methyl), and compounds of formula (AK), using similar procedures and conditions described previously. Compounds of formula (V) are known or can be prepared from known reagents using known methods.

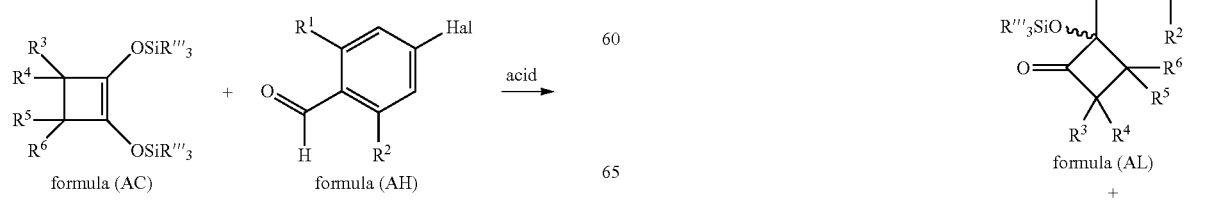

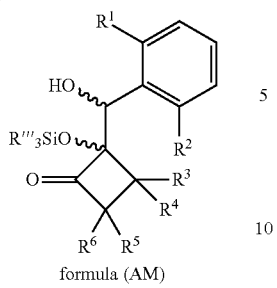

formula (AM)

↓ Pinacol rearrangement

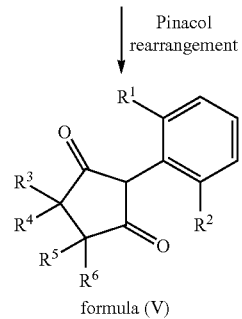

formula (V)

In a further approach, a compound of formula (A), wherein X is methyl, may be prepared by reacting a compound of formula (AN) with a with an aryllead tricarboxylate, in the presence of a suitable ligand and in a suitable solvent. Similar reactions are described in the literature (see for example M. Muehlebach et al., WO08/071,405; J. Pinhey, B. Rowe, *Aust. J. Chem.*, (1979), 32, 1561-6; J. Morgan, J. Pinhey, *J. Chem. Soc. Perkin Trans.* 1, (1990), 3, 715-20). Preferably the aryllead tricarboxylate is an aryllead triacetate of formula (AO). Preferably the ligand is a nitrogen containing heterocycle such as N,N-dimethylaminopyridine, 1,10-phenanthroline pyridine, bipyridine, or imidazole, and one to ten equivalents of ligand with respect to a compound of formula (AN) is preferably used. Most preferably the ligand is N,N-dimethylaminopyridine. The solvent is preferably chloroform, dichloromethane or toluene, most preferably chloroform, or a mixture of chloroform and toluene. Preferably the reaction is conducted at a temperature of −10° C. to 100° C., most preferably at 40-90° C.).

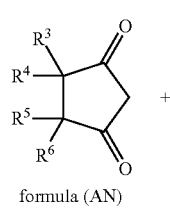

formula (AN)

+

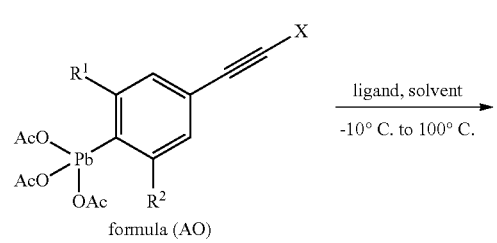

formula (AO)

ligand, solvent
−10° C. to 100° C.
→

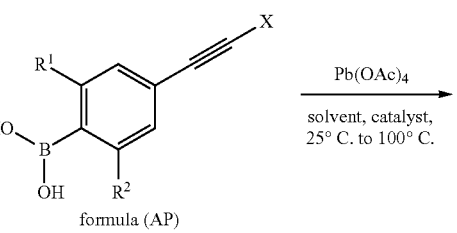

formula (A)

Compounds of formula (AN) are known compounds or can be prepared from known reagents using known methods.

A compound of formula (AO), wherein X is methyl, may be prepared from a compound of formula (AP) by treatment with lead tetraacetate in a suitable solvent (for example chloroform) at 25° C. to 10° C. (preferably 25-50° C.), and optionally in the presence of a catalyst such as mercury diacetate, according to procedures described in the literature (for example see, K. Shimi, G. Boyer, J-P. Finet and J-P. Galy, *Letters in Organic Chemistry*, (2005), 2, 407-409; J. Morgan and J. Pinhey, *J. Chem. Soc. Perkin Trans.* 1; (1990), 3, 715-720).

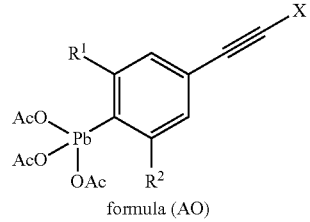

formula (AP)

Pb(OAc)₄
solvent, catalyst,
25° C. to 100° C.
→ formula (AO)

An aryl boronic acid of formula (AP), wherein X is methyl, may be prepared from an aryl halide of formula (AQ), wherein X is methyl and Hal is bromine or iodine, by known methods (see, for example, W. Thompson and J. Gaudino, *J. Org. Chem.*, (1984), 49, 5237-5243 and R. Hawkins et al., *J. Am. Chem. Soc.*, (1960), 82, 3053-3059). Thus an aryl halide of formula (AQ) may be treated with an alkyl lithium or alkyl magnesium halide at low temperature, and the aryl magnesium or aryl lithium reagent obtained is allowed to react with a trialkyl borate, B(OR″)₃, preferably trimethylborate, to give an aryl dialkylboronate which may be hydrolysed to the desired boronic acid of formula (AP) under acidic conditions. Alternatively the same overall transformation of compound (AQ) to compound (AP) may be achieved through a palladium-catalysed borylation reaction under known conditions using known reagents (see for example T. Ishiyama, M. Murata, N. Miyaura, *J. Org. Chem.* (1995), 60, 7508-7501; and K. L. Billingsley, T. E. Barder, S. L. Buchwald, *Angew. Chem. Int. Ed.* (2007), 46, 5359-5363), followed by hydrolysis of the intermediate boronate ester.

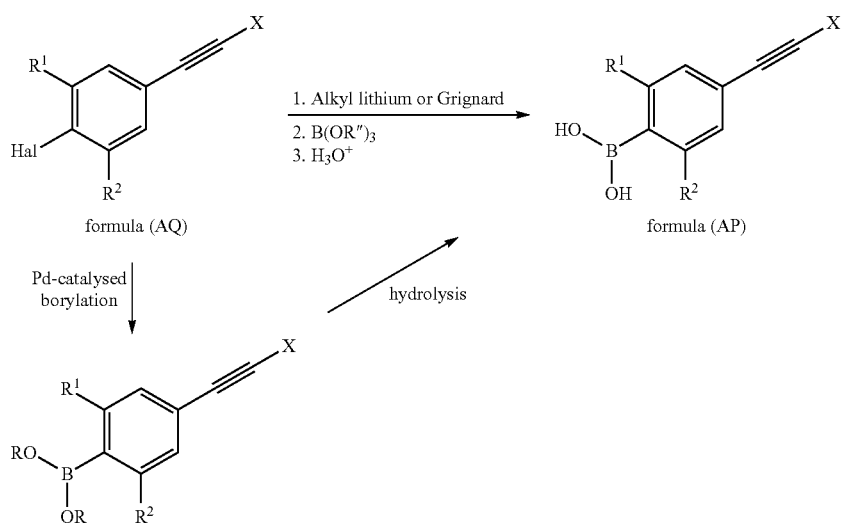

In an alternative approach, a compound of formula (A), wherein X is methyl, may be prepared by the reaction of a compound of formula (AR), wherein Ar is an aryl moiety (preferably phenyl) with an arylboronic acid of formula (AP) in the presence of a suitable palladium catalyst, a suitable base, an optionally in the presence of a suitable ligand or additive, and in a suitable solvent.

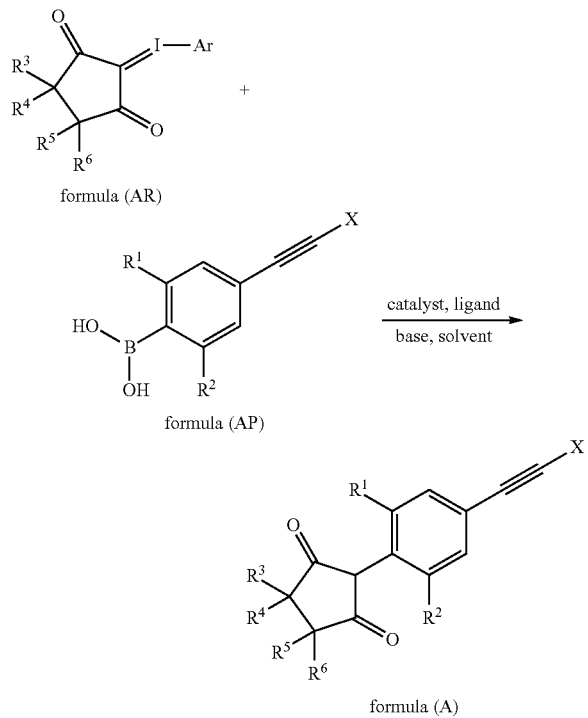

Suitable palladium catalysts include, for example palladium(II) dihalides, palladium(II) acetate and palladium(II) sulfate, and is preferably palladium(II) acetate. Suitable ligands include triphenylphosphine, tricyclopentylphosphine, tricyclohexylphosphine, 2-dicyclo-hexylphosphino-2',6'-dimethoxybiphenyl, 2-dicyclohexylphosphino-2',4',6'-triisopropyl-biphenyl, 1,1'-bis(diphenylphosphino)ferrocene and 1,2-bis(diphenylphosphino)ethane. The reaction may also be carried out in the presence of other additives, such as tetralkylammonium salts, for example, tetrabutylammonium bromide. Suitable bases include alkali metal hydroxides, especially lithium hydroxide. A suitable solvent is aqueous 1,2-dimethoxyethane.

A compound of formula (AR), wherein Ar is phenyl, may be prepared from a compound of formula (AN) by treatment with a hypervalent iodine reagent such as a (diacetoxy)iodobenzene or iodosylbenzene and a base such as aqueous sodium carbonate, lithium hydroxide or sodium hydroxide in a solvent such as water or an aqueous alcohol such as aqueous ethanol according to the procedures of K. Schank and C. Lick, *Synthesis* (1983), 392; R. Moriarty et al, *J. Am. Chem. Soc.*, (1985), 107, 1375, or of Z. Yang et al., *Org. Lett.*, (2002), 4 (19), 3333:

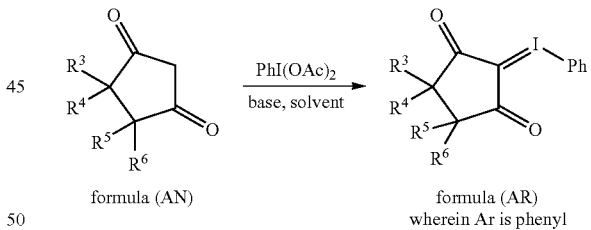

In a further approach, a compound of formula I (wherein X is methyl and G is preferably methyl or ethyl) may be prepared by reacting a compound of formula (AS) (wherein G is preferably $C_{1-4}$ alkyl, and Hal is a halogen, preferably bromine or iodine), with an arylboronic acid of formula (AP) in the presence of a suitable palladium catalyst (for example 0.001-50% palladium(II) acetate with respect to compound (AS)) and a base (for example 1 to 10 equivalents potassium phosphate with respect to compound (AS)) and preferably in the presence of a suitable ligand (for example 0.001-50% (2-dicyclohexylphosphino)-2',6'-dimethoxybiphenyl with respect to compound (AS)), and in a suitable solvent (for example toluene), preferably between 25° C. and 200° C. Similar couplings are known in the literature (see for example, Y. Song, B. Kim and J.-N. Heo, *Tetrahedron Letters*

(2005), 46 (36), 5987-5990). A compound of formula I can be converted to a compound of formula (A) by hydrolysis under known conditions.

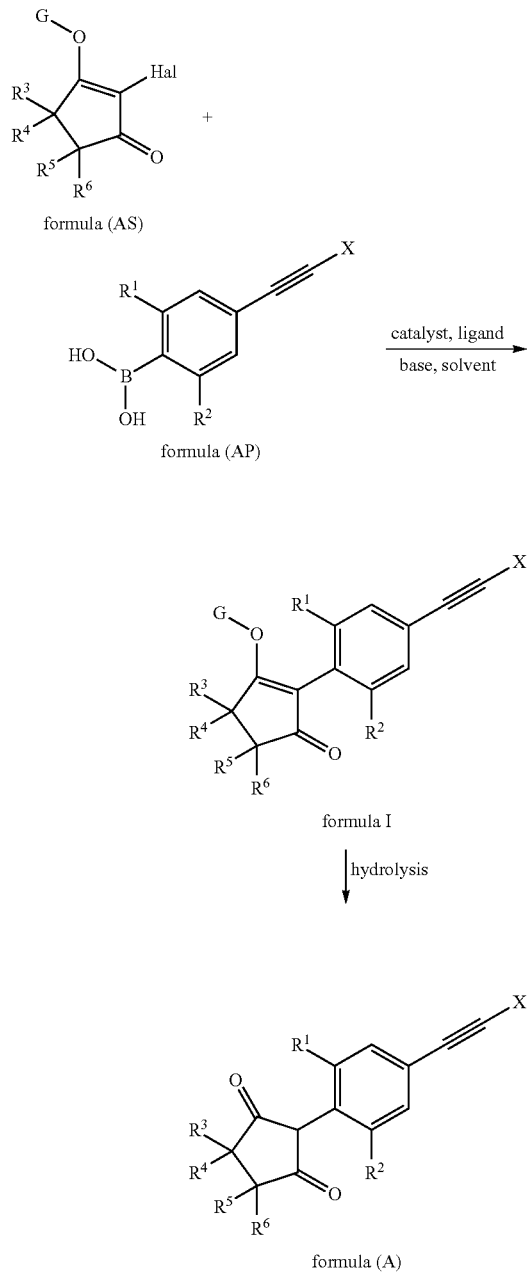

formula (AS)

formula (AP)

formula I hydrolysis formula (A)

A compound of formula (AS) may be prepared by halogenating a compound of formula (AN), followed by reaction of the resulting halide of formula (AU) with a $C_1$-$C_4$ alkyl halide or tri-$C_1$-$C_4$-alkylorthoformate under known conditions, for example by the procedures of R. Shepherd and A. White (*J. Chem. Soc. Perkin Trans.* 1 (1987), 2153-2155) and Y.-L. Lin et al. (*Bioorg. Med. Chem.* (2002), 10, 685-690). Alternatively, a compound of formula (AS) may be prepared by reacting a compound of formula (AN) with a $C_1$-$C_4$ alkyl halide or a tri-$C_1$-$C_4$-alkylorthoformate, and halogenating the resulting enol ether of formula (AT) under known conditions (see for example Y. Song, B. Kim and J.-N. Heo, *Tetrahedron Letters* (2005), 46 (36), 5987-5990).

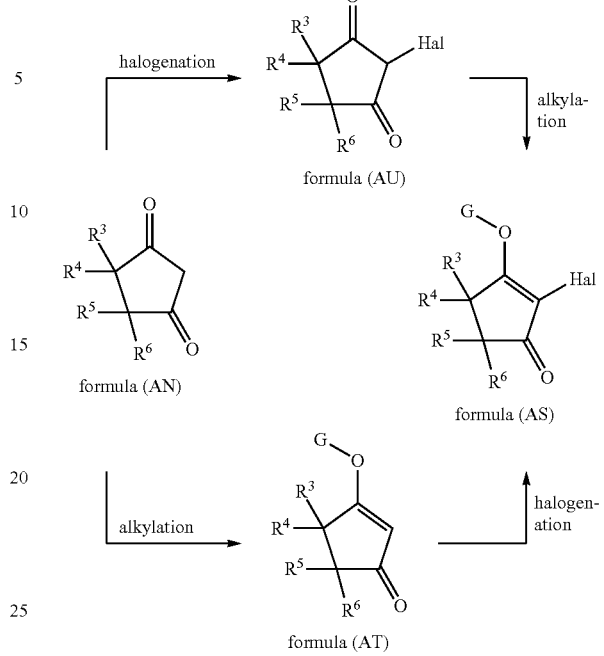

formula (AN)

formula (AU)

formula (AT)

formula (AS)

In a further approach, a compound of formula (AN), wherein X is methyl, may be prepared by reacting a compound of formula (Y) with a compound of formula (AQ) in the presence of a suitable palladium catalyst (for example 0.001-50% palladium(II) acetate with respect to compound (AN)) and a base (for example 1 to 10 equivalents potassium phosphate with respect to compound (AN)) and preferably in the presence of a suitable ligand (for example 0.001-50% (2-dicyclohexylphosphino)-2',4',6'-triisopropylbiphenyl with respect to compound (AN)), and in a suitable solvent (for example dioxane), preferably between 25° C. and 200° C. and optionally under microwave heating.

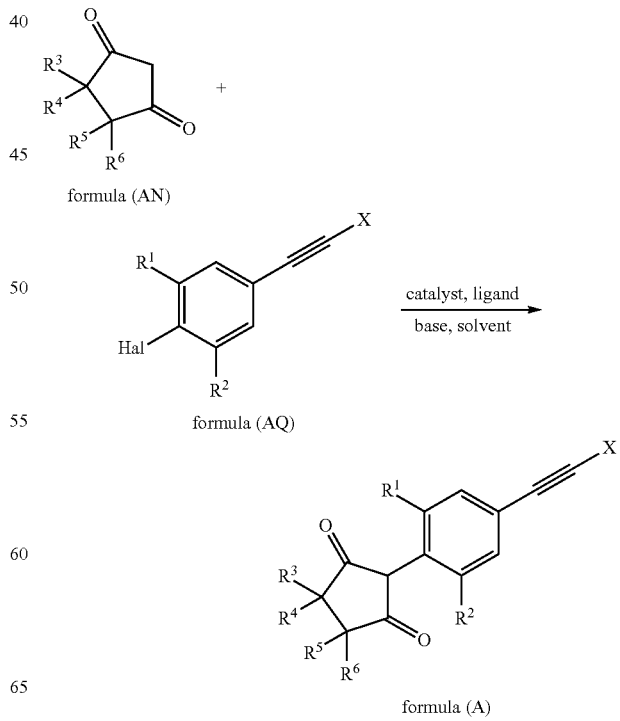

formula (AN)

formula (AQ)

formula (A)

Similar couplings are known in the literature (see for example, S. Buchwald et al., J. Am. Chem. Soc. (2000), 122, 1360-1370; B. Hong et al. WO 2005/000233). Alternatively, a compound of formula (A) may be prepared by reacting a compound of formula (AN) with a compound of formula (AQ) in the presence of a suitable copper catalyst (for example 0.001-50% copper(I) iodide with respect to compound (AN)) and a base (for example 1 to 10 equivalents cesium carbonate with respect to compound (AN)) and preferably in the presence of a suitable ligand (for example 0.001-50% L-proline with respect to compound (AN)), and in a suitable solvent (for example dimethylsulfoxide), preferably between 25° C. and 200° C. Similar couplings are known in the literature (see for example, Y. Jiang et al., *Synlett*, (2005), 18, 2731-2734, and X. Xie et al., *Organic Letters* (2005), 7 (21), 4693-4695).

Similarly, a compound of formula (P) can also be prepared using similar methods described previously, starting from compounds (AV), (AW) and (AX) which are known or can be prepared from known reagents using known methods.

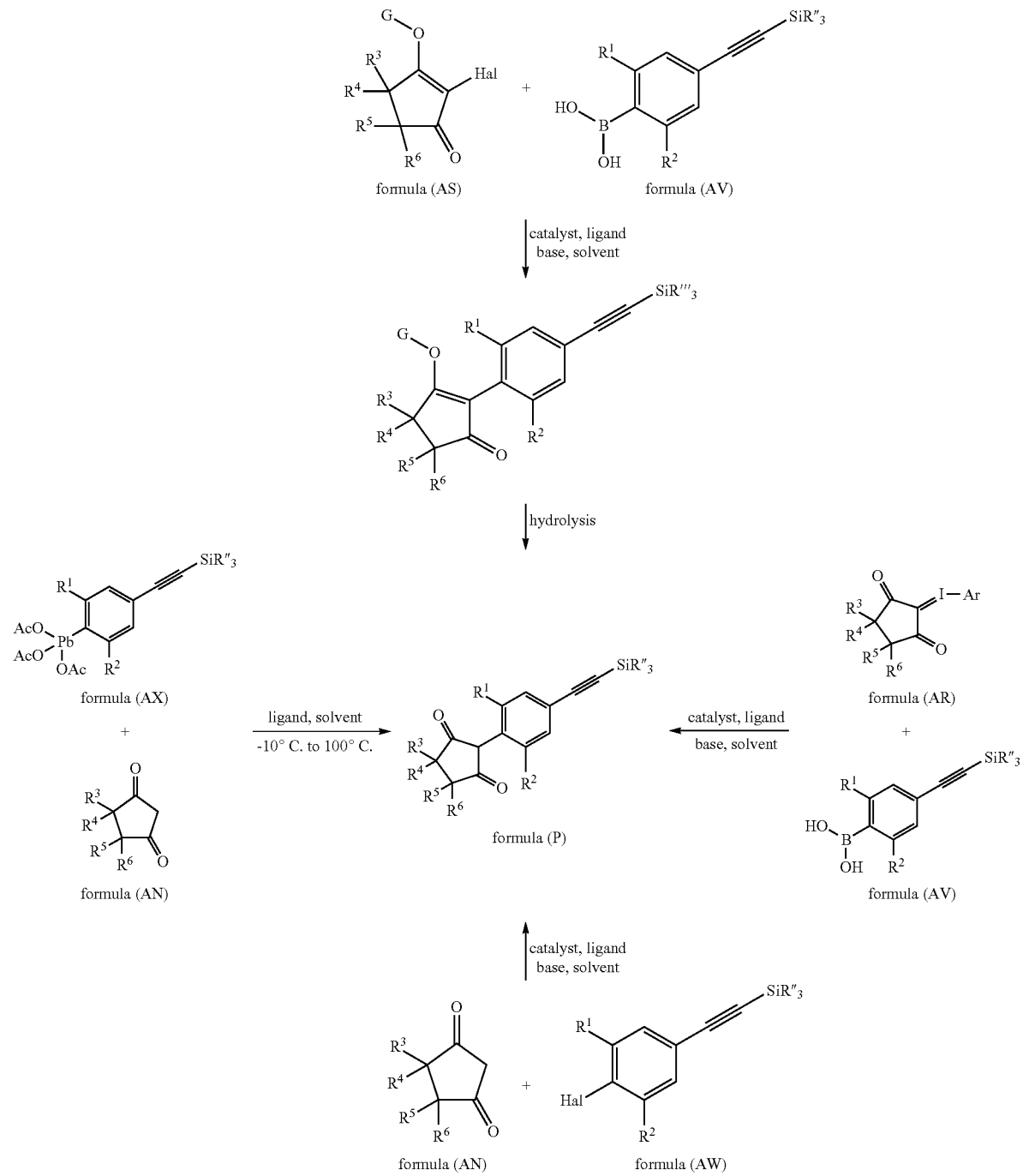

Similarly, a compound of formula (L) can also be prepared using similar methods described previously, starting from compounds (AY), (AZ) and (AAA) which are known or can be prepared from known reagents using known methods.

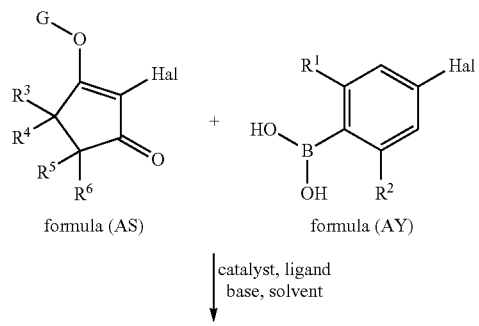
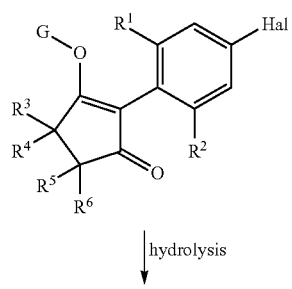
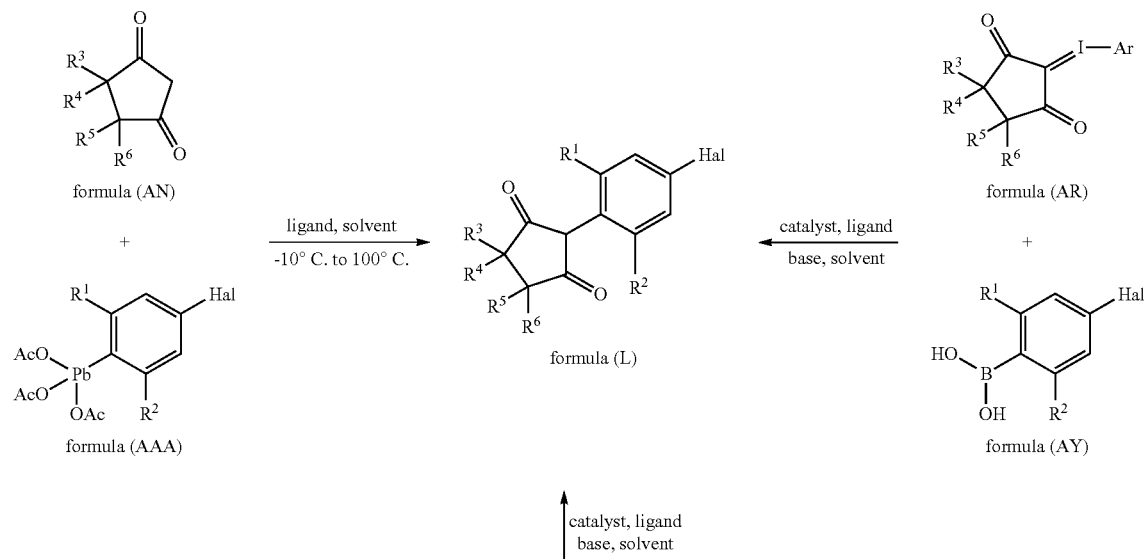
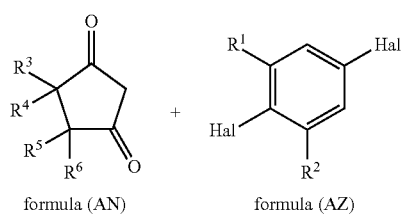

Additionally, a compound of formula (V) can also be prepared using similar methods described previously, starting from compounds (AAB), (AAC) and (AAD) which are known or can be prepared from known reagents using known methods.

described for coupling a compound of formula (AN) and a compound of formula (AQ) to produce a compound of formula (AAF)), to produce a compound of formula (AJ) which is then reduced under standard conditions (for a similar example see T. N. Wheeler, CA1113959). The aniline (AAG)

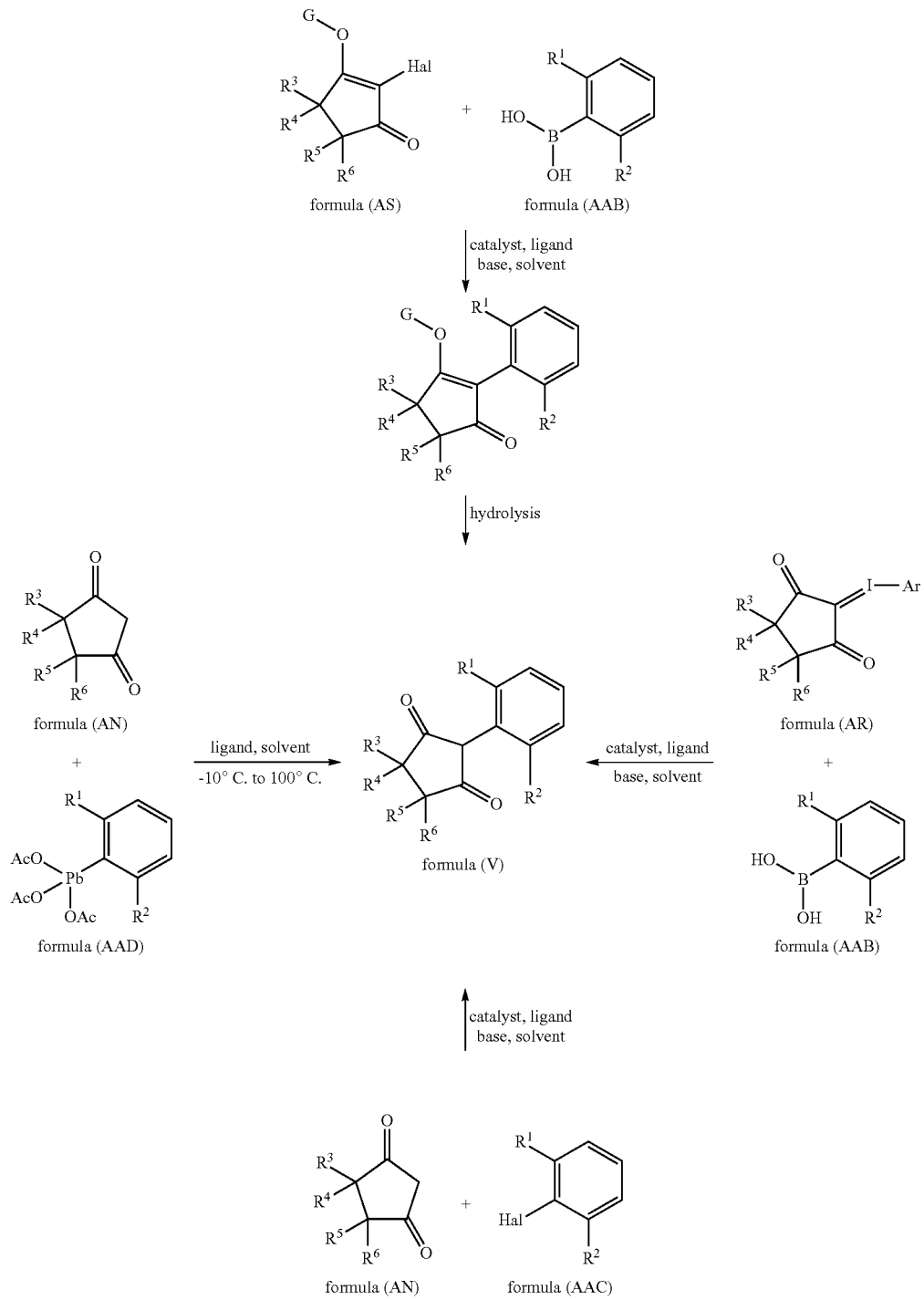

Furthermore, a compound of formula (L) can be prepared by reacting a compound of formula (AN) with a halonitrobenzene of formula (AAE) (under conditions similar to those described for coupling a compound of formula (AN) and a compound of formula (AQ) to produce a compound of formula (AAF)), to produce a compound of formula (AJ) which is then reduced under standard conditions (for a similar example see T. N. Wheeler, CA1113959). The aniline (AAG) is then converted to the aryl halide (L) under Sandmeyer conditions (for a similar example see T. N. Wheeler, CA1113959).

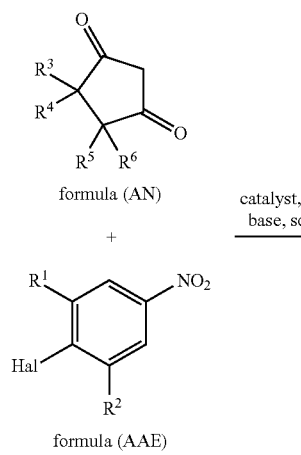

formula (AN)

+

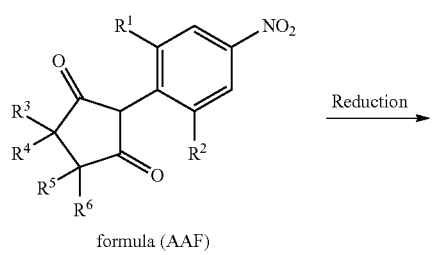

formula (AAE)

catalyst, ligand
base, solvent
⟶

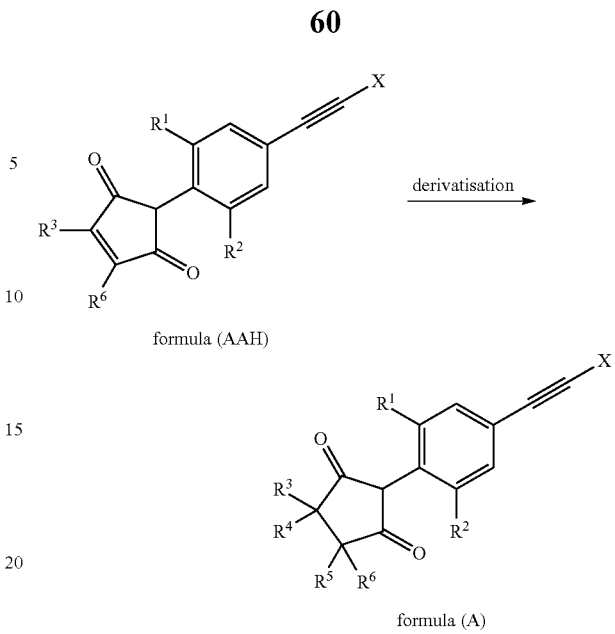

formula (AAH)

derivatisation ⟶ formula (A)

For example, a compound of formula (AAH), wherein X is methyl, may be reacted with a suitable nucleophile, Nuc-H, optionally in the presence of a suitable base and a suitable solvent to give compounds of formula (A), wherein X is methyl and $R^5$ is the group Nuc resulting from nucleophilic attack and $R^4$ is hydrogen.

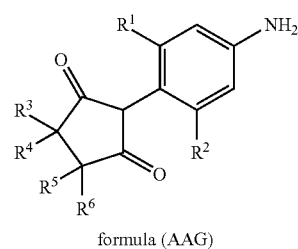

formula (AAF)

Reduction ⟶

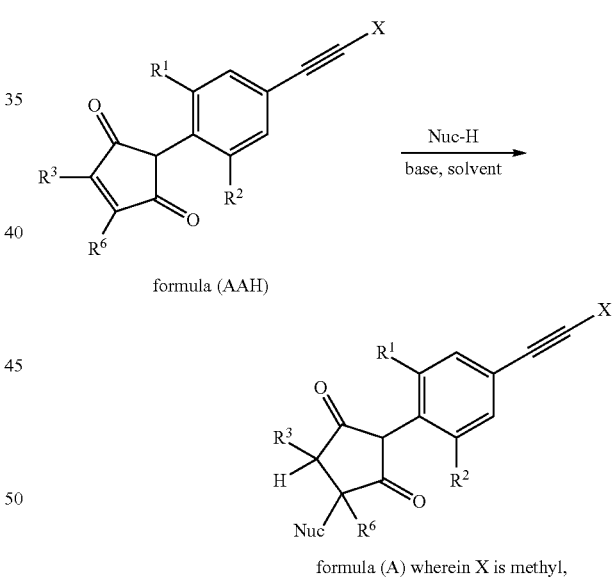

formula (AAH)

Nuc-H
base, solvent
⟶ formula (A) wherein X is methyl,
$R^5$ is Nuc and $R^4$ is H formula (AAG)

Sandmeyer ↓

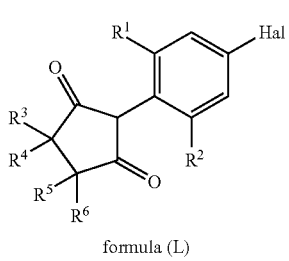

formula (L)

In a further approach, a compound of formula (A), wherein X is methyl, may be prepared by derivatisation of a compound of formula (AAH), which is a compound of formula I, wherein X is methyl, G is hydrogen and $R^4$ and $R^5$ together form a bond. Compounds of formula (AAH) are α,β-unsaturated cyclic diones and undergo reactions in the presence of reagents known to effect transformations of α,β-unsaturated ketones to give additional compounds of formula (A).

Suitable nucleophiles, Nuc-H, include, but are not limited to, optionally substituted $C_1$-$C_6$alkylthiols, optionally substituted arylthiols, optionally substituted heteroarylthiols optionally substituted $C_1$-$C_6$alkyl alcohols and optionally substituted $C_3$-$C_7$cyclic alcohols (including $C_3$-$C_6$ alicyclic alcohols, 4-6 membered heterocyclic alcohols, phenols and heteroaromatic alcohols).

A compound of formula (AAH), wherein X is methyl, will also participate in cycloaddition reactions under suitable conditions to afford additional compounds of formula (A).

For example, a compound of formula (AAH), wherein X is methyl, may be reacted with a suitable 1,3-diene of formula (AAI), wherein $R_a$ represents a suitable substituent (such as $C_1$-$C_4$alkyl, $C_1$-$C_4$alkoxy or tri-$C_1$-$C_4$alkylsilyloxy), and n is 0, 1 or 2, under suitable conditions to give a compound of formula (A) wherein $R^4$ and $R^5$ together with the atoms to which they are joined form an unsaturated six-membered ring.

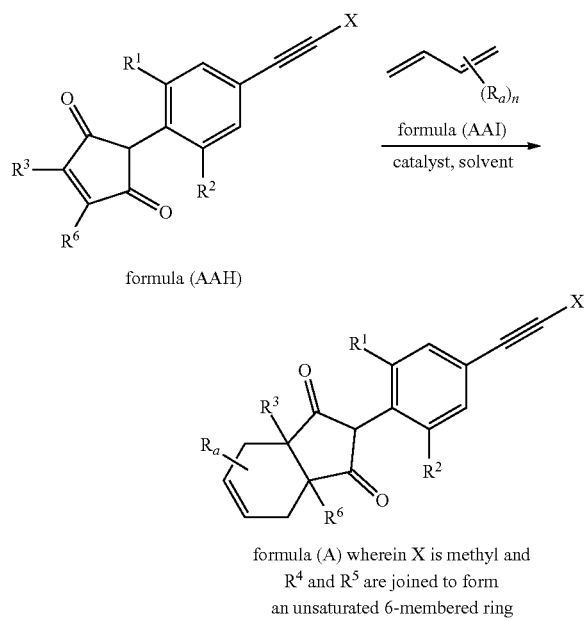

formula (A) wherein X is methyl and
$R^4$ and $R^5$ are joined to form
an unsaturated 6-membered ring Suitable 1,3-dienes include 1,3-butadiene (or an equivalent, for instance 2,5-dihydrothiophene-1,1-dioxide), and substituted 1,3-butadienes. Similarly, a compound of formula (AAH), wherein X is methyl, may also be reacted with cyclic dienes of formula (AAJ) such as cyclopentadiene (W is —$CH_2$— and $R_b$ is hydrogen), substituted cyclopentadienes, cyclohexa-1,3-diene (W is —$CH_2$—$CH_2$— and $R_b$ is hydrogen), substituted cyclopentadienes, furan (W is oxygen and $R_b$ is hydrogen) and substituted furans.

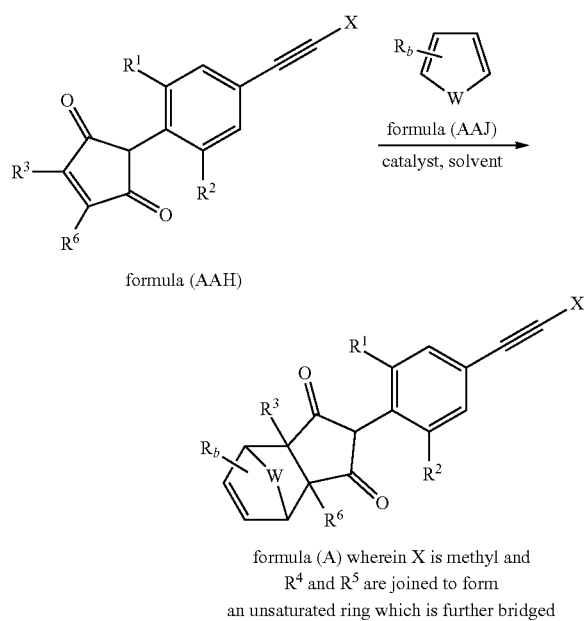

formula (A) wherein X is methyl and
$R^4$ and $R^5$ are joined to form
an unsaturated ring which is further bridged Those skilled in the art will appreciate that cyclic dienes of formula (AAJ) bearing a wide variety of substituents $R_b$ will undergo cycloaddition reactions with a compound of formula (AAH) to give new compounds of formula (A), under appropriate conditions (for example, in the presence or absence of Lewis acid catalysts, such as aluminium chloride, bismuth (III) chloride, bismuth(II) trifluoromethanesulfonate, boron trifluoride, cerium(III) chloride, copper(I) trifluoromethanesulfonate, diethylaluminium chloride, hafnium(IV) chloride, iron(III) chloride, lithium perchlorate, lithium trifluoromethanesulfonate, magnesium bromide, magnesium iodide, scandium(III) trifluoromethanesulfonate, tin(IV) chloride, titanium(IV) chloride, titanium(IV) isopropoxide, trimethyl aluminium, N-trimethylsilyl-bis(trifluoromethanesulfonyl)imide, trimethylsilyl trifluoromethane-sulfonate, ytterbium(III) trifluoromethanesulfonate, zinc iodide and zirconium(IV) chloride, and in the presence or absence of solvents such as chloroform, dichloromethane, diethyl ether, ethanol, methanol, perfluorinated alkanes such as perfluorohexane, toluene, water, and ionic liquids such as 1-butyl-3-methylimidazolium tetrafluoroborate and 1-butyl-3-methylimidazolium hexafluorophosphate, and at normal atmospheric pressure or under high pressure conditions), as described, for example by G. Silvero et al., *Tetrahedron* (2005), 61, 7105-7111; I. Hemeon et al., *Synlett*, (2002), 11, 1815-1818; S. Otto and J. Engberts, *Pure Appl. Chem.* (2000), 72 (7), 1365-1372; R. Breslow, *Acc. Chem. Res.*, (1991), 24 (6), 159-164; K. Hara et al., *Org. Lett.*, (2005), 7 (25), 5621-5623; J, Augé et al., *Synlett*, (2000), 6, 877-879, B. Garrigues and A. Oussaid, *J. Organometallic Chem.*, (1989), 585, 253-255; B. Mathieu and L. Ghosez, *Tetrahedron Lett.*, (1997), 38 (31), 5497-5500; M. Ordoñez et al., *Tetrahedron Asymmetry*, (1996), 7 (9), 2675-2686; S. Kobayashi et al., *Tetrahedron Lett.*, (1993), 34 (23), 3755-3758; C. Cativiela et al., U. Pindur et al., *Chem. Rev.*, (1993), 93, 741-761; *Tetrahedron*, (1992), 48 (31), 6467-6476; J. Aubé et al., *J. Am. Chem. Soc.*, (1992), 114, 5466-5467; S. Danishefsky and M. Bednarski, *Tetrahedron Lett.*, (1985), 26 (21), 2507-2508 and references therein); Q. Chu, W. Zhang and D. Curran, *Tetrahedron Lett.*, (2006), 47, 9287-9290; K. Ishihara and K. Nakano, *J. Am. Chem. Soc.*, (2005), 127 (30), 10504-10505; and A. Northrup and D. MacMillan, (2002), *J. Am. Chem. Soc.*, 124 (11), 2458-2460).

The reaction of compounds of formula (AAH) with compounds of formula (AAI) or with compounds of formula (AAJ) provides compounds of formula (A) wherein $R^4$ and $R^5$ are joined to form an unsaturated ring. Such compounds are alkenes, which may undergo reactions typical of alkenes (for example reduction, halogenation or cross-coupling) to produce further compounds of formula (A).

A compound of formula (AAH), wherein X is methyl, may also act as a dipolarophile and will therefore undergo a range of 3+2 cycloaddition reactions with suitable dipolar reagents under suitable conditions. For example, a compound of formula (AAH) may react with a nitrile oxide of formula (AAK), wherein $R_c$ is a suitable substituent (for example $C_1$-$C_4$alkyl or aryl), or with a nitrone of formula (AAL), wherein $R_e$, $R_f$ and $R_g$ are suitable substituents (for example hydrogen or $C_1$-$C_4$alkyl), under appropriate conditions to give further compounds of formula (A), wherein $R^4$ and $R^5$ together with the atoms to which they are attached form an isoxazoline or isoxazolidine ring respectively.

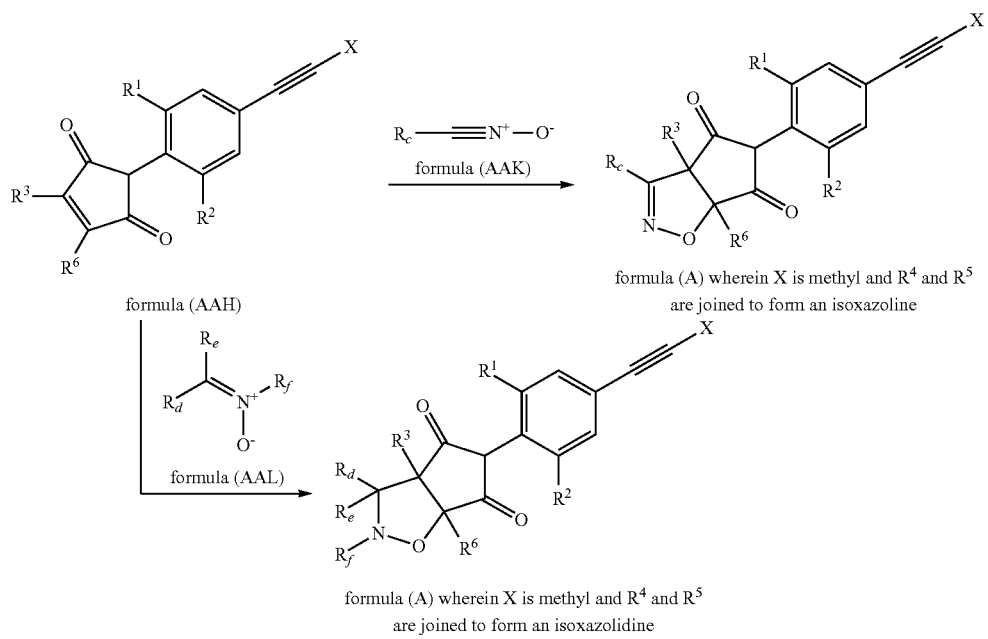

formula (A) wherein X is methyl and $R^4$ and $R^5$ are joined to form an isoxazoline formula (A) wherein X is methyl and $R^4$ and $R^5$ are joined to form an isoxazolidine Suitable conditions for effecting 3+2 cycloadditions are described, for example, by L. Deng and Y. Hu, *Synth. Commun.* (2007), 37, 157-163; E. Kantorowski et al., *J. Org. Chem.*, (1998), 63, 5272-5274; and by V. Jager and I. MOller, *Tetrahedron* (1985), 41 (17), 3519-3528.

In a further approach, a compound of formula (A), wherein X is methyl and $R^5$ is Nuc (and Nuc is as previously defined) may be prepared by the hydrolysis of a compound of formula I, wherein G is $C_1$-$C_4$alkyl, under acidic conditions.

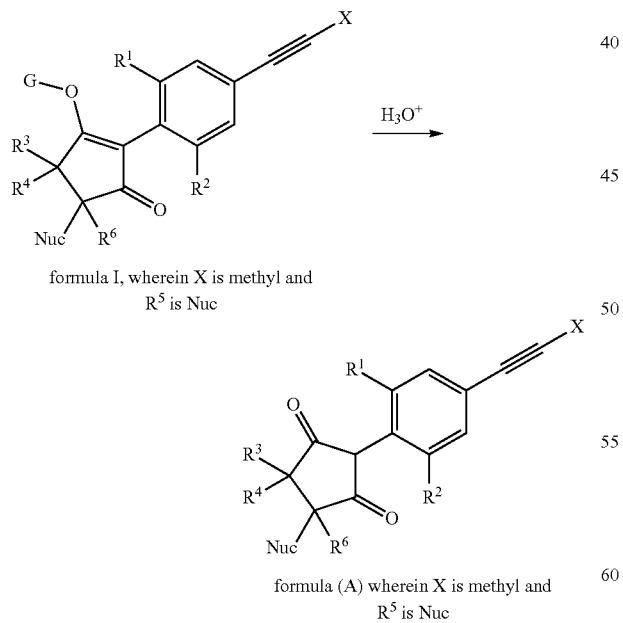

formula I, wherein X is methyl and $R^5$ is Nuc formula (A) wherein X is methyl and $R^5$ is Nuc A compound of formula I (wherein X is methyl, G is $C_1$-$C_4$alkyl and $R^5$ is Nuc) may be prepared from a compound of formula I (wherein X is methyl, $R^5$ is Hal and Hal is chlorine, bromine or iodine), by treatment with a nucleophile, Nuc-H, optionally in the presence of a suitable base and in a suitable solvent. Suitable conditions for effecting nucleophilic substitution reactions are described, for example, by J. March, Advanced Organic Chemistry Third Edition, ed J. Wiley and Sons, 1985.

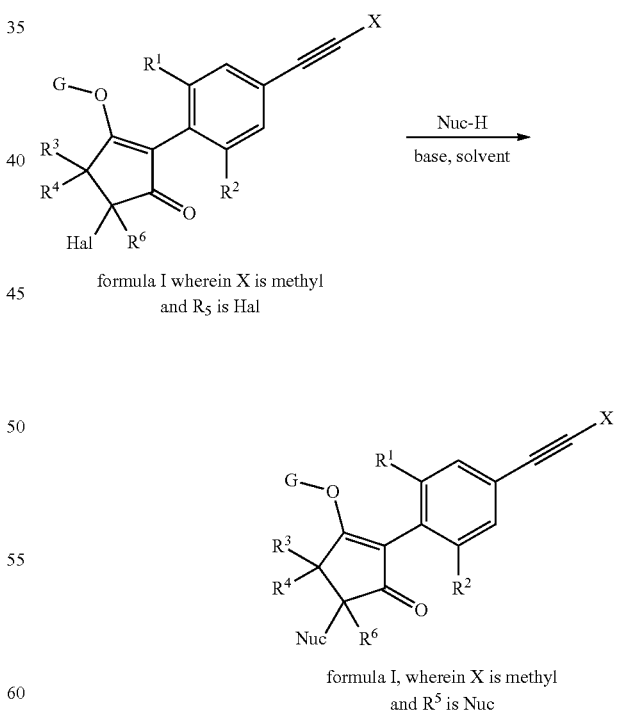

formula I wherein X is methyl and $R_5$ is Hal formula I, wherein X is methyl and $R^5$ is Nuc A compound of formula I, wherein X is methyl and $R^5$ is Hal, may be prepared from a compound of formula I, wherein X is methyl and $R^5$ is hydrogen, by halogenation.

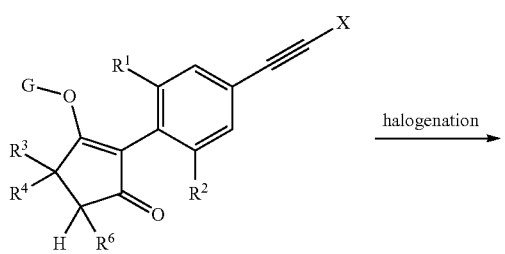

formula I, wherein X is methyl
and R⁵ is hydrogen

↓ halogenation

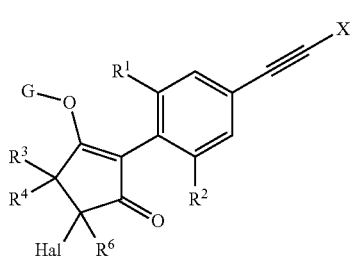

formula I wherein X is methyl
and R₅ is Hal

For example, a compound of formula I, wherein X is methyl, Hal is chlorine and G is $C_1$-$C_4$alkyl, may be prepared by reacting a compound of formula I, wherein X is methyl and $R^5$ is hydrogen, with copper(II) chloride and lithium chloride according to the procedure of E. Kosower et al., *J. Org. Chem.*, (1963), 28, 630. Alternatively a compound of formula (AM), wherein X is methyl, Hal is bromine and G is $C_1$-$C_4$alkyl, may be prepared treating a compound of formula I, wherein $R^5$ is hydrogen, with dibutylboryl trifluoromethanesulfonate and N-bromosuccinimide, by methods similar to those described by P. Page et al., *Tetrahedron* (1995), 51 (4), 1285-1294).

Alternatively, a compound of formula (A), wherein X is methyl and $R^4$ and $R^5$ are hydrogen, may be prepared by reduction of a compound of formula (AAH) under conditions which are compatible with the substrate, for example in the presence of sodium borohydride and cuprous chloride, as described by M. Narisada, I. Horibe, F. Watanabe and K. Takeda, *Journal of Organic Chemistry* (1989), 54 (22), 5308-13.

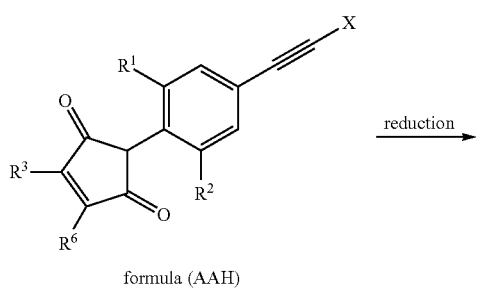

formula (AAH)

↓ reduction

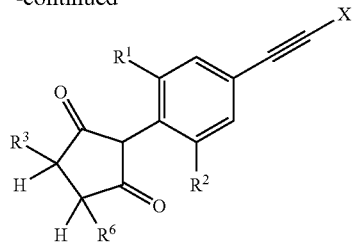

formula (A) wherein X is methyl and
$R^4$ and $R^5$ is hydrogen

A compound of formula (AAH), wherein X is methyl, may be prepared by oxidising a compound of formula (AAM) in a suitable solvent such as toluene, acetone, chloroform, dichloromethane or 1,4-dioxane. A wide range of oxidants is suitable for effecting this transformation, including inorganic oxidants such as chromium trioxide, pyridinium dichromate, manganese dioxide and aluminium alkoxides such as aluminium isopropoxide, as well as organic oxidants such as 2,3-dichloro-5,6-dicyano-p-benzoquinone and hypervalent iodine oxidants such as 1,1,1,-tris(acetyloxy)-1,1-dihydro-1,2-benziodoxol-3-(1H)-one (Dess-Martin periodinane), Suitable procedures are described, for example, by K. Saito and H. Yamachika, U.S. Pat. No. 4,371,711. and by G. Piancatelli et al., *Tetrahedron* (1978), 34, 2775. The use of chromium trioxide in a mixture of sulfuric acid and acetone (Jones reagent) is preferred.

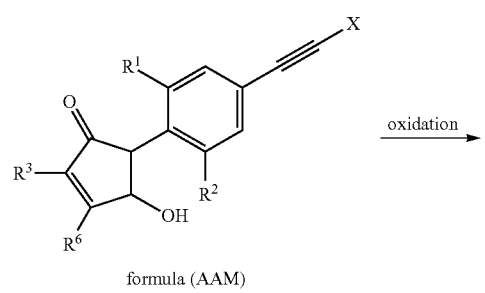

formula (AAM)

↓ oxidation

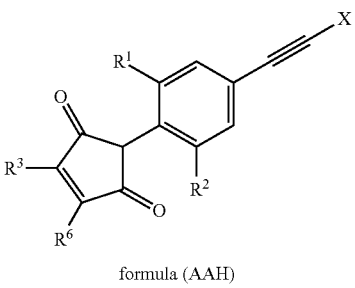

formula (AAH)

A compound of formula (AAM), wherein X is methyl, may be prepared from a compound of formula (AAN) by treatment with a suitable acid catalyst in the presence of water and optionally in the presence of a suitable solvent.

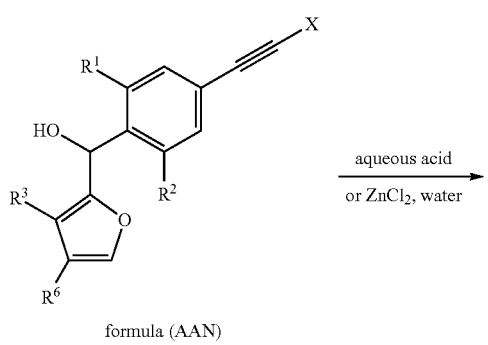

formula (AAN)

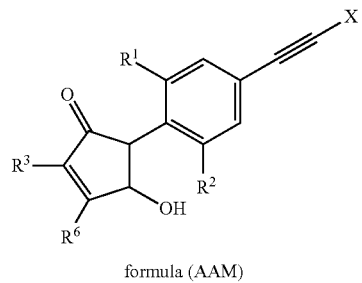

formula (AAM)

For example, a compound of formula (AAN), wherein X is methyl, may be converted to a compound of formula (AAM) in the presence of an aqueous solution of an acid such as phosphoric acid or polyphosphoric acid under conditions described, for example by K. Saito and H. Yamachika, U.S. Pat. No. 4,371,711. Alternatively a compound of formula (AAM), wherein X is methyl, may be prepared from a compound of formula (AAN) by rearrangement in the presence of a Lewis acid catalyst such as zinc chloride according to the procedure of G. Piancatelli et al., *Tetrahedron*, (1978), 34, 2775.

A compound of formula (AAN), wherein X is methyl, may be prepared by the addition of a suitable organometallic reagent such as an arylmagnesium halide of formula (AAQ) wherein X is methyl and Hal is a halide such as chloride, bromide or iodide, or an aryllithium reagent of formula (AAP) or a diarylzinc reagent of formula (AAO) to a furan-2-carboxaldehyde of formula (AAR) according to known procedures (see, for example G. Panda et al., *Tetrahedron Lett.*, (2005), 46, 3097).

The organometallic reagents of formula (AAQ), formula (AAP) and formula (AAO), wherein X is methyl, may be made by known methods from a compound of formula (AQ).

Additionally, a compound of formula I, wherein X is methyl and $R^5$ is hydrogen, can be prepared by the reduction of a compound of formula (AAS), wherein $R_f$ and $R_g$ are suitable substituents, under similar conditions to those described to convert a compound of formula (AAH) to a compound of formula (A), wherein X is methyl and $R^4$ and $R^5$ are hydrogen.

formula (AAS)

formula I, wherein X is methyl and $R^5$ is hydrogen

A compound of formula (AAS), wherein X is methyl, can be prepared, for example, from a compound of formula I (wherein X is methyl, $R^5$ and $R^6$ are hydrogen and G is preferably methyl) and compound of formula (AAT), under basic conditions, followed by elimination. Suitable bases include lithium diisopropylamide, sodium hexamethyldisilazide, potassium tert-butoxide and the reaction is preferably conducted in a suitable (such as tetrahydrofuran) at a temformula (AAR)      formula (AAQ)      formula (AAP)

formula (AAO)

formula (AAN)

perature between −80° C. and 30° C. (see, for example, Drege, E. et al. *Tetrahedron Letters* (2005), 46 (42), 7263-7266 and Drege, E. et al., *Eur. J. Org. Chem.* (2006), (21), 4825-4840). Compounds of formula (AAT) are known compounds, or can be prepared from known compounds using known methods.

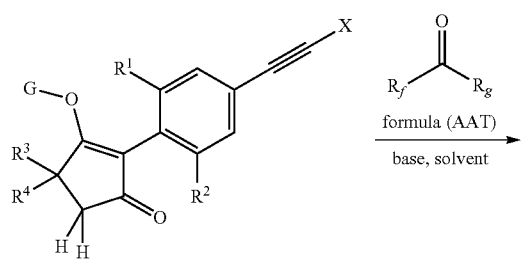

formula (AAT)
base, solvent

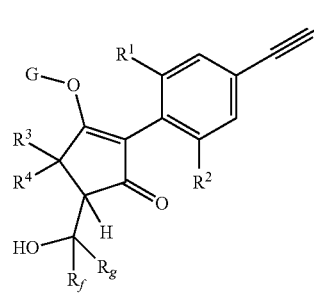

formula I, wherein X is methyl and R⁵ and R⁶ is hydrogen

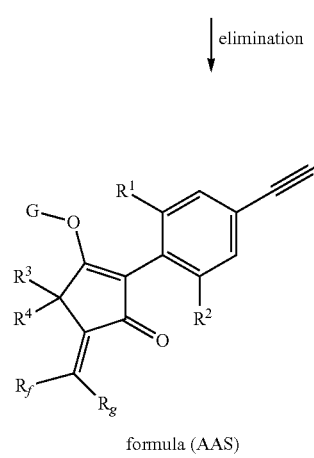

↓ elimination formula (AAS)

Furthermore, a compounds of formula I, wherein X is methyl, can be obtained by reacting compounds of formula I (wherein X is methyl, R⁵ is hydrogen and G is preferably methyl), with compounds of formula (AAU) wherein LG is a leaving group such as halogen (preferably iodide or bromide) or an activated alcohol (preferably mesylate, tosylate or triflate) under under basic conditions. Suitable bases include lithium diisopropylamide, sodium hexamethyldisilazide, potassium tert-butoxide and the reaction is preferably conducted in a suitable (such as tetrahydrofuran) at a temperature between −80° C. and 30° C. Similar reactions are described by Gulias, M. et al. *Org. Lett.* (2003), 5 (11), 1975-1977. Compounds of formula (AAU) are known compounds, or can be prepared from known compounds using known reagents.

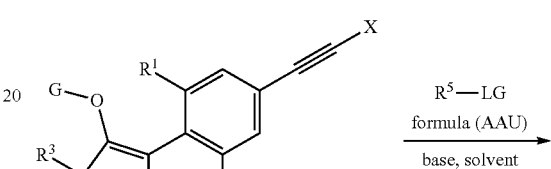

R⁵—LG
formula (AAU)
base, solvent formula I, wherein X is methyl and R⁵ is hydrogen

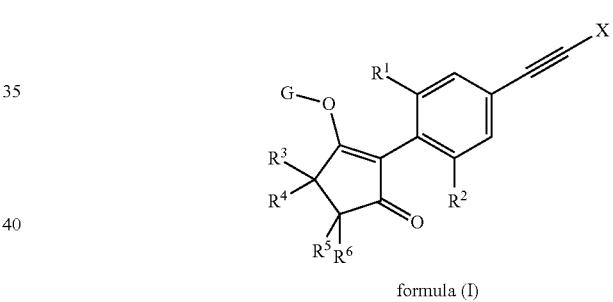

formula (I)

Using similar chemistry, a compound of formula (P) can be prepared by the derivitisation of a compound of formula (AAV), a compound of formula (AAX) or a compound of formula (AAY). Compounds of formula (AAV), (AAX) and (AAY) can be prepared by routes analogous to those described previously.

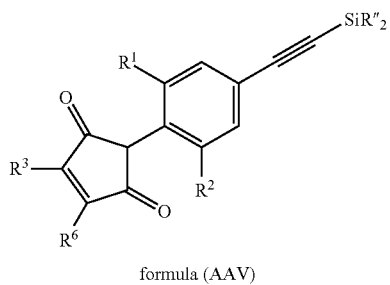

formula (AAV)

derivitisation →

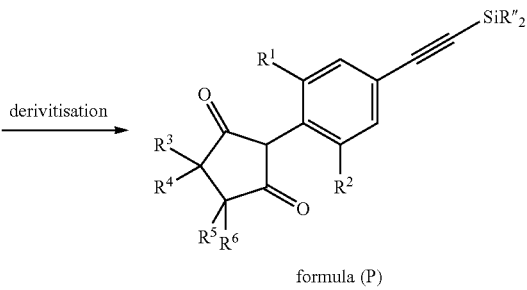

formula (P)

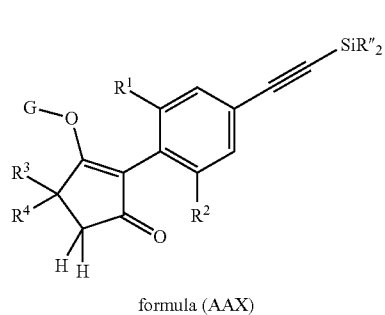

formula (AAX)

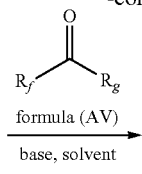

formula (AV)

base, solvent

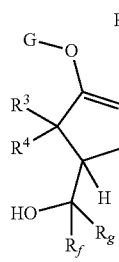

elimination

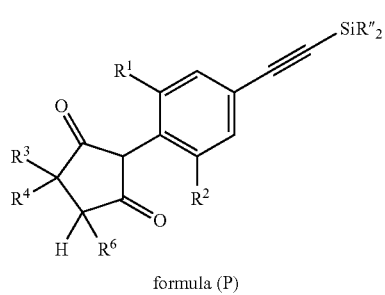

formula (P)

← hydrolysis

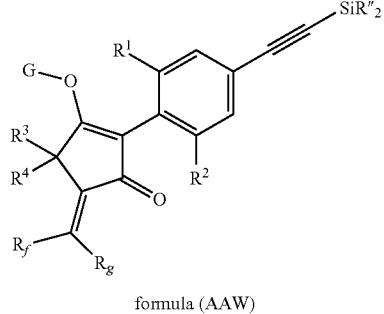

formula (AAW)

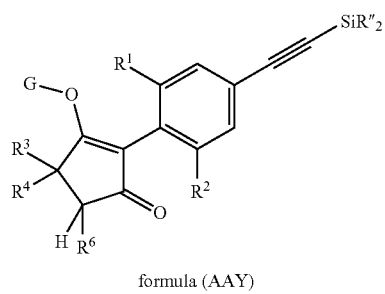

formula (AAY)

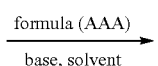

$R^5$—LG
formula (AAA)
base, solvent

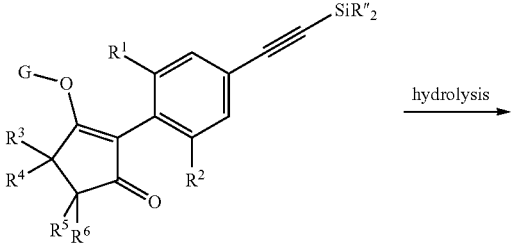

hydrolysis →

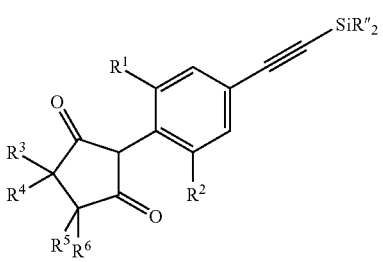

formula (P)

Similarly, using similar chemistry, a compound of formula (L) can be prepared by the derivitisation of a compound of formula (AAZ), a compound of formula (AAAB) or a compound of formula (AAAC), using similar chemistry to that described above. Compounds of formula (AAZ), (AAAB) and (AAAC) can be prepared by routes analogous to those described previously.

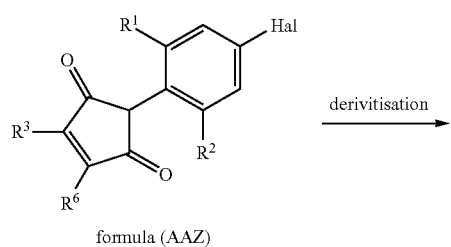

formula (AAZ)

derivitisation →

-continued

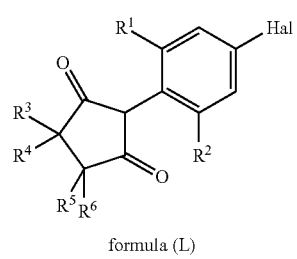

formula (L)

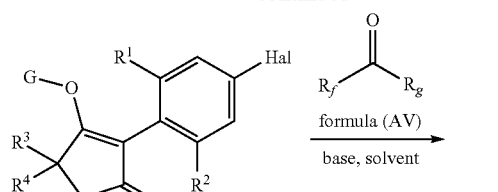

formula (AAAB)

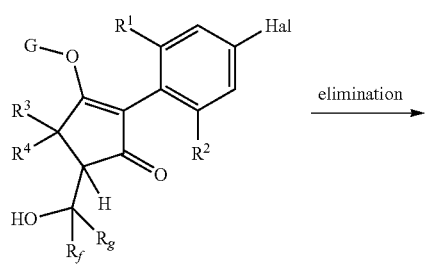

formula (AAAA)

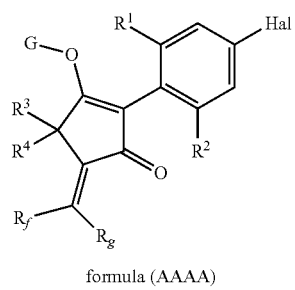

formula (L)

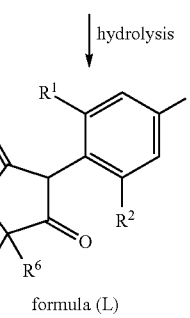

formula (AAAC)

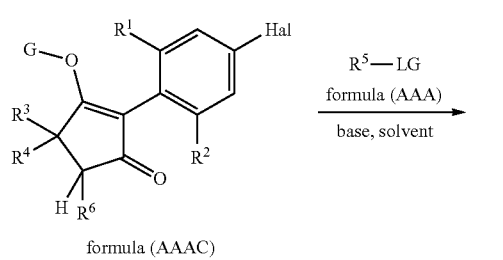

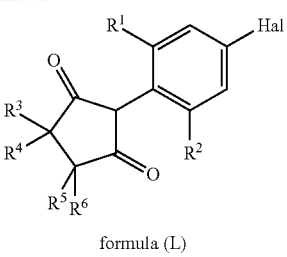

formula (L)

Finally, using similar chemistry, a compound of formula (V) can be prepared by the derivitisation of a compound of formula (AAD), a compound of formula (AAAF) or a compound of formula (U). Compounds of formula (AAAD), (AAAF) and (U) can be prepared by routes analogous to those described previously.

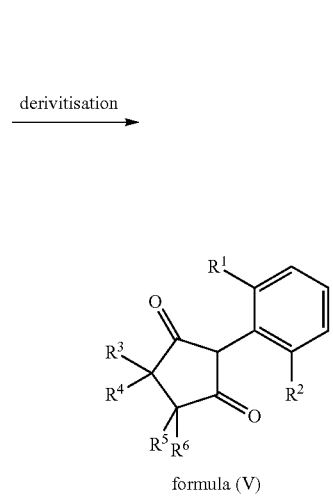

formula (AAAD)

formula (V)

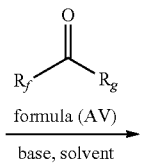

formula (AAAF)

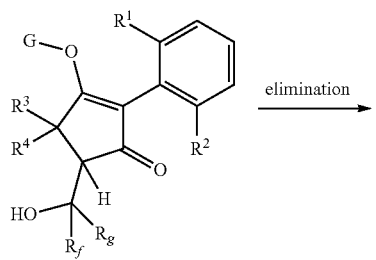

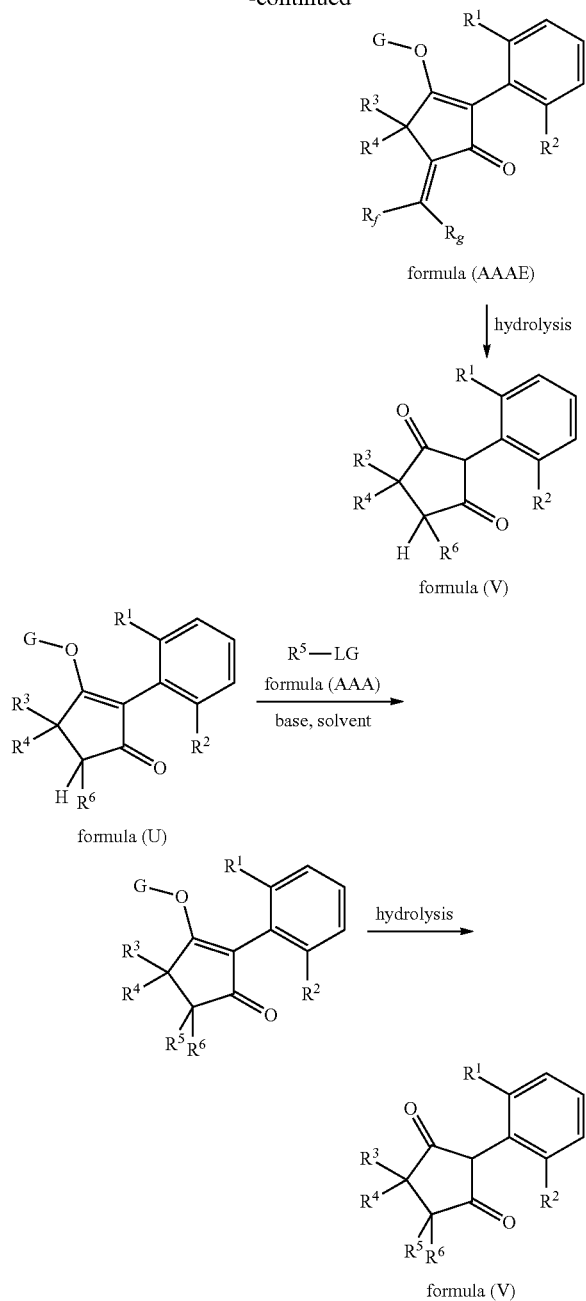

formula (AAAE)

↓ hydrolysis formula (V)

formula (U) →[R⁵—LG, formula (AAA), base, solvent]

→ hydrolysis formula (V)

Herbicidal Compositions

In another aspect, the present invention provides a herbicidal composition, e.g. for use in a method of controlling weeds (e.g. monocotyledonous such as grassy weeds) in crops of useful plants, which composition comprises a compound of formula (I) as defined herein (e.g. a herbicidally effective amount thereof), and a substantially-inert agrochemically acceptable substance (e.g. an agrochemically acceptable carrier, diluent and/or solvent, an agrochemically acceptable adjuvant, an agrochemically acceptable emulsifier/surfactant/surface-active substance, and/or another agrochemically acceptable additive).

In a further aspect, the present invention provides a herbicidal composition, e.g. for use in a method of controlling weeds (e.g. monocotyledonous such as grassy weeds) in crops of useful plants, comprising a compound of formula (I) as defined herein (e.g. a herbicidally effective amount thereof), and an agrochemically acceptable carrier, diluent and/or solvent.

In all aspects of the invention, the compound of the formula (I) is optionally present (e.g. where chemically possible) as an agrochemically acceptable salt thereof.

The compounds of formula (I) according to the invention can be used as crop protection agents in unmodified form, as obtained by synthesis, but, for use as herbicides, they are generally formulated into herbicidal compositions (formulations), e.g. in a variety of ways, containing one or more substantially-inert agrochemically acceptable substances (e.g. an agrochemically acceptable carrier, diluent and/or solvent, an agrochemically acceptable adjuvant, an agrochemically acceptable emulsifier/surfactant/surface-active substance, and/or another agrochemically acceptable additive).

The formulations (herbicidal compositions) can be in various physical forms, for example in the form of dusting powders, gels, wettable powders, coated or impregnated granules for manual or mechanical distribution on target sites, water-dispersible granules, water-soluble granules, emulsifiable granules, water-dispersible tablets, effervescent compressed tablets, water-soluble tapes, emulsifiable concentrates, microemulsifiable concentrates, oil-in-water (EW) or water-in-oil (WO) emulsions, other multiphase systems such as oil/water/oil and water/oil/water products, oil flowables, aqueous dispersions, oily dispersions, suspoemulsions, capsule suspensions, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. The active ingredient may be incorporated into microfibers or micro-rods formed of polymers or polymerizable monomers and having diameter of about 0.1 to about 50 microns and aspect ratio of between about 10 and about 1000.

Such formulations can either be used directly or are diluted prior to use. They can then be applied through suitable ground or aerial application spray equipment or other ground application equipment such as central pivot irrigation systems or drip/trickle irrigation means. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be contained in fine microcapsules consisting of a core and a polymeric shell. Microcapsules usually have a diameter of from 0.1 to 500 microns. They contain active ingredients in an amount of about from 25 to 95% by weight of the capsule weight. The active ingredients can be present in the form of liquid technical material, in the form of a suitable solution, in the form of fine particles in solid or liquid dispersion or as a monolithic solid. The encapsulating membranes comprise, for example, natural and synthetic gums, cellulose, styrene-butadiene copolymers or other similar suitable membrane forming material, polyacrylonitrile, polyacrylate, polyester, polyamides, polyureas, polyurethane, aminoplast resins or chemically modified starch or other polymers that are known to the person skilled in the art in this connection.

Alternatively it is possible for fine so called "microcapsules" to be formed wherein the active ingredient is present in the form of finely divided particles in a solid matrix of a base substance, but in that case the microcapsule is not encapsulated with a diffusion limiting membrane as outlined in the preceding paragraph.

The active ingredients may be adsorbed on a porous carrier. This may enable the active ingredients to be released into their surroundings in controlled amounts (e.g. slow release). Other forms of controlled release formulations are granules or powders in which the active ingredient is dispersed or dissolved in a solid matrix consisting of a polymer, a wax or a suitable solid substance of lower molecular weight. Suitable polymers are polyvinyl acetates, polystyrenes, polyolefins, polyvinyl alcohols, polyvinyl pyrrolidones, alkylated polyvinyl pyrrolidones, copolymers of polyvinyl pyrrolidones and maleic anhydride and esters and half-esters thereof, chemically modified cellulose esters like carboxymethyl cellulose, methyl cellulose, hydroxyethyl cellulose, examples of suitable waxes are polyethylene wax, oxidized polyethylene wax, ester waxes like montan waxes, waxes of natural origin like carnauba wax, candelilla wax, bees wax etc.

Other suitable matrix materials for slow release formulations are starch, stearin, lignin.

The formulation adjuvants suitable for the preparation of the compositions according to the invention are known per se.

As liquid carriers there may be used: water, aromatic solvents such as toluene, m-xylene, o-xylene, p-xylene and mixtures thereof, cumene, aromatic hydrocarbon blends with boiling ranges between 140 and 320° C. known under various trademarks like Solvesso®, Shellsol A®, Caromax®, Hydrosol®, paraffinic and isoparaffinic carriers such as paraffin oils, mineral oils, de-aromatized hydrocarbon solvents with boiling ranges between 50 and 320° C. known for instance under the trademark Exxsol®, non-dearomatized hydrocarbon solvents with boiling ranges between 100 and 320° C. known under the tradename Varsol®, isoparaffinic solvents with boiling ranges between 100 and 320° C. known under tradenames like Isopar® or Shellsol T®, hydrocarbons such as cyclohexane, tetrahydronaphthalene (tetralin), decahydronaphthalene, alpha-pinene, d-limonene, hexadecane, isooctane, ester solvents such as ethyl acetate, n/i-butyl acetate, amyl acetate, i-bornyl acetate, 2-ethylhexyl acetate, $C_6$-$C_{18}$ alkyl esters of acetic acid known under the tradename Exxate®, lactic acid ethylester, lactic acid propylester, lactic acid butylester, benzyl benzoate, benzyl lactate, dipropyleneglycol dibenzoate, dialkyl esters of succinic, maleic and fumaric acid and polar solvents like N-methylpyrrolidone, N-ethyl pyrrolidone, $C_3$-$C_{18}$-alkyl pyrrolidones, gamma-butyrolactone, dimethylsulfoxide, N,N-dimethylformamide, N,N-dimethylacetamide, N,N-dimethyllactamide, $C_4$-$C_{18}$ fatty acid dimethylamides, benzoic acid dimethylamide, acetonitrile, acetone, methyl ethyl ketone, methyl-isobutyl ketone, isoamyl ketone, 2-heptanone, cyclohexanone, isophorone, methyl isobutenyl ketone (mesityl oxide), acetophenone, ethylene carbonate, propylene carbonate, butylene carbonate, alcoholic solvents and diluents such as methanol, ethanol, propanol, n/iso-butanol, n/iso-pentanol, 2-ethyl hexanol, n-octanol, tetrahydrofurfuryl alkohol, 2-methyl-2,4-pentanediol, 4-hydroxy-4-methyl-2-pentanon, cyclohexanol, benzyl alcohol, ethylene glycol, ethylene glycol butyl ether, ethylene glycol methyl ether, diethylene glycol, diethylene glycol butyl ether, diethylene glycol ethyl ether, diethylene glycol methyl ether, propylene glycol, dipropylene glycol, dipropylene glycol methyl ether and other similar glycol ether solvents based on ethylene glycol, propylene glycol and butylene glycol feedstocks, triethylene glycol, polyethylene glycol (PEG 400), polypropylenglycols with molecular masses of 400-4000, glycerol, glycerol acetate, glycerol diacetate, glycerol triacetate, 1,4-dioxane, diethylene glycol abietate, chlorobenzene, chlorotoluene, fatty acid esters such as methyl octanoate, isopropyl myristate, methyl laurate, methyl oleate, mixture of $C_8$-$C_{10}$ fatty acid methyl esters, rape seed oil methyl and ethyl esters, soy bean oil methyl and ethyl esters, vegetable oils, fatty acids such as oleic acid, linoleic acid, linolenic acid, esters of phosphoric and phosphonic acid such as triethyl phosphate, $C_3$-$C_{18}$-tris-alkyl phosphates, alkylaryl phosphates, bis-octyl-octyl phosphonates.

Water is generally the carrier of choice for the dilution of the concentrates.

Suitable solid carriers are, for example, talc, titanium dioxide, pyrophyllite clay, silica (fumed or precipated silica and optionally functionalised or treated, for instance silanised), attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in the EPA CFR 180.1001. (c) & (d). Powdered or granulated fertilisers can also be used as solid carriers.

A large number of surface-active substances can advantageously be used both in solid and in liquid formulations, especially in those formulations which can be diluted with a carrier prior to use. Surface-active substances may be anionic, cationic, amphoteric, non-ionic or polymeric and they may be used as emulsifying, wetting, dispersing or suspending agents or for other purposes. Typical surface-active substances include, for example, salts of alkyl sulfates, such as diethanolammonium lauryl sulfate; Sodium lauryl sulfate, salts of alkylarylsulfonates, such as calcium or sodium dodecylbenzenesulfonate; alkylphenol-alkylene oxide addition products, such as nonylphenol ethoxylates; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, compatibility agents and solubilisers and also liquid and solid fertilisers.

The formulations may also comprise additional active substances, for example further herbicides, herbicide safeners, plant growth regulators, fungicides or insecticides.

The compositions according to the invention can additionally include an additive (commonly referred to as an adjuvant), comprising a mineral oil, an oil of vegetable or animal origin, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsifiable vegetable oil, such as AMIGO® (Loveland Products Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is AGNIQUE ME 18 RD-F® (Cognis). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic, cationic or amphoteric surfactants. Examples of suitable anionic, non-ionic, cationic or amphoteric surfactants are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant). Also preferred are silicone surfactants, especially polyalkyl-oxide-modified heptamethyltrisiloxanes, which are commercially available e.g. as SILWET L-77®, and also perfluorinated surfactants. The concentration of surface-active substances in relation to the total additive is generally from 1 to 50% by weight. Examples of oil additives that consist of mixtures of oils or mineral oils or derivatives thereof with surfactants are TURBOCHARGE®, ADIGOR® (both (Syngenta Crop Protection AG), ACTIPRON® (BP Oil UK Limited), AGRI-DEX® (Helena Chemical Company).

The said surface-active substances may also be used in the formulations alone, that is to say without oil additives.

Furthermore, the addition of an organic solvent to the oil additive/surfactant mixture can contribute to a further enhancement of action. Suitable solvents are, for example, SOLVESSO® and AROMATIC® solvents (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF). Further oil additives that are preferred according to the invention are SCORE® and ADIGOR® (both Syngenta Crop Protection AG).

In addition to the oil additives listed above, in order to enhance the activity of the compositions according to the invention it is also possible for formulations of alkylpyrrolidones, (e.g. AGRIMAX® from ISP) to be added to the spray mixture. Formulations of synthetic latices, such as, for example, polyacrylamide, polyvinyl compounds or poly-1-p-menthene (e.g. BOND®, COURIER® or EMERALD®) can also be used.

Such adjuvant oils as described in the preceding paragraphs may be employed as the carrier liquid in which an active compound is dissolved, emulsified or dispersed as appropriate to the physical form of the active compound.

The pesticidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1-2000 g/ha, preferably 1-1000 g/ha and most preferably at 1-500 g/ha.

Preferred Formulations have Especially the Following Representative Compositions:
(%=percent by weight):
Emulsifiable Concentrates:
active ingredient: 1 to 95%, preferably 60 to 90%
surface-active agents: 1 to 30%, preferably 5 to 20%
solvents as liquid carrier: 1 to 80%, preferably 1 to 35%
Dusts:
active ingredient: 0.1 to 10%, preferably 0.1 to 5%
solid carriers: 99.9 to 90%, preferably 99.9 to 99%
Suspension Concentrates:
active ingredient: 5 to 75%, preferably 10 to 50%
water: 94 to 24%, preferably 88 to 30%
surface-active agents: 1 to 40%, preferably 2 to 30%
Wettable Powders:
active ingredient: 0.5 to 90%, preferably 1 to 80%
surface-active agents: 0.5 to 20%, preferably 1 to 15%
solid carriers: 5 to 95%, preferably 15 to 90%
Granules:
active ingredient: 0.1 to 30%, preferably 0.1 to 15%
solid carriers: 99.5 to 70%, preferably 97 to 85%
Waterdispersible Granules:
active ingredient: 1 to 90%, preferably 10 to 80%
surface-active agents: 0.5 to 80%, preferably 5 to 30%
solid carriers: 90 to 10%, preferably 70 to 30%

The following Examples further illustrate, but do not limit, the invention.

| F1. Emulsifiable concentrates | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP (N-methyl-2-pyrrolidone) | — | 10% | — | 20% |
| aromatic hydrocarbon mixture $C_9$-$C_{12}$ | 85% | 68% | 65% | 16% |

Emulsions of any desired concentration can be prepared from such concentrates by, dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | 40% | 50% | — | — |
| polyethylene glycol MW 400 | 20% | 10% | — | — |

-continued

| F2. Solutions | a) | b) | c) | d) |
|---|---|---|---|---|
| NMP (N-methyl-2-pyrrolidone) | — | — | 50% | 10% |
| aromatic hydrocarbon mixture $C_9$-$C_{12}$ | 35% | 30% | — | — |

The solutions are suitable for application undiluted or after dilution with water.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient | 0.1% | 5% | 15% |
| highly dispersed silica | 0.9% | 2% | 2% |
| inorganic carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly dispersed silica | 0.9% | 1% | 2% |
| inorganic carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

| F6. Extruded granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Water-dispersible granules | a) | b) | c) | d) |
|---|---|---|---|---|
| active ingredient | 5% | 10% | 40% | 90% |
| sodium lignosulfonate | 20% | 20% | 15% | 7% |
| dibutyl naphthalene sulfonate | 5% | 5% | 4% | 2% |
| Gum arabic | 2% | 1% | 1% | 1% |
| Diatomaceous earth | 20% | 30% | 5% | — |
| Sodium sulfate | — | 4% | 5% | — |
| kaolin | 48% | 30% | 30% | — |

The active ingredient is mixed and ground with the adjuvants and the mixture is moistened with water. The resulting mixture is extruded and then dried in a stream of air.

| F8. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F9. Suspension concentrates | a) | b) | c) | d) |
|---|---|---|---|---|
| active ingredient | 3% | 10% | 25% | 50% |
| propylene glycol | 5% | 5% | 5% | 5% |
| nonylphenol polyglycol ether (15 mol of ethylene oxide) | — | 1% | 2% | — |
| sodium lignosulfonate | 3% | 3% | 7% | 6% |
| heteropolysacharide (Xanthan) | 0.2% | 0.2% | 0.2% | 0.2% |
| 1,2-benzisothiazolin-3-one | 0.1% | 0.1% | 0.1% | 0.1% |
| silicone oil emulsion | 0.7% | 0.7% | 0.7% | 0.7% |
| water | 87% | 79% | 62% | 38% |

The finely ground active ingredient is intimately mixed with the adjuvants, yielding a suspension concentrate from which suspensions of any desired concentration can be prepared by dilution with water.

Herbicidal Uses—Crops of Useful Plants, Weeds, Application Rates, et al.

In a further aspect, the present invention provides a method of controlling weeds (e.g. monocotyledonous such as grassy weeds) in crops of useful plants, which comprises applying a compound of the formula (I), or a herbicidal composition comprising such a compound, to the weeds and/or to the plants and/or to the locus thereof.

In a further aspect, the present invention provides a herbicidal composition, in particular for use in a method of controlling weeds (e.g. monocotyledonous such as grassy weeds) in crops of useful plants, comprising a compound of formula (I) as defined herein (e.g. a herbicidally effective amount thereof), and an agrochemically acceptable carrier, diluent and/or solvent.

In all aspects of the invention, the compound of the formula (I) is optionally present (e.g. where chemically possible) as an agrochemically acceptable salt thereof.

In one embodiment, the herbicidal composition also comprises one or more further herbicides, e.g. as mixture partner(s) for the compound of formula (I), and/or a safener. See the combinations and mixtures section herein for more details of examples of these.

In all aspects of the invention (e.g. the methods of use of the invention), crops of useful plants, e.g. in which the compounds or compositions according to the invention can be used, comprise (e.g. are), in particular, cereals (e.g. non-oat cereals, in particular wheat, barley, rye and/or triticale), rice, corn (maize), sugarcane, soybean, cotton, rape (e.g. oilseed rape or canola), sunflower, sugarbeet, peanut and/or plantation crops.

Preferably, in all aspects of the invention, the crops of useful plants, e.g. in which the compounds or compositions according to the invention can be used, comprise (e.g. are) cereals (e.g. non-oat cereals, in particular wheat, barley, rye and/or triticale), rice, corn (maize), sugarcane, soybean, cotton, rape (e.g. oilseed rape or canola), sunflower and/or sugarbeet; more preferably, cereals (e.g. non-oat cereals, in particular wheat, barley, rye and/or triticale), rice, corn (maize) and/or soybean.

The term "crops" is to be understood as also including crops that have been rendered tolerant to herbicides or classes of herbicides (for example ALS, GS, EPSPS, PPO and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

In all aspects of the invention, the weeds, e.g. to be controlled and/or growth-inhibited, may be either monocotyledonous (e.g. grassy) and/or dicotyledonous weeds. Preferably the weeds, e.g. to be controlled and/or growth-inhibited, comprise or are monocotyledonous weeds, more preferably grassy monocotyledonous weeds.

In all aspects of the invention, typically, the monocotyledonous (preferably grassy) weeds, e.g. to be controlled and/or growth-inhibited, comprise (e.g. are) weeds from the genus *Agrostis, Alopecurus, Apera, Avena, Brachiaria, Bromus, Cyperus* (a genus of sedges), *Digitaria, Echinochloa, Eriochloa, Fimbristylis* (a genus of sedges), *Juncus* (a genus of rushes), *Leptochloa, Lolium, Monochoria, Panicum, Phalaris, Poa, Rottboellia, Sagittaria, Scirpus* (a genus of sedges), *Setaria* and/or *Sorghum*; in particular: *Alopecurus myosuroides* (ALOMY, English name "blackgrass"), *Apera spica-venti, Avena fatua* (AVEFA, English name "wild oats"), *Avena ludoviciana, Avena sterilis, Avena sativa* (English name "oats" (volunteer)), *Brachiaria plantaginia, Bromus tectorum, Digitaria sanguinalis* (DIGSA), *Echinochloa crusgalli* (English name "common barnyard grass", ECHCG), *Echinochloa oryzoides, Echinochloa colona* or *colonum, Eriochloa villosa* (English name "woolly cupgrass"), *Leptochloa chinensis, Leptochloa panicoides, Lolium perenne* (LOLPE, English name "perennial ryegrass"), *Lolium multiflorum* (LOLMU, English name "Italian ryegrass"), *Lolium persicum* (English name "Persian darnel"), *Lolium rigidum, Panicum miliaceum* (English name "wild proso millet"), *Phalaris minor, Phalaris paradoxa, Poa annua* (POAAN, English name "annual bluegrass"), *Scirpus maritimus, Scirpus juncoides, Setaria viridis* (SETVI, English name "green foxtail"), *Setaria faberi* (SETFA, English name "giant foxtail"), *Setaria lutescens* (English name "yellow foxtail") and/or *Sorghum halapense* (English name "Johnson grass").

In one preferred embodiment of all aspects of the invention, the monocotyledonous weeds, e.g. to be controlled and/or growth-inhibited, are grassy weeds; in which case they typically comprise (e.g. are) weeds from the genus *Agrostis, Alopecurus, Apera, Avena, Brachiaria, Bromus, Digitaria, Echinochloa, Eriochloa, Leptochloa, Lolium, Panicum, Phalaris, Poa, Rottboellia, Setaria* and/or *Sorghum*.

In one particular embodiment of all aspects of the invention, the grassy monocotyledonous weeds, e.g. to be controlled and/or growth-inhibited, are "warm-season" grassy weeds; in which case they typically comprise (e.g. are) weeds from the genus *Brachiaria, Digitaria, Echinochloa, Eriochloa, Leptochloa, Panicum, Setaria* and/or *Sorghum*.

In another particular embodiment of all aspects of the invention, the grassy monocotyledonous weeds, e.g. to be controlled and/or growth-inhibited, are "cool-season" grassy weeds; in which case they typically comprise (e.g. are) weeds from the genus *Agrostis, Alopecurus, Apera, Avena, Bromus, Lolium* and/or *Poa*.

In non-oat cereal crops such as wheat and/or barley, control and/or growth inhibition of weeds from the genus *Alopecurus, Apera, Avena*, especially *Avena fatua, Bromus, Lolium, Phalaris*, and/or *Setaria* is preferred; in particular *Alopecurus, Avena* (especially *Avena fatua*), *Lolium* and/or *Setaria* (especially *Setaria viridis, Setaria lutescens* and/or *Setaria faberi*).

In all aspects of the invention, in a particular embodiment, the weeds, e.g. to be controlled and/or growth-inhibited e.g. by applying a compound of formula (I), may be grassy monocotyledonous weeds (e.g. *Alopecurus, Apera, Avena, Brachiaria, Bromus, Digitaria, Echinochloa, Eriochloa, Lolium, Panicum, Phalaris, Poa, Setaria* and/or *Sorghum* weeds), which are resistant to one or more ACCase inhibitor herbicides (ACCase=acetyl-coenzyme A carboxylase) selected from the group consisting of pinoxaden, clodinafop-propargyl, fenoxaprop-P-ethyl, diclofop-methyl, fluazifop-P-butyl, haloxyfop-P-methyl, quizalofop-P-ethyl, propaquizafop, cyhalofop-butyl, clethodim, sethoxydim, cycloxydim, tralkoxydim and butroxydim;

and/or which are resistant to glyphosate;

and/or which are resistant to one or more ALS inhibitor herbicides (ALS=acetolactate synthase), such as one or more sulfonyl urea herbicides (e.g. iodosulfuron-methyl, mesosulfuron-methyl, tribenuron-methyl, triasulfuron, prosulfuron, sulfosulfuron, pyrazosulfuron-ethyl, bensulfuron-methyl, nicosulfuron, or any other sulfonyl urea herbicide disclosed in The Pesticide Manual, 15th edition, 2009, ed. C.D.S. Tomlin, British Crop Protection Council) and/or one or more triazolopyrimidine herbicides (e.g. florasulam, pyroxsulam or penoxsulam) and/or one or more pyrimidinyl-(thio or oxy)-benzoate herbicides (e.g. bispyribac-sodium or pyriftalid) and/or one or more sulfonylamino-carbonyl-triazolinone herbicides (e.g. thiencarbazone-methyl, propoxycarbazone-sodium or flucarbazone-sodium). Such resistant (in particular ACCase-inhibitor-resistant, glyphosate-resistant, and/or ALS-inhibitor-resistant) grassy weeds can more particularly comprise *Alopecurus myosuroides, Apera spica-venti, Avena fatua, Avena sterilis, Digitaria sanguinalis, Echinochloa colona, Echinochloa crus-galli, Lolium multiflorum, Lolium rigidum, Lolium perenne, Phalaris minor, Phalaris paradoxa, Setaria viridis, Setaria faberi* and/or *Sorghum halapense.*

In an even more particular embodiment of the invention, the compound of formula (I) can be applied to grassy monocotyledonous weeds (e.g. selected from one of the above-mentioned list(s) of grassy weeds):

(a1) which are resistant to one or more ACCase inhibitor herbicides (e.g. selected from the above-mentioned list of ACCase inhibitor herbicides) at least partly by means of mutation (e.g. substitution) of one or more amino acids on the ACCase target site in the weed (e.g. see S. B. Powles and Qin Yu, "Evolution in Action: Plants Resistant to Herbicides", *Annu. Rev. Plant Biol.,* 2010, 61, pp. 317-347, e.g. see pages 325-327 therein in particular Table 3, incorporated herein by reference, for examples of such resistant weeds and/or amino acid substitutions); and/or (a2) which are resistant to glyphosate at least partly by means of mutation (e.g. substitution) of one or more amino acids on the EPSPS target site in the weed targeted by glyphosate (e.g. see above-mentioned S. B. Powles and Qin Yu article, pp. 327-329); and/or (a3) which are resistant to one or more ALS inhibitor herbicides (e.g. selected from the above-mentioned list of ALS inhibitor herbicides) at least partly by mutation (e.g. substitution) of one or more amino acids on the ALS target site in the weed (e.g. see S. B. Powles and Qin Yu, "Evolution in Action: Plants Resistant to Herbicides", *Annu. Rev. Plant Biol.,* 2010, 61, pp. 317-347, e.g. see pages 322-324 therein in particular Table 2, incorporated herein by reference, for examples of such resistant weeds and/or amino acid substitutions); and/or (b) which are resistant to: one or more ACCase inhibitor herbicides (e.g. selected from the above-mentioned list), and/or glyphosate, and/or one or more ALS inhibitor herbicides (e.g. selected from the above-mentioned list); at least partly by metabolic-type herbicidal resistance e.g. at least partly by cytochrome P450-mediated herbicide metabolism (e.g. see S. B. Powles and Qin Yu, "Evolution in Action: Plants Resistant to Herbicides", *Annu. Rev. Plant Biol.,* 2010, 61, pp. 317-347, e.g. see Table 4 on page 328 therein, incorporated herein by reference, for examples of such resistant weeds).

Typically, dicotyledonous weeds, e.g. to be controlled, comprise (e.g. are) *Abutilon, Amaranthus, Chenopodium, Chrysanthemum, Galium, Ipomoea, Kochia, Nasturtium, Polygonum, Sida, Sinapsis, Solanum, Stellaria, Viola, Veronica* and/or *Xanthium.*

Areas under cultivation, and/or the locus (e.g. of weeds and/or of crops of useful plants), are to be understood as including land where the crop plants are already growing as well as land intended for the cultivation of those crop plants.

In all aspects of the invention, the rate of application of the compound of formula (I) (which optionally may be an agrochemically acceptable salt thereof) is generally from 1 to 2000 g of the compound of formula (I) per hectare (ha) (measured as the salt-free compound), in particular from 5 to 1000 or from 10 to 500 g/ha, preferably from 20 to 300 g/ha, of the compound of formula (I) (measured as the salt-free compound).

In all aspects of the invention, the compound of formula (I) or salt thereof can be applied pre- and/or post-emergence, but preferably is applied post-emergence.

Combinations and Mixtures

In a further aspect, the present invention provides a herbicidal composition, e.g. for use in a method of controlling weeds (e.g. monocotyledonous such as grassy weeds) in crops of useful plants, comprising a compound of formula (I) as defined herein (e.g. a herbicidally effective amount thereof), and an agrochemically acceptable carrier, diluent and/or solvent, and also comprising one or more further herbicides, and/or a safener.

In all aspects of the invention, the compound of the formula (I) is optionally present (e.g. where chemically possible) as an agrochemically acceptable salt thereof.

Examples of these mixtures/compositions, comprising one or more further herbicides and/or a safener, follow.

The compounds of formula I according to the invention can be used in combination with one or more further herbicides, e.g. as mixture partner(s) for the compound of formula (I).

Preferably, in these mixtures, the compound of the formula I is one of those compounds listed in Tables 1 to 22 or Table 23 and/or the exemplified compounds (e.g. one of Compounds A-1 to A-19, or A-20 to A-34) as disclosed herein e.g. hereinbelow.

The following mixtures of the compound of formula I with one or more further herbicides are particularly disclosed:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fenoxasulfone (CAS Reg. No. 639826-16-7), compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+fluorochloridone, compound of formula I+fluoroxypyr, compound of formula I+fluoroxypyr-meptyl, compound of formula I+fluoroxypyr-butomethyl, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glufosinate-P, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+ipfencarbazone (CAS Reg. No. 212201-70-2), compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+metazosulfuron (NC-620, CAS Reg. No. 868680-84-6), compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyrisulfuron (TH-547, CAS Reg. No. 570415-88-2), compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS Reg. No. 353292-31-6), compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636), compound of formula I+BAY747 (CAS Reg. No. 335104-84-2), compound of formula I+topramezone (CAS Reg. No. 210631-68-8), compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula I+4-hydroxy-3-[[2-(3-methoxypropyl)-6-(difluoromethyl)-3-pyridinyl]carbonyl]-bicyclo[3.2.1]oct-3-en-2-one, compound of formula (I)+either one of compounds A-1 to A-168 or D-1 to D-43 disclosed on pages 87-109 and 227-233 respectively of WO 2008/071405 A1 or a compound covered by claim 14 of WO 2008/071405 A1 (Syngenta Participations AG and Syngenta Limited) these parts of which are incorporated herein by reference (in particular compound of formula (I)+one of compounds A-4, A-45, A-64, A-65, A-66, A-167, D-7, D-16, D-23 or D-26 disclosed in WO 2008/071405 A1, these parts of which are incorporated herein by reference), compound of formula (I)+one of compounds A-1, A-2, A-3, A-4, A-5, A-6, A-7, A-8, A-9, A-10 or A-11 (e.g. compound A-5 or A-6) disclosed in pages 7-8 of WO 2011/073615 A2 (Syngenta Limited) these parts of which are incorporated herein by reference, compound of formula (I)+one of compounds A-12, A-13, A-14, A-15 or A-16 (in particular compound A-13) disclosed in pages 10-11 of WO 2011/073616 A2 these parts of which are incorporated herein by reference (Syngenta Limited), compound of formula (I)+one of the specific herbicidal compounds disclosed in WO 2010/059676 (Dow, e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (Dow, e.g. as defined in one of the examples therein and/or e.g. can be plus cloquintocet-mexyl or another safener) these parts of which are incorporated herein by reference, and compound of formula (I)+one of the specific herbicidal compounds disclosed in WO 2010/059671 (Dow, e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+aminocyclopyrachlor (which is 6-amino-5-chloro-2-cyclopropylpyrimidine-4-carboxylic acid, CAS Reg. No. 858956-08-8), compound of formula I+aminocyclopyrachlor-methyl (which is methyl 6-amino-5-chloro-2-cyclopropylpyrimidine-4-carboxylate, CAS Reg. No. 858954-83-3), compound of formula I+aminocyclopyrachlor-potassium (which is potassium 6-amino-5-chloro-2-cyclopropylpyrimidine-4-carboxylate, CAS Reg. No. 858956-35-1), compound of formula I+saflufenacil (which is N'-{2-chloro-4-fluoro-5-[1,2,3,6-tetrahydro-3-methyl-2,6-dioxo-4-(trifluoromethyl)pyrimidin-1-yl]benzoyl}-N-isopropyl-N-methylsulfamide, CAS Reg. No. 372137-35-4), compound of formula I+iofensulfuron (which is 1-(2-iodophenylsulfonyl)-3-(4-methoxy-6-methyl-1,3,5-triazin-2-yl)urea, CAS Reg. No. 1144097-22-2), compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2), compound of formula I+clacyfos (which is dimethyl[(1RS)-1-(2,4-dichlorophenoxyacetoxy)ethyl]phosphonate, also named Ivxiancaolin or Iüxiancaolin, CAS Reg. No. 215655-76-8), compound of formula I+cyclopyrimorate (which is 6-chloro-3-(2-cyclopropyl-6-methylphenoxy)pyridazin-4-yl morpholine-4-carboxylate, CAS Reg. No. 499231-24-2), or compound of formula I+triafamone (which is N-[2-[(4,6-dimethoxy-1,3,5-triazin-2-yl)carbonyl]-6-fluorophenyl]-N-methyl-1,1-difluoromethanesulfonamide, CAS Reg. No. 874195-61-6).

The mixing partners for the compound of formula (I) are optionally in the form of an ester or a salt (in particular an agrochemically acceptable salt) thereof (e.g. where chemically possible). The above-mentioned mixing partners for the compound of formula (I), are generally mentioned e.g. in The Pesticide Manual, 15th Edition, 2009, ed. C.D.S. Tomlin, British Crop Production Council.

For applications in cereals, the following mixtures are preferred: compound of formula I+aclonifen, compound of formula I+amidosulfuron, compound of formula I+aminopyralid, compound of formula I+beflubutamid, compound of formula I+benfluralin, compound of formula I+bifenox, compound of formula I+bromoxynil, compound of formula I+butafenacil, compound of formula I+carbetamide, compound of formula I+carfentrazone, compound of formula I+carfentrazone-ethyl, compound of formula I+chlorotoluron, compound of formula I+chlorpropham, compound of formula I+chlorsulfuron, compound of formula I+cinidon-ethyl, compound of formula I+clodinafop, compound of formula I+clodinafop-propargyl, compound of formula I+clopyralid, compound of formula I+2,4-D, compound of formula I+dicamba, compound of formula I+dichlobenil, compound of formula I+dichlorprop, compound of formula I+diclofop, compound of formula I+diclofop-methyl, compound of formula I+difenzoquat, compound of formula I+difenzoquat metilsulfate, compound of formula I+diflufenican, compound of formula I+diquat, compound of formula I+diquat dibromide, compound of formula I+fenoxaprop-P, compound of formula I+fenoxaprop-P-ethyl, compound of formula I+flamprop-M, compound of formula I+florasulam, compound of formula I+fluazifop-P-butyl, compound of formula I+flucarbazone, compound of formula I+flucarbazone-sodium, compound of formula I+flufenacet, compound of formula I+flupyrsulfuron, compound of formula I+flupyrsulfuron-methyl-sodium, compound of formula I+fluorochloridone, compound of formula I+fluoroxypyr, compound of formula I+fluoroxypyr-meptyl, compound of formula I+fluoroxypyr-butomethyl, compound of formula I+flurtamone, compound of formula I+imazamethabenz-methyl, compound of formula I+imazamox, compound of formula I+iodosulfuron, compound of formula I+iodosulfuron-methyl-sodium, compound of formula I+ioxynil, compound of formula I+isoproturon, compound of formula I+linuron, compound of formula I+MCPA, compound of formula I+mecoprop, compound of formula I+mecoprop-P, compound of formula I+mesosulfuron, compound of formula I+mesosulfuron-methyl, compound of formula I+mesotrione, compound of formula I+metribuzin, compound of formula I+metsulfuron, compound of formula I+metsulfuron-methyl, compound of formula I+pendimethalin, compound of formula I+picolinafen, compound of formula I+pinoxaden, compound of formula I+prodiamine, compound of formula I+propanil, compound of formula I+propoxycarbazone, compound of formula I+propoxycarbazone-sodium, compound of formula I+prosulfocarb, compound of formula I+pyrasulfotole, compound of formula I+pyridate, compound of formula I+pyroxasulfone (KIH-485), compound of formula I+pyroxsulam compound of formula I+sulfosulfuron, compound of formula I+tembotrione, compound of formula I+terbutryn, compound of formula I+thifensulfuron, compound of formula I+thiencarbazone, compound of formula I+thifensulfuron-methyl, compound of formula I+topramezone, compound of formula I+tralkoxydim, compound of formula I+triallate, compound of formula I+triasulfuron, compound of formula I+tribenuron, compound of formula I+tribenuron-methyl, compound of formula I+trifluralin, compound of formula I+trinexapac-ethyl and compound of formula I+tritosulfuron, compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula (I)+one of the specific herbicidal compounds disclosed in WO 2010/059676 (Dow, e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (Dow, e.g. as defined in one of the examples therein and/or e.g. can be plus cloquintocet-mexyl or another safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), or compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2);

wherein the mixing partners for the compound of formula (I) may also be in the form of an ester or a salt (in particular an agrochemically acceptable salt) thereof.

For applications in cereals, particularly preferred is a mixture comprising: a compound of formula (I)+amidosulfuron, compound of formula (I)+aminopyralid, compound of formula (I)+beflubutamid, compound of formula (I)+bromoxynil, compound of formula (I)+carfentrazone, compound of formula (I)+carfentrazone-ethyl, compound of formula (I)+chlorotoluron, compound of formula (I)+chlorsulfuron, compound of formula (I)+clodinafop, compound of formula (I)+clodinafop-propargyl, compound of formula (I)+clopyralid, compound of formula (I)+2,4-D, compound of formula (I)+dicamba, compound of formula (I)+difenzoquat, compound of formula (I)+difenzoquat metilsulfate, compound of formula (I)+diflufenican, compound of formula (I)+fenoxaprop-P, compound of formula (I)+fenoxaprop-P-ethyl, compound of formula (I)+florasulam, compound of formula (I)+flucarbazone, compound of formula (I)+flucarbazone-sodium, compound of formula (I)+flufenacet, compound of formula (I)+flupyrsulfuron, compound of formula (I)+flupyrsulfuron-methyl-sodium, compound of formula (I)+fluoroxypyr, compound of formula I+fluoroxypyr-meptyl, compound of formula I+fluoroxypyr-butomethyl, compound of formula (I)+ flurtamone, compound of formula (I)+iodosulfuron, compound of formula (I)+iodosulfuron-methyl-sodium, compound of formula (I)+MCPA, compound of formula (I)+mesosulfuron, compound of formula (I)+mesosulfuron-methyl, compound of formula (I)+metsulfuron, compound of formula (I)+metsulfuron-methyl, compound of formula (I)+pendimethalin, compound of formula (I)+picolinafen, compound of formula (I)+pinoxaden, compound of formula (I)+prosulfocarb, compound of formula (I)+pyrasulfotole, compound of formula (I)+pyroxasulfone (KIH-485), compound of formula (I)+pyroxsulam, compound of formula (I)+sulfosulfuron, compound of formula (I)+thifensulfuron, compound of formula (I)+thifensulfuron-methyl, compound of formula I+topramezone, compound of formula (I)+tralkoxydim, compound of formula (I)+triasulfuron, compound of formula (I)+tribenuron, compound of formula (I)+tribenuron-methyl, compound of formula (I)+trifluralin, compound of formula (I)+trinexapac-ethyl, compound of formula (I)+tritosulfuron, compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula (I)+one of the specific herbicidal compounds disclosed in WO 2010/059676 (Dow, e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (Dow, e.g. as defined in one of the examples therein and/or e.g. can be plus cloquintocet-mexyl or another safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), or compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2);

wherein the mixing partners for the compound of formula (I) may also be in the form of an ester or a salt (in particular an agrochemically acceptable salt) thereof.

For applications in rice, the following mixtures are preferred: compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+butachlor, compound of formula (I)+cafenstrole, compound of formula (I)+cinosulfuron, compound of formula (I)+clomazone, compound of formula (I)+clomeprop, compound of formula (I)+cyclosulfamuron, compound of formula (I)+cyhalofop, compound of formula (I)+cyhalofop-butyl, compound of formula (I)+2,4-D, compound of formula (I)+daimuron, compound of formula (I)+dicamba, compound of formula (I)+diquat, compound of formula (I)+diquat dibromide, compound of formula (I)+esprocarb, compound of formula (I)+ethoxysulfuron, compound of formula (I)+fenoxaprop-P, compound of formula (I)+fenoxaprop-P-ethyl, compound of formula I+fenoxasulfone (CAS Reg. No. 639826-16-7), compound of formula (I)+fentrazamide, compound of formula (I)+florasulam, compound of formula (I)+glufosinate-ammonium, compound of formula (I)+glyphosate, compound of formula (I)+halosulfuron, compound of formula (I)+halosulfuron-methyl, compound of formula (I)+imazosulfuron, compound of formula I+ipfencarbazone (CAS Reg. No. 212201-70-2), compound of formula (I)+MCPA, compound of formula (I)+mefenacet, compound of formula (I)+mesotrione, compound of formula (I)+metamifop, compound of formula I+metazosulfuron (NC-620, CAS Reg. No. 868680-84-6), compound of formula (I)+metsulfuron, compound of formula (I)+metsulfuron-methyl, compound of formula (I)+n-methyl glyphosate, compound of formula (I)+orthosulfamuron, compound of formula (I)+oryzalin, compound of formula (I)+oxadiargyl, compound of formula (I)+oxadiazon, compound of formula (I)+paraquat dichloride, compound of formula (I)+pendimethalin, compound of formula (I)+penoxsulam, compound of formula (I)+pretilachlor, compound of formula (I)+profoxydim, compound of formula (I)+propanil, compound of formula I+propyrisulfuron (TH-547, CAS Reg. No. 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl, compound of formula (I)+either one of compounds A-1 to A-168 or D-1 to D-43 disclosed on pages 87-109 and 227-233 respectively of WO 2008/071405 A1 or a compound covered by claim 14 of WO 2008/071405 A1 (Syngenta Participations AG and Syngenta Limited) these parts of which are incorporated herein by reference (in particular compound of formula (I)+one of compounds A-4, A-45, A-64, A-65, A-66, A-167, D-7, D-16, D-23 or D-26 disclosed in WO 2008/071405 A1, these parts of which are incorporated herein by reference), compound of formula (I)+one of compounds A-1, A-2, A-3, A-4, A-5, A-6, A-7, A-8, A-9, A-10 or A-11 (e.g. compound A-5 or A-6) disclosed in pages 7-8 of WO 2011/073615 A2 (Syngenta Limited) these parts of which are incorporated herein by reference, compound of formula (I)+one of compounds A-12, A-13, A-14, A-15 or A-16 (in particular compound A-13) disclosed in pages 10-11 of WO 2011/073616 A2 these parts of which are incorporated herein by reference (Syngenta Limited), compound of formula (I)+one of the specific herbicidal compounds disclosed in WO 2010/059671 (Dow, e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl) pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl) pyridine-2-carboxylate, CAS Reg. No. 943831-98-9), compound of formula I+iofensulfuron (which is 1-(2-iodophenyl-sulfonyl)-3-(4-methoxy-6-methyl-1,3,5-triazin-2-yl)urea, CAS Reg. No. 1144097-22-2), compound of formula I+iofensulfuron-sodium (which is sodium N-(2-iodophenyl-sulfonyl)-N'-(4-methoxy-6-methyl-1,3,5-triazin-2-yl)carbamimidate, CAS Reg. No. 1144097-30-2), or compound of formula I+triafamone (which is N-[2-[(4,6-dimethoxy-1,3,5-triazin-2-yl)carbonyl]-6-fluorophenyl]-N-methyl-1,1-difluoromethanesulfonamide, CAS Reg. No. 874195-61-6);

wherein the mixing partners for the compound of formula (I) may also be in the form of an ester or a salt (in particular an agrochemically acceptable salt) thereof; are particularly preferred.

For applications in rice, particularly preferred is a mixture comprising: a compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+clomazone, compound of formula (I)+clomeprop, compound of formula (I)+cyhalofop, compound of formula (I)+cyhalofop-butyl, compound of formula (I)+2,4-D, compound of formula (I)+daimuron, compound of formula (I)+dicamba, compound of formula (I)+esprocarb, compound of formula (I)+ethoxysulfuron, compound of formula (I)+fenoxaprop-P, compound of formula (I)+fenoxaprop-P-ethyl, compound of formula I+fenoxasulfone (CAS Reg. No. 639826-16-7), compound of formula (I)+fentrazamide, compound of formula (I)+florasulam, compound of formula (I)+halosulfuron, compound of formula (I)+halosulfuron-methyl, compound of formula (I)+imazosulfuron, compound of formula I+ipfencarbazone (CAS Reg. No. 212201-70-2), compound of formula (I)+MCPA, compound of formula (I)+mefenacet, compound of formula (I)+mesotrione, compound of formula I+metazosulfuron (NC-620, CAS Reg. No. 868680-84-6), compound of formula (I)+metsulfuron, compound of formula (I)+metsulfuron-methyl, compound of formula (I)+orthosulfamuron, compound of formula (I)+oxadiargyl, compound of formula (I)+oxadiazon, compound of formula (I)+pendimethalin, compound of formula (I)+penoxsulam, compound of formula (I)+pretilachlor, compound of formula I+propyrisulfuron (TH-547, CAS Reg. No. 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron, compound of formula (I)+trinexapac-ethyl, compound of formula (I)+either one of compounds A-1 to A-168 or D-1 to D-43 disclosed on pages 87-109 and 227-233 respectively of WO 2008/071405 A1 or a compound covered by claim 14 of WO 2008/071405 A1 (Syngenta Participations AG and Syngenta Limited) these parts of which are incorporated herein by reference (in particular compound of formula (I)+one of compounds A-4, A-45, A-64, A-65, A-66, A-167, D-7, D-16, D-23 or D-26 disclosed in WO 2008/071405 A1, these parts of which are incorporated herein by reference), compound of formula (I)+one of compounds A-1, A-2, A-3, A-4, A-5, A-6, A-7, A-8, A-9, A-10 or A-11 (e.g. compound A-5 or A-6) disclosed in pages 7-8 of WO 2011/073615 A2 (Syngenta Limited) these parts of which are incorporated herein by reference, compound of formula (I)+one of compounds A-12, A-13, A-14, A-15 or A-16 (in particular compound A-13) disclosed in pages 10-11 of WO 2011/073616 A2 these parts of which are incorporated herein by reference (Syngenta Limited), compound of formula (I)+one of the specific herbicidal compounds disclosed in WO 2010/059671 (Dow, e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl) pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl) pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2), or compound of formula I+triafamone (which is N-[2-[(4,6-dimethoxy-1,3,5-triazin-2-yl)carbonyl]-6-fluorophenyl]-N-methyl-1,1-difluoromethanesulfonamide, CAS Reg. No. 874195-61-6);

wherein the mixing partners for the compound of formula (I) may also be in the form of an ester or a salt (in particular an agrochemically acceptable salt) thereof.

In the above-mentioned compositions or mixtures comprising a compound of formula (I) (e.g. a compound from Tables 1 to 23 and/or one of Compounds A-1 to A-34 herein) and one or more further herbicides, the weight ratio of the compound of formula (I) to each further herbicide can vary over a large range and is, typically, from 500:1 to 1:200, especially from 200:1 to 1:100, more especially from 100:1 to 1:50, even more especially from 40:1 to 1:20. Typically, these weight ratios are measured as the free compound(s), i.e. excluding the weight of any associated salt counterion(s).

Alternatively or additionally, in herbicidal compositions, the compounds of formula (I) according to the invention can be used in combination with a safener. Preferably, in these herbicidal compositions or mixtures, the compound of the formula I is one of those compounds listed in Tables 1 to 22 or Table 23 and/or the exemplified compounds (e.g. one of Compounds A-1 to A-19, or A-20 to A-34) below. The following mixtures with safeners, especially, come into consideration in the present invention:

compound of formula I+cloquintocet-mexyl, compound of formula I+cloquintocet acid or an agrochemically acceptable salt thereof, compound of formula I+fenchlorazole-ethyl, compound of formula I+fenchlorazole acid or an agrochemically acceptable salt thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl) amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148, or compound of formula I+PPG-1292.

The above-mentioned safeners and herbicides are described, for example, in the Pesticide Manual, Twelfth Edition, British Crop Protection Council, 2000; or The Pesticide Manual, 15$^{th}$ edition, 2009, ed. C.D.S. Tomlin, British Crop Production Council. R-29148 is described, for example by P. B. Goldsbrough et al., Plant Physiology, (2002), Vol. 130 pp. 1497-1505 and references therein, PPG-1292 is known from WO09211761 and N-(2-methoxybenzoyl)-4-[(methylaminocarbonyl)amino]benzenesulfonamide is known from EP365484.

Especially preferably, in a composition or mixture comprising a compound of formula (I) (e.g. a compound from Tables 1 to 23 or one of Compounds A-1 to A-19, or A-20 to A-34) and a safener, the safener comprises (e.g. is) benoxacor, cloquintocet-mexyl, cloquintocet acid or an agrochemically acceptable salt thereof, cyprosulfamide, mefenpyr-diethyl and/or N-(2-methoxybenzoyl)-4-[(methylaminocarbonyl)amino]benzenesulfonamide. Even more preferably, the safener comprises (e.g. is) cloquintocet-mexyl, cloquintocet acid or an agrochemically acceptable salt thereof, and/or mefenpyr-diethyl; in particular for use on non-oat cereals such as wheat, barley, rye and/or triticale. Cloquintocet-mexyl is particularly valuable and is the most preferred safener, especially for use on non-oat cereals such as wheat, barley, rye and/or triticale.

In the above-mentioned compositions or mixtures comprising a compound of formula (I) (e.g. a compound from Tables 1 to 23 and/or one of Compounds A-1 to A-34 herein) with a safener, the weight ratio of the compound of formula (I) to the safener can vary over a large range and is, typically, from 200:1 to 1:200, especially from 50:1 to 1:50, more especially from 20:1 to 1:20, even more especially from 20:1 to 1:10. Preferably, the safener comprises (e.g. is) cloquintocet-mexyl, cloquintocet acid or an agrochemically acceptable salt thereof, and/or mefenpyr-diethyl, and the weight ratio of the compound of formula (I) to the safener is from 20:1 to 1:10, more preferably from 15:1 to 1:2. Typically, these weight ratios are measured as the free compound(s), i.e. excluding the weight of any associated salt counterion(s).

Application rates of herbicide and/or safener: The rate of application of safener relative to the herbicide (e.g. compounds of formula (I) is largely dependent upon the mode of application. In the case of field treatment, generally from 0.001 to 5.0 kg (e.g. from 1 to 1000 g) of safener per ha, preferably from 0.001 to 0.5 kg (in particular from 2 to 200 g or from 5 to 200 g) of safener per ha; and/or generally from 0.001 to 2 kg of herbicide (e.g. compound of formula (I)) per ha, but preferably from 0.005 to 1 kg (more preferably from 10 to 300 g or from 20 to 200 g) of herbicide (e.g. compound of formula (I)) per ha, are applied. ha=hectare. Typically, these application rates are measured as the free compound, i.e. excluding the weight of any associated salt counterion(s). In field treatment, the application of the herbicide (e.g. compound of formula (I)) is preferably post-emergence.

The herbicidal compositions according to the invention are suitable for all methods of application customary in agriculture, such as, for example, pre-emergence application, post-emergence application and seed dressing. Depending upon the intended use, the safeners can be used for pretreating the seed material of the crop plant (dressing the seed or seedlings) or introduced into the soil before or after sowing, followed by the application of the (unsafened) compound of the formula (I), optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field treatment, generally from 0.001 to 5.0 kg of safener/ha, preferably from 0.001 to 0.5 kg of safener/ha, are applied. ha=hectare. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10000 ppm, preferably from 100 to 1000 ppm.

It is preferred to apply the other herbicide together with one of the safeners mentioned above.

EXAMPLES

The following Examples illustrate the invention further but do not limit the invention.

PREPARATION EXAMPLES

Those skilled in the art will appreciate that certain compounds described below are β-ketoenols, and as such may exist as a single tautomer or as a mixture of keto-enol and diketone tautomers, as described, for example by J. March, Advanced Organic Chemistry, third edition, John Wiley and Sons. The compounds shown below, and in Table T1 are drawn as an arbitrary single enol tautomer, but it should be inferred that this description covers both the diketone form and any possible enols which could arise through tautomerism. Where more than one tautomer is observed in proton NMR, the data shown are for the mixture of tautomers. Furthermore, some of the compounds shown below are drawn as single enantiomers for the purposes of simplicity, but unless specified as single enantiomers, these structures should be construed as representing a mixture of enantiomers. Additionally, some of the compounds can exist as diastereoisomers, and it should be inferred that these can be present as a mixture of diastereoisomers or as any possible single diastereoisomer. Within the detailed experimental section the diketone tautomer is chosen for naming purposes, even if the predominant tautomer is the enol form.

Preparation Examples

Example 1

Preparation of 2-(2,6-Dimethyl-4-prop-1-ynylphenyl)cyclopentane-1,3-dione (Compound A-1)

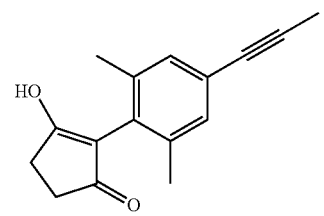 [SMILES: CC#Cc1cc(C)c(C2=C(O)CCC2=O)c(C)c1]

Step 1: Preparation of 2-(4-Bromo-2,6-dimethylphenyl)cyclopentane-1,3-dione

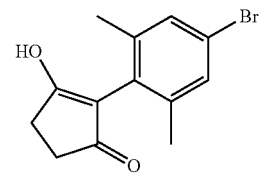

To a solution of 2-(4-bromo-2,6-dimethylphenyl)cyclopent-4-ene-1,3-dione (described in WO 2010/089210) (50 g, 0.18 mol) in acetic acid (2000 ml) at 25-30°C. is added zinc powder (82.3 g, 1.26 mol). The resulting suspension is heated to 90°C. for 2 hours, followed by cooling to room temperature then filtration through a bed of diatomaceous earth. The residue is washed with methanol (100 ml×2) and the solution is concentrated in vacuo. Distilled water is added and the crude product is extracted with ethyl acetate (500 ml×3). Organic fractions are combined then washed with distilled water, brine, then dried over sodium sulfate, filtered and the filtrate concentrated in vacuo to afford 2-(4-bromo-2,6-dimethylphenyl)cyclopentane-1,3-dione. This material is used directly in the next step without further purification.

Step 2: Preparation of 2-(4-Bromo-2,6-dimethylphenyl)-3-methoxycyclopent-2-enone

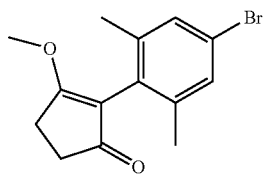 [SMILES: COC1=C(c2c(C)cc(Br)cc2C)C(=O)CC1]

To a solution of 2-(4-bromo-2,6-dimethylphenyl)cyclopentane-1,3-dione (40 g, 0.143 mol) in acetone (2000 ml) is added anhydrous potassium carbonate (98.5 g, 0.714 mol) and iodomethane (45 ml, 0.72 mol). The resulting mixture is stirred at 25-30°C. for 16 hours, then volatile solvents are removed in vacuo, and the residue is diluted with distilled water (200 ml) and extracted with ethyl acetate (3×500 ml). Organic fractions are combined, washed with distilled water, brine, then dried over sodium sulphate, filtered and the filtrate concentrated in vacuo. The crude product is purified by flash column chromatography to afford 2-(4-bromo-2,6-dimethylphenyl)-3-methoxycyclopent-2-enone.

Step 3: Preparation of 2-(2,6-Dimethyl-4-prop-1-ynylphenyl)-3-methoxycyclopent-2-enone

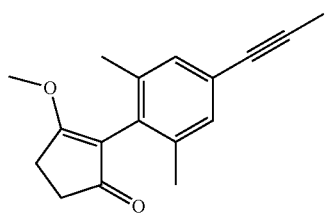 [SMILES: CC#Cc1cc(C)c(C2=C(OC)CCC2=O)c(C)c1]

To a solution of anhydrous zinc bromide (1.41 g, 6.3 mmol) in anhydrous tetrahydrofuran (8.0 ml) under nitrogen at 0°C., is added propynylmagnesium bromide (15.7 ml, 6.3 mmol, 0.4 M solution in tetrahydrofuran) dropwise. The reaction mixture is then allowed to warm to room temperature and stir for 10 minutes, then cooled again to 0°C. To this mixture is then added [1,1'-bis(diphenylphosphino)ferrocene]dichloropalladium(II) (0.102 g, 0.13 mmol), followed by a solution of 2-(4-bromo-2,6-dimethylphenyl)-3-methoxycyclopent-2-enone (0.370 g, 1.25 mmol) in anhydrous tetrahydrofuran (4.0 ml). The reaction mixture is heated at reflux for 4.5 hours, then allowed to cool to room temperature followed by quenching with saturated aqueous ammonium chloride (10 ml). Ethyl acetate is added, and the mixture is filtered through a bed of diatomaceous earth and the phases separated. The aqueous phase is extracted again with ethyl acetate (×3) and combined organics are washed with brine, dried over magnesium sulfate, filtered and the filtrate concentrated in vacuo. The residue is purified by flash column chromatography (ethyl acetate and isohexane as eluant) to afford 2-(2,6-dimethyl-4-prop-1-ynylphenyl)-3-methoxycyclopent-2-enone.

Step 4: Preparation of 2-(2,6-Dimethyl-4-prop-1-ynylphenyl)cyclopentane-1,3-dione

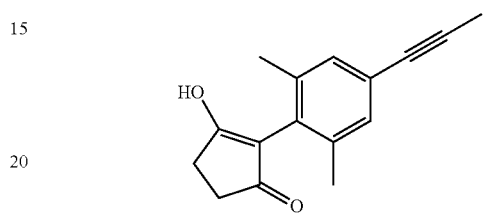

To a solution of 2-(2,6-dimethyl-4-prop-1-ynylphenyl)-3-methoxycyclopent-2-enone (0.193 g, 0.76 mmol) in acetone (2.0 ml) is added 2M hydrochloric acid (2.0 ml). The mixture is heated at 60°C. under microwave irradiation for 20 minutes, then distilled water and ethyl acetate are added and the phases separated. The aqueous phase is extracted with ethyl acetate (×3), and combined organic fractions are washed with brine, dried over magnesium sulfate, filtered and the filtrate concentrated in vacuo. The crude product is purified by flash column chromatography (ethyl acetate and isohexane as eluant) to afford 2-(2,6-dimethyl-4-prop-1-ynylphenyl)cyclopentane-1,3-dione.

Example 2

Preparation of rac-2-(2,6-Dimethyl-4-prop-1-ynylphenyl)-4-(pyridin-2-ylmethyl)cyclopentane-1,3-dione

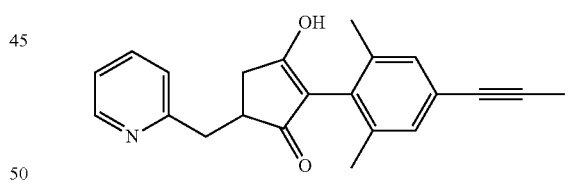

Step 1: Preparation of 2-(4-Bromo-2,6-dimethylphenyl)-5-(hydroxypyridin-2-ylmethyl)-3-methoxycyclopent-2-enone

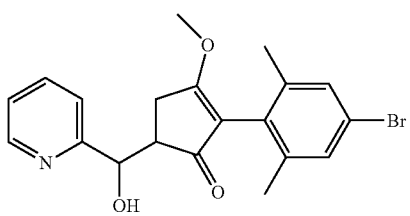 [SMILES: COC1=C(c2c(C)cc(Br)cc2C)C(=O)C(C(O)c2ccccn2)C1]

To a solution of 2-(4-bromo-2,6-dimethylphenyl)-3-methoxycyclopent-2-enone (5 g, 17 mmol) in anhydrous tetrahydrofuran (50 ml) under nitrogen atmosphere is added lithium bis(trimethylsilyl)amide (22.4 ml, 20 mmol, 0.9M solution in tetrahydrofuran) dropwise at −75°C. The resulting solution is stirred at this temperature for 40 minutes, then a second solution of pyridine-2-carboxaldehyde (2.18 g, 20 mmol) in anhydrous tetrahydrofuran (50 ml) is added over 20 minutes. The resulting solution is stirred at −75°C. for 2 hours, then allowed to warm to room temperature and stir for a further 2 hours. The reaction mixture is quenched with ice cold water (30 ml), extracted with ethyl acetate (3×100 ml), then dried over sodium sulfate, filtered and the filtrate is concentrated in vacuo to afford 2-(4-bromo-2,6-dimethylphenyl)-5-(hydroxypyridin-2-ylmethyl)-3-methoxycyclopent-2-enone. This material is used directly in the next step without further purification.

Step 2: Preparation of 2-(4-Bromo-2,6-dimethylphenyl)-3-methoxy-5-[1-pyridin-2-ylmethylidene]cyclopent-2-enone

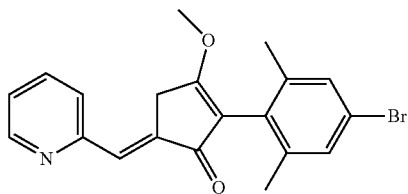 [SMILES: COC1=C(c2c(C)cc(Br)cc2C)C(=O)/C(=C/c2ccccn2)C1]

To a solution of 2-(4-bromo-2,6-dimethylphenyl)-5-(hydroxypyridin-2-ylmethyl)-3-methoxycyclopent-2-enone (7.2 g, 17.9 mmol) in dichloromethane (200 ml) at 0°C. is added triethylamine (7.0 ml, 53.8 mmol) dropwise, then methanesulfonyl chloride (6 ml, 53.8 mmol). The reaction mixture is allowed to warm to room temperature, then is stirred overnight and quenched with ice cold water. The organic phase is separated and the aqueous phase is extracted with ethyl acetate (100 ml×3). The combined organic fractions are concentrated in vacuo and the residue is re-dissolved in methanol (250 ml) and stirred for 10 minutes. To this suspension is then added potassium carbonate (8.1 g, 58.7 mmol), and the reaction mixture is stirred for 4-5 hours at 25-30°C. Volatile solvents are removed under vacuum and the crude product is diluted with distilled water and extracted with ethyl acetate (150 ml×3). The combined organic fractions are washed with distilled water, brine, then dried over sodium sulfate, filtered and the filtrate is concentrated in vacuo. The crude product is purified by flash column chromatography to afford 2-(4-bromo-2,6-dimethylphenyl)-3-methoxy-5-[1-pyridin-2-ylmethylidene]cyclopent-2-enone.

Step 3: Preparation of rac-2-(4-Bromo-2,6-dimethylphenyl)-3-methoxy-5-pyridin-2-ylmethylcyclopent-2-enone

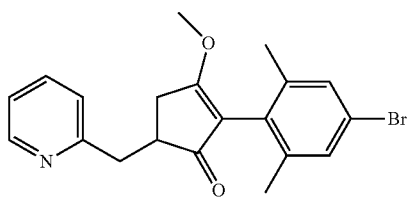 [SMILES: COC1=C(c2c(C)cc(Br)cc2C)C(=O)C(Cc2ccccn2)C1]

To a solution of 2-(4-bromo-2,6-dimethylphenyl)-3-methoxy-5-[1-pyridin-2-ylmethylidene]cyclopent-2-enone (2.8 g, 7.3 mmol) in acetic acid (30 ml) is added zinc powder (2.3 g, 36.5 mmol) at 25-30°C. The resulting suspension is stirred at 25-30°C. for 6-7 hours, then filtered through a bed of diatomaceous earth and washed with methanol (20 ml×2). The filtrate is concentrated under vacuum, water is added and the crude product is extracted with ethyl acetate (50 ml×3). The combined organic fractions are washed with distilled water, brine, dried over sodium sulfate, filtered and the filtrate concentrated in vacuo. The crude is purified by flash column chromatography to afford rac-2-(4-bromo-2,6-dimethylphenyl)-3-methoxy-5-pyridin-2-ylmethylcyclopent-2-enone.

Step 4: Preparation of rac-2-(2,6-Dimethyl-4-prop-1-ynylphenyl)-3-methoxy-5-pyridin-2-ylmethylcyclopent-2-enone

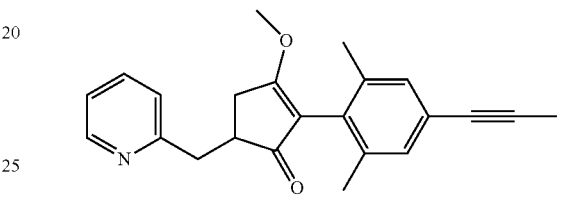

To a degassed solution of rac-2-(4-bromo-2,6-dimethylphenyl)-3-methoxy-5-pyridin-2-ylmethylcyclopent-2-enone (1.0 g, 2.5 mmol) in toluene (10 ml) is added tributyl (1-propynyl)tin (1.55 ml, 5.18 mmol) and tetrakistriphenylphosphine palladium(0) (0.5 g, 0.5 mmol) under a nitrogen atmosphere. The reaction mixture is heated at 130°C. for 40 minutes under microwave irradiation, then diluted with distilled water (20 ml) and extracted with ethyl acetate (50 ml×2). The combined organic fractions are washed with distilled water, brine, dried over sodium sulfate, filtered and the filtrate concentrated in vacuo to afford rac-2-(2,6-dimethyl-4-prop-1-ynylphenyl)-3-methoxy-5-pyridin-2-ylmethylcyclopent-2-enone. This material is used directly in the next step without further purification.

Step 5: Preparation of rac-2-(2,6-Dimethyl-4-prop-1-ynylphenyl)-4-pyridin-2-ylmethylcyclopentane-1,3-dione

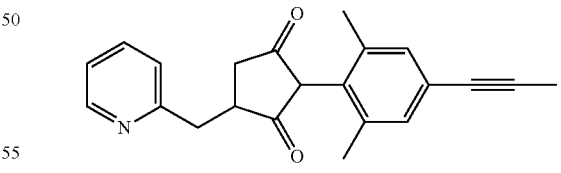

A solution of rac-2-(2,6-dimethyl-4-prop-1-ynylphenyl)-3-methoxy-5-pyridin-2-ylmethylcyclopent-2-enone (0.5 g, 1.45 mmol) in acetone (10 ml) and 2N hydrochloric acid (5 ml) is heated at 80°C. under microwave irradiation for 40 minutes. Volatile solvents are removed in vacuo and residue is diluted with distilled water (50 ml) and extracted with ethyl acetate (3×50 ml). The combined organic fractions are washed again with distilled water, brine, dried over sodium sulfate, filtered and the filtrate concentrated in vacuo. The crude product is purified by flash column chromatography to afford rac-2-(2,6-Dimethyl-4-prop-1-ynylphenyl)-4-pyridin-2-ylmethylcyclopentane-1,3-dione.

Example 3

Preparation of rac-2-(4-Chloroethynyl-2,6-dimethylphenyl)-4-(pyridin-2-ylmethyl)cyclopentane-1,3-dione

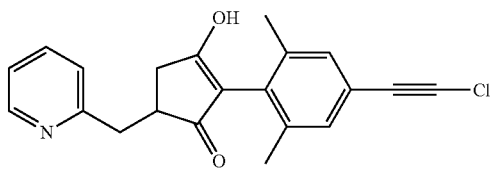

Step 1: Preparation of rac-2-(4-Ethynyl-2,6-dimethylphenyl)-3-methoxy-5-pyridin-2-ylmethylcyclopent-2-enone

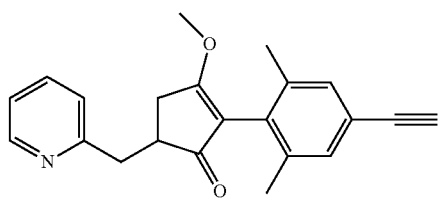 [SMILES: C#Cc1cc(C)c(C2=C(OC)CC(Cc3ccccn3)C2=O)c(C)c1]

To a mixture of rac-2-(4-bromo-2,6-dimethylphenyl)-3-methoxy-5-pyridin-2-ylmethylcyclopent-2-enone (0.50 g, 1.29 mmol), cesium fluoride (0.39 g, 2.59 mmol) and copper (I) iodide (0.025 g, 0.129 mmol) in N,N-dimethylformamide (5.0 ml) is added [1,1'-bis(diphenylphosphino)ferrocene]dichloropalladium(II) (0.053 g, 0.065 mmol) and ethynyltributylstannane (1.22 g, 3.88 mmol). The reaction mixture is heated at 110°C. under microwave irradiation for 60 mins, then allowed to cool to room temperature and is quenched with distilled water (20 ml) and extracted with ethyl acetate. The combined organic fractions are dried over magnesium sulfate, filtered and the filtrate evaporated in vacuo. The crude product is purified by flash column chromatography (0-8% methanol in dichloromethane as eluant) to afford rac-2-(4-ethynyl-2,6-dimethylphenyl)-3-methoxy-5-pyridin-2-ylmethylcyclopent-2-enone.

Step 2: Preparation of rac-2-(4-Chloroethynyl-2,6-dimethylphenyl)-3-methoxy-5-pyridin-2-ylmethylcyclopent-2-enone

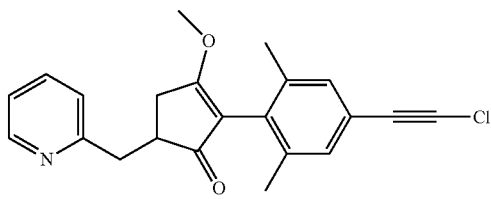 [SMILES: COC1=C(c2c(C)cc(C#CCl)cc2C)C(=O)C(Cc2ccccn2)C1]

To a mixture of rac-2-(4-ethynyl-2,6-dimethylphenyl)-3-methoxy-5-pyridin-2-ylmethylcyclopent-2-enone (0.20 g, 0.60 mmol) and silver (I) acetate (0.01 g, 0.06 mmol) in acetone (2.0 ml) is added N-chlorosuccimide (0.10 g, 0.72 mmol) and the solution is heated at reflux overnight. The reaction mixture is filtered, the filtrate evaporated in vacuo, and the residue purified by flash column chromatography (0-8% methanol in dichloromethane as eluant) to afford rac-2-(4-chloroethynyl-2,6-dimethylphenyl)-3-methoxy-5-pyridin-2-ylmethylcyclopent-2-enone.

Step 3: Preparation of rac-2-(4-Chloroethynyl-2,6-dimethylphenyl)-4-pyridin-2-ylmethylcyclopentane-1,3-dione

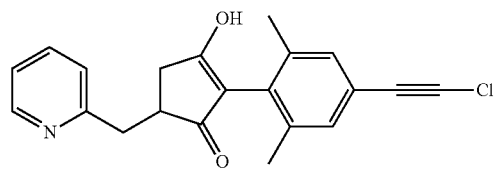 [SMILES: Cc1cc(C#CCl)cc(C)c1C1=C(O)CC(Cc2ccccn2)C1=O]

Aqueous 2M hydrochloric acid (1.20 ml) is added to a solution of rac-2-(4-chloroethynyl-2,6-dimethylphenyl)-3-methoxy-5-pyridin-2-ylmethylcyclopent-2-enone (0.120 g, 0.33 mmol) in acetone (1.20 ml), and the reaction mixture is heated at 60°C. for 2 hours. The solution is then concentrated in vacuo, and the crude product is purified by preparative reverse phase HPLC to afford rac-2-(4-chloroethynyl-2,6-dimethylphenyl)-4-pyridin-2-ylmethylcyclopentane-1,3-dione.

Example 4

Preparation of 2-(2,6-Dimethyl-4-prop-1-ynylphenyl)-4-(tetrahydropyran-4-ylmethyl)cyclopentane-1,3-dione

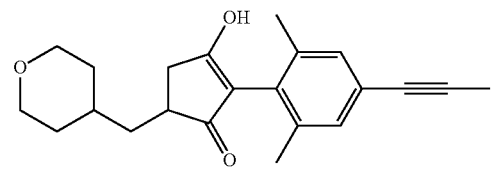

Step 1: Preparation of 2-(4-Bromo-2,6-dimethylphenyl)-5-[hydroxy(tetrahydropyran-4-yl)methyl]-3-methoxycyclopent-2-enone

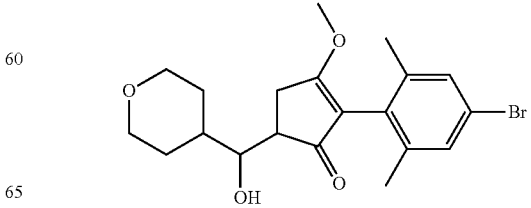

To a solution of 2-(4-bromo-2,6-dimethylphenyl)-3-methoxycyclopent-2-enone (7.5 g, 26.0 mmol) in anhydrous tetrahydrofuran (70 ml) under a nitrogen atmosphere is added lithium bis(trimethylsilyl)amide (44.6 ml, 31.0 mmol, 0.7M in tetrahydrofuran) dropwise at −75°C. After stirring for 40 minutes at this temperature a second solution of tetrahydropyranyl-4-carboxaldehyde (5.90 g, 52.0 mmol) in tetrahydrofuran (70 ml) is added over 20 minutes, and the resulting solution is stirred at −75°C. for 2 hours. After warming to room temperature the mixture is stirred for a further 2 hours, then is quenched with ice cold water (100 ml) and extracted with ethyl acetate (3×150 ml). Organics are combined, dried over sodium sulphate, filtered and the filtrate is concentrated in vacuo to afford 2-(4-bromo-2,6-dimethylphenyl)-5-[hydroxy(tetrahydropyran-4-yl)methyl]-3-methoxycyclopent-2-enone. This material is used directly in the next step without further purification.

Step 2: Preparation of 2-(4-Bromo-2,6-dimethylphenyl)-4-[1-(tetrahydropyran-4-yl)methylidene]cyclopentane-1,3-dione

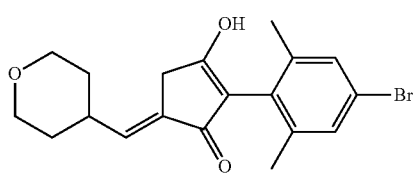 [SMILES: Cc1cc(Br)cc(C)c1C1=C(O)C/C(=C\C2CCOCC2)C1=O]

A solution of 2-(4-bromo-2,6-dimethylphenyl)-5-[hydroxy(tetrahydropyran-4-yl)methyl]-3-methoxycyclopent-2-enone (16.0 g, 39.0 mmol) in a mixture of acetone (320 ml) and 2N hydrochloric acid (160 ml) is heated at 13°C. under microwave irradiation for 40 minutes. Volatile solvents are removed in vacuo, followed by the addition of distilled water (250 ml) and extraction with ethyl acetate (3×150 ml). The combined organic extracts are washed with water, brine, dried over sodium sulphate, then filtered and the filtrate concentrated in vacuo. The residue is finally purified by flash column chromatography to afford 2-(4-bromo-2,6-dimethylphenyl)-4-[1-(tetrahydropyran-4-yl)methylidene]cyclopentane-1,3-dione.

Step 3: Preparation of rac-2-(4-Bromo-2,6-dimethylphenyl)-4-(tetrahydropyran-4-ylmethyl)cyclopentane-1,3-dione

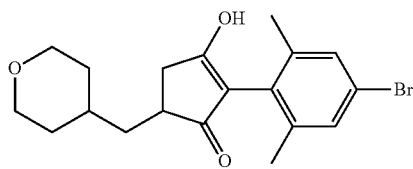 [SMILES: Cc1cc(Br)cc(C)c1C1=C(O)CC(CC2CCOCC2)C1=O]

A solution of 2-(4-bromo-2,6-dimethylphenyl)-4-[1-(tetrahydropyran-4-yl)methylidene]cyclopentane-1,3-dione (0.10 g, 0.26 mmol) in methanol (100 ml) is passed over a cartridge of 10% platinum carbon under a 20 bar hydrogen atmosphere. The reaction mixture is then concentrated in vacuo, and the crude product is purified by flash column chromatography (hexane/ethyl acetate as eluant) to afford rac-2-(4-bromo-2,6-dimethylphenyl)-4-(tetrahydropyran-4-ylmethyl)cyclopentane-1,3-dione.

Step 4: Preparation of rac-2,2-Dimethylpropionic acid 2-(4-bromo-2,6-dimethylphenyl)-3-oxo-4-(tetrahydropyran-4-ylmethyl)cyclopent-1-enyl ester

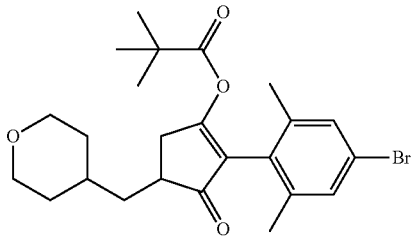 [SMILES: Cc1cc(Br)cc(C)c1C1=C(OC(=O)C(C)(C)C)CC(CC2CCOCC2)C1=O]

To a solution of rac-2-(4-bromo-2,6-dimethylphenyl)-4-(tetrahydropyran-4-ylmethyl)cyclopentane-1,3-dione (1.0 g, 2.6 mmol) in dichloromethane (20 ml) is added triethylamine (1.09 ml, 7.8 mmol) then pivaloyl chloride (1.10 ml, 7.8 mmol), and the resulting solution is stirred at room temperature for 4 hours. The reaction mixture is diluted with dichloromethane (100 ml), washed with distilled water (50 ml×3), and the organic fractions are combined, dried over sodium sulphate, filtered and the filtrate concentrated in vacuo to afford rac-2,2-dimethylpropionic acid 2-(4-bromo-2,6-dimethylphenyl)-3-oxo-4-(tetrahydropyran-4-ylmethyl)cyclopent-1-enyl ester. This material is used directly in the next step without further purification.

Step 5: Preparation of rac-2-(2,6-Dimethyl-4-prop-1-ynylphenyl)-4-(tetrahydropyran-4-ylmethyl)cyclopentane-1,3-dione

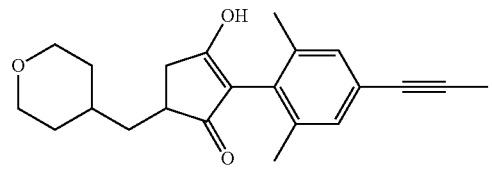 [SMILES: CC#Cc1cc(C)c(C2=C(O)CC(CC3CCOCC3)C2=O)c(C)c1]

To a degassed solution of rac-2,2-dimethylpropionic acid 2-(4-bromo-2,6-dimethylphenyl)-3-oxo-4-(tetrahydropyran-4-ylmethyl)cyclopent-1-enyl ester (0.20 g, 0.43 mmol) in toluene (4 ml) under a nitrogen atmosphere is added tributyl (1-propynyl)tin (0.39 ml, 1.29 mmol) and tetrakistriphenylphosphine palladium(0) (0.10 g, 0.086 mmol). The reaction mixture is then heated at 130°C. under microwave irradiation for 45 minutes, followed by quenching with distilled water (20 ml) and extraction with ethyl acetate (50 ml×2). The combined organic fractions are washed with water, brine, dried over sodium sulphate, filtered and the filtrate is concentrated in vacuo. The residue is then dissolved in methanol (1.0 ml) and 2N sodium hydroxide solution (0.5 ml) is added followed by stirring at 25°C. for 3 hours. The solvent is evaporated in vacuo and the crude product is diluted with distilled water, acidified with 2N hydrochloric acid then extracted with ethyl acetate (50 ml×3). The combined organic fractions are washed with water, brine, dried over sodium sulphate, filtered and the filtrate is concentrated in vacuo to afford rac-2-(2,6-dimethyl-4-prop-1-ynylphenyl)-4-(tetrahydropyran-4-ylmethyl)cyclopentane-1,3-dione.

Example 5

Preparation of (1RS,2SR,6RS,7SR)-4-(2,6-dimethyl-4-prop-1-ynylphenyl)-10-oxatricyclo[5.2.1.0²,⁶]decane-3,5-dione

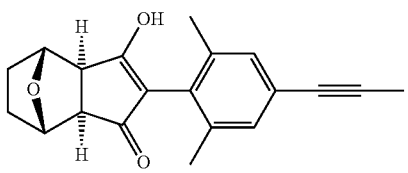

Step 1: Preparation of (1RS,2SR,6RS, 7SR)-4-(4-Bromo-2,6-dimethylphenyl)-5-methoxy-10-oxa-tricyclo[5.2.1.0²,⁶]dec-4-en-3-one

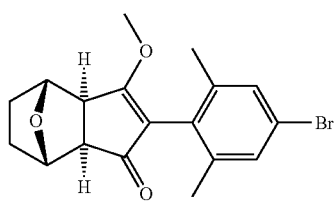

To a suspension of 4-(4-Bromo-2,6-dimethylphenyl)-10-oxatricyclo[5.2.1.0*2,6*]decane-3,5-dione (1.0 g, 2.86 mmol) (reported in WO 2009019005) in acetone (50 ml) is added potassium carbonate (0.59 g, 4.3 mmol) followed by iodomethane (2.0 g, 0.89 ml, 14 mmol). The mixture is stirred at room temperature for 18 hours then acetone is removed in vacuo and the residue is partitioned between water and ethyl acetate. The crude product is extracted with ethyl acetate and the combined organic fractions are washed with distilled water then brine, dried over magnesium sulfate, filtered and concentrated in vacuo to afford (1RS,2SR,6RS,7SR)-4-(4-bromo-2,6-dimethylphenyl)-5-methoxy-10-oxa-tricyclo[5.2.1.0²,⁶]dec-4-en-3-one.

Step 2: Preparation of (1RS,2SR,6RS,7SR)-4-(2,6-Dimethyl-4-prop-1-ynylphenyl)-10-oxatricyclo[5.2.1.0²,⁶]decane-3,5-dione

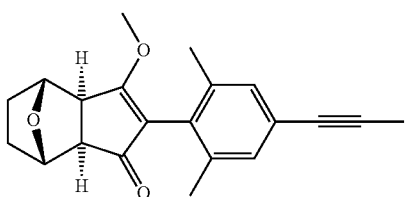

To (1RS,2SR,6RS,7SR)-4-(4-bromo-2,6-dimethylphenyl)-5-methoxy-10-oxa-tricyclo[5.2.1.0²,⁶]dec-4-en-3-one (0.40 g, 1.10 mmol), cesium fluoride (0.34 g, 2.20 mmol), cuprous iodide (0.04 g, 0.22 mmol) and [1,1'-bis(diphenylphosphino)ferrocene]dichloropalladium(II) (0.12 g, 0.17 mmol) under nitrogen atmosphere is added anhydrous dimethylformamide (3.8 g, 4 ml, 51 mmol) followed by tributyl (prop-1-ynyl)stannane (1.10 g, 1.0 ml, 3.3 mmol). The mixture is heated at 120°C. under microwave irradiation for 60 minutes then diluted with water (50 ml) and ethyl acetate (50 ml) and filtered through a bed of diatomaceous earth. The residue is washed with ethyl acetate and the crude product is extracted with ethyl acetate (50 ml×2). The combined organic fractions are washed with distilled water then brine, dried over magnesium sulfate, filtered and concentrated in vacuo. The crude product is purified by flash column chromatography to afford (1RS,2SR,6RS,7SR)-4-(2,6-dimethyl-4-prop-1-ynylphenyl)-10-oxatricyclo[5.2.1.0²,⁶]decane-3,5-dione.

Step 4: Preparation of (1RS,2SR,6RS,7SR)-4-(2,6-dimethyl-4-prop-1-ynylphenyl)-10-oxatricyclo [5.2.1.0²,⁶]decane-3,5-dione

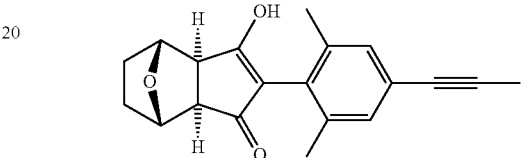

(1RS,2SR,6RS,7SR)-4-(2,6-dimethyl-4-prop-1-ynylphenyl)-10-oxatricyclo[5.2.1.0²,⁶]decane-3,5-dione (0.17 g, 0.52 mmol) is dissolved in morpholine (2.0 g, 2.0 ml, 23 mmol) and heated to 100°C. with stirring for 2.25 hours. The mixture is allowed to cool to room temperature and concentrated in vacuo. The residue is dissolved in ethyl acetate (15 ml) and washed with 2M hydrochloric acid (15 ml×3) followed by brine (15 ml) then dried over magnesium sulfate, filtered and concentrated in vacuo. The crude product is purified by flash column chromatography to afford (1RS,2SR, 6RS,7SR)-4-(2,6-dimethyl-4-prop-1-ynylphenyl)-10-oxatricyclo[5.2.1.0²,⁶]decane-3,5-dione.

Example 5A

Chiral HPLC Separation of Compound A-2 and/or Example 2 into Enantiomer Compounds A-6 and A-5

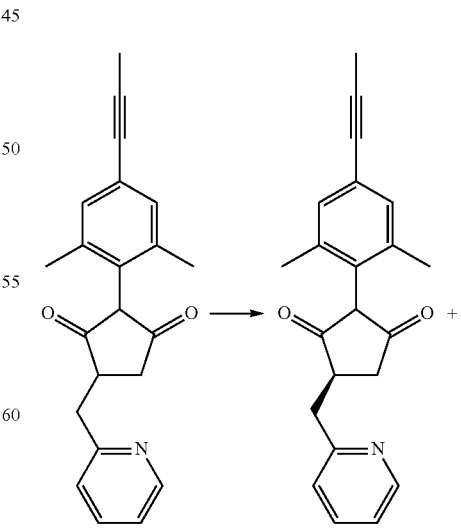

Compound A-2 and/or Example 2          Compound A-6

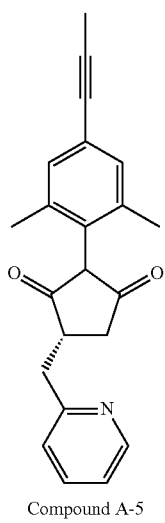

Compound A-5

Compound A-2, and/or Example 2 (racemic), was separated into the enantiomer compounds A-6 and A-5 using a chiral HPLC column, by the following method and under the following conditions.

The chiral HPLC column used was a (s,s) WhelkO1-5 micron −21 mm×250 mm HPLC column, manufactured by Regis Technologies, Inc. In this column, the chiral stationary phase is (S,S) 1-(3-5-dinitrobenzamido)-1,2,3,4-tetrahydrophenanthrene.

The solvent system used as an eluent for the column was a 50:50 (by volume) mixture of Solvent A and Solvent B, in which:

Solvent A is isohexane containing 0.1% v/v of glacial acetic acid, and

Solvent B is a mixture of isopropanol (90% v/v) and acetonitrile (10% v/v) containing 0.1% v/v of glacial acetic acid.

Other conditions were as follows:

Flow rate through column: 21 ml/minute. Run time: 20 minutes.

Loading (compound loaded onto column): 25 mg/ml of compound in 50:50 isopropanol/isohexane.

Volume of sample (compound) injected per run=1000 microliters.

Number of injections of compound=17.

Amount of racemic compound A-2 used: 420 mg

Chiral HPLC on a total of 420 mg of compound A-2 under the above conditions gave 163 mg of compound A-6 (100% enantiomeric excess (e.e.), retention time 13.98 minutes under the above conditions) and 158 mg of compound A-5 (98.6% enantiomeric excess (e.e.), retention time 16.03 minutes under the above conditions).

Abbreviation: HPLC=high performance (or high pressure) liquid chromatography.

Note 1: The absolute structure and enantiomeric configuration of Compound A-6 has been confirmed to be that shown herein (e.g. that shown hereinabove), because a crystal of Compound A-6 has been obtained which has been analysed to confirm this structure and enantiomeric configuration, e.g. by an X-ray crystal structure analysis.

Note 2: The above procedure using chiral HPLC can be used to separate the enantiomers of other compounds of the invention. Chiral columns which might be useful to achieve this are as follows:

(s,s) WhelkO1-5 micron −21 mm×250 mm HPLC column, manufactured by Regis Technologies, Inc [in this column, the chiral stationary phase is (S,S) 1-(3-5-dinitrobenzamido)-1,2,3,4-tetrahydrophenanthrene];

Kromasil® AmyCoat™[whose chiral stationary phase is tris-(3,5-dimethylphenyl)carbamoyl amylose];

Kromasil® CelluCoat™[whose chiral stationary phase is tris-(3,5-dimethylphenyl)carbamoyl cellulose];

Chiralpak® IA [whose chiral stationary phase is a (3,5-dimethylphenyl)carbamate derivative of amylose];

Chiralpak® IB [whose chiral stationary phase is tris-(3,5-dimethylphenyl)carbamate derivative of cellulose];

Chiralpak® IC [whose chiral stationary phase is cellulose tris(3,5-dichlorophenyl)carbamate];

Lux® Amylose-2 [whose chiral stationary phase is amylose tris(5-chloro-2-methylphenylcarbamate)]; or Lux® Cellulose-2 [whose chiral stationary phase is Cellulose tris(3-chloro-4-methylphenylcarbamate)].

Example 6

Example of a preparation of compound of formula (I) in which G=Methyl by a decarboxylative coupling reaction of the corresponding 2-(4-bromo-2,6-dimethyl-phenyl)-3-methoxy-cyclopent-2-en-1-one derivative with but-2-ynoic acid: Synthesis of 2-(2,6-dimethyl-4-prop-1-ynyl-phenyl)-3-methoxy-5-(2-pyridylmethyl)-cyclopent-2-en-1-one

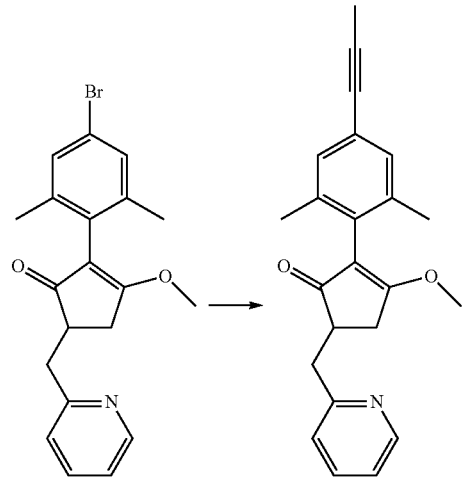

To a flask charged with 2-(4-bromo-2,6-dimethyl-phenyl)-3-methoxy-5-(2-pyridylmethyl)cyclopent-2-en-1-one (328 mg, 0.8491 mmol) was added but-2-ynoic acid (0.9340 mmol), bis(triphenylphosphine) palladium(II) dichloride (0.04245 mmol, 0.03010 g) and 1,4-bis-(diphenylphosphino)butane (0.08491 mmol, 0.03621 g), and the vessel purged with $N_2$. DMSO (3 ml) was added, followed by tetrabutylammonium fluoride (1 mol/L) in tetrahydrofuran (1.698 mL, 1.698 mmol), and the reaction heated to 110°C. under N2 for 40 minutes. The reaction was diluted with EtOAc (25 ml), washed with saturated aqueous ammonium chloride (25 ml) and brine (2×25 ml) and the organic layer removed and allowed to stand overnight. The organic layer was dry loaded onto silica and purified by flash chromatography on $SiO_2$ using a 50-100% gradient of EtOAc in hexane to give the desired compound as a colourless oil (193 mg, 66%). $^1$H NMR (400 MHz, CDCl$_3$) δ ppm 8.49-8.56 (m, 1H), 7.60 (td, 1H), 7.24 (d, 1H), 7.11-7.18 (m, 1H), 7.07 (d, 2H), 3.70 (s, 3H), 3.40 (dd, 1H), 3.07-3.18 (m, 1H), 2.96-3.05 (m, 1H), 2.84-2.90 (m, 2H), 2.09 (s, 3H), 2.02 (s, 3H), 1.91 (s, 3H).

Intermediate 1: Synthesis of 6-[[3-(4-bromo-2,6-dimethyl-phenyl)-4-methoxy-2-oxo-cyclopent-3-en-1-yl]methyl]-2-methylsulfanyl-pyridine-3-carbonitrile

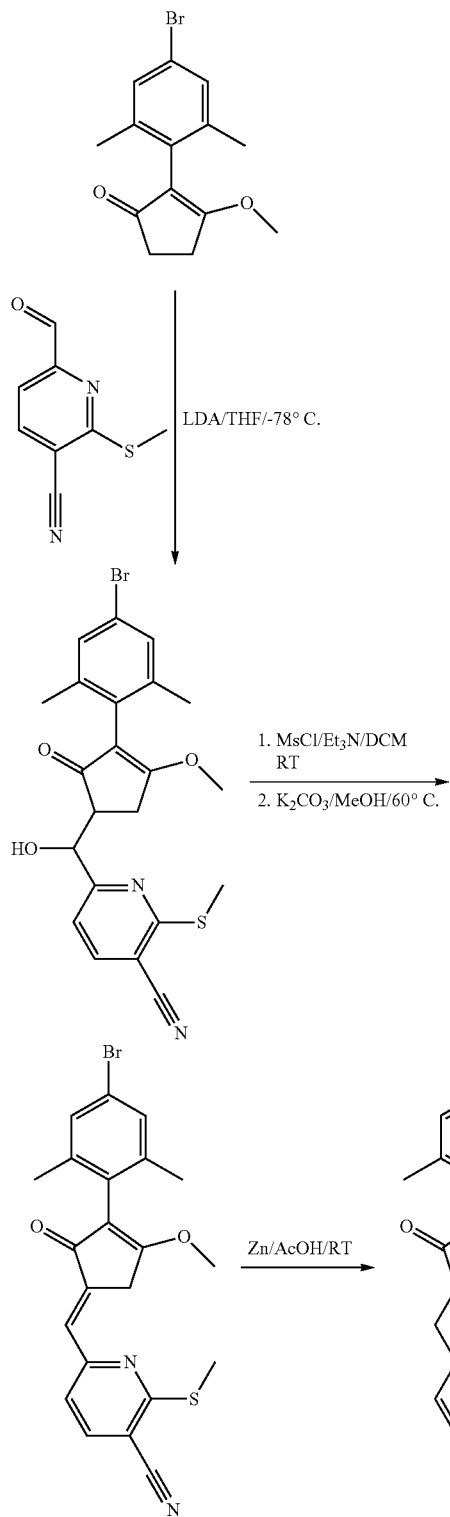

Abbreviations:
RT=room temperature.
LDA=lithium diisopropylamide.
THF=tetrahydrofuran.
DCM=dichloromethane.

Intermediate 2: Synthesis of 6-[[3-(4-bromo-2,6-dimethyl-phenyl)-4-methoxy-2-oxo-cyclopent-3-en-1-yl]methyl]-2-methylsulfonyl-pyridine-3-carbonitrile

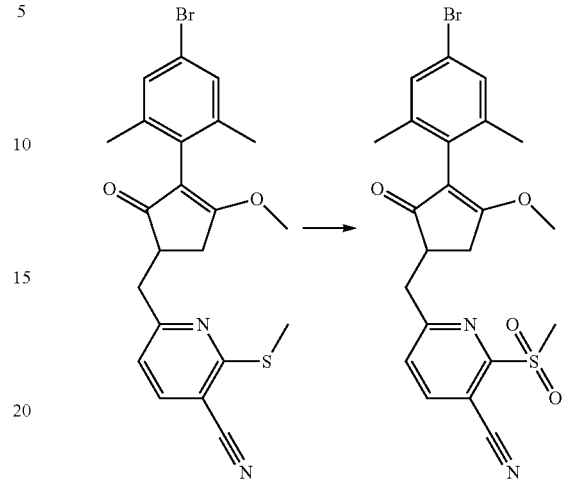

To a solution of 6-[[3-(4-bromo-2,6-dimethyl-phenyl)-4-methoxy-2-oxo-cyclopent-3-en-1-yl]methyl]-2-methylsulfanyl-pyridine-3-carbonitrile (3.87 mmol, 1.77 g) in $CH_2Cl_2$ (15 ml) at 0°C. was added urea hydrogen peroxide (9.67 mmol, 0.938 g) followed by slow addition of a solution of trifluoroacetic anhydride (9.67 mmol, 2.03 g, 1.34 mL) in $CH_2Cl_2$ (3 ml). The reaction was stirred at 0°C. for 3.5 hours and then further urea hydrogen peroxide (0.3 g) and trifluoroacetic anhydride (0.4 ml in 2 ml of $CH_2Cl_2$) were added. The reaction was stirred at 0°C. for a further 30 minutes and then quenched with 10% aqueous sodium metabisulphite (20 mL) and extracted into $CH_2Cl_2$ (3×20 mL). The combined organic extracts were dried over $MgSO_4$, filtered and concentrated under reduced pressure to give an orange gum. The crude product was purified by column chromatography on $SiO_2$ using a hexane: EtOAc gradient to yield the desired compound (1.00 g, 53%) as a yellow foam. $^1H$ NMR (400 MHz, $CDCl_3$) (diagnostic peaks) δ ppm 8.19 (d, 1H), 7.58 (1H, d), 7.22 (s, 2H), 3.52 (s, 3H), 3.39 (s, 3H), 2.10 (s, 3H), 2.05 (s, 3H).

Intermediate 3: Synthesis of 6-[[3-(4-bromo-2,6-dimethyl-phenyl)-4-methoxy-2-oxo-cyclopent-3-en-1-yl]methyl]-2-(methylamino)pyridine-3-carbonitrile

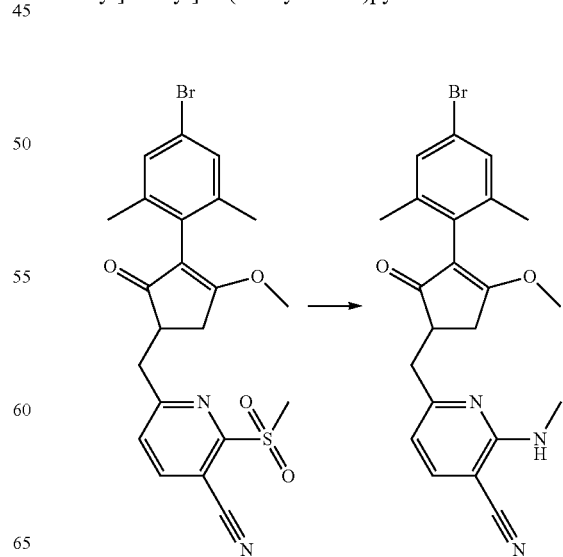

To 6-[[3-(4-bromo-2,6-dimethyl-phenyl)-4-methoxy-2-oxo-cyclopent-3-en-1-yl]methyl]-2-methylsulfonyl-pyridine-3-carbonitrile (2.043 mmol, 1 g) was added a solution of methylamine (5.1 ml of a 2M solution in tetrahydrofuran, 10.22 mmol). The reaction was stirred at room temperature for three hours and then concentrated under reduced pressure to give a brown gum. The crude product was purified by column chromatography on SiO$_2$ using a hexane: EtOAc gradient to yield the desired compound (890 mg, 99%) as an orange solid. $^1$H NMR (400 MHz, CDCl$_3$) (diagnostic peaks) δ ppm 7.55 (d, 1H), 7.18 (d, 2H), 6.45 (d, 1H), 3.55 (s, 3H), 3.05 (d, 3H), 2.15 (s, 3H), 2.00 (s, 3H).

Example 7

Synthesis of 6-[[3-(2,6-dimethyl-4-prop-1-ynyl-phenyl)-4-methoxy-2-oxo-cyclopent-3-en-1-yl]methyl]-2-(methylamino)pyridine-3-carbonitrile

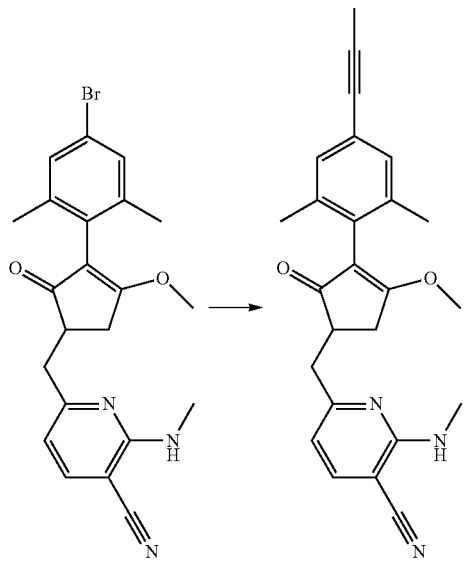

A microwave vial was charged with 6-[[3-(4-bromo-2,6-dimethyl-phenyl)-4-methoxy-2-oxo-cyclopent-3-en-1-yl]methyl]-2-(methylamino)pyridine-3-carbonitrile (150 mg, 0.34 mmol), caesium fluoride (CsF, 104 mg, 0.68 mmol), copper(I) iodide (CuI, 13 mg, 0.068 mmol), dichloro[1,1'-bis(diphenylphosphino)ferrocene]palladium(II) dichloromethane adduct (37 mg, 0.05 mmol), tributyl(prop-1-ynyl)stannane (125 mg, 0.41 mmol) and N,N-dimethylformamide (1.5 ml), sealed and heated at 120°C. under microwave irradiation for 60 minutes. Further caesium fluoride (52 mg, 0.34 mmol), copper(I) iodide (6.5 mg, 0.034 mmol), dichloro[1,1'-bis(diphenylphosphino)ferrocene]palladium(II) dichloromethane adduct (18.5 mg, 0.025 mmol) and tributyl(prop-1-ynyl)stannane (63 mg, 0.21 mmol) were added and the reaction heated at 120 C under microwave irradiation for a further 30 minutes. The reaction was allowed to cool to room temperature, diluted with water (10 ml) and diethyl ether (10 ml) and filtered through Celite. The filtrate phases were separated and the aqueous phase extracted with further diethyl ether (2×10 ml). The combined organic extracts were washed with brine (10 ml), dried over MgSO$_4$, filtered and evaporated to dryness under reduced pressure. The crude product was dissolved in EtOAc, absorbed onto silica and purified by flash chromatography on silica using an EtOAc/isohexane gradient to give the desired product (32 mg, 24%) as a yellow gum. $^1$H NMR (400 MHz, CDCl$_3$) 7.45 (d, 1H), 7.05 (2×s, 2×1H), 6.45 (d, 1H), 5.20 (br, 1H), 3.50 (s, 3H), 3.50-3.40 (m, 1H), 3.20-3.15 (m, 1H), 3.05 (d, 3H), 2.80-2.05 (m, 3H), 2.15 (s, 3H), 2.05 (s, 3H), 1.95 (s, 3H).

Example 8

Synthesis of 6-[[3-(2,6-dimethyl-4-prop-1-ynyl-phenyl)-2,4-dioxo-cyclopentyl]methyl]-2-(methylamino)pyridine-3-carbonitrile (Compound A-23)

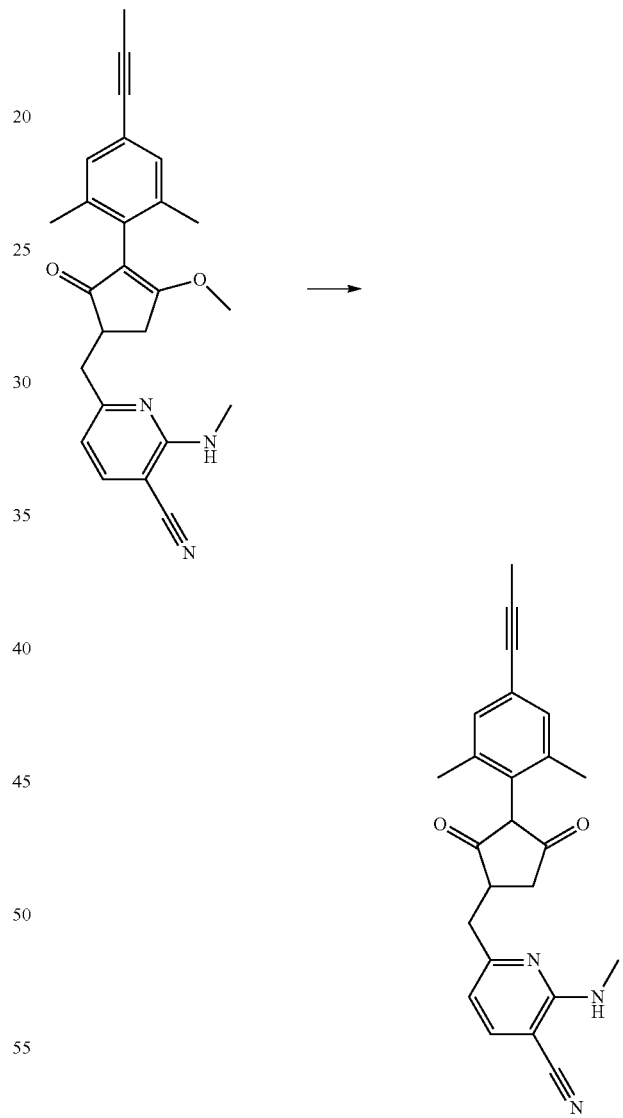

To a stirred solution of 6-[[3-(2,6-dimethyl-4-prop-1-ynyl-phenyl)-4-methoxy-2-oxo-cyclopent-3-en-1-yl]methyl]-2-(methylamino)pyridine-3-carbonitrile (34 mg, 0.085 mmol) in acetone (1 ml) was added 2M aqueous HCl (1 ml). The reaction was heated at 60°C. for 5 hours and then allowed to cool to room temperature. The reaction was concentrated under reduced pressure and then 2M aqueous K$_2$CO$_3$ solution (2 ml) added to the residue. The pH was adjusted to about 5.5 with saturated NH₄Cl solution and then extracted with dichloromethane (3×10 ml). The combined organics were dried over MgSO₄, filtered and evaporated to dryness under reduced pressure to give the desired compound (28 mg, 85%) as a brown gum. ¹H NMR (400 MHz, CDCl₃) 7.71 (d, 1H), 7.09 (s, 2H), 6.63 (d, 1H), 5.60 (br, 1H), 2.96-3.36 (m, 7H), 2.37-2.45 (m, 1H), 2.13 (s, 6H), 2.02 (s, 3H).

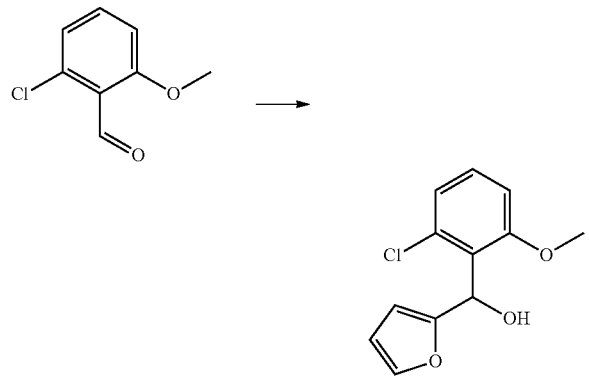

Intermediate 4: Synthesis of (2-chloro-6-methoxy-phenyl)-(2-furyl)methanol

To a solution of furan (10.7 mL, 147 mmol) in anhydrous tetrahydrofuran (100 mL) under an N₂ atmosphere at −10°C. was added n-butyl lithium (65 mL of a 2.5M solution in hexanes, 162 mmol) dropwise over 35 minutes (the internal temperature was maintained at less than −7°C.). The mixture was stirred at this temperature for 1 hour 35 minutes before adding a solution of 2-chloro-6-methoxy-benzaldehyde (27.6 g, 162 mmol) in anhydrous tetrahydrofuran (100 mL) dropwise over 1 h 30 (internal temperature approx −5°C.). On completion of addition, the reaction mixture was warmed to room temperature and stirred at this temperature for 18 hours. Water (100 mL) was added then the mixture was diluted with EtOAc (100 ml). The phases were separated and aqueous phase was extracted into EtOAc (2×100 ml). The combined organics extracts were washed with brine (50 ml), dried over MgSO₄ and concentrated to a yellow oil. The crude product was adsorbed onto silica and purified by flash chromatography over silica using an EtOAc/isohexane gradient to give the desired product (33.9 g, 97%) as a yellow solid. ¹H NMR (400 MHz, CDCl₃) δ ppm 7.37 (d, 1H), 7.25-7.21 (m, 1H), 7.05 (dd, 1H), 6.89 (d, 1H), 6.34-6.29 (m, 2H), 6.06 (dt, 1H), 4.38 (d, 1H), 3.87 (s, 3H).

Intermediate 5: Scheme for synthesis of 2-(2-chloro-6-methoxy-phenyl)-3-methoxy-cyclopent-2-en-1-one

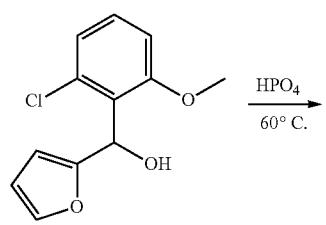

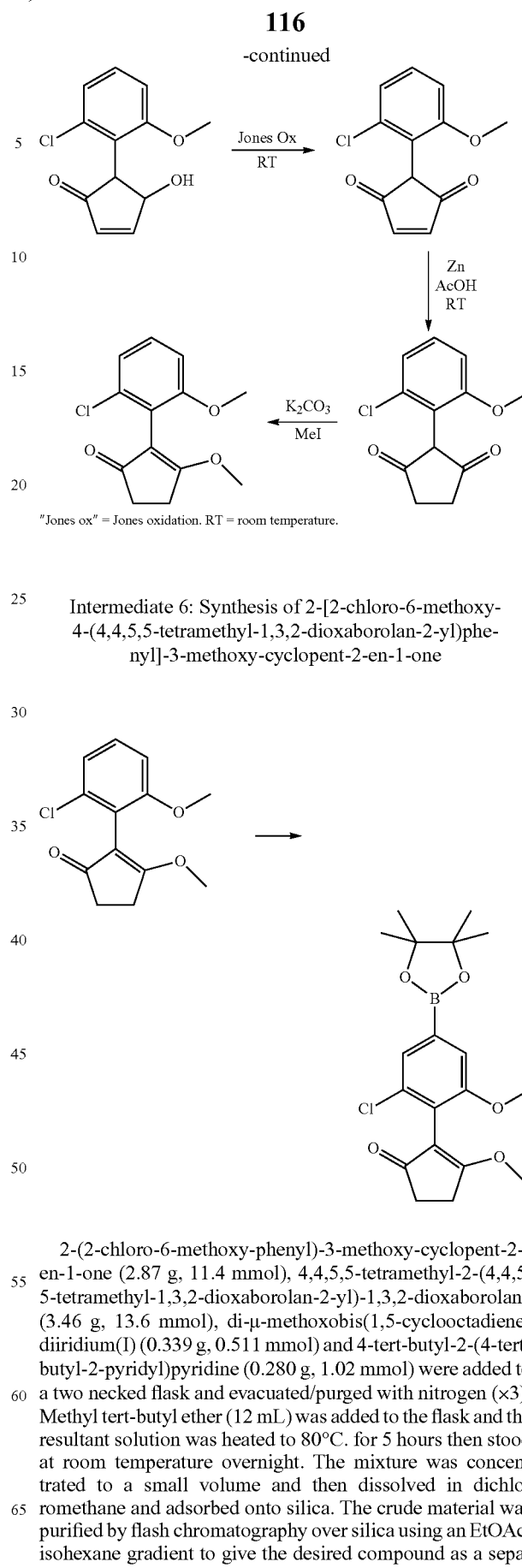

"Jones ox" = Jones oxidation. RT = room temperature.

Intermediate 6: Synthesis of 2-[2-chloro-6-methoxy-4-(4,4,5,5-tetramethyl-1,3,2-dioxaborolan-2-yl)phenyl]-3-methoxy-cyclopent-2-en-1-one 2-(2-chloro-6-methoxy-phenyl)-3-methoxy-cyclopent-2-en-1-one (2.87 g, 11.4 mmol), 4,4,5,5-tetramethyl-2-(4,4,5,5-tetramethyl-1,3,2-dioxaborolan-2-yl)-1,3,2-dioxaborolane (3.46 g, 13.6 mmol), di-µ-methoxobis(1,5-cyclooctadiene)diiridium(I) (0.339 g, 0.511 mmol) and 4-tert-butyl-2-(4-tert-butyl-2-pyridyl)pyridine (0.280 g, 1.02 mmol) were added to a two necked flask and evacuated/purged with nitrogen (×3). Methyl tert-butyl ether (12 mL) was added to the flask and the resultant solution was heated to 80°C. for 5 hours then stood at room temperature overnight. The mixture was concentrated to a small volume and then dissolved in dichloromethane and adsorbed onto silica. The crude material was purified by flash chromatography over silica using an EtOAc/isohexane gradient to give the desired compound as a separable mixture of atropisomers with identical spectral data (3.60 g, 67%). $^1$H NMR (400 MHz, CDCl$_3$) δ ppm 7.50 (s, 1H), 7.21 (s, 1H), 3.83 (s, 3H), 3.74 (s, 3H), 2.78-2.76 (m, 2H), 2.63-2.60 (m, 2H), 1.34 (s, 12H).

Intermediate 7: Synthesis of 2-(4-bromo-2-chloro-6-methoxy-phenyl)-3-methoxy-cyclopent-2-en-1-one

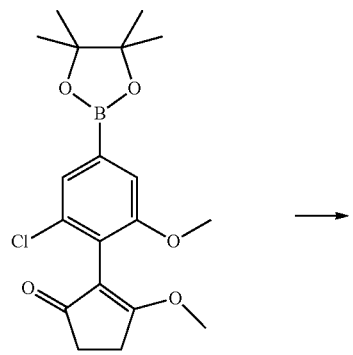

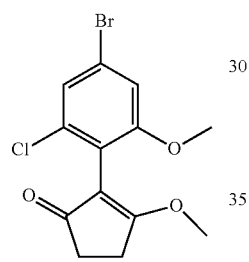

To a stirred solution of 2-[2-chloro-6-methoxy-4-(4,4,5,5-tetramethyl-1,3,2-dioxaborolan-2-yl)phenyl]-3-methoxy-cyclopent-2-en-1-one (2.381 g, 6.288 mmol) in methanol (60 mL) and a solution of copper dibromide (2.809 g, 12.58 mmol) in water (60 mL) was added. The reaction was heated at reflux for 3 hours under an atmosphere of nitrogen. The reaction was allowed to cool to room temperature, and dichloromethane (100 mL) was added followed by water (20 mL). The mixture was stirred at room temperature for 3 hours and then stood at room temperature overnight. The reaction mixture was extracted with dichloromethane (2×50 ml) and the combined organic extracts washed with brine (30 ml), dried over MgSO$_4$ and evaporated to dryness under reduced pressure. The residue was dissolved in acetone (78.5 mL) K$_2$CO$_3$ (1.02 g, 7.42 mmol) was added followed by iodomethane (1.54 mL, 24.7 mmol). The mixture was stirred at room temperature for 18 hours then stood at room temperature for 24 hours. The reaction was evaporated to dryness under reduced pressure and the residue was partitioned between water (50 ml) and EtOAc (50 ml). The phases were separated and the aqueous was extracted with EtOAc (2×40 ml). The combined organic phases were washed with brine (30 ml), dried over MgSO$_4$, filtered and evaporated to dryness under reduced pressure to give a brown gum. The crude product was dissolved in dichloromethane and absorbed onto silica and purified by flash chromatography over silica using a MeOH/dichloromethane gradient to give the desired product (1.27 g) as a brown solid. $^1$H NMR (400 MHz, CDCl$_3$) δ ppm 7.22 (s, 1H), 6.95 (s, 1H), 3.80 (s, 3H), 3.78 (s, 3H), 2.80-2.78 (m, 2H), 2.63-2.61 (m, 2H).

Intermediate 8: Synthesis of 2-(4-bromo-2-chloro-6-methoxy-phenyl)-3-methoxy-5-prop-2-ynyl-cyclopent-2-en-1-one

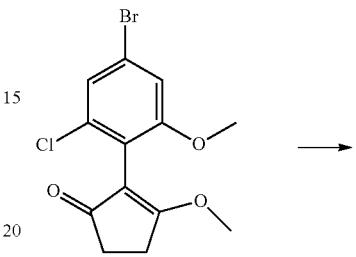

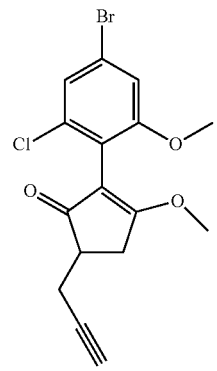

To a stirred solution of 2-(4-bromo-2-chloro-6-methoxy-phenyl)-3-methoxy-cyclopent-2-en-1-one (0.500 g, 1.51 mmol) in anhydrous tetrahydrofuran (10 mL) under an nitrogen atmosphere at −78°C. was added KHMDS (potassium hexamethyldisilazide) (1.81 mL of a 1.0M solution in tetrahydrofuran, 1.81 mmol) dropwise and the reaction was allowed to stir at this temperature for 55 minutes. Propargyl bromide (80 wt % in toluene, 0.202 mL, 1.81 mmol) was diluted in anhydrous tetrahydrofuran (2.5 mL) under an nitrogen atmosphere and then added dropwise to the reaction mixture. The reaction was stirred at −78°C. for 30 minutes and then allowed to warm to room temperature over 18 hours. The reaction was quenched by addition of saturated aqueous ammonium chloride solution (10 mL) followed by EtOAc (10 mL). Water (1 mL) was added and then the phases were separated and aqueous was extracted with further EtOAc (2×10 ml). The combined organic extracts were washed with brine (10 ml), dried over MgSO$_4$, filtered and evaporated to dryness under reduced pressure to give an orange gum. The crude product was dissolved in dichloromethane, adsorbed onto silica and purified by flash chromatography over silica using a dichloromethane/MeOH gradient to give the desired product (254 mg, 46%) as a yellow gum. $^1$H NMR (400 MHz, CDCl$_3$) δ ppm 7.23 (s, 1H), 6.95 (s, 1H), 3.78 (s, 3H), 3.66 (s, 3H), 3.14-3.10 (m, 1H), 2.79-2.51 (m, 4H), 2.00 (s, 1H).

Example 9

Synthesis of 2-(2-chloro-6-methoxy-4-prop-1-ynyl-phenyl)-3-methoxy-5-prop-2-ynyl-cyclopent-2-en-1-one

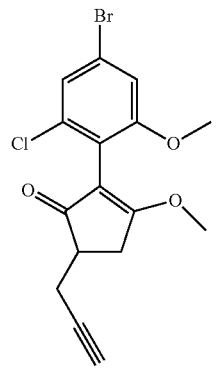

A microwave vial was charged with 2-(4-bromo-2-chloro-6-methoxy-phenyl)-3-methoxy-5-prop-2-ynyl-cyclopent-2-en-1-one (0.147 g, 0.398 mmol), but-2-ynoic acid (0.0368 g, 0.437 mmol), dichlorobis(triphenylphosphine)palladium(II) (0.0141 g, 0.0199 mmol) and 1,4-bis-(diphenylphosphino)butane (0.0170 g, 0.0398 mmol) was sealed and dimethyl sulfoxide (2 mL) was added via syringe followed by tetrabutylammonium fluoride (1 mol/L) in tetrahydrofuran (0.795 mL, 0.795 mmol) and then the solution was heated under microwave irradiation at 110°C. for 40 minutes. The reaction was cooled to room temperature, poured into water (20 ml) and diluted with EtOAc (10 ml). The phases were separated and the aqueous phase was extracted into ethyl acetate (2×10 ml). The combined organic extracts were washed with brine (10 ml), dried over MgSO$_4$, filtered and evaporated to dryness under reduced pressure to give a yellow gum, 230 mg. The residue was dissolved in dichloromethane, adsorbed onto silica and purified by flash chromatography over silica using an EtOAc/isohexane gradient to give the desired compound as a yellow gum (42 mg, 32%) as a seperable mixture of atropisomers. $^1$H NMR (400 MHz, CDCl$_3$) δ ppm 7.09 (s, 1H), 6.82 (s, 1H), 3.77 (s, 3H), 3.64 (s, 3H), 3.11-3.09 (m, 1H), 2.74-2.51 (m, 4H), 2.05 (s, 3H), 1.99 (s, 1H).

Example 10

Synthesis of 2-(2-chloro-6-methoxy-4-prop-1-ynyl-phenyl)-4-prop-2-ynyl-cyclopentane-1,3-dione (Compound A-31)

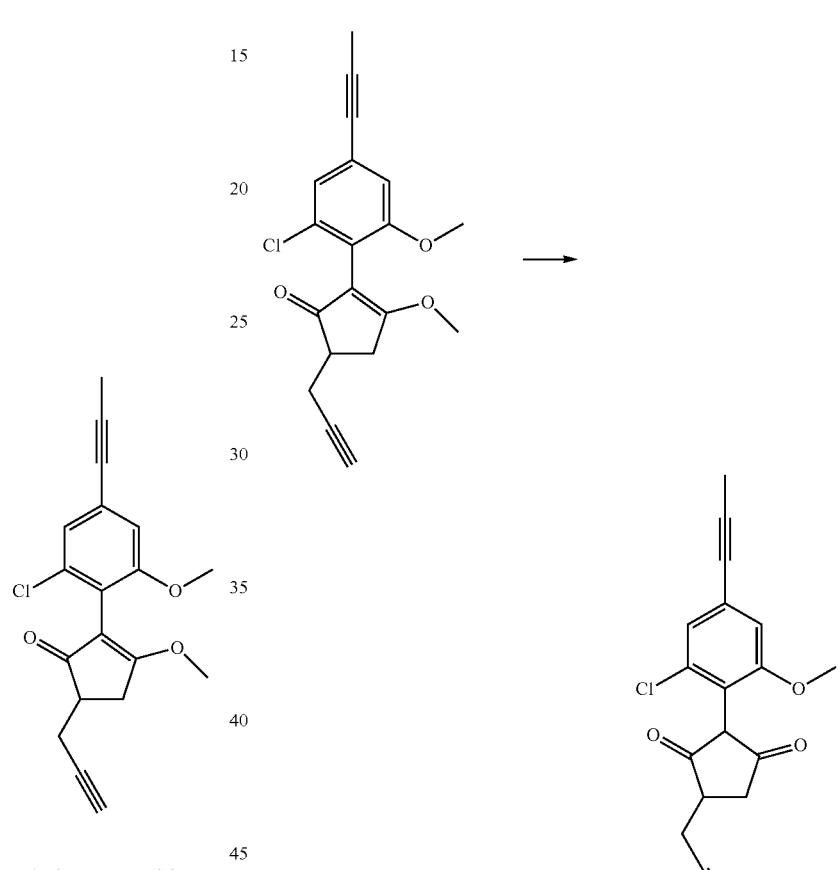

A solution of 2-(2-chloro-6-methoxy-4-prop-1-ynyl-phenyl)-3-methoxy-5-prop-2-ynyl-cyclopent-2-en-1-one (0.042 g, 0.1277 mmol) in acetone (1.5 mL) and 2M aqueous HCl (0.5 mL) was heated under microwave irradiation at 100°C. for 30 minutes. The reaction mixture was allowed to cool to room temperature, and then was diluted with dichloromethane (5 ml) and water (5 ml), and then was separated by elution through a phase separation cartridge, washing with more dichloromethane. The organic filtrate was evaporated to dryness under reduced pressure to give a yellow solid. The crude product was dissolved in dichloromethane and adsorbed onto silica and then purified by flash chromatography over silica using an EtOAc/isohexane gradient to give the desired product as a mixture of atropisomers. $^1$H NMR (400 MHz, CDCl$_3$) δ ppm 7.13 (s, 1H), 6.85 (s, 1H), 3.79 (s, 3H), 2.99-2.56 (m, 5H), 2.06 (s, 3H), 2.00 (s, 1H).

Intermediate 9: Synthesis of 2-[2,6-dichloro-4-(4,4,5,5-tetramethyl-1,3,2-dioxaborolan-2-yl)phenyl]-3-methoxy-cyclopent-2-en-1-one

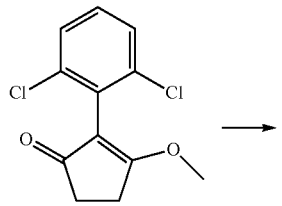

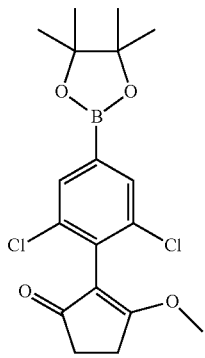

A microwave vessel was charged with 4-tert-butyl-2-(4-tert-butyl-2-pyridyl)pyridine (32 mg, 0.117 mmol), 4,4,5,5-tetramethyl-2-(4,4,5,5-tetramethyl-1,3,2-dioxaborolan-2-yl)-1,3,2-dioxaborolane (3.53 g, 13.6 mmol) and di-μ-methoxobis(1,5-cyclooctadiene)diiridium(I) (77 mg, 0.117 mmol). The vessel was purged with a nitrogen/evacuation cycle three times and methyl tert-butyl ether (10 ml) added. The now red/brown reaction mixture was then added to a second microwave vial containing 2-(2,6-dichlorophenyl)-3-methoxy-cyclopent-2-en-1-one (1.00 g, 3.89 mmol) in methyl tert-butyl ether (5 ml). The vial was sealed and heated at 80°C. for 1 hour under microwave irradiation. The reaction mixture was cooled, adsorbed onto silica and purified by flash chromatography on silica using a EtOAc/isohexane gradient to give the desired product as a white solid (1.67 g, contaminated with pinacol by-products). $^1$H NMR (400 MHz, CDCl$_3$) δ ppm 7.65 (s, 2H), 3.75 (s, 3H), 2.82-2.78 (m, 2H), 2.65-2.60 (m, 2H), 1.25 (s, 12H).

Intermediate 10: Synthesis of 2-(4-bromo-2,6-dichloro-phenyl)-3-methoxy-cyclopent-2-en-1-one

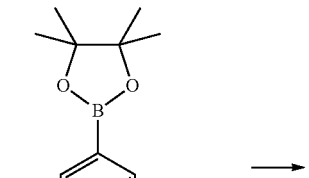

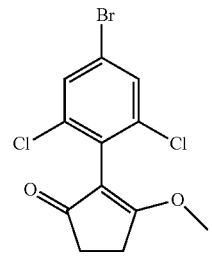

To a stirred solution of 2-[2,6-dichloro-4-(4,4,5,5-tetramethyl-1,3,2-dioxaborolan-2-yl)phenyl]-3-methoxy-cyclopent-2-en-1-one (1.49 g, 3.89 mmol) in MeOH (39 ml) was added CuBr$_2$ (2.61 g, 11.7 mmol) in water (39 ml). The reaction was heated at 85 C for 2 hours. The MeOH was removed under reduced pressure and the residue extracted with EtOAc (30 ml). The organic phase was washed with saturated aqueous NH$_4$Cl solution (2×20 ml). The combined aqueous washings were extracted with EtOAc (2×20 ml). The combined organics were dried over MgSO$_4$, filtered and evaporated to dryness under reduced pressure. The residue was dissolved in acetone (30 ml) and K$_2$CO$_3$ (650 mg, 4.67 mmol) and MeI (0.266 ml, 4.28 mmol) added. The reaction was stirred at room temperature for 4 hours, then diluted with H$_2$O (50 ml) and extracted with CH$_2$Cl$_2$ (3×30 ml). The combined organic extracts were dried over MgSO$_4$, filtered and evaporated to dryness under reduced pressure to give the desired product (0.96 g, 73%) as a pale yellow solid. $^1$H NMR (400 MHz, CDCl3) δppm 7.52 (s, 2H), 3.85 (s, 3H), 2.85-2.80 (2H, m), 2.65-2.60 (2H, m).

Intermediate 11: Synthesis of (5E)-2-(4-bromo-2,6-dichloro-phenyl)-3-methoxy-5-(2-pyridylmethylene)cyclopent-2-en-1-one

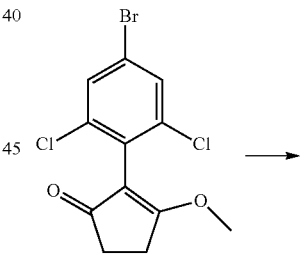

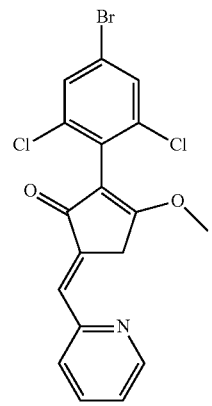

To a stirred solution of 2-(4-bromo-2,6-dichloro-phenyl)-3-methoxy-cyclopent-2-en-1-one (0.86 g, 2.56 mmol) in anhydrous tetrahydrofuran (17 ml) at 0°C. under an nitrogen atmosphere was added dropwise potassium hexamethyldisilazide (2.81 ml of a 1.0M solution in tetrahydrofuran, 2.81 mmol) over 10 minutes followed by dropwise addition of a solution of pyridine-2-carbaldehyde (0.268 ml, 2.81 mmol) in tetrahydrofuran (1 ml) over 5 minutes. The reaction was stirred at 0°C. for 10 minutes and then allowed to warm to room temperature over 1.5 hours. The reaction was quenched with saturated aqueous NH$_4$Cl (25 ml) and extracted with EtOAc (3×25 ml). The combined organic extracts were washed with brine (15 ml), dried over MgSO$_4$, filtered and evaporated to dryness under reduced pressure. The crude product was purified by flash chromatography over silica using an EtOAc/isohexane gradient to give the desired product (250 mg, 20%). $^1$H NMR (400 MHz, CDCl3) δ ppm 8.70 (d, 1H), 7.70 (dd, 1H), 7.55 (s, 2H), 7.45 (d, 1H), 7.40 (s, 1H), 7.25-7.20 (m, 1H), 4.05 (s, 2H), 3.95 (s, 3H).

Intermediate 12: Synthesis of 2-(4-bromo-2,6-dichloro-phenyl)-3-methoxy-5-(2-pyridylmethyl) cyclopent-2-en-1-one

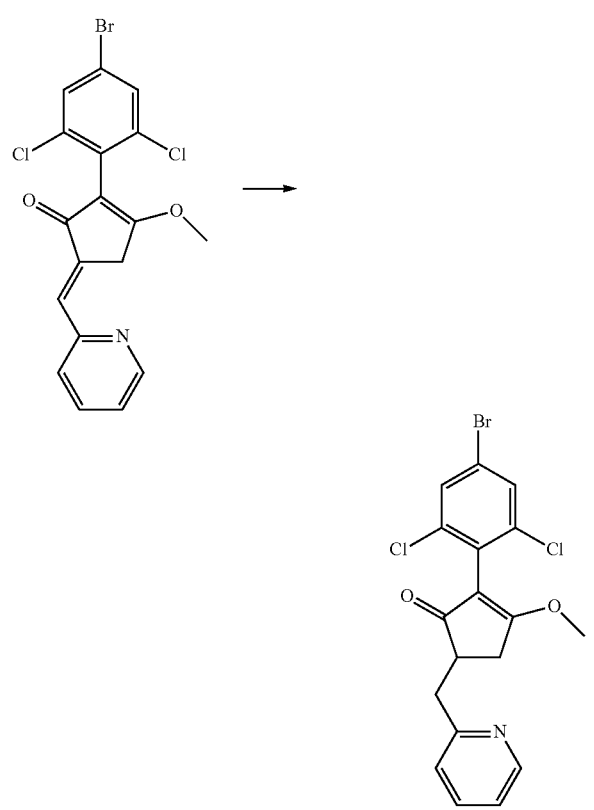

To a stirred solution of (5E)-2-(4-bromo-2,6-dichloro-phenyl)-3-methoxy-5-(2-pyridylmethylene)cyclopent-2-en-1-one (235 mg, 0.55 mmol) in glacial AcOH (2.4 ml) at 0°C. was added zinc dust (126 mg, 1.94 mmol) portionwise over 10 minutes. The reaction was stirred at room temperature for 2 hours and then diluted with EtOAc (25 ml), filtered through Celite and washed through with further EtOAc (2×20 ml). The filtrate was evaporated to dryness under reduced pressure and then azeotroped with toluene and then MeOH to give the desired product (235 mg, 99%) as a brown gum. $^1$H NMR (400 MHz, CDCl3) δ ppm 8.52 (d, 1H), 7.60 (dd, 1H), 7.45 (2×s, 2×1H), 7.25 (d, 1H), 7.15 (dd, 1H), 3.80 (s, 3H), 3.45-3.35 (1H, m), 3.20-3.10 (m, 1H), 3.00-2.90 (1H, m), 2.90-2.85 (m, 2H).

Example 11

Synthesis of 2-(2,6-dichloro-4-prop-1-ynyl-phenyl)-3-methoxy-5-(2-pyridylmethyl)cyclopent-2-en-1-one

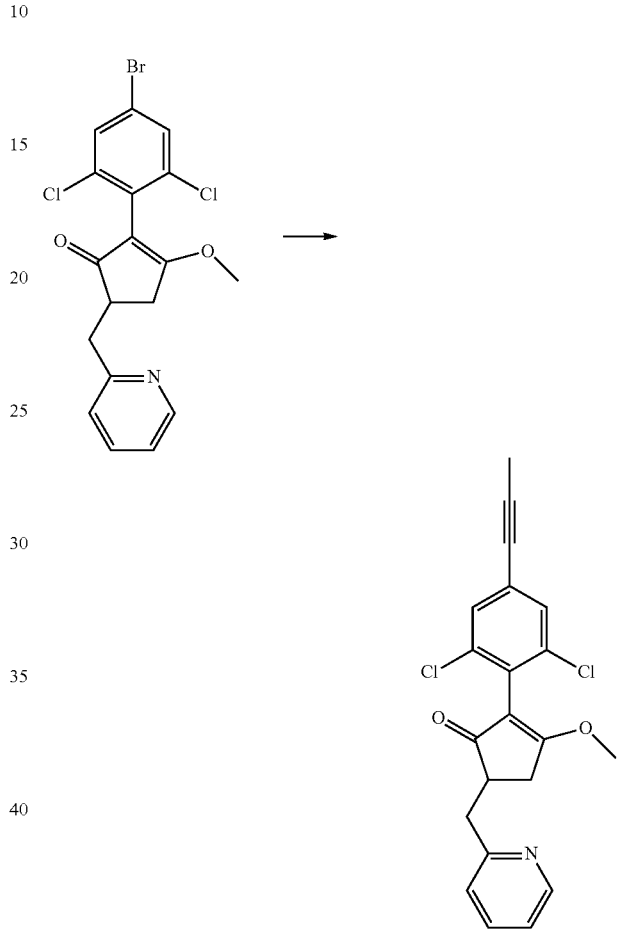

A microwave vial was charged with 2-(4-bromo-2,6-dichloro-phenyl)-3-methoxy-5-(2-pyridylmethyl)cyclopent-2-en-1-one (90 mg, 0.21 mmol), caesium fluoride (CsF, 64 mg, 0.42 mmol), copper(I) iodide (CuI, 8 mg, 0.042 mmol), dichloro[1,1'-bis(diphenylphosphino)ferrocene]palladium (II) dichloromethane adduct (23 mg, 0.032 mmol), tributyl(prop-1-ynyl)stannane (83 mg, 0.25 mmol) and N,N-dimethylformamide (0.9 ml), sealed and heated at 120°C. under microwave irradiation for 30 minutes. Further caesium fluoride (32 mg, 0.21 mmol), copper(I) iodide (4 mg, 0.021 mmol), dichloro[1,1'-bis(diphenylphosphino)ferrocene]palladium(II) dichloromethane adduct (12 mg, 0.016 mmol) and tributyl(prop-1-ynyl)stannane (42 mg, 0.13 mmol) were added and the reaction heated at 120°C. under microwave irradiation for a further 30 minutes. The reaction was allowed to cool to room temperature, diluted with water (10 ml) and Et$_2$O (10 ml) and filtered through Celite. The filtrate phases were separated and the aqueous phase extracted with further Et$_2$O (2×10 ml). The combined organic extracts were washed with brine (10 ml), dried over MgSO$_4$, filtered and evaporated to dryness under reduced pressure. The crude product was dissolved in EtOAc, absorbed onto silica and purified by flash chromatography on silica using an EtOAc/isohexane gradient to give the desired product (26 mg, 32%). ¹H NMR (400 MHz, CDCl3)δ ppm 8.50 (d, 1H), 7.60 (dd, 1H), 7.30 (2×s, 2×1H), 7.25 (d, 1H), 7.15 (dd, 1H), 3.75 (s, 3H), 3.40-3.35 (m, 1H), 3.20-3.10 (m, 1H), 3.00-2.90 (m, 1H), 2.85-2.80 (m, 2H), 2.05 (s, 3H).

Example 12

Synthesis of 2-(2,6-dichloro-4-prop-1-ynyl-phenyl)-4-(2-pyridylmethyl)cyclopentane-1,3-dione (Compound A-32)

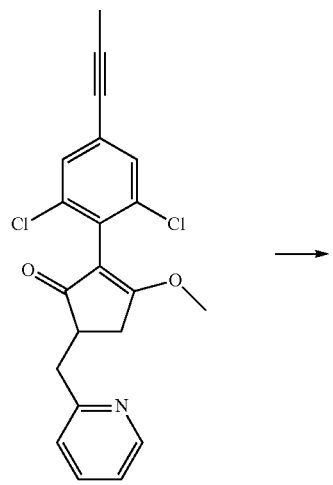

→

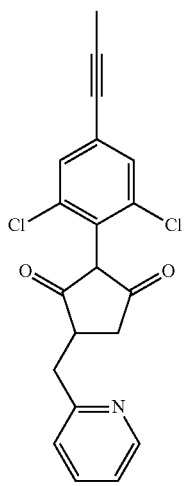

A mixture of 2-(2,6-dichloro-4-prop-1-ynyl-phenyl)-3-methoxy-5-(2-pyridylmethyl)cyclopent-2-en-1-one (41 mg, 0.106 mmol) and morpholine (1 ml) were heated at 10°C. for 4 hours. The reaction was cooled to room temperature and evaporated to dryness under reduced pressure. The residue was partitioned between EtOAc (10 ml) and saturated aqueous NH₄Cl (10 ml). The organic phase was washed with further saturated aqueous NH₄Cl (5 ml), brine (5 ml), dried over MgSO₄, filtered and evaporated to dryness under reduced pressure. The crude product was purified on the FractionLynx to give the desired product (14 mg, 36%). ¹H NMR (400 MHz, CDCl3) δ ppm 8.50 (d, 1H), 7.85 (dd, 1H), 7.40 (d, 1H), 7.35-7.30 (m, 3H), 6.10 (br, 1H), 3.40-3.25 (m, 3H), 3.05 (dd, 1H), 2.40 (dd, 1H), 2.05 (s, 3H).

Additional compounds in Table T1 below (e.g. Compounds A-1 to A-34) were prepared (or are likely to be preparable) by method(s) similar to one or more of the preparative methods described hereinabove, using appropriate starting materials.

TABLE T1

| Compound Number | Structure | ¹H NMR (CDCl₃ unless stated) or other physical data |
| --- | --- | --- |
| A-1 | 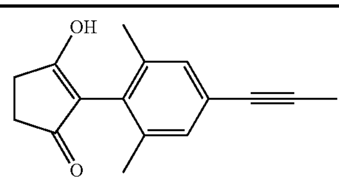 | δ (delta) (MeOD): 7.05 (s, 2H), 2.68 (s, 4H), 2.06 (s, 6H), 2.00 (s, 3H). |
| A-2 | 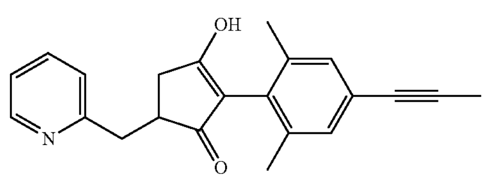 [SMILES: CC#Cc1cc(C)c(C2=C(O)CC(Cc3ccccn3)C2=O)c(C)c1] | δ (delta) 8.41 (d, 1 H), 7.78 (m, 1 H), 7.35 (d, 1H), 7.29 (t, 1H), 7.04 (d, 2H), 3.26 (m, 3H), 2.97 (dd, 1H), 2.4 (d, 1H), 2.12 (s, 3H), 2.11 (s, 3H), 1.93 (s, 3H). |
| A-3 | 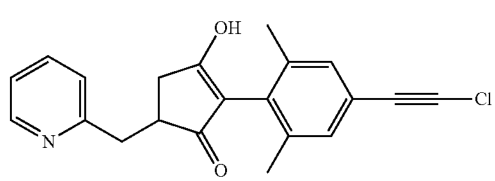 [SMILES: Cc1cc(C#CCl)cc(C)c1C1=C(O)CC(Cc2ccccn2)C1=O] | δ (delta) (MeOD): 8.70-8.75 (br. d, 1H), 8.38-8.44 (dt, 1H), 7.93-7.98 (d, 1H), 7.80-7.86 (t, 1H), 7.15-7.18 (s, 2H), 3.30-3.51 (m, 3H), 2.98-3.06 (dd, 1H), 2.56-2.63 (dd, 1H), 2.10-2.11 (s, 3H), 2.11-2.12 (s, 3H). |

TABLE T1-continued

| Compound Number | Structure | ¹H NMR (CDCl₃ unless stated) or other physical data |
|---|---|---|
| A-4 | 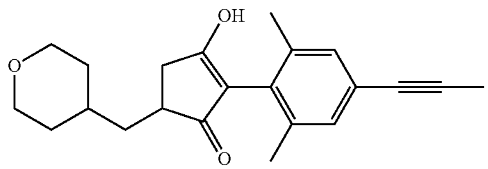 [SMILES: CC#Cc1cc(C)c(C2=C(O)CC(CC3CCOCC3)C2=O)c(C)c1] | δ (delta) (MeOD): 7.23 (s, 1H), 7.1 (s, 1H) 3.96 (t, 2H), 3.4-3.5 (m, 2H), 2.92-2.8 (m, 2H), 2.4 (d, 1H), 2.07 (s, 3H), 2.05 (s, 3H), 2.0 (s, 3H), 1.90-1.65 (m, 4H), 1.40-1.30 (m, 3H). |
| A-5 | 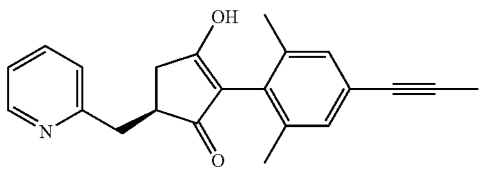 [SMILES: CC#Cc1cc(C)c(C2=C(O)C[C@H](Cc3ccccn3)C2=O)c(C)c1] | δ (delta) 8.41 (d, 1H), 7.78 (m, 1H), 7.35 (d, 1H), 7.29 (t, 1H), 7.04 (d, 2H), 3.26 (m, 3H), 2.97 (dd, 1H), 2.4 (d, 1H), 2.12 (s, 3H), 2.11 (s, 3H), 1.93 (s, 3H). |
| A-6 | 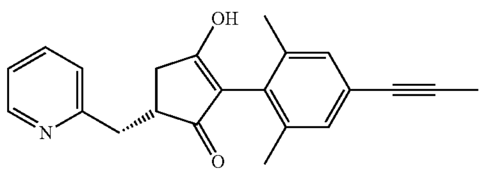 | δ (delta) 8.41 (d, 1H), 7.78 (m, 1H), 7.35 (d, 1H), 7.29 (t, 1H), 7.04 (d, 2H), 3.26 (m, 3H), 2.97 (dd, 1H), 2.4 (d, 1H), 2.12 (s, 3H), 2.11 (s, 3H), 1.93 (s, 3H). |
| A-7 | 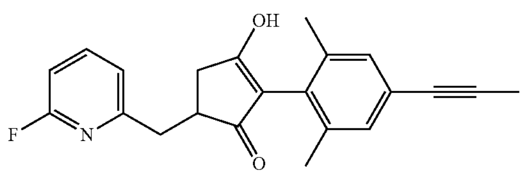 [SMILES: CC#Cc1cc(C)c(C2=C(O)CC(Cc3cccc(F)n3)C2=O)c(C)c1] | δ (delta) 7.88-7.83 (m, 1H), 7.2 (d, 1H), 7.08 (d, 2H), 6.91 (d, 1H), 3.3-3.25 (m, 3H), 3.01-2.92 (m, 1H), 2.4 (d, 1H), 2.12 (s, 3H), 2.09 (s, 3H), 2.01 (s, 3H). |
| A-8 | 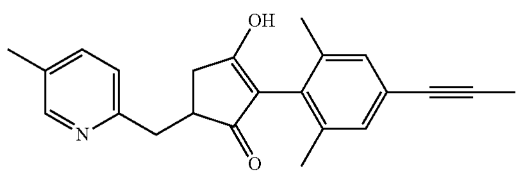 [SMILES: CC#Cc1cc(C)c(C2=C(O)CC(Cc3ccc(C)cn3)C2=O)c(C)c1] | δ (delta) 8.28 (s, 1H), 7.63 (d, 1H), 7.29 (d, 1H), 7.1 (d, 2H), 3.3-3.24 (m, 3H) 3.01 (dd, 1H), 2.41 (d, 1H), 2.37 (s, 3H), 2.15 (s, 3H), 2.13 (s, 3H), 2.02 (s, 3H). |
| A-9 | 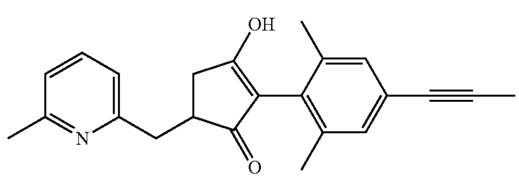 [SMILES: CC#Cc1cc(C)c(C2=C(O)CC(Cc3cccc(C)n3)C2=O)c(C)c1] | δ (delta) 7.64 (t, 1H), 7.15-7.2 (m, 2H), 7.03 (d, 2H), 3.25-3.4 (m, 3H), 3.0 (dd, 1H), 2.6 (s, 3H), 2.4 (d, 1H), 2.15 (s, 3H), 2.14 (s, 3H), 2.02 (s, 3H). |
| A-10 | 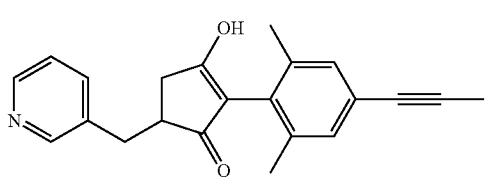 [SMILES: CC#Cc1cc(C)c(C2=C(O)CC(Cc3cccnc3)C2=O)c(C)c1] | δ (delta) 7.9-7.94 (m, 2H), 7.65 (d, 1H), 7.23-7.27 (m, 1H), 6.89 (s, 1H), 6.85 (s, 1H), 5.35 (br s, 1H), 3.1-3.2 (m, 2H), 3.0 (d, 1H), 2.7 (dd, 1H), 2.2 (d, 1H), 2.07 (s, 3H), 2.03 (s, 3H), 1.98 (s, 3H). |
| A-11 | 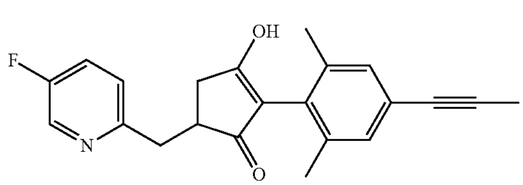 [SMILES: CC#Cc1cc(C)c(C2=C(O)CC(Cc3ccc(F)cn3)C2=O)c(C)c1] | δ (delta) 8.35 (d, 1H), 7.54-7.59 (m, 1H), 7.39-7.42 (m, 1H), 7.1 (d, 2H), 3.27-3.4 (m, 3H), 3.02 (dd, 1H), 2.4 (d, 1H), 2.14 (s, 3H), 2.13 (s, 3H), 2.02 (s, 3H). |

TABLE T1-continued

| Compound Number | Structure | ¹H NMR (CDCl₃ unless stated) or other physical data |
|---|---|---|
| A-12 | 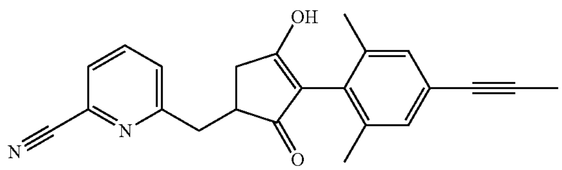 [SMILES: CC#Cc1cc(C)c(C2=C(O)CC(Cc3cccc(C#N)n3)C2=O)c(C)c1] | δ (delta) 7.86 (t, 1H), 7.66 (d, 1H), 7.5 (d, 1H), 7.06 (d, 2H), 3.2-3.4 (m, 3H), 2.9 (dd, 1H), 2.42 (d, 1H), 2.13 (s, 3H), 2.06 (s, 3H), 2.05 (s, 3H). |
| A-13 | 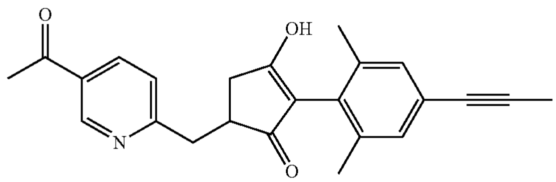 [SMILES: CC#Cc1cc(C)c(C2=C(O)CC(Cc3ccc(C(C)=O)cn3)C2=O)c(C)c1] | δ (delta) 13.5 (br. s, 1H), 9.01 (d, 1H), 8.33 (dd, 1H), 7.5 (d, 1H), 7.08 (d, 2H), 3.34 (s, 3H), 3.01 (dd, 1H), 2.63 (s, 3H), 2.41 (d, 1H), 2.16 (s, 3H), 2.13 (s, 3H), 2.02 (s, 3H). |
| A-14 | 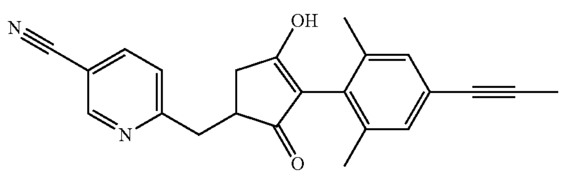 [SMILES: CC#Cc1cc(C)c(C2=C(O)CC(Cc3ccc(C#N)cn3)C2=O)c(C)c1] | δ (delta) 13.5 (br. s, 1H), 8.75 (s, 1H), 8.04 (s, 1H), 7.45-7.65 (m, 1H), 7.05 (d, 2H), 3.35 (s, 3H), 3.0 (dd, 1H), 2.4 (d, 1H), 2.15 (s, 3H), 2.05 (s, 3H), 2.05 (s, 3H). |
| A-15 | 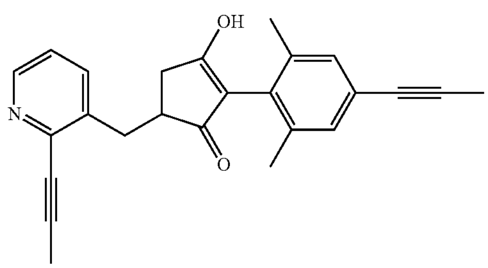 [SMILES: CC#Cc1cc(C)c(C2=C(O)CC(Cc3cccnc3C#CC)C2=O)c(C)c1] | δ (delta) 8.22 (d, 1H), 7.7 (d, 1H), 7.2-7.23 (m, 1H), 7.06 (s, 2H), 3.36 (d, 1H), 3.02 (s, 2H), 2.68 (dd, 1H), 2.5 (d, 1 H), 2.11 (s, 3H), 2.06 (s, 3H), 2.05 (s, 3H), 1.86 (s, 3H). |
| A-16 | 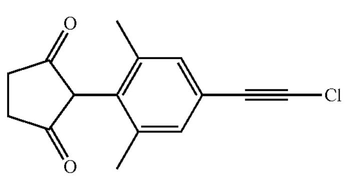 [SMILES: Cc1cc(C#CCl)cc(C)c1C1C(=O)CCC1=O] | δ (delta) (d-DMSO): 7.14 (s, 2H), 2.69 (s, 4H), 2.08 (s, 6H). |
| A-17 | 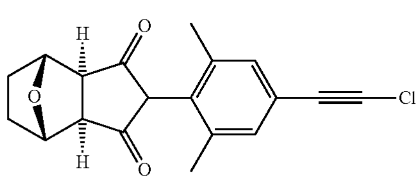 | δ (delta) (d-DMSO): 7.13 (s, 2H), 4.59 (dd, 2H), 2.86 (s, 2H), 2.07 (s, 6H), 1.82-1.80 (m, 2H), 1.68-1.65 (m, 2H). |
| A-18 | 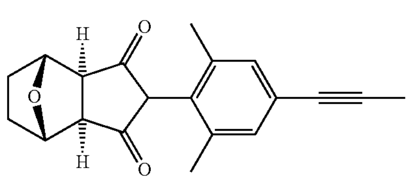 | δ (delta) (d-DMSO): 7.04 (s, 2H), 4.60-4.58 (m, 2H), 2.85 (s, 2H), 2.04 (s, 6H), 2.00 (s, 3H), 1.83-1.80 (m, 2H), 1.68-1.65 (m, 2H). |

TABLE T1-continued

| Compound Number | Structure | ¹H NMR (CDCl₃ unless stated) or other physical data |
|---|---|---|
| A-19 | 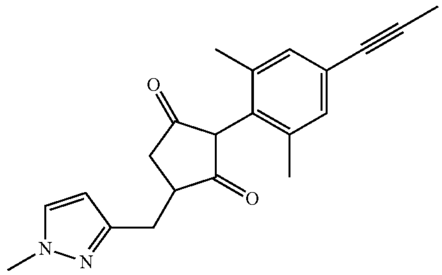 [SMILES: CC#Cc1cc(C)c(C2C(=O)CC(Cc3ccn(C)n3)C2=O)c(C)c1] | δ (delta) (MeOD) 7.46 (d, 1H), 7.02 (d, 2 H), 6.11 (d, 1H), 3.82 (s, 3H), 3.03-3.16 (m, 2H) 2.70-2.94 (m, 2H), 2.44-2.57 (m, 1H), 2.05 (s, 3H), 1.99 (s, 3H), 1.91 (s, 3H). |
| A-20 | 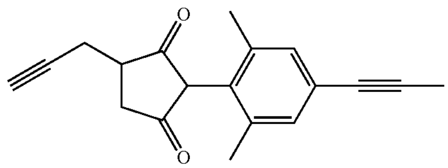 [SMILES: C#CCC1CC(=O)C(c2c(C)cc(C#CC)cc2C)C1=O] | δ (delta) (d₆-DMSO) 6.99 (s, 2H), 2.83-2.64 (br.m, 3H), 2.58-2.48 (br.m, 2H), 2.43-2.32 (br.m, 1H), 1.99 (s, 6H), 1.98 (s, 3H). |
| A-21 | 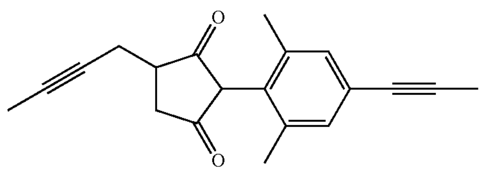 [SMILES: CC#CCC1CC(=O)C(c2c(C)cc(C#CC)cc2C)C1=O] | δ (delta) (MeOD) 7.03 (s, 2H), 2.91-2.77 (m, 2H), 2.70-2.49 (m, 3H), 2.11 (s, 3H), 2.06 (s, 3H), 1.99 (s, 3H), 1.70 (s, 3H). |
| A-22 | 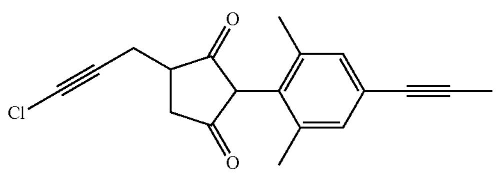 [SMILES: CC#Cc1cc(C)c(C2C(=O)CC(CC#CCl)C2=O)c(C)c1] | δ (delta) (MeOD) 7.04 (s, 2H), 2.95-2.82 (m, 2H), 2.76-2.51 (m, 3H), 2.11 (s, 3H), 2.05 (s, 3H), 1.99 (s, 3H). |
| A-23 | 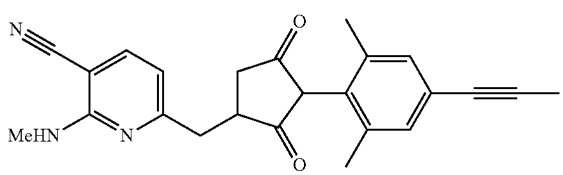 [SMILES: CC#Cc1cc(C)c(C2C(=O)CC(Cc3ccc(C#N)c(NC)n3)C2=O)c(C)c1] | δ (delta) 7.71 (d, 1H), 7.09 (s, 2H), 6.63 (d, 1H), 5.60 (br, 1H), 2.96-3.36 (m, 7H), 2.37-2.45 (m, 1H), 2.13 (s, 6H), 2.02 (s, 3H). |
| A-24 | 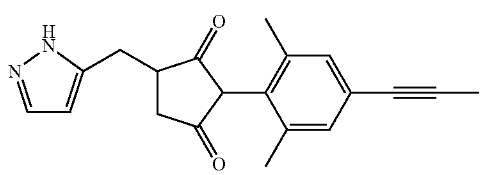 [SMILES: CC#Cc1cc(C)c(C2C(=O)CC(Cc3ccn[nH]3)C2=O)c(C)c1] | δ (delta) 7.26 (s, 1 H), 7.12 (d, 2 H), 6.18 (d, 1 H), 3.35 (br s, 1 H), 3.21 (d, 1 H), 2.87-3.05 (m, 2 H), 2.38 (dd, 1 H), 2.13 (s, 3 H), 2.09 (s, 3 H), 2.04 (s, 3 H). |
| A-25 | 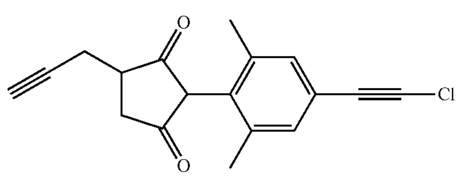 [SMILES: C#CCC1CC(=O)C(c2c(C)cc(C#CCl)cc2C)C1=O] | δ (delta) (MeOD) 7.13 (s, 2H), 2.98-2.81 (m, 2H), 2.73-2.67 (m, 3H), 2.31 (s, 1H), 2.12 (s, 3H), 2.07 (s, 3H). |
| A-26 | 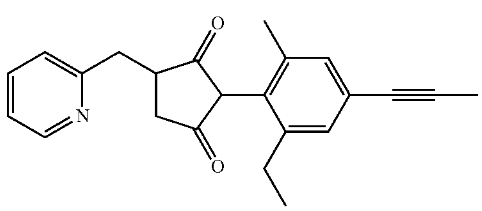 [SMILES: CC#Cc1cc(C)c(C2C(=O)CC(Cc3ccccn3)C2=O)c(CC)c1] | δ (delta) (MeOD) 8.53 (d, 1 H), 7.82-8.01 (m, 1 H), 7.46-7.60 (m, 1 H), 7.35-7.44 (m, 1 H), 6.98-7.28 (m, 2 H), 3.29-3.36 (m, 2 H), 3.11-3.23 (m, 1 H), 2.80-2.90 (m, 1 H), 2.48 (dt, 1 H), 2.30-2.44 (m, 2 H), 2.06 (s, 1.5 H), 1.99-2.02 (m, 4.5 H), 0.99-1.11 (m, 3 H). |

TABLE T1-continued

| Compound Number | Structure | ¹H NMR (CDCl₃ unless stated) or other physical data |
|---|---|---|
| A-27 | 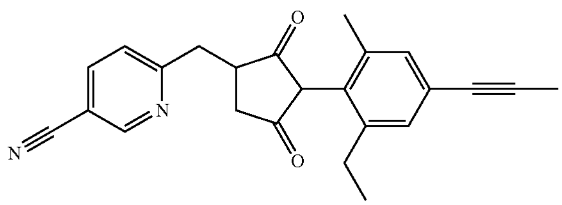 [SMILES: CC#Cc1cc(C)c(C2C(=O)CC(Cc3ccc(C#N)cn3)C2=O)c(CC)c1] | δ (delta) 8.70 (s, 1H), 7.99 (d, 1H), 7.43 (d, 1H), 6.90-7.10 (2H, m), 3.29 (3H, br), 2.90-3.00 (1H, m), 2.25-2.40 (3H, m), 1.85 (6H, m), 0.90-1.10 (3H, m). |
| A-28 | 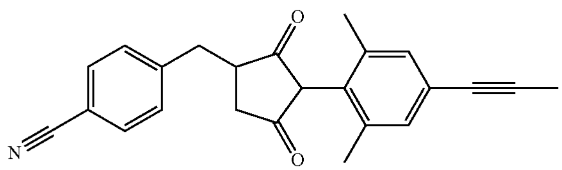 [SMILES: CC#Cc1cc(C)c(C2C(=O)CC(Cc3ccc(C#N)cc3)C2=O)c(C)c1] | δ (delta) (MeOD) 7.65 (d, 2H), 7.47 (d, 2H), 7.02 (d, 2H), 3.29-3.23 (m, 1H), 3.18-3.09 (m, 1H), 2.97-2.87 (m, 1H), 2.80-2.70 (m, 1H), 2.40 (d, 1H), 2.04 (s, 3H), 1.99 (s, 3H), 1.89 (s, 3H). |
| A-29 | 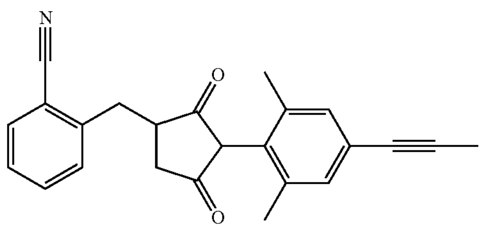 [SMILES: CC#Cc1cc(C)c(C2C(=O)CC(Cc3ccccc3C#N)C2=O)c(C)c1] | δ (delta) (MeOD) 7.72 (d, 1H), 7.61 (t, 1H), 7.53 (d, 1H), 7.41 (t, 1H), 7.03 (s, 2H), 3.50-3.42 (m, 1H), 3.24-3.14 (m, 1H), 3.05-2.96 (m, 1H), 2.81-2.72 (m, 1H), 2.48-2.38 (m, 1H), 2.05 (s, 3H), 2.00 (s, 6H). |
| A-30 | 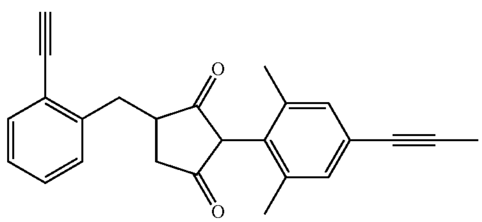 [SMILES: C#Cc1ccccc1CC1CC(=O)C(c2c(C)cc(C#CC)cc2C)C1=O] | δ (delta) (MeOD) 7.51 (d, 1H), 7.40-7.27 (m, 2H), 7.26-7.19 (m, 1H), 7.07 (s, 2H), 3.78 (s, 1H), 3.52-3.43 (m, 1H), 3.27-3.16 (m, 1H), 3.00-2.91 (m, 1H), 2.71-2.61 (m, 1H), 2.60-2.49 (m, 1H), 2.09 (s, 3H), 2.01 (2 × s, 6H). |
| A-31 | 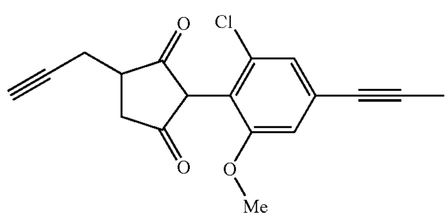 [SMILES: C#CCC1CC(=O)C(c2c(Cl)cc(C#CC)cc2OC)C1=O] | δ (delta) 7.13 (br. s, 1H), 6.85 (br. s, 1H), 3.79 (d, 3H), 2.99-2.83 (m, 2H), 2.76-2.50 (m, 3H), 2.06 (s, 3H), 2.01-1.98 (m, 1H). |
| A-32 | 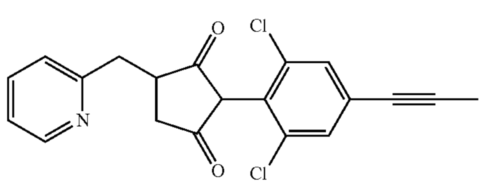 [SMILES: CC#Cc1cc(Cl)c(C2C(=O)CC(Cc3ccccn3)C2=O)c(Cl)c1] | δ (delta) 8.50 (d, 1H), 7.85 (dd, 1H), 7.40 (d, 1H), 7.35-7.30 (m, 3H), 6.10 (br, 1H), 3.40-3.25 (m, 3H), 3.05 (dd, 1H), 2.40 (dd, 1H), 2.05 (s, 3H). |
| A-33 | 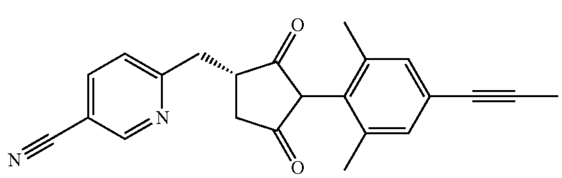 [SMILES: CC#Cc1cc(C)c(C2C(=O)C[C@H](Cc3ccc(C#N)cn3)C2=O)c(C)c1] | |

TABLE T1-continued

| Compound Number | Structure | 1H NMR (CDCl3 unless stated) or other physical data |
|---|---|---|
| A-34 | 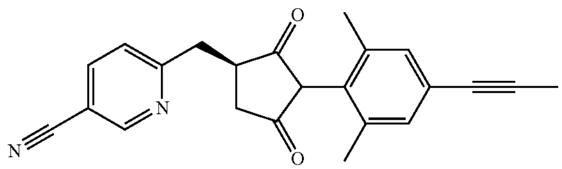 [SMILES: CC#Cc1cc(C)c(C2C(=O)C[C@@H](Cc3ccc(C#N)cn3)C2=O)c(C)c1] | |

It should be noted that certain compounds of the invention exist as a mixture of isomers, including atropisomers, noted above, under the conditions used to obtain the $^1$H NMR data. Where this has occurred, the characterising data are reported for all isomers present at ambient temperature in the specified solvent. Unless otherwise stated, proton NMR spectra were recorded at ambient temperature. Compounds characterised by HPLC-MS were analysed using one of two methods described below.

The compounds of the following Tables 1 to 22 are further examples of the present invention. These compounds are optionally obtained in an analogous manner to the manner in which one or more of Compounds A-1 to A-34 are obtained.

Table 1 covers 26 compounds of the following formula

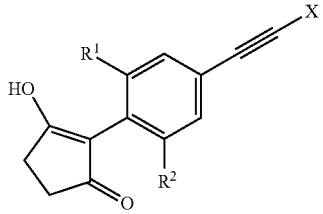

wherein X, $R^1$ and $R^2$ are as defined in Table 1.

TABLE 1

| Compound Number | $R^1$ | $R^2$ | X |
|---|---|---|---|
| 1.01 | Methyl | Hydrogen | Methyl |
| 1.02 | Methyl | Methyl | Methyl |
| 1.03 | Methyl | Chlorine | Methyl |
| 1.04 | Methyl | Methoxy | Methyl |
| 1.05 | Methyl | Ethynyl | Methyl |
| 1.06 | Methyl | Ethyl | Methyl |
| 1.07 | Methyl | Vinyl | Methyl |
| 1.08 | Chlorine | Hydrogen | Methyl |
| 1.09 | Chlorine | Chlorine | Methyl |
| 1.10 | Chlorine | Methoxy | Methyl |
| 1.11 | Chlorine | Ethynyl | Methyl |
| 1.12 | Chlorine | Ethyl | Methyl |
| 1.13 | Chlorine | Vinyl | Methyl |
| 1.14 | Methyl | Hydrogen | Chlorine |
| 1.15 | Methyl | Methyl | Chlorine |
| 1.16 | Methyl | Chlorine | Chlorine |
| 1.17 | Methyl | Methoxy | Chlorine |
| 1.18 | Methyl | Ethynyl | Chlorine |
| 1.19 | Methyl | Ethyl | Chlorine |
| 1.20 | Methyl | Vinyl | Chlorine |
| 1.21 | Chlorine | Hydrogen | Chlorine |
| 1.22 | Chlorine | Chlorine | Chlorine |
| 1.23 | Chlorine | Methoxy | Chlorine |
| 1.24 | Chlorine | Ethynyl | Chlorine |

TABLE 1-continued

| Compound Number | $R^1$ | $R^2$ | X |
|---|---|---|---|
| 1.25 | Chlorine | Ethyl | Chlorine |
| 1.26 | Chlorine | Vinyl | Chlorine |

Table 2 covers 26 compounds of the following formula

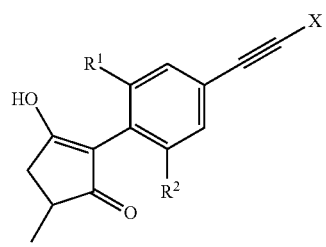

wherein X, $R^1$ and $R^2$ are as defined in Table 1.

Table 3 covers 26 compounds of the following formula

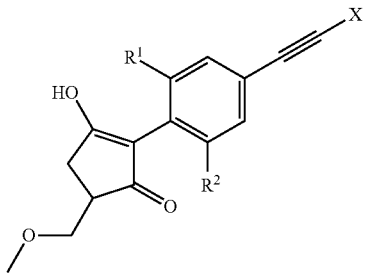

wherein X, $R^1$ and $R^2$ are as defined in Table 1.

Table 4 covers 26 compounds of the following formula

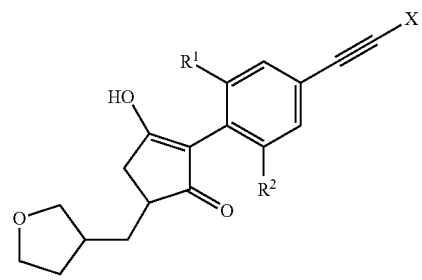

wherein X, $R^1$ and $R^2$ are as defined in Table 1.

Table 5 covers 26 compounds of the following formula

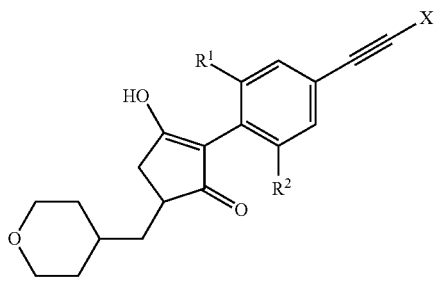

wherein X, R¹ and R² are as defined in Table 1.

Table 6 covers 26 compounds of the following formula

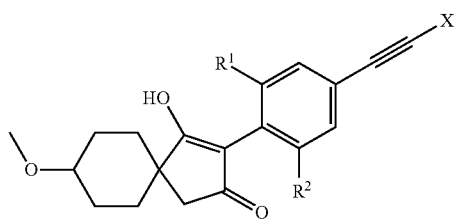

wherein X, R¹ and R² are as defined in Table 1.

Table 7 covers 26 compounds of the following formula

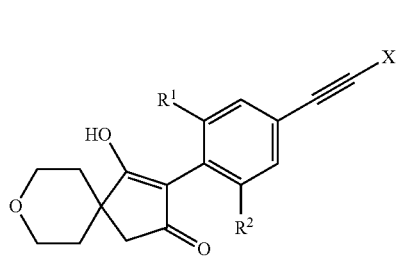

wherein X, R¹ and R² are as defined in Table 1.

Table 8 covers 26 compounds of the following formula

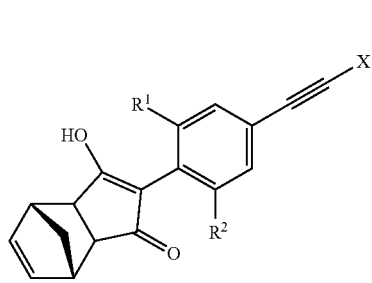

wherein X, R¹ and R² are as defined in Table 1.

Table 9 covers 26 compounds of the following formula

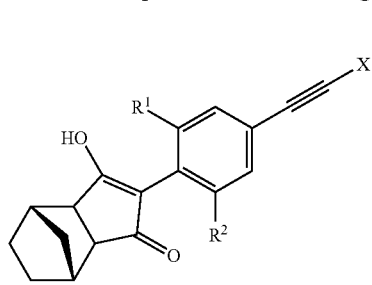

wherein X, R²¹ and R² are as defined in Table 1.

Table 10 covers 26 compounds of the following formula

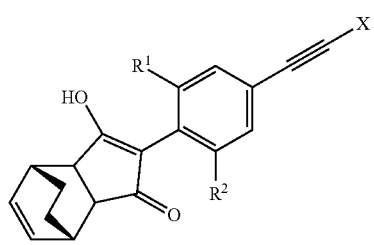

wherein X, R¹ and R² are as defined in Table 1.

Table 11 covers 26 compounds of the following formula

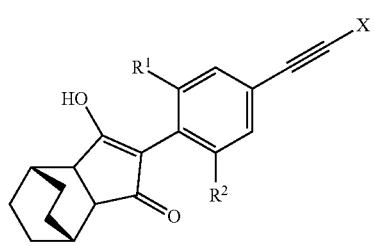

wherein X, R¹ and R² are as defined in Table 1.

Table 12 covers 26 compounds of the following formula

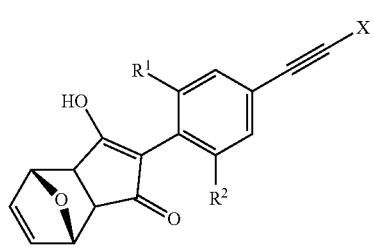

wherein X, R¹ and R² are as defined in Table 1.

Table 13 covers 26 compounds of the following formula

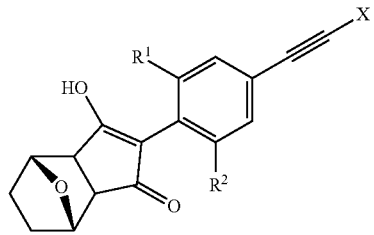

wherein X, R¹ and R² are as defined in Table 1.

Table 14 covers 26 compounds of the following formula

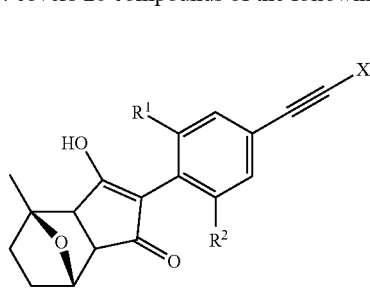

wherein X, R¹ and R² are as defined in Table 1.

Table 15 covers 26 compounds of the following formula

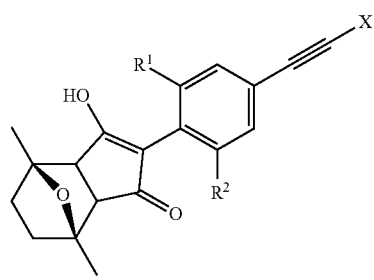

wherein X, R$^1$ and R$^2$ are as defined in Table 1.

Table 16 covers 26 compounds of the following formula

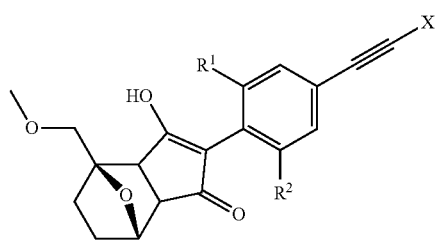

wherein X, R$^1$ and R$^2$ are as defined in Table 1.

Table 17 covers 26 compounds of the following formula

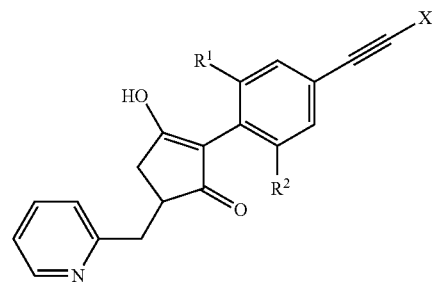

wherein X, R$^1$ and R$^2$ are as defined in Table 1.

Table 18 covers 26 compounds of the following formula

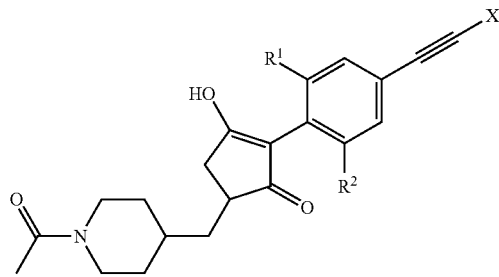

wherein X, R$^1$ and R$^2$ are as defined in Table 1.

Table 19 covers 26 compounds of the following formula

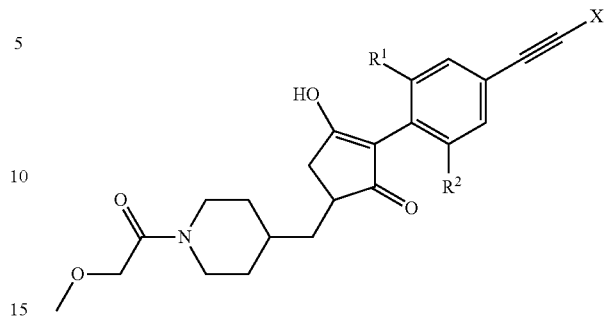

wherein X, R$^1$ and R$^2$ are as defined in Table 1.

Table 20 covers 26 compounds of the following formula

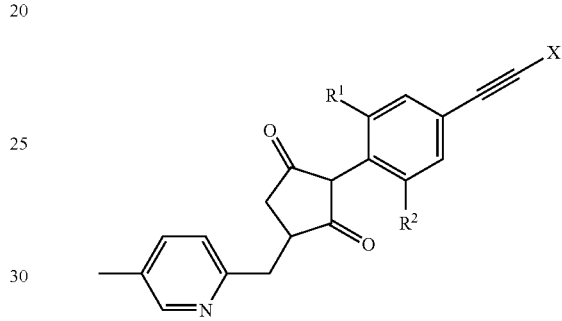

wherein X, R$^1$ and R$^2$ are as defined in Table 1.

Table 21 covers 26 compounds of the following formula

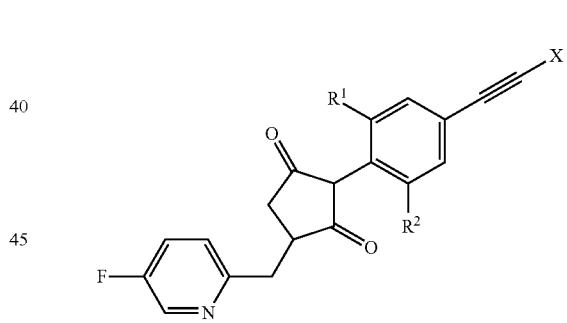

wherein X, R$^1$ and R$^2$ are as defined in Table 1.

Table 22 covers 26 compounds of the following formula

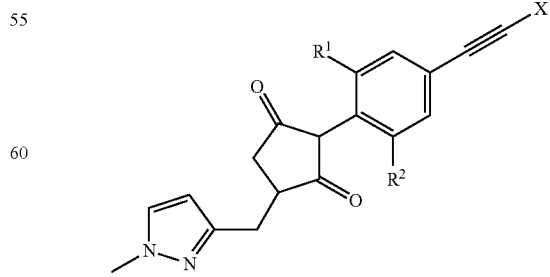

wherein X, R$^1$ and R$^2$ are as defined in Table 1.

Table 23 covers 26 compounds of the following formula

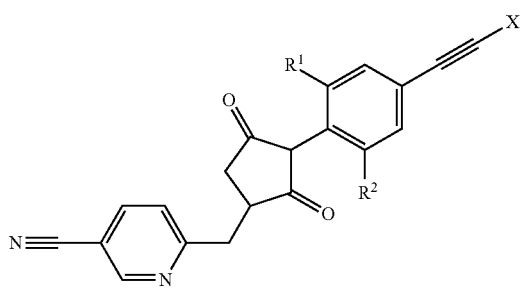

wherein X, $R^1$ and $R^2$ are as defined in Table 1.

Example of Preparation of Compounds in which G is Other than Hydrogen, from Compounds in which G is Hydrogen Preparation of [2-(2,6-dimethyl-4-prop-1-ynyl-phenyl)-3-oxo-4-(2-pyridylmethyl)cyclopenten-1-yl] isopropylsulfanylformate (Compound P-9)

To a solution of the 2-(2,6-dimethyl-4-prop-1-ynyl-phenyl)-4-(2-pyridylmethyl)cyclopentane-1,3-dione (0.100 g, 0.302 mmol) in dichloromethane (3.02 mL) was added N-ethyl-N-isopropyl-propan-2-amine (1.51 mmol, 0.265 mL). The reaction was then cooled in the freezer for 30 minutes before addition of S-isopropyl chlorothioformate (0.075 ml, 0.603 mmol), and then the reaction mixture was stirred overnight at room temperature. The reaction was then washed with water, dried and reduced in vacuo. The crude product was then purified by column chromatography, eluting with acetonitrile and dichloromethane, to give the desired product (23 mg, 18%). The product was characterised by HPLC, as follows.

HPLC (High-Performance Liquid Chromatography) Method

The compounds are analysed using a Waters Fraction Lynx HPLC system comprising a 2767 injector/collector with a 2525 gradient pump, CFO, 2996 photodiode array, 2420 ELSD and Micromass ZQ2000 equipped with a Waters XBridge dC18 column (column length 50 mm, internal diameter of column 4.6 mm, particle size 3.5 microns). The analysis was conducted using a six minute run time, according to the following gradient table:

| Time (mins) | Solvent A (%) | Solvent B (%) | Flow (ml/min) |
|---|---|---|---|
| 0.00 | 95.0 | 5.0 | 2.5 |
| 5.34 | 0.0 | 100 | 2.5 |
| 5.69 | 0.0 | 100 | 2.5 |
| 5.70 | 95.0 | 5.0 | 2.5 |
| 6.00 | 95.0 | 5.0 | 2.5 |

Solvent A = Water with 10 mM ammonium acetate;
Solvent B = Acetonitrile.

The characteristic values obtained for each compound were the retention time (recorded in minutes) and the molecular ion, typically the cation $M+H^+$.

The following Compounds P-1 to P-23 are further examples of the present invention. Most or all of these were made using substantially the above-mentioned preparation method, but varying the halogen-containing reactant (e.g. the chlorine-containing reactant, usually an acid chloride) as the structure of the "G" group (the group attached to oxygen) in the product structures below varied. The $MH^+$ and retention time, as measured using substantially the above-mentioned HPLC method, are given.

| Compound Number | Structure | MH+ | Retention time (min) |
|---|---|---|---|
| P-1 | 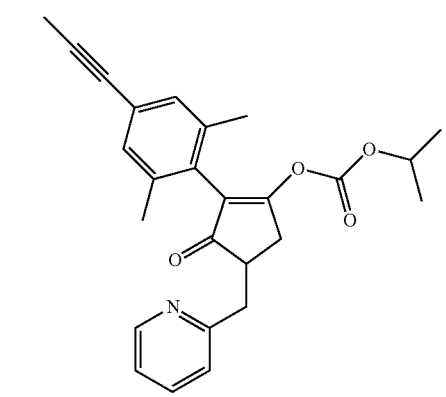 [SMILES: CC#Cc1cc(C)c(C2=C(OC(=O)OC(C)C)CC(Cc3ccccn3)C2=O)c(C)c1] | 418 | 4.48 |

-continued

| Compound Number | Structure | MH+ | Retention time (min) |
|---|---|---|---|
| P-2 | 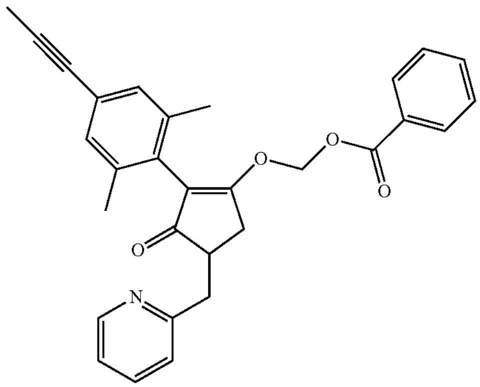 [SMILES: CC#Cc1cc(C)c(C2=C(OCOC(=O)c3ccccc3)CC(Cc3ccccn3)C2=O)c(C)c1] | 466 | 4.51 |
| P-3 | 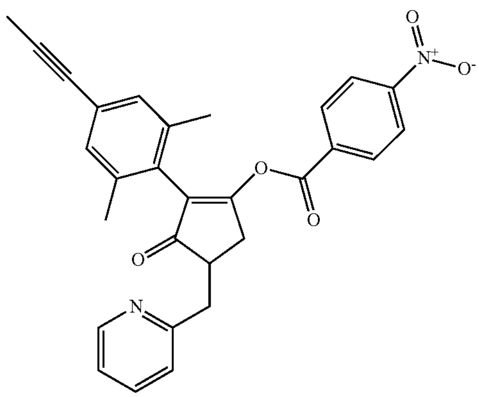 [SMILES: CC#Cc1cc(C)c(C2=C(OC(=O)c3ccc([N+](=O)[O-])cc3)CC(Cc3ccccn3)C2=O)c(C)c1] | 481 | 4.66 |
| P-4 | 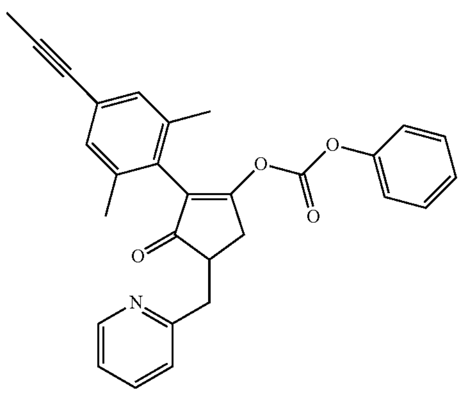 [SMILES: CC#Cc1cc(C)c(C2=C(OC(=O)Oc3ccccc3)CC(Cc3ccccn3)C2=O)c(C)c1] | 452 | 4.66 |
| P-5 | 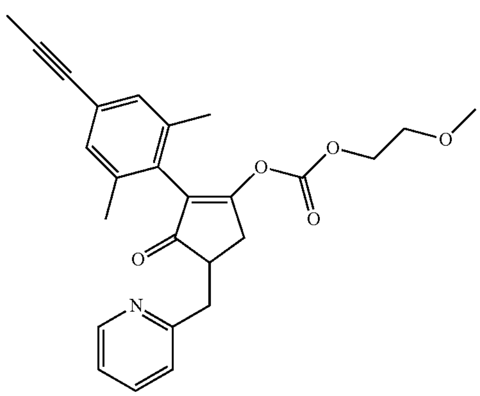 [SMILES: CC#Cc1cc(C)c(C2=C(OC(=O)OCCOC)CC(Cc3ccccn3)C2=O)c(C)c1] | 434 | 4.12 |

-continued

| Compound Number | Structure | MH+ | Retention time (min) |
|---|---|---|---|
| P-6 | 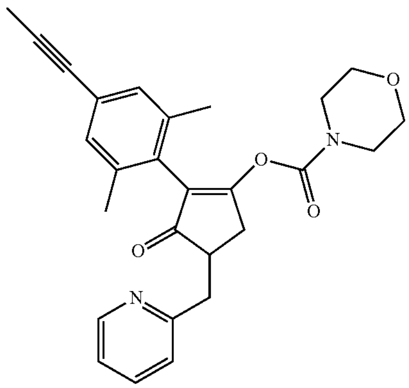 [SMILES: CC#Cc1cc(C)c(C2=C(OC(=O)N3CCOCC3)CC(Cc3ccccn3)C2=O)c(C)c1] | 445 | 3.91 |
| P-7 | 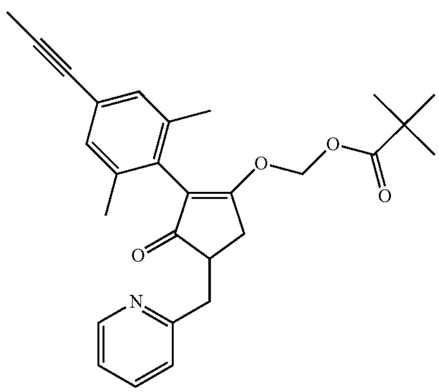 [SMILES: CC#Cc1cc(C)c(C2=C(OCOC(=O)C(C)(C)C)CC(Cc3ccccn3)C2=O)c(C)c1] | 446 | 4.53 |
| P-8 | 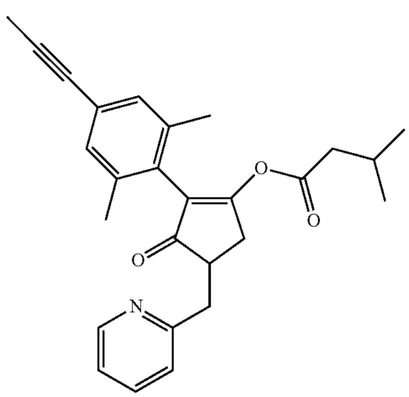 [SMILES: CC#Cc1cc(C)c(C2=C(OC(=O)CC(C)C)CC(Cc3ccccn3)C2=O)c(C)c1] | 416 | 4.8 |
| P-9 | 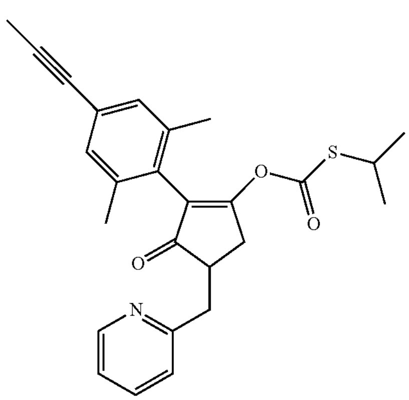 | 434 | 4.92 |

-continued

| Compound Number | Structure | MH+ | Retention time (min) |
|---|---|---|---|
| P-10 | 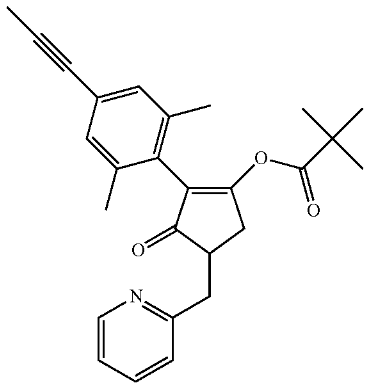 [SMILES: CC#Cc1cc(C)c(C2=C(OC(=O)C(C)(C)C)CC(Cc3ccccn3)C2=O)c(C)c1] | 416 | 4.87 |
| P-11 | 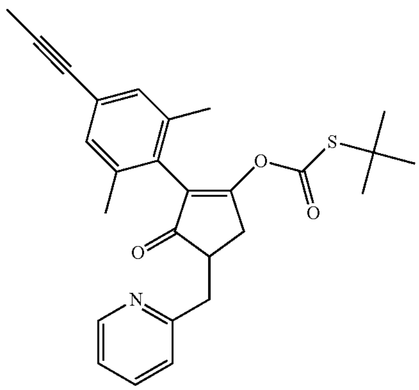 [SMILES: CC#Cc1cc(C)c(C2=C(OC(=O)SC(C)(C)C)CC(Cc3ccccn3)C2=O)c(C)c1] | 448 | 5.13 |
| P-12 | 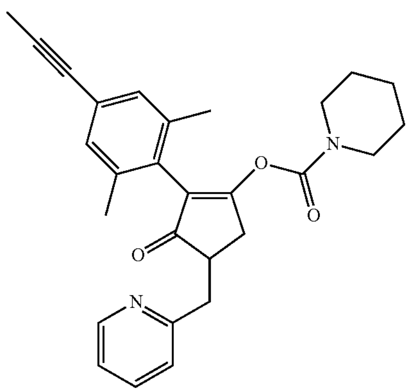 [SMILES: CC#Cc1cc(C)c(C2=C(OC(=O)N3CCCCC3)CC(Cc3ccccn3)C2=O)c(C)c1] | 444 | 4.49 |
| P-13 | 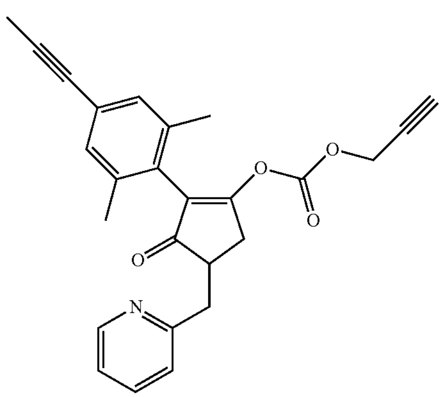 [SMILES: C#CCOC(=O)OC1=C(c2c(C)cc(C#CC)cc2C)C(=O)C(Cc2ccccn2)C1] | 414 | 4.22 |

-continued

| Compound Number | Structure | MH+ | Retention time (min) |
|---|---|---|---|
| P-14 | 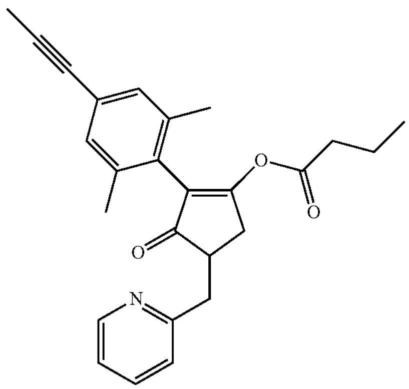 [SMILES: CC#Cc1cc(C)c(C2=C(OC(=O)CCC)CC(Cc3ccccn3)C2=O)c(C)c1] | 402 | 4.57 |
| P-15 | 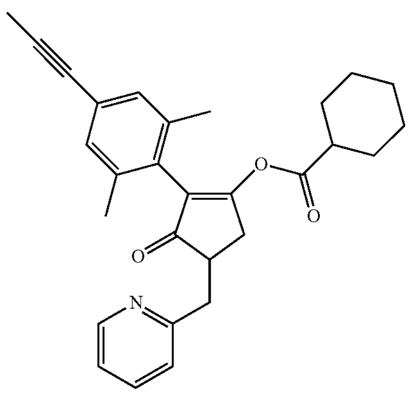 [SMILES: CC#Cc1cc(C)c(C2=C(OC(=O)C3CCCCC3)CC(Cc3ccccn3)C2=O)c(C)c1] | 442 | 5.2 |
| P-16 | 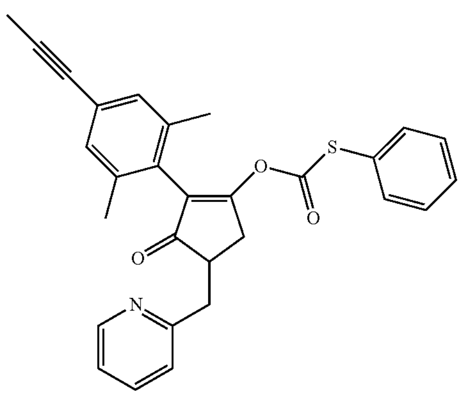 [SMILES: CC#Cc1cc(C)c(C2=C(OC(=O)Sc3ccccc3)CC(Cc3ccccn3)C2=O)c(C)c1] | 468 | 5.02 |
| P-17 | 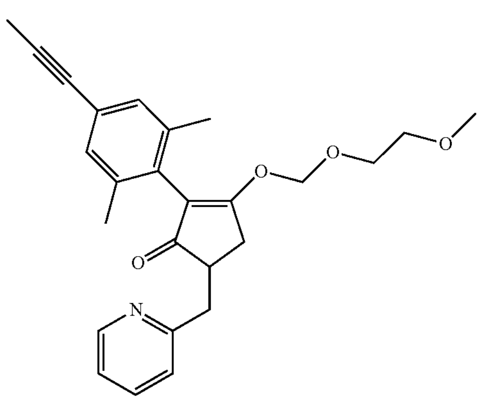 [SMILES: CC#Cc1cc(C)c(C2=C(OCOCCOC)CC(Cc3ccccn3)C2=O)c(C)c1] | 420 | 3.84 |

-continued
| Compound Number | Structure | MH+ | Retention time (min) |
|---|---|---|---|
| P-18 | 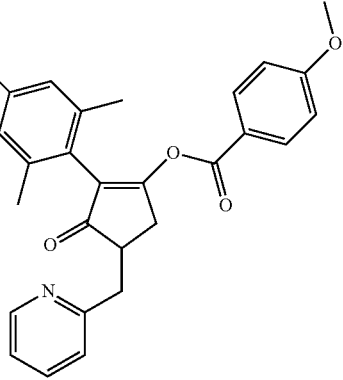 | 466 | 4.71 |
| P-19 | 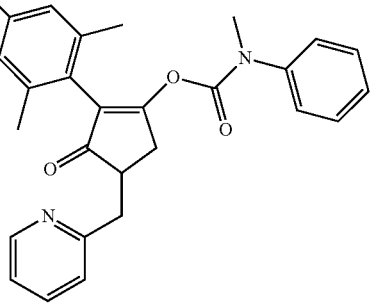 | 465 | 4.52 |
| P-20 | 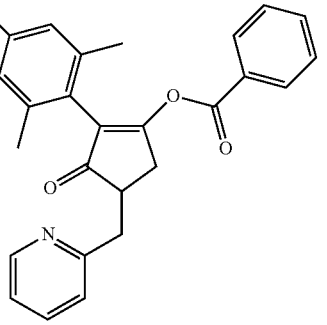 | 436 | 4.76 |
| P-21 | 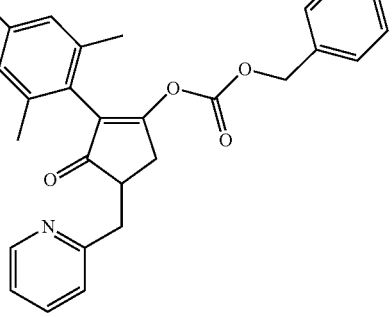 | 466 | 4.72 |

-continued

| Compound Number | Structure | MH+ | Retention time (min) |
|---|---|---|---|
| P-22 | 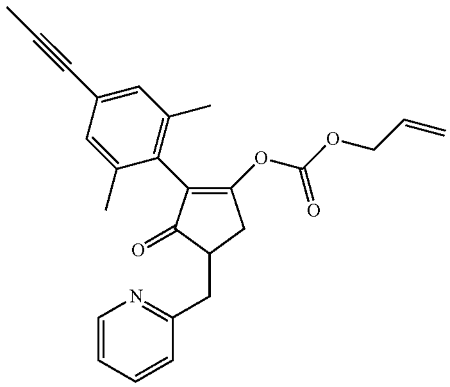 [SMILES: C=CCOC(=O)OC1=C(c2c(C)cc(C#CC)cc2C)C(=O)C(Cc2ccccn2)C1] | 416 | 4.38 |
| P-23 | 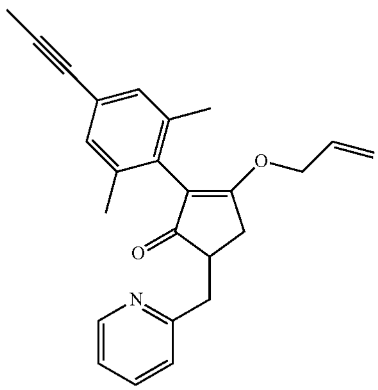 [SMILES: C=CCOC1=C(c2c(C)cc(C#CC)cc2C)C(=O)C(Cc2ccccn2)C1] | 372 | 4.09 |

BIOLOGICAL EXAMPLES

Biological Example 1

Glasshouse Screen for Herbicidal Activity

Seeds of a variety of test species were sown in standard soil in pots. After cultivation for one day (pre-emergence) or after 8 days cultivation (post-emergence) under controlled conditions in a glasshouse (at 24/16°C., day/night; 14 hours light; 65% humidity), the plants were sprayed with an aqueous spray solution derived from the formulation of the "technical" (i.e. unformulated) active ingredient in acetone/water (50:50) solution containing 0.5% Tween 20 (polyoxyethylene sorbitan monolaurate, CAS Registry Number 9005-64-5). The test plants were then grown in a glasshouse under controlled conditions in a glasshouse (at 24/16°C., day/night; 14 hours light; 65% humidity) and watered twice daily. After 13 days for pre- or post-emergence, the test was evaluated visually, and an assessed percentage phytotoxicity score given for each herbicidal application on each plant/weed species (with 100%=total damage to plant; 0%=no damage to plant).

Pre- and post-emergence herbicide application tests using two different selections of weeds follow.

Biological Example 1

Pre-Emergence Herbicidal Activity

Test plants: *Alopecurus myosuroides* (ALOMY), *Setaria faberi* (SETFA), *Echinochloa crus-galli* (ECHCG), *Solanum nigrum* (SOLNI), *Amaranthus retroflexus* (AMARE) and *Ipomoea hederacea* (IPOHE). ALOMY, SETFA and ECHCG are grassy monocotyledonous weeds. SOLNI, AMARE and IPOHE are dicotyledonous (broadleaved) weeds.

| Compound Number | Application Rate (g/ha) | SOLNI | AMARE | SEFTA | ALOMY | ECHCG | IPOHE |
|---|---|---|---|---|---|---|---|
| A-1 | 250 | 0 | 0 | 80 | 100 | 100 | 0 |
| A-3 | 250 | 90 | 90 | 100 | 90 | 100 | 70 |
| A-16 | 250 | 10 | 40 | 90 | 50 | 100 | 0 |
| A-17 | 250 | 80 | 100 | 100 | 80 | 100 | 80 |
| A-18 | 250 | 80 | 100 | 100 | 100 | 100 | 80 |

Test plants: *Lolium perenne* (LOLPE), *Alopecurus myosuroides* (ALOMY), *Echinochloa crus-galli* (ECHCG), and *Avena fatua* (AVEFA). All four of these are grassy monocotyledonous weeds.

| Compound Number | Application Rate (g/ha) | LOLPE | ALOMY | ECHCG | AVEFA |
|---|---|---|---|---|---|
| A-2 | 250 | 100 | 100 | 100 | 70 |
| A-4 | 250 | 100 | 100 | 100 | 70 |
| A-8 | 250 | 100 | 100 | 100 | 100 |
| A-9 | 250 | 100 | 100 | 100 | 100 |
| A-10 | 250 | 100 | 80 | 100 | 90 |
| A-11 | 250 | 100 | 90 | 100 | 70 |
| A-12 | 250 | 90 | 90 | 100 | 80 |
| A-13 | 250 | 80 | 80 | 100 | 80 |
| A-14 | 250 | 90 | 90 | 90 | 50 |
| A-15 | 250 | 100 | 90 | 100 | 70 |
| A-19 | 250 | 100 | 100 | 100 | 100 |
| A-20 | 250 | 100 | 100 | 100 | 90 |
| A-21 | 250 | 100 | 100 | 100 | 60 |
| A-22 | 250 | 90 | 90 | 100 | 80 |
| A-23 | 250 | 80 | 80 | 100 | 80 |
| A-24 | 250 | 100 | 100 | 100 | 80 |
| A-25 | 250 | 100 | 90 | 100 | 70 |
| A-26 | 250 | 100 | 100 | 100 | 100 |
| A-27 | 250 | 100 | 90 | 100 | 90 |
| A-28 | 250 | 90 | 70 | 100 | 70 |
| A-29 | 250 | 50 | 50 | 80 | 100 |

Biological Example 1

Post-Emergence Herbicidal Activity

Test plants: *Alopecurus myosuroides* (ALOMY), *Setaria faberi* (SETFA), *Echinochloa crus-galli* (ECHCG), *Solanum nigrum* (SOLNI), *Amaranthus retroflexus* (AMARE) and *Ipomoea hederacea* (IPOHE). ALOMY, SETFA and ECHCG are grassy monocotyledonous weeds. SOLNI, AMARE and IPOHE are dicotyledonous (broadleaved) weeds.

| Compound Number | Application Rate (g/ha) | SOLNI | AMARE | SEFTA | ALOMY | ECHCG | IPOHE |
|---|---|---|---|---|---|---|---|
| A-1 | 250 | 10 | 0 | 70 | 90 | 100 | 30 |
| A-3 | 250 | 70 | 60 | 100 | 90 | 100 | 30 |
| A-16 | 250 | 20 | 10 | 70 | 50 | 100 | 10 |
| A-17 | 250 | 70 | 10 | 90 | 80 | 100 | 70 |
| A-18 | 250 | 80 | 30 | 100 | 100 | 100 | 80 |

Test plants: *Lolium perenne* (LOLPE), *Alopecurus myosuroides* (ALOMY), *Echinochloa crus-galli* (ECHCG), and *Avena fatua* (AVEFA). All four of these are grassy monocotyledonous weeds.

| Compound Number | Application Rate (g/ha) | LOLPE | ALOMY | ECHCG | AVEFA |
|---|---|---|---|---|---|
| A-2 | 250 | 100 | 100 | 100 | 100 |
| A-4 | 250 | 100 | 90 | 100 | 100 |
| A-5 | 250 | 80 | 80 | 90 | 90 |
| A-6 | 250 | 100 | 100 | 100 | 100 |
| A-7 | 250 | 100 | 100 | 100 | 90 |
| A-8 | 250 | 100 | 100 | 100 | 100 |
| A-9 | 250 | 100 | 90 | 100 | 100 |
| A-10 | 250 | 100 | 90 | 100 | 90 |
| A-11 | 250 | 100 | 100 | 100 | 90 |
| A-12 | 250 | 90 | 90 | 100 | 100 |
| A-13 | 250 | 80 | 70 | 100 | 80 |
| A-14 | 250 | 100 | 100 | 100 | 90 |
| A-15 | 250 | 100 | 90 | 100 | 100 |
| A-19 | 250 | 100 | 100 | 100 | 100 |
| A-20 | 250 | 100 | 100 | 100 | 90 |
| A-21 | 250 | 100 | 100 | 100 | 80 |
| A-22 | 250 | 80 | 60 | 100 | 0 |
| A-23 | 250 | 90 | 100 | 100 | 90 |
| A-24 | 250 | 100 | 100 | 100 | 100 |
| A-25 | 250 | 100 | 90 | 100 | 100 |
| A-26 | 250 | 100 | 100 | 100 | 100 |
| A-27 | 250 | 90 | 70 | 100 | 100 |
| A-28 | 250 | 90 | 90 | 100 | 80 |
| A-29 | 250 | 100 | 100 | 100 | 80 |

Biological Example 2

Comparative Herbicidal Data

Comparative herbicidal data are given for certain exemplified compounds with 4-(prop-1-ynyl)-2,6-dimethylphenyl or 4-(chloroethynyl)-2,6-dimethylphenyl headgroups, compared to the corresponding comparative compounds with 4-ethynyl-2,6-dimethylphenyl headgroups, as follows.

Except where specified otherwise, the glasshouse screen for herbicidal activity is substantially the same as that presented in Biological Example 1 hereinabove. The weed abbreviations are as defined in Biological Example 1.

It can be seen from the results bellow that, for those exemplified compounds with 4-(prop-1-ynyl)-2,6-dimethylphenyl or 4-(chloroethynyl)-2,6-dimethylphenyl headgroups whose results are given below in Biological Example 2, these are generally more potent herbicides when used post-emergence against the grassy monocotyledonous weed species tested and under the conditions tested, compared to the corresponding comparative compounds with 4-ethynyl-2,6-dimethylphenyl headgroups tested under comparable conditions.

Biological Example 2

Post-Emergence Herbicidal Activity (Comparative Data)

Table B2(A)—Post-emergence herbicidal activities (percentage phytotoxicity) at 62.5 g/ha application rate are as follows:

| Compound no. | Structure | LOLPE | ALOMY | ECHCG | AVEFA | SETFA |
|---|---|---|---|---|---|---|
| A-2 | 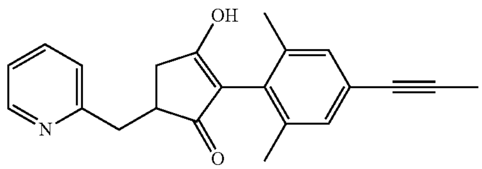 [SMILES: CC#Cc1cc(C)c(C2=C(O)CC(Cc3ccccn3)C2=O)c(C)c1] | 100 | 100 | 100 | 90 | not tested |
| A-3 | 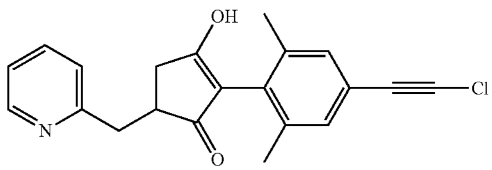 [SMILES: Cc1cc(C#CCl)cc(C)c1C1=C(O)CC(Cc2ccccn2)C1=O] | not tested | 90 | 100 | not tested | 90 |
| Comparative example X-1 | 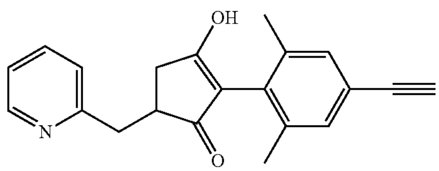 [SMILES: C#Cc1cc(C)c(C2=C(O)CC(Cc3ccccn3)C2=O)c(C)c1] | 100 | 100 | 80 | 90 | not tested |
| A-4 | 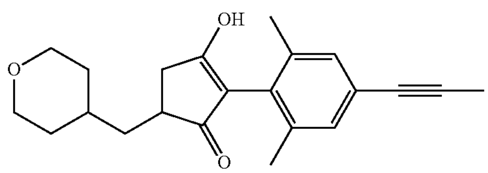 [SMILES: CC#Cc1cc(C)c(C2=C(O)CC(CC3CCOCC3)C2=O)c(C)c1] | 100 | 90 | 100 | 100 | not tested |
| Comparative example X-2 | 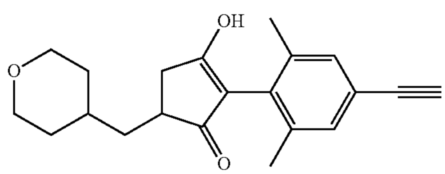 [SMILES: C#Cc1cc(C)c(C2=C(O)CC(CC3CCOCC3)C2=O)c(C)c1] | 90 | 90 | 90 | 90 | not tested |
| A-1 | 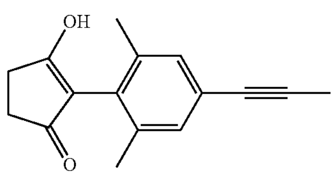 [SMILES: CC#Cc1cc(C)c(C2=C(O)CCC2=O)c(C)c1] | not tested | 80 | 100 | not tested | 60 |
| A-16 | 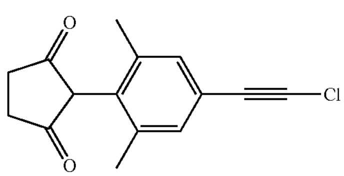 [SMILES: Cc1cc(C#CCl)cc(C)c1C1C(=O)CCC1=O] | not tested | 10 | 90 | not tested | 80 |
| Comparative example X-3 | 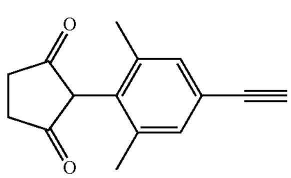 [SMILES: C#Cc1cc(C)c(C2C(=O)CCC2=O)c(C)c1] | not tested | 0 | 20 | not tested | 0 |
| A-17 | 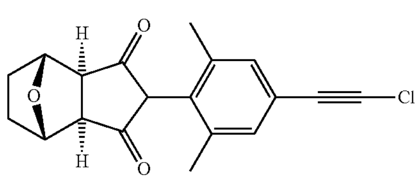 | not tested | 70 | 100 | not tested | 80 |

| Compound no. | Structure | LOLPE | ALOMY | ECHCG | AVEFA | SETFA |
|---|---|---|---|---|---|---|
| A-18 | 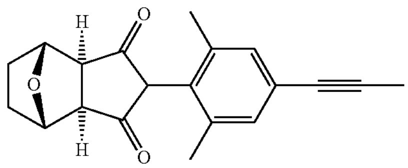 | not tested | 100 | 100 | not tested | 90 |
| Comparative example X-4 | 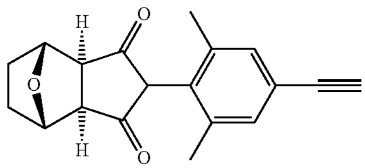 | not tested | 80 | 80 | not tested | 40 |

Table B2(B)—Post-emergence herbicidal activities (percentage phytotoxicity) at 15.625 g/ha application rate are as follows:

| Compound no. | Structure | LOLPE | ALOMY | ECHCG | AVEFA | SETFA |
|---|---|---|---|---|---|---|
| A-2 | 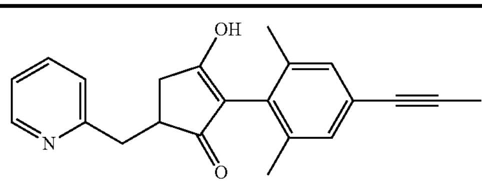 | 100 | 90 | 100 | 80 | not tested |
| A-3 | 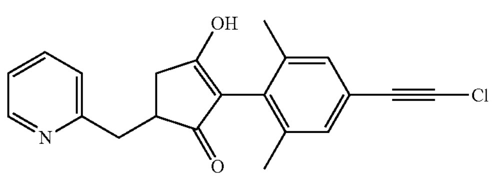 [SMILES: Cc1cc(C#CCl)cc(C)c1C1=C(O)CC(Cc2ccccn2)C1=O] | not tested | 90 | 100 | not tested | 80 |
| Compar. example X-1 | 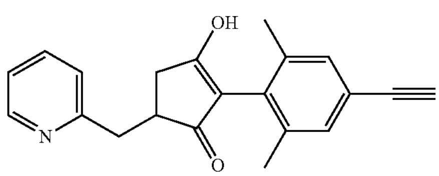 [SMILES: C#Cc1cc(C)c(C2=C(O)CC(Cc3ccccn3)C2=O)c(C)c1] | 60 | 60 | 70 | 50 | not tested |
| A-4 | 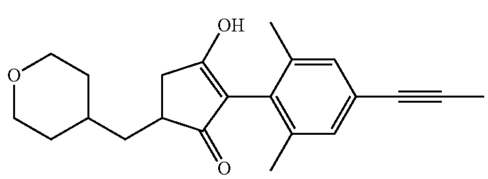 [SMILES: CC#Cc1cc(C)c(C2=C(O)CC(CC3CCOCC3)C2=O)c(C)c1] | 100 | 70 | 100 | 100 | not tested |
| Comparative example X-2 | 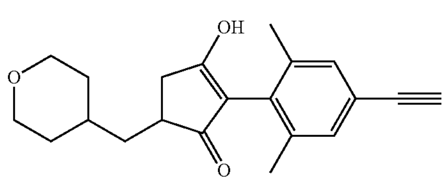 [SMILES: C#Cc1cc(C)c(C2=C(O)CC(CC3CCOCC3)C2=O)c(C)c1] | 80 | 60 | 70 | 90 | not tested |

-continued

| Compound no. | Structure | LOLPE | ALOMY | ECHCG | AVEFA | SETFA |
|---|---|---|---|---|---|---|
| A-1 | 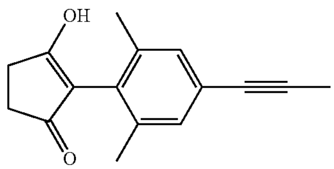 [SMILES: CC#Cc1cc(C)c(C2=C(O)CCC2=O)c(C)c1] | not tested | 20 | 70 | not tested | 40 |
| A-16 | 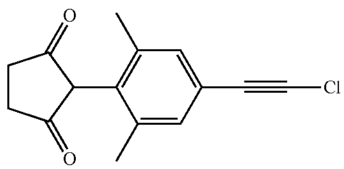 [SMILES: Cc1cc(C#CCl)cc(C)c1C1C(=O)CCC1=O] | not tested | 10 | 70 | not tested | 0 |
| Comparative example X-3 | 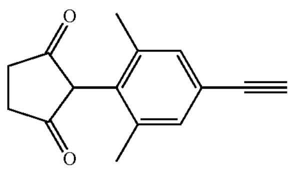 [SMILES: C#Cc1cc(C)c(C2C(=O)CCC2=O)c(C)c1] | not tested | 0 | 0 | not tested | 0 |
| A-17 | 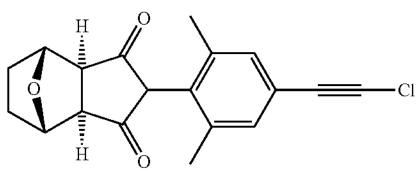 | not tested | 60 | 100 | not tested | 80 |
| A-18 | 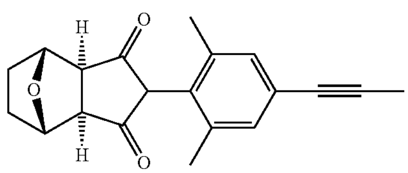 | not tested | 90 | 100 | not tested | 70 |
| Comparative example X-4 | 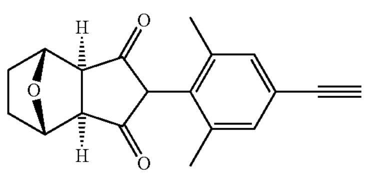 | not tested | 30 | 80 | not tested | 40 |

Notes regarding the Comparative Examples X-1, X-2, and X-4:

Comparative Example X-1

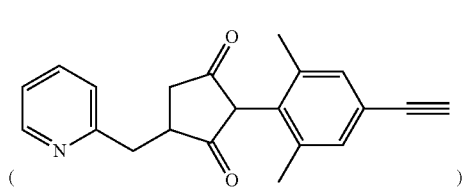 [SMILES: C#Cc1cc(C)c(C2C(=O)CC(Cc3ccccn3)C2=O)c(C)c1]

is disclosed as Compound T65 on page 83 of WO 2010/069834 A1 (Syngenta Participations AG and Syngenta Limited), whose compounds were stated to have herbicidal properties.

Comparative Example X-2

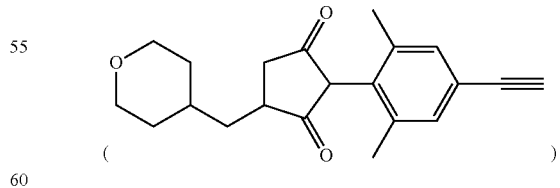

is disclosed in Table 19 on pages 126-127 of WO 2010/000773 A1, with reference to the substituent definitions of compound 1.042 in Table 1 on pages 113-114 of WO 2010/000773 A1. WO 2010/000773 A1 (Syngenta Limited) discloses 5-(heterocyclylalkyl)-3-hydroxy-2-phenylcyclopent-2-enone compounds and certain derivatives thereof as herbicides.

Comparative Example X-4

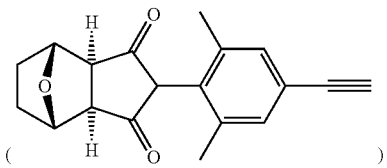

is covered by, but is not specifically disclosed in, WO 2009/019005 A2 (Syngenta Limited), whose compounds were stated to have herbicidal properties. [Therefore, a further aspect of the present invention provides a compound having the following structure:

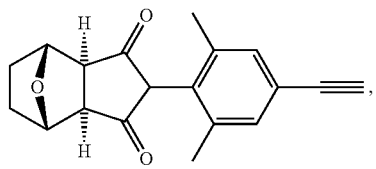

or an agrochemically acceptable salt thereof.] WO 2009/019005 A2 does disclose the following compound in Table 35 on page 139, with reference to the substituent definitions of compound 1.001 in Table 1 on page 110 of WO 2009/019005 A2:

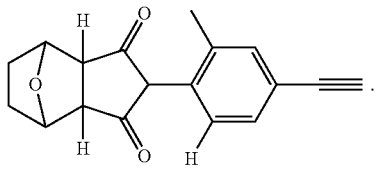 [SMILES: C#Cc1ccc(C2C(=O)C3C4CCC(O4)C3C2=O)c(C)c1]

Biological Example 3

Glasshouse Screen for Herbicidal Activity

Test Method: Seeds of a variety of test species are sown in standard soil in pots. After cultivation for one day (pre-emergence) or after 12 days cultivation (post-emergence) under controlled conditions in a glasshouse (warm climate species at 24/18°C., cool climate species at 20/16°C., both at day/night; 16 hours light; 65% humidity), the plants are sprayed with an aqueous spray solution derived from the formulation of the "technical"(i.e. unformulated) active ingredient dissolved in acetone plus IF50, at a 1:20 ratio of "technical"active ingredient to IF50. The IF50 contains about 10.56 weight % Emulsogen EL™(castor oil ethoxylate, CAS Registry number 61791-12-6), about 42.22 weight % N-methylpyrrolidone, and about 42.22 weight % DPG-Monoethyl ether (dipropylene glycol mono-ethyl ether). The adjuvant X-77 (a mixture of alkyl aryl polyoxyethylene glycols and free fatty acids in isopropanol, CAS Registry number 11097-66-8) is added to the aqueous spray solution to form a 0.2% v/v solution, before spraying onto the plants.

The test plants are then grown in a glasshouse under controlled conditions in a glasshouse (at 24/18°C. or 20/16°C., day/night; 16 hours light; 65% humidity) and watered twice daily. After 15 days after application of the herbicide (15 DAA) (for post-emergence), and after 20 DAA (for pre-emergence), the test is evaluated visually, and an assessed percentage phytotoxicity score is given for each herbicidal application on each plant/weed species (with 100%=total damage to plant; 0%=no damage to plant).

Inter alia the following plant species are tested:

| Latin species name | Common English name | BAYER plant species code |
|---|---|---|
| Cool climate species: | | |
| Triticum aestivum | wheat | TRZAW |
| Alopecurus myosuroides | blackgrass | ALOMY |
| Avena fatua | wild oats | AVEFA |
| Lolium perenne | perennial ryegrass | LOLPE |
| Warm climate species: | | |
| Echinochloa crus galli | barnyardgrass | ECHCG |

Biological Example 3

Post-Emergence Herbicidal Activity

The post-emergence herbicidal activity results on some grassy weeds and on wheat (TRZAW) for some compounds of the invention (which have prop-1-ynyl groups at the 4-position of the phenyl ring) and for some comparative examples (which do not have prop-1-ynyl groups at the 4-position of the phenyl ring), are as follows. These give an approximate indication of the level of selectivity on wheat for these tested compounds, when a herbicide safener such as cloquintocet-mexyl is not used:

| Compound Number | Application rate (g/ha) | TRZAW | ALOMY | AVEFA | LOLPE | ECHCG |
|---|---|---|---|---|---|---|
| A-2 | 30 | 30 | 90 | 70 | 90 | 100 |
| A-4 | 30 | 80 | 100 | 80 | 100 | 100 |
| A-7 | 30 | 40 | 70 | 40 | 80 | 80 |
| A-8 | 30 | 40 | 80 | 70 | 90 | 70 |
| A-9 | 30 | 20 | 70 | 30 | 50 | 70 |
| A-11 | 30 | 40 | 90 | 70 | 80 | 100 |
| A-14 | 30 | 20 | 70 | 0 | 70 | 90 |
| A-19 | 30 | 70 | 100 | 90 | 80 | 100 |
| A-19 | 15 | 20 | 80 | 40 | 30 | 70 |
| A-18 | 8 | 40 | 70 | 30 | 80 | 80 |
| Compound T71, from WO 2010/069834 | 30 | 80 | 100 | 100 | 90 | 100 |
| Compound 1 in Table 22, from WO 2010/069834 | 30 | 70 | 100 | 90 | 70 | 90 |
| Compound 27 in Table 17, from WO 2010/069834 | 30 | 50 | 70 | 30 | 10 | 100 |
| A-1 | 125 | 40 | 70 | 0 | 50 | 80 |
| A-7 | 60 | 50 | 80 | 50 | 90 | 100 |
| A-9 | 60 | 30 | 80 | 30 | 100 | 100 |

-continued

| Compound Number | Application rate (g/ha) | TRZAW | ALOMY | AVEFA | LOLPE | ECHCG |
|---|---|---|---|---|---|---|
| A-10 | 60 | 50 | 80 | 50 | 40 | 80 |
| A-11 | 60 | 50 | 100 | 100 | 100 | 100 |
| A-14 | 60 | 40 | 90 | 60 | 80 | 90 |
| A-15 | 60 | 30 | 50 | 80 | 40 | 80 |

Notes:
Compound T71 disclosed in WO 2010/069834 (Syngenta) is

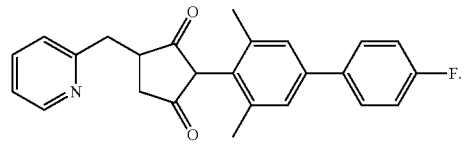 [SMILES: Cc1cc(-c2ccc(F)cc2)cc(C)c1C1C(=O)CC(Cc2ccccn2)C1=O]

Compound 1 in Table 22, disclosed in WO 2010/069834, is

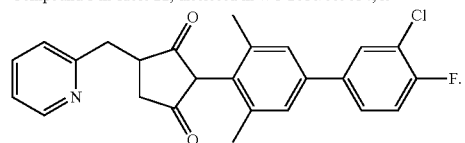

Compound 27 in Table 17, disclosed in WO 2010/069834, is:

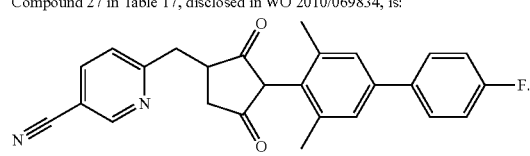

Biological Example 4

Post-Emergence Herbicidal Activity & Cereal Crop Phytotoxicity Data at 30 and 60 g/ha for Various Compounds, with or without 50 g/ha Cloquintocet-Mexyl Safener Biological Example 4A Previously-Formulated Compounds Seeds of a variety of test species are sown in standard soil in pots. After cultivation for 14 days under controlled conditions in a glasshouse (at 22/16°C., day/night; 16 hours light; 65% humidity), the plants are sprayed with the test compounds. The test plants are then grown on under controlled conditions in the glasshouse (at 22/16°C., day/night; 16 hours light; 65% humidity) and are watered twice daily. After 14 days the test is evaluated visually (100%=total damage to plant; 0%=no damage to plant). Post-emergence herbicidal activity (phytotoxicity) data, on certain grassy monocotyledonous weeds and cereal crops in a glasshouse, are measured 14 days after application of the herbicide (14 DAA), inter alia for post-emergence application rates of 30 or 60 g/ha of the test herbicide, with or without 50 g/ha of cloquintocet-mexyl safener applied at substantially the same time as the herbicide.

Herbicidal activity (phytotoxicity) is evaluated visually, and an assessed percentage phytotoxicity score is given for each herbicidal application on each plant species (with 100%=total damage to plant; 0%=no damage to plant). Two repetitions are made for each experiment and the mean herbicidal activity (phytotoxicity) data is reported.

Biological Example 4A is used on previously-formulated compounds, typically compounds previously formulated as an emulsifiable concentrates (EC), wherein the EC contains the herbicidal compound under test dissolved in one or more organic solvents, and wherein the EC also contains one or more surfactants or emulsifiers. In the test method, the EC containing the herbicide (plus a cloquintocet-mexyl formulation if this is also present) is generally diluted with water to form an emulsion, and the resulting emulsion is sprayed onto the emerged weed and/or crop plants.

For the testing of Compounds A-5 and A-6, each of these compounds was separately formulated into an emulsifiable concentrate containing 10% w/w of the herbicidal compound, 9% w/w of castor oil ethoxylate (an emulsifier, present as Emulsogen™EL360), 6% w/w of calcium dodecylbenzenesulfonate (linear) (an emulsifier, present as Nansa™EVM 63B), 3% w/w of tristyrylphenol ethoxylate having 16 moles of ethoxylation per mole of molecule (an emulsifier, present as Soprophor™BSU), 10% w/w of benzyl benzoate (as solvent), 20% w/w of 1-methyl-2-pyrrolidone (as solvent), and the remainder of N-octyl-2-pyrrolidone (as solvent). The solvents and surfactants/emulsifiers were first mixed together, to form a "blank" EC, and the herbicidal compound was then added to and dissolved in this solvent and emulsifier mixture to prepare the emulsifiable concentrate, to give an EC formulation/composition containing approximately 100 g/L of active herbicidal compound.

In the tests of Compounds A-5 and A-6, the cloquintocet-mexyl was pre-formulated as a formulation/composition containing 10% w/w cloquintocet-mexyl, 6% w/w Emulsogen™ EL360 (as emulsifier), 4% w/w Nansa™EVM 63B (as wetting agent), 1% w/w Drapex™39 (epoxidised soybean oil), 20% w/w 1-methyl-2-pyrrolidone (as solvent), and the remainder as Solvesso™200ND (a mixture of heavy aromatic hydrocarbons, as a solvent).

A selection of results according to the method of Biological Example 4A for Compounds A-5 and A-6 (which are the two enantiomers of one compound) are as follows. Two repetitions are made for each experiment; the mean herbicidal activity (phytotoxicity) data is reported.

Biological Example 4A

Post-Emergence Herbicidal Activity (% Phytotoxicity) on Grassy Monocotyledonous Weeds—at 14 Days after Application

| Compound | Application Rate (g/ha) | cloquintocetmexyl application rate (g/ha) | AVEFA | LOLMU | SETVI | POAAN | ALOMY |
|---|---|---|---|---|---|---|---|
| A-5 | 60 | 0 | 83 | 95 | 98 | 18 | 93 |
| A-5 | 60 | 50 | 68 | 99 | 95 | 5 | 98 |
| A-5 | 30 | 0 | 58 | 93 | 80 | 0 | 58 |
| A-5 | 30 | 50 | 23 | 68 | 85 | 13 | 63 |
| A-6 | 60 | 0 | 100 | 100 | 100 | 94 | 100 |
| A-6 | 60 | 50 | 99 | 100 | 100 | 85 | 100 |

-continued

| Compound | Application Rate (g/ha) | cloquintocetmexyl application rate (g/ha) | AVEFA | LOLMU | SETVI | POAAN | ALOMY |
|---|---|---|---|---|---|---|---|
| A-6 | 30 | 0 | 98 | 100 | 100 | 65 | 100 |
| A-6 | 30 | 50 | 90 | 100 | 100 | 48 | 100 |

Test plants: *Avena fatua* (AVEFA), *Lolium multiflorum* (LOLMU), *Setaria viridis* (SETVI), *Poa annua* (POAAN), *Alopecurus myosuroides* (ALOMY). All five of these are grassy monocotyledonous weeds.

Biological Example 4A

Post-Emergence Phytotoxicity (%) on Cereal Crops—at 14 Days after Application

| Compound | Application Rate (g/ha) | cloquintocet-mexyl application rate (g/ha) | Winter Wheat "Hereward" | Spring Wheat "Teal" | Spring Barley "Harrington" | Winter Barley "Suzuka" |
|---|---|---|---|---|---|---|
| A-5 | 60 | 0 | 53 | 80 | 88 | 65 |
| A-5 | 60 | 50 | 0 | 0 | 18 | 0 |
| A-5 | 30 | 0 | 40 | 43 | 73 | 33 |
| A-5 | 30 | 50 | 0 | 0 | 3 | 0 |
| A-6 | 60 | 0 | 80 | 94 | 98 | 98 |
| A-6 | 60 | 50 | 20 | 45 | 48 | 25 |
| A-6 | 30 | 0 | 65 | 78 | 95 | 93 |
| A-6 | 30 | 50 | 15 | 25 | 13 | 10 |

Biological Example 4B

Not-Previously-Formulated Compounds

Seeds of a variety of test species are sown in standard soil in pots. After cultivation for 14 days under controlled conditions in a glasshouse (at 22/16°C., day/night; 16 hours light; 65% humidity), the plants are sprayed with an aqueous spray solution derived from the formulation of the technical active ingredient dissolved in acetone plus IF50 containing 10.56 wt % Emulsogen™EL (castor oil ethoxylate, CAS Registry number 61791-12-6)

42.22 wt % N-Methyl pyrrolidone 42.22 wt % dipropylene glycol monoethyl ether at a 1:20 ratio of (technical active ingredient:IF50). The adjuvant Adigor™(an adjuvant containing inter alia methylated rapeseed oil, e.g. available from Syngenta) is added to form a 0.5% v/v solution. The test plants are then grown on under controlled conditions in the glasshouse (at 22/16°C., day/night; 16 hours light; 65% humidity) and are watered twice daily. After 14 days the test is evaluated (100%=total damage to plant; 0%=no damage to plant).

Post-emergence herbicidal activity (phytotoxicity) data, on certain grassy monocotyledonous weeds and cereal crops in a glasshouse, are measured 14 days after application of the herbicide (14 DAA), for (a) a post-emergence application rate of 60 g/ha of the test herbicide with or without 50 g/ha of cloquintocet-mexyl safener applied at substantially the same time as the herbicide, and (b) for a post-emergence application rate of 30 g/ha of the test herbicide with 50 g/ha of cloquintocet-mexyl safener applied at substantially the same time as the herbicide. Herbicidal activity (phytotoxicity) is evaluated visually, and an assessed percentage phytotoxicity score is given for each herbicidal application on each plant species (with 100%=total damage to plant; 0%=no damage to plant). Two repetitions are made for each experiment, and the mean herbicidal activity (phytotoxicity) data is reported.

It can bee seen that Biological Example 4B is run under a slightly different protocol to Biological Example 4A, in that it uses "technical"(i.e. unformulated, not-previously-formulated) herbicidal compound.

A selection of the results obtained in Biological Example 4B for Compounds A-8, A-11, A-14, A-19 and A-26, are as follows:

Biological Example 4B

Post-Emergence Herbicidal Activity (% Phytotoxicity) on Grassy Monocotyledonous Weeds—at 14 Days after Application

| Compound | Application Rate g/ha | cloquintocet-mexyl application rate (g/ha) | AVEFA | LOLMU | SETVI | POAAN | ALOMY |
|---|---|---|---|---|---|---|---|
| A-8 | 60 | 0 | 97 | 92 | 75 | 80 | 94 |
| A-8 | 60 | 50 | 95 | 94 | 75 | 75 | 94 |
| A-8 | 30 | 50 | 45 | 68 | 55 | 65 | 63 |
| A-11 | 60 | 0 | 93 | 95 | 98 | 75 | 85 |
| A-11 | 60 | 50 | 88 | 88 | 97 | 75 | 85 |

-continued

| Compound | Application Rate g/ha | cloquintocet-mexyl application rate (g/ha) | AVEFA | LOLMU | SETVI | POAAN | ALOMY |
|---|---|---|---|---|---|---|---|
| A-11 | 30 | 50 | 50 | 68 | 89 | 70 | 73 |
| A-14 | 60 | 0 | 83 | 100 | 100 | 85 | 97 |
| A-14 | 60 | 50 | 80 | 97 | 100 | 85 | 97 |
| A-14 | 30 | 50 | 38 | 88 | 99 | 83 | 78 |
| A-19 | 60 | 0 | 99 | 100 | 100 | 92 | 100 |
| A-19 | 60 | 50 | 99 | 100 | 100 | 92 | 100 |
| A-19 | 30 | 50 | 90 | 100 | 100 | 80 | 100 |
| A-19 | 15 | 50 | 88 | 98 | 99 | 75 | 99 |
| A-26 | 60 | 0 | 100 | 100 | 100 | 73 | 100 |
| A-26 | 60 | 50 | 100 | 100 | 100 | 70 | 100 |
| A-26 | 30 | 50 | 100 | 100 | 100 | 33 | 100 |
| A-26 | 15 | 50 | 99 | 100 | 95 | 13 | 99 |
| A-26 | 7.5 | 50 | 83 | 90 | 68 | 0 | 97 |

Test plants: *Avena fatua* (AVEFA), *Lolium multiflorum* (LOLMU), *Setaria viridis* (SETVI), *Poa annua* (POAAN), *Alopecurus myosuroides* (ALOMY). All five of these are grassy monocotyledonous weeds.

Biological Example 4B

Post-Emergence Phytotoxicity (%) on Cereal Crops—at 14 Days after Application

| Compound | Application Rate (g/ha) | cloquintocet-mexyl application rate (g/ha) | Winter Wheat "Hereward" | Spring Wheat "Teal" | Spring Barley "Harrington" | Winter Barley "Suzuka" |
|---|---|---|---|---|---|---|
| A-8 | 60 | 0 | 63 | 73 | 85 | 73 |
| A-8 | 60 | 50 | 45 | 25 | 75 | 60 |
| A-8 | 30 | 50 | 13 | 0 | 18 | 9 |
| A-11 | 60 | 0 | 55 | 38 | 58 | 68 |
| A-11 | 60 | 50 | 8 | 15 | 13 | 33 |
| A-11 | 30 | 50 | 3 | 8 | 8 | 8 |
| A-14 | 60 | 0 | 80 | 83 | 95 | 97 |
| A-14 | 60 | 50 | 78 | 65 | 95 | 93 |
| A-14 | 30 | 50 | 30 | 13 | 70 | 45 |
| A-19 | 60 | 0 | 89 | 90 | 98 | 97 |
| A-19 | 60 | 50 | 75 | 83 | 94 | 95 |
| A-19 | 30 | 50 | 65 | 73 | 38 | 55 |
| A-19 | 15 | 50 | 58 | 23 | 3 | 3 |
| A-26 | 60 | 0 | 99 | 100 | 100 | 100 |
| A-26 | 60 | 50 | 98 | 97 | 100 | 100 |
| A-26 | 30 | 50 | 90 | 93 | 99 | 100 |
| A-26 | 15 | 50 | 80 | 78 | 80 | 53 |
| A-26 | 7.5 | 50 | 30 | 23 | 10 | 4 |

Biological Example 5

Soil Persistence Analytical Data

Biological Example 5A

"DT50" Soil Persistence Method

Field soil is sieved to 2 mm. Approximately 900 g of soil is treated with solutions of each chemical dissolved in water/methanol (9:1 v/v) for all substances to give a final soil concentration of approximately 0.4 mg of each compound for each treatment. The treatments are made drop-wise using a syringe. Each treated soil is thoroughly mixed and 150 g soil removed in order to provide triplicate 0 DAT samples. The remaining soil is stored in a plastic tub provided with ventilation holes in the lid, at 20°C. in a controlled environment room. Moisture contents of treated samples are measured at regular intervals and maintained at the starting levels (see table below) by addition of water. The units are sampled by removal of 50 g of soil at intervals up to 56 DAT and the samples stored at −20°C. until required for analysis.

20 g samples from each timepoint are extracted by shaking with acetonitrile/1 M ammonium hydroxide (80:20 v/v) for all substances, followed by centrifugation.

After extraction the samples are diluted with water 10-fold for all solutions and analysed by LC-MS/MS. Degradation kinetics, and an estimated half-life (T½) of the compound in the particular soil, can then be calculated using simple first order assumptions.

Abbreviations:

DAT=days after start of treatment or test.

LC-MS=liquid chromatography/mass spectrometry.

MS=mass spectrometry.

Characterizing data for 5 types of soil which can be used in the above method follows.

TABLE 5.1

Soil Characterization Data

| Soil | Soil Classification | pH H$_2$O | pH 0.01M CaCl$_2$ | % OM | CEC meq/100 g | Particle Size Analysis % Sand | % Silt | % Clay | Moisture Content used in Study (%) |
|---|---|---|---|---|---|---|---|---|---|
| 18 Acres | sandy clay loam | 6.3 | 5.8 | 5.6 | 20.3 | 49 | 24 | 27 | about 30 |
| Gartenacker | loam | 7.2 | 6.9 | 5.0 | 10.9 | 43 | 44 | 13 | about 36 |
| Marsillargues | silty clay loam | 8.1 | 7.5 | 2.0 | 9.7 | 5 | 54 | 41 | about 22 |
| Krone | silty clay loam | 7.2 | 5.9 | 1.7 | 18.4 | 20 | 65 | 15 | about 34 |
| Pappelacker | loamy sand | 7.3 | 6.9 | 3.5 | 6.2 | 77 | 15 | 8 | about 30 |
| East Anglia 1 | sandy loam | 8.0 | 7.4 | 2.3 | 5.7 | 71 | 16 | 13 | about 30 |

Abbreviations and Notes for Table 5.1:

OM = organic matter (% in the soil).

CEC = cation exchange capacity for the soil.

The particle size analyses (percentages of sand, silt and clay) are approximate.

18 Acres sandy clay loam soil is taken from a United Kingdom (UK) site close to Syngenta Limited, Jealott's Hill International Research Centre, Bracknell, Berkshire RG42 6EY, UK (soil collection site is on Hawthorn Lane, GPS location X=51.454442, Y=−0.720644). Gartenacker loam soil is from Les Barges, Valais, Switzerland (GPS location X=46.331300, Y=6.924100). Marsillargues silty clay loam soil is from Marsillargues, Hérault, France (GPS location X=43.606356, Y=4.142253). Krone silty clay loam soil is from Möhlin, Aargau, Switzerland (GPS location X=47.555283, Y=7.854136). Pappelacker loamy sand soil is from Les Barges, Valais, Switzerland (GPS location X=46.331300, Y=6.924100). East Anglia 1 soil is from Melton Constable, Norfolk, United Kingdom (GPS location X=52.869000, Y=1.097000). GPS=Global Positioning System.

Biological Example 5B

"RASP"Soil Persistence Method

Field soil (of the type "18 Acres", as described in Biological Example 5A and Table 5.1 above) is sieved to 2 mm. The sieved soil is wetted up with distilled water, mixing thoroughly until it reaches "field capacity". "Field capacity"is determined by the finger test as the point where the soil is wet to the touch but does not "ball up". Usually, the moisture content of the soil used is about 25%.

For each compound tested, 6×50 mL polypropylene centrifuge tubes containing 10 g±0.5 g of soil at field capacity are used. Each tube lid has a 2 mm hole to allow for air circulation during the incubation period.

4×10 microliters of treatment solutions of the compounds to be tested are applied to the surface of the soil in groups of 6 tubes. 4×10 microliter drops are also dispensed into the treatment check vials and these are diluted to 1 mL with acetonitrile; at this point additional samples can be prepared for HPLC method development if required.

Two of the tubes containing the treated soil are capped and immediately frozen as T0 (day zero) samples. The remaining four samples are capped with lids containing a 2 mm hole drilled into the lid and incubated in controlled environment cabinets for the correct time interval at 20°C., 80% relative humidity.

After both one and four weeks incubation, two tubes from each treatment are removed from the cabinets, the lids are replaced for ones lacking ventilation holes and the tubes are frozen. When the samples are ready for analysis, a zero time, 1 week and 4 week sample for each compound is removed from the freezer and allowed to thaw. Immediately after thawing, 40 mL of extraction solution is added to the samples.

Samples are extracted using a mixture such as 80:20 (v/v) acetonitrile/1 M ammonium hydroxide solution.

After addition of the extraction solvent, the tubes are capped and shaken on a flatbed shaker for 1 hour. After shaking, the tubes are centrifuged at 3000 rpm for 5 minutes.

All samples from the test are analysed by UPLC-MS. For example, the samples are typically run on an acetonitrile/0.2% acetic acid solvent gradient and scanned from 150 to 750 amu (atomic mass units) in both electrospray positive and negative modes.

For each compound, the molecular ion giving the best sensitivity is chosen and a single ion monitoring method is set up. The method development samples are re-analysed using the selected ion monitoring methods to check that suitable sensitivity is obtained.

Degradation kinetics, and an estimated half-life (T½) of the compound in the soil, can then be calculated using simple first order assumptions.

Abbreviations:

UPLC=Ultra Performance Liquid Chromatography. MS=mass spectrometry. HPLC=High Performance Liquid Chromatography.

Soil Persistence Results from Biological Examples 5A (DT50 Test) and 5B (RASP Test)

The estimated approximate half-life (T½) or half-lives of the tested compound(s) in the relevant soil(s), measured using substantially the above two methods, were found to be as follows. A "NT"means that the compound was not tested in the test method shown:

| Compound Number | Structure | RASP Test: estimated soil T½ (except where shown otherwise) | DT50 Test: estimated soil T½; and soil type used |
|---|---|---|---|
| A-6 | 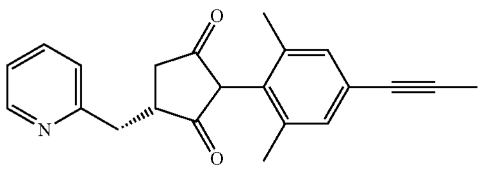 | NT | 4 days (Krone)<br>8 days (18 Acres)<br>6 days (East Anglia 1)<br>5 days (Gartenacker)<br>4 days (Pappelacker) |
| A-8 | 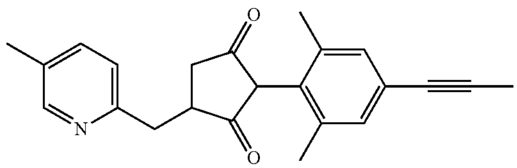 [SMILES: CC#Cc1cc(C)c(C2C(=O)CC(Cc3ccc(C)cn3)C2=O)c(C)c1] | NT | 7 days (18 Acres)<br>3 days (Gartenacker)<br>6 days (Marsillargues) |
| A-14 | 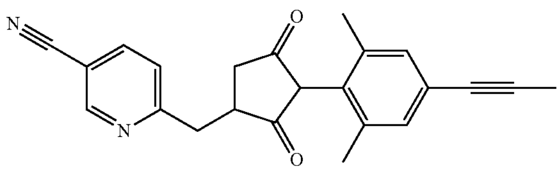 [SMILES: CC#Cc1cc(C)c(C2C(=O)CC(Cc3ccc(C#N)cn3)C2=O)c(C)c1] | estimated soil T½ < 1 week | <1 day (18 Acres)<br>1 day (Gartenacker)<br>1 day (Marsillargues) |
| A-19 | 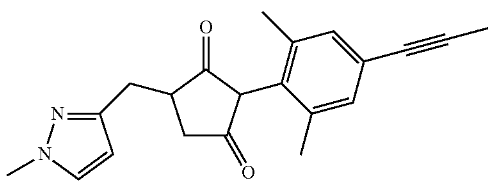 [SMILES: CC#Cc1cc(C)c(C2C(=O)CC(Cc3ccn(C)n3)C2=O)c(C)c1] | % of compound remaining at 0, 1 and 4 weeks = 80, 79 and 80% respectively. | NT |
| A-20 | 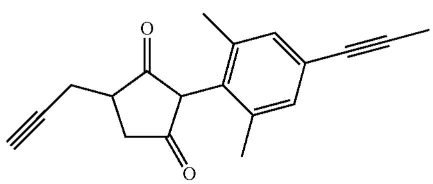 [SMILES: C#CCC1CC(=O)C(c2c(C)cc(C#CC)cc2C)C1=O] | estimated soil T½ = about 4 weeks | NT |
| A-23 | 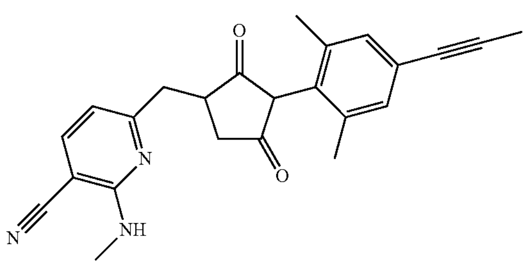 [SMILES: CC#Cc1cc(C)c(C2C(=O)CC(Cc3ccc(C#N)c(NC)n3)C2=O)c(C)c1] | estimated soil T½ = about 2 weeks | NT |
| A-26 | 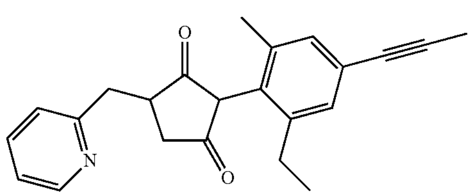 [SMILES: CC#Cc1cc(C)c(C2C(=O)CC(Cc3ccccn3)C2=O)c(CC)c1] | estimated soil T½ = about 4 weeks | NT |

| Compound Number | Structure | RASP Test: estimated soil T½ (except where shown otherwise) | DT50 Test: estimated soil T½; and soil type used |
|---|---|---|---|
| A-27 | 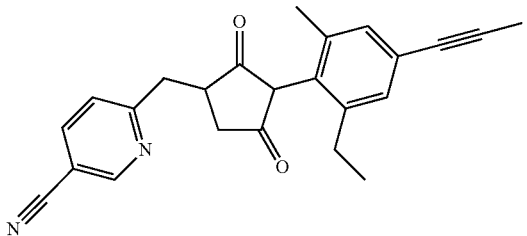 [SMILES: CC#Cc1cc(C)c(C2C(=O)CC(Cc3ccc(C#N)cn3)C2=O)c(CC)c1] | estimated soil T½ being measured | NT |

The above results are preliminary indications that at least Compounds A-6, A-8, A-14, A-20, A-23 and A-26 apparently have quite a low half-life within soil, i.e. quite a low soil persistence, which may lead to certain environmental and/or regulatory advantages such as: the compound not persisting for too long in the environment after spraying on a field, and/or possibly a reduced potential to leach into and/or to negatively affect groundwater.

The invention claimed is:

1. A compound of formula (I):

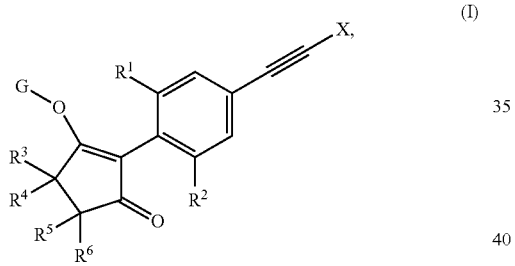

wherein:

X is methyl or chlorine;

$R^1$ is methyl or chlorine;

$R^2$ is hydrogen, methyl, ethyl, n-propyl, cyclopropyl, vinyl, ethynyl, fluorine, chlorine, bromine, methoxy, ethoxy or fluoromethoxy;

$R^3$, $R^4$ and $R^5$, independently of each other, are hydrogen, $C_1$-$C_5$alkyl, $C_2$-$C_4$ alkenyl, $C_2$-$C_4$alkynyl, $C_1$-$C_2$fluoroalkyl or $C_1$-$C_3$alkoxy$C_1$-$C_3$alkyl; and $R^6$ is: hydrogen; $C_1$-$C_5$alkyl; $C_2$-$C_4$ alkenyl; $C_2$-$C_4$alkynyl; $R^{6AA}$—C≡C—$CH_2$—; $C_1$-$C_2$fluoroalkyl; $C_1$-$C_3$alkoxy$C_1$-$C_3$alkyl; $C_1$-$C_3$alkylthio$C_1$-$C_3$alkyl; $C_1$-$C_3$alkylsulfinyl$C_1$-$C_3$alkyl; $C_1$-$C_3$alkylsulfonyl$C_1$-$C_3$alkyl; $C_3$-$C_4$cycloalkyl; or an unsubstituted 4, 5 or 6 membered monocyclic heterocyclyl having one ring heteroatom independently selected from oxygen, sulfur and nitrogen, and attached at a ring carbon atom within the heterocyclyl;

or $R^6$ is Q-$(CH_2)_m$—CH($R^7$)—, wherein m is 0 or 1, and either $R^7$ is hydrogen or $R^7$ and $R^5$ together are a bond, and Q is an optionally substituted heterocyclyl as defined below;

or $R^6$ is Het-CH($R^8$)—, wherein either $R^8$ is hydrogen or $R^8$ and $R^5$ together are a bond, and Het is an optionally substituted heteroaryl as defined below;

or $R^6$ is $C_3$-$C_6$cycloalkyl$C_1$-$C_2$alkyl-; or is $C_4$-$C_6$cycloalkyl$C_1$-$C_2$alkyl- substituted, at a cycloalkyl ring-carbon atom which is not the ring-carbon atom attached to the —$C_1$-$C_2$alkyl- moiety and which is not bonded directly to the ring-carbon atom attached to the —$C_1$-$C_2$alkyl- moiety, by one or two ring substituents which independently are: =N—O—$R^{10}$, oxo (=O), $C_1$-$C_4$alkoxy, $C_1$-$C_2$haloalkoxy, 2—($C_1$-$C_3$alkoxy)-ethoxy, $C_3$-$C_5$cycloalkyloxy, ($C_3$-$C_5$cycloalkyl)methoxy, $C_2$-$C_3$alkenyl-$CH_2$-oxy, $C_1$-$C_3$alkyl or $C_1$-$C_2$fluoroalkyl; or benzyloxy in which the phenyl ring is optionally substituted by one or two substituents independently being methyl, methoxy, $C_1$fluoroalkoxy, fluorine or chlorine;

or $R^6$ is benzyl optionally substituted on its phenyl ring by one or two substituents which independently are: cyano, —C≡C —$R^{6A}$, —C($R^{6B}$)=C($R^{6C}$)($R^{6CC}$), —C(O) —$R^{6D}$, —S(O)$_2$—$R^{6E}$, —N($R^{6F}$)($R^{6G}$), $C_1$-$C_3$alkoxy, $C_1$-$C_2$fluoroalkoxy, cyclopropyloxy, $CH_2$=CH—$CH_2$—O—, HC≡C—$CH_2$—O—, halogen, $C_1$-$C_2$alkyl, or $C_1$fluoroalkyl;

or $R^3$ and $R^4$ taken together are —$(CH_2)_{n1}$— or —$(CH_2)_{n2}$—$X^1$—$(CH_2)_{n3}$— and $R^5$ and $R^6$ are as defined herein, or $R^5$ and $R^6$ taken together are —$(CH_2)_{n1}$, — or —$(CH_2)_{n2}$—$X^1$—$(CH_2)_{n3}$— and $R^3$ and $R^4$ are as defined herein;

or $R^4$ and $R^6$ taken together are —C($R^{11}$)($R^{12}$)—C($R^{13}$)($R^{14}$)—C($R^{15}$)($R^{16}$)—C($R^{17}$)($R^{18}$)—, —C($R^{11}$)($R^{12}$)—C($R^{13}$)=C($R^{15}$)—C($R^{17}$)($R^{18}$)—, or —CH($R^{19}$)—C($R^{20}$)($R^{21}$)—CH($R^{22}$)—;

wherein Q is a 4 to 7 membered monocyclic or an 8 to 11 membered fused bicyclic heterocyclyl, having one or two ring heteroatoms independently selected from oxygen, sulfur and nitrogen;

and wherein the heterocyclyl Q is optionally substituted by 1 or 2 ring-carbon substituents independently being $C_1$-$C_3$alkyl, $C_1$-$C_2$fluoroalkyl or oxo (=O), and/or is optionally substituted by one $C_1$-$C_4$alkyl, $C_1$-$C_2$fluoroalkyl, $C_1$-$C_4$alkoxy, $C_1$-$C_2$fluoroalkoxy, $R^9$—C(O)— or $C_1$-$C_2$alkyl-S(O)$_2$— substituent on a ring nitrogen if present, and/or is optionally substituted by one or two oxo (=O) substituents on a ring sulfur if present;

wherein Het is a heteroaryl, attached at a ring-carbon, which is optionally substituted by 1, 2 or 3 ring-carbon substituents independently being $C_1$-$C_3$alkyl, $C_1$-$C_2$fluoroalkyl, $C_1$-$C_3$alkyl-C(O)—, $C_1$-$C_2$fluoroalkyl-C(O)—, —C(O)—N($R^{6H}$)($R^{6J}$), —S(O)$_2$—R$^{6E}$, —N(R$^{6F}$)(R$^{6G}$), hydroxy (including any oxo tautomer), C$_2$-C$_3$alkenyl, —C(R$^{6BB}$)=C(R$^{6C1}$)(R$^{C2}$), C$_2$-C$_3$alkynyl, —C≡C—R$^{6AA}$, C$_1$-C$_3$alkoxy, C$_1$-C$_2$fluoroalkoxy, cyclopropyloxy, CH$_2$=CH—CH$_2$—O—, HC≡C—CH$_2$—O—, halogen, cyano or nitro;

provided that any non-fluorine halogen, alkoxy, fluoroalkoxy, cyclopropyloxy, CH$_2$=CH-CH$_2$—O—or HC≡C—CH$_2$—O—, is not substituted at any ring-carbon bonded directly to a ring-nitrogen of the heteroaryl;

and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one C$_1$-C$_3$alkyl, C$_1$-C$_2$fluoroalkyl, C$_1$-C$_3$alkyl-C(O)—, C$_1$-C$_2$fluoroalkyl-C(O)—or C$_1$-C$_2$alkyl-S(O)$_2$—substituent;

wherein:
R$^{6A}$ is hydrogen, methyl, C$_1$fluoroalkyl, fluorine, chlorine or bromine;
R$^{6AA}$ is C$_1$fluoroalkyl, fluorine, chlorine or bromine;
R$^{6B}$, R$^{6C}$ and R$^{6CC}$ independently are hydrogen, methyl, C$_1$fluoroalkyl, fluorine or chlorine;
provided that R$^{6B}$, R$^{6C}$ and R$^{6CC}$ in total contain no more than one carbon atom, and R$^{6B}$, R$^{6C}$ and R$^{6CC}$ in total comprise no more than one chlorine; and
R$^{6BB}$, R$^{6C1}$ and R$^{6C2}$ independently are hydrogen, methyl, C$_1$fluoroalkyl, fluorine or chlorine;
provided that R$^{6BB}$, R$^{6C1}$ and R$^{6C2}$ in total contain no more than one carbon atom, and R$^{6BB}$, R$^{6C1}$ and R$^{6C2}$ in total comprise no more than one chlorine; and provided that —C(R$^{6BB}$)=C(R$^{6C1}$) R$^{6C2}$) is not C$_2$-C$_3$alkenyl; and
R$^{6D}$ and R$^{6E}$ independently are C$_1$-C$_3$alkyl, C$_1$fluoroalkyl, or —N(R$^{6H}$)(R$^{6J}$);
R$^{6F}$ is —C(O)—C$_1$-C$_2$alkyl, —C(O)—C$_1$fluoroalkyl, —S(O)$_2$-C$_1$-C$_2$alkyl, —S(O)$_2$-C$_1$fluoroalkyl, C$_1$-C$_2$alkyl, or C$_1$fluoroalkyl;
R$^{6G}$ and R$^{6J}$ independently are hydrogen, methyl or C$_1$fluoroalkyl; and
R$^{6H}$ is hydrogen, C$_1$-C$_2$alkyl (e.g. methyl), or C$_1$fluoroalkyl;
and wherein R$^9$ is C$_1$-C$_4$alkyl, C$_2$-C$_4$alkenyl attached at a carbon atom partaking in the C=C double bond, C$_1$-C$_2$fluoroalkyl, C$_1$-C$_2$alkoxymethyl-, C$_1$-C$_3$alkoxy, cyclopropyl, furanyl, morpholin-4-yl, isoxazol-3-yl, 5-methyl-isoxazol-3-yl, pyrazol-5-yl, 3-methylpyrazol-5-yl, 1-methylpyrazol-5-yl, 1,3-dimethylpyrazol-5-yl; or phenyl or phenyl substituted by 1 or 2 substituents independently being methyl, ethyl, C$_1$fluoroalkyl, methoxy, C$_1$fluoroalkoxy, fluorine or chlorine;
wherein R$^{10}$ and R$^{23}$ are independently hydrogen, C$_1$-C$_4$alkyl, C$_1$-C$_2$fluoroalkyl, 2-(C$_1$-C$_3$alkoxy)-ethyl, C$_3$-C$_5$cycloalkyl or (C$_3$-C$_5$cycloalkyl)methyl;
wherein X$^1$ is O, S, S(O), S(O)$_2$, NH, N(C$_1$-C$_3$alkyl), N(C$_1$-C$_3$alkoxy), C(H)(C$_1$-C$_2$alkyl), C(C$_1$-C$_2$alkyl)$_2$, C(H)(C$_1$-C$_3$alkoxy) or C(Me)(C$_1$-C$_2$alkoxy); and
n1 is 2, 3, 4 or 5; and
n2 and n3 are independently 1, 2 or 3 provided that n2+n3 is 2, 3 or 4;
wherein:
R$^{11}$ and R$^{18}$ are both hydrogen, or R$^{11}$ and R$^{18}$ are taken together and form an —O— or —C$_1$-C$_2$alkylene-bridge; and
R$^{12}$ and R$^{17}$ are independently hydrogen, C$_1$-C$_3$alkyl or C$_1$-C$_2$alkoxyC$_1$-C$_2$alkyl;

R$^{13}$, R$^{14}$ and R$^{15}$ are independently hydrogen, C$_1$-C$_3$alkyl or C$_1$-C$_2$alkoxyC$_1$-C$_2$alkyl, provided that one, two or all of R$^{13}$, R$^{14}$ and R$^{15}$ are hydrogen; and
R$^{16}$ is hydrogen; C$_1$-C$_3$alkyl; C$_1$-C$_2$alkoxyC$_1$-C$_2$alkyl; phenyl optionally substituted by 1, 2 or 3 of, independently, methyl, C$_1$fluoroalkyl, methoxy, C$_1$fluoroalkoxy, methylthio, fluorine, chlorine, cyano or nitro; or pyridinyl attached at a ring-carbon and optionally substituted by 1, 2 or 3 ring-carbon substituents independently being methyl, C$_1$fluoroalkyl, methoxy, C$_1$fluoroalkoxy, hydroxy (including any oxo tautomer), fluorine, chlorine, cyano or nitro, provided that any chlorine, methoxy or C$_1$fluoroalkoxy is not substituted at any ring-carbon bonded directly to the ring-nitrogen of the pyridinyl;
and wherein:
R$^{19}$ and R$^{22}$ are independently hydrogen, C$_1$-C$_3$alkyl or C$_1$-C$_2$alkoxyC$_1$-C$_2$alkyl; and
R$^{20}$ and R$^{21}$ are independently hydrogen, C$_1$-C$_3$alkyl or C$_1$-C$_2$alkoxyC$_1$-C$_2$alkyl;
or R$^{20}$ and R$^{21}$ taken together are oxo (=O), =N—O—R$^{23}$, or =CH$_2$;
or R$^{20}$ and R$^{21}$, together with the carbon atom to which they are attached, form a 5, 6 or 7 membered saturated heterocyclyl, wherein the heterocyclyl has two ring heteroatoms independently being oxygen or sulfur and which are not directly bonded to each other, and wherein the heterocyclyl is optionally substituted by 1, 2 or 3 ring-carbon substituents independently being C$_1$-C$_2$alkyl;
and wherein:
G is hydrogen; an agriculturally acceptable metal, or an agriculturally acceptable sulfonium or ammonium group; or G is C$_1$-C$_8$alkyl, C$_2$-C$_8$fluoroalkyl, phenylC$_1$-C$_8$alkyl (wherein the phenyl is optionally substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, C$_1$-C$_3$alkylthio, C$_1$-C$_3$alkylsulfinyl, C$_1$-C$_3$alkylsulfonyl, halogen, cyano or nitro), heteroarylC$_1$-C$_8$alkyl (wherein the heteroaryl is optionally substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, C$_1$-C$_3$alkylthio, C$_1$-C$_3$alkylsulfinyl, C$_1$-C$_3$ alkylsulfonyl, halogen, cyano or nitro), C$_2$-C$_7$alkenyl-CH$_2$—, C$_2$-C$_7$alkenyl-CH(Me)-, C$_2$-C$_7$alkenyl-CMe$_2$-, C$_2$-C$_4$fluoroalkenyl-CH$_2$—, C$_2$-C$_7$alkynyl-CH$_2$—, —C(X$^a$)—R$^a$, —C(X$^b$)—X$^c$—R$^b$, —C(X$^d$)—N(R$^c$)—R$^d$, —SO$_2$—R$^e$, —P(X$^e$)(R$^f$)—R$^g$ or —CH$_2$—X$^f$—R$^h$;
wherein X$^a$, X$^b$, X$^c$, X$^d$, X$^e$ and X$^f$ are independently of each other oxygen or sulfur; and wherein
R$^a$ is H, C$_1$-C$_{21}$alkyl, C$_2$-C$_{21}$alkenyl, C$_2$-C$_{18}$alkynyl, C$_1$-C$_{10}$fluoroalkyl, C$_1$-C$_{10}$cyanoalkyl, C$_1$-C$_{10}$nitroalkyl, C$_1$-C$_{10}$aminoalkyl, C$_1$-C$_5$alkylamino(C$_1$-C$_5$)alkyl, C$_2$-C$_8$dialkylamino(C$_1$-C$_5$)alkyl, C$_3$-C$_7$cycloalkyl(C$_1$-C$_5$)alkyl, C$_1$-C$_5$alkoxy(C$_1$-C$_5$)alkyl, C$_3$-C$_5$alkenyloxy(C$_1$-C$_5$)alkyl, C$_3$-C$_5$alkynyloxy(C$_1$-C$_5$)alkyl, C$_1$-C$_5$alkylthio(C$_1$-C$_5$)alkyl, C$_1$-C$_5$alkylsulfinyl(C$_1$-C$_5$)alkyl, C$_1$-C$_5$alkylsulfonyl(C$_1$-C$_5$)alkyl, C$_2$-C$_8$alkylideneaminoxy(C$_1$-C$_5$)alkyl, C$_1$-C$_5$alkylcarbonyl(C$_1$-C$_5$)alkyl, C$_1$-C$_5$alkoxycarbonyl(C$_1$-C$_5$)alkyl, aminocarbonyl(C$_1$-C$_5$)alkyl, C$_1$-C$_5$alkylaminocarbonyl(C$_1$-C$_5$)alkyl, C$_2$-C$_8$dialkylaminocarbonyl(C$_1$-C$_5$)alkyl, C$_1$-C$_5$alkylcarbonylamino(C$_1$-C$_5$)alkyl, N—(C$_1$-C$_5$) alkylcarbonyl-N—(C$_1$-C$_5$)alkylamino(C$_1$-C$_5$)alkyl, C$_3$-C$_6$trialkylsilyl(C$_1$-C$_5$)alkyl, phenyl(C$_1$-C$_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl$C_1$-$C_5$alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkyl-thio, $C_1$-$C_3$alkylsulfinyl, $C_1$-$C_3$alkylsulfonyl, halogen, cyano, or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or by nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino or $C_3$-$C_7$cycloalkoxy;

or $R^c$ and $R^d$, together with the nitrogen to which they are bonded, form an unsubstituted 4, 5, 6 or 7 membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$alkoxy, $C_1$-$C_{10}$fluoroalkoxy, $C_1$-$C_5$alkylamino or di($C_1$-$C_4$alkyl)amino;

$R^f$ and $R^g$ are are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$fluoroalkoxy, $C_1$-$C_5$alkylamino or di($C_1$-$C_4$alkyl)amino; or benzyloxy or phenoxy, wherein the benzyl and phenyl groups are in turn optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino ($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl ($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), phenoxy($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryloxy($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or phenyl-C(O)— or $C_1$-$C_6$alkyl-C(O)—;

wherein "heteroaryl" means an aromatic ring system containing at least one ring heteroatom and consisting either of a single ring or of two fused rings;

and wherein the compound of formula (I) is optionally present as an agrochemically acceptable salt thereof.

2. A compound as claimed in claim 1, wherein $R^6$ is not $R^{6AA}$—C≡C—CH$_2$—, and is not optionally substituted benzyl;

wherein Het is a heteroaryl, attached at a ring-carbon, which is optionally substituted by 1, 2 or 3 ring-carbon substituents independently being $C_1$-$C_3$alkyl, $C_1$-$C_2$fluoroalkyl, $C_1$-$C_3$alkyl-C(O)—, $C_1$-$C_2$fluoroalkyl-C(O)—, hydroxy (including any oxo tautomer), $C_2$-$C_3$alkenyl, $C_2$-$C_3$alkynyl, $C_1$-$C_3$alkoxy, $C_1$-$C_2$fluoroalkoxy, halogen, cyano or nitro; provided that any non-fluorine halogen, alkoxy or fluoroalkoxy is not substituted at any ring-carbon bonded directly to a ring-nitrogen of the heteroaryl;

and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$— substituent;

and wherein $R^h$ is not phenyl-C(O)— or $C_1$-$C_6$alkyl-C(O)—.

3. A compound as claimed in claim 1, wherein G is hydrogen; an agriculturally acceptable metal, or an agriculturally acceptable sulfonium or ammonium group; or G is —C($X^a$)—$R^a$ or —C($X^b$)—$X^c$—$R^b$, wherein $X^a$, $R^a$, $X^b$, $X^c$, and $R^b$ are as defined in claim 1.

4. A compound as claimed in claim 1, wherein, when G is —C($X^a$)—$R^a$ or —C($X^b$)—$X^c$—$R^b$, then $X^a$, $X^b$ and $X^c$ are oxygen, $R^a$ is $C_1$-$C_{10}$alkyl, $C_2$-$C_6$alkenyl, $C_2$-$C_6$alkynyl, $C_3$-$C_6$cycloalkyl or $C_1$-$C_4$alkoxy$C_1$-$C_4$alkyl; and $R^b$ is $C_1$-$C_{10}$alkyl, $C_2$-$C_5$alkenyl-$CH_2$—, $C_2$-$C_4$alkenyl-CH(Me)-, $C_2$-$C_5$alkynyl-$CH_2$—, $C_2$-$C_4$alkynyl-CH(Me)-, $C_3$-$C_6$cycloalkyl or $C_1$-$C_4$alkoxy$C_1$-$C_4$alkyl.

5. A compound as claimed in claim 1, wherein X is methyl.

6. A compound as claimed in claim 1, wherein $R^1$ is methyl.

7. A compound as claimed in claim 1, wherein X is methyl, and $R^1$ is methyl.

8. A compound as claimed in claim 1, wherein $R^2$ is hydrogen, methyl, ethyl, ethynyl, chlorine, methoxy or fluoromethoxy.

9. A compound as claimed in claim 1, wherein $R^2$ is methyl.

10. A compound as claimed in claim 1, wherein $R^3$, $R^4$ and $R^5$ are hydrogen;
or $R^3$ and $R^5$ are hydrogen, and $R^4$ and $R^6$ taken together are —C($R^{11}$)($R^{12}$)—C($R^{13}$)($R^{14}$)—C($R^{15}$)($R^{16}$)—C($R^{17}$)($R^{18}$)—, —C($R^{11}$)($R^{12}$)—C($R^{13}$)=C($R^{15}$) —C($R^{17}$)($R^{18}$)—, or —CH($R^{19}$)—C($R^{20}$)($R^{21}$)—CH($R^{22}$)—.

11. A compound as claimed in in claim 1, wherein:
$R^6$ is Q-CH($R^7$)— in which $R^7$ is hydrogen;
or $R^6$ is Het-CH($R^8$)— in which $R^8$ is hydrogen;
or $R^4$ and $R^6$ taken together are —C($R^{11}$)($R^{12}$)—C($R^{13}$)($R^{14}$)—C($R^{15}$)($R^{16}$) —C($R^{17}$)($R^{18}$)— or —C($R^{11}$)($R^{12}$)—C($R^{13}$)=C($R^{15}$)—C($R^{17}$)($R^{18}$)—.

12. A compound as claimed in claim 1, wherein:
$R^6$ is Q-CH($R^7$)— or Het-CH($R^8$)—; and
$R^7$ and $R^8$ are hydrogen.

13. A compound as claimed in claim 1: Q is a 4, 5 or 6 membered monocyclic heterocyclyl, having one ring heteroatom selected from oxygen, sulfur and nitrogen;
and wherein the heterocyclyl Q is optionally substituted by one $R^9$—C(O)— or $C_1$-$C_2$alkyl-S(O)$_2$— substituent on a ring nitrogen if present, and/or is optionally substituted by one or two oxo (=O ) substituents on a ring sulfur if present; and wherein:
Q is attached at a ring carbon atom to the —(CH$_2$)$_m$—CH($R^7$)— or —CH($R^7$)—moiety; and
in Q, the one ring heteroatom is not directly bonded to the ring atom which is the position of attachment to the —(CH$_2$)$_m$—CH($R^7$)— or —CH($R^7$)— moiety.

14. A compound as claimed in claim 1, wherein Q is one of the sub-formulae Q$_2$, or Q$_7$:

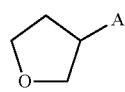  Q$_2$

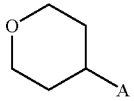  Q$_7$ wherein A is the position of attachment to the —(CH$_2$)$_m$—CH($R^7$)— or —CH($R^7$)— moiety.

15. A compound as claimed in any preceding claim, wherein:
Het is a monocyclic heteroaryl, attached at a ring-carbon, which is optionally substituted by 1 or 2 ring-carbon substituents independently being $C_1$-$C_2$alkyl, $C_1$fluoroalkyl, $C_1$-$C_2$alkyl-C(O)—, $C_1$fluoroalkyl-C(O)—, hydroxy (including any oxo tautomer), ethynyl, prop-1-ynyl, $C_1$-$C_2$alkoxy, $C_1$fluoroalkoxy, fluorine, chlorine, bromine, cyano or nitro, provided that any chlorine, bromine, alkoxy or fluoroalkoxy is not substituted at any ring-carbon bonded directly to a ring-nitrogen of the heteroaryl;
and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$—substituent.

16. A compound as claimed in claim 1, wherein Het is an optionally substituted monocyclic heteroaryl, attached at a ring-carbon, which is:
pyridinyl, pyrazolyl, imidazolyl, pyrazinyl, pyrimidinyl, pyridazinyl, triazolyl, tetrazol-5-yl, oxazolyl, thiazolyl, isoxazolyl, isothiazolyl or oxadiazolyl; optionally present as an agrochemically acceptable salt thereof.

17. A compound as claimed in claim 1, wherein Het is an optionally substituted monocyclic heteroaryl, attached at a ring-carbon, which is:
pyridinyl, pyrazolyl, imidazolyl, pyrazinyl, pyrimidinyl, or pyridazinyl; optionally present as an agrochemically acceptable salt thereof.

18. A compound as claimed in claim 1, wherein Het is an optionally substituted monocyclic heteroaryl, attached at a ring-carbon, which is: pyridin-2-yl or pyrazol-3yl; optionally present as an agrochemically acceptable salt thereof.

19. A compound as claimed in claim 1, wherein, in Het, any ring-carbon atom, which is directly bonded to the ring atom which is the point of attachment to the —CH($R^8$)— moiety, is unsubstituted.

20. A compound as claimed in claim 1, wherein:
$R^{10}$ and $R^{23}$ are independently hydrogen, $C_1$-$C_2$alkyl or $C_1$fluoroalkyl;
$X^1$ is O, NH, NMe, N(OMe), C(H)($C_1$-$C_3$alkoxy), or C(Me)($C_1$-$C_2$alkoxy);
n1 is 4 or 5; and
n2 and n3 are independently 1 or 2 provided that n2+n3 is 3 or 4.

21. A compound as claimed in claim 1, wherein, when $R^4$ and $R^6$ taken together are —C($R^{11}$)($R^{12}$)—C($R^{13}$)($R^{14}$)—C($R^{15}$)($R^{16}$)—C($R^{17}$)($R^{18}$)— or —C($R^{11}$)($R^{12}$)—C ($R^{13}$)=C($R^{15}$) —C($R^{17}$)($R^{18}$)—, then $R^4$ and $R^6$ taken together are:

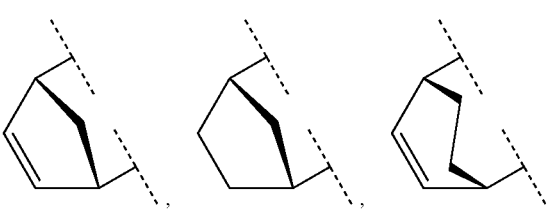

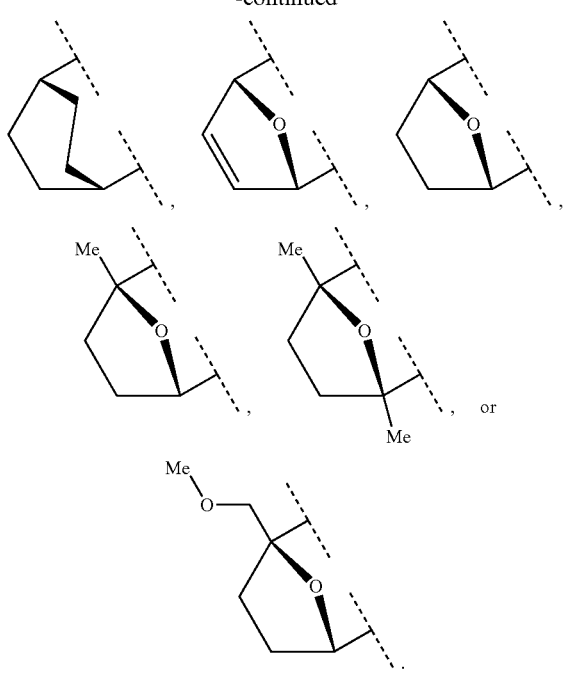
22. A compound as claimed in claim 1, as illustrated below, optionally present as an agrochemically acceptable salt thereof:
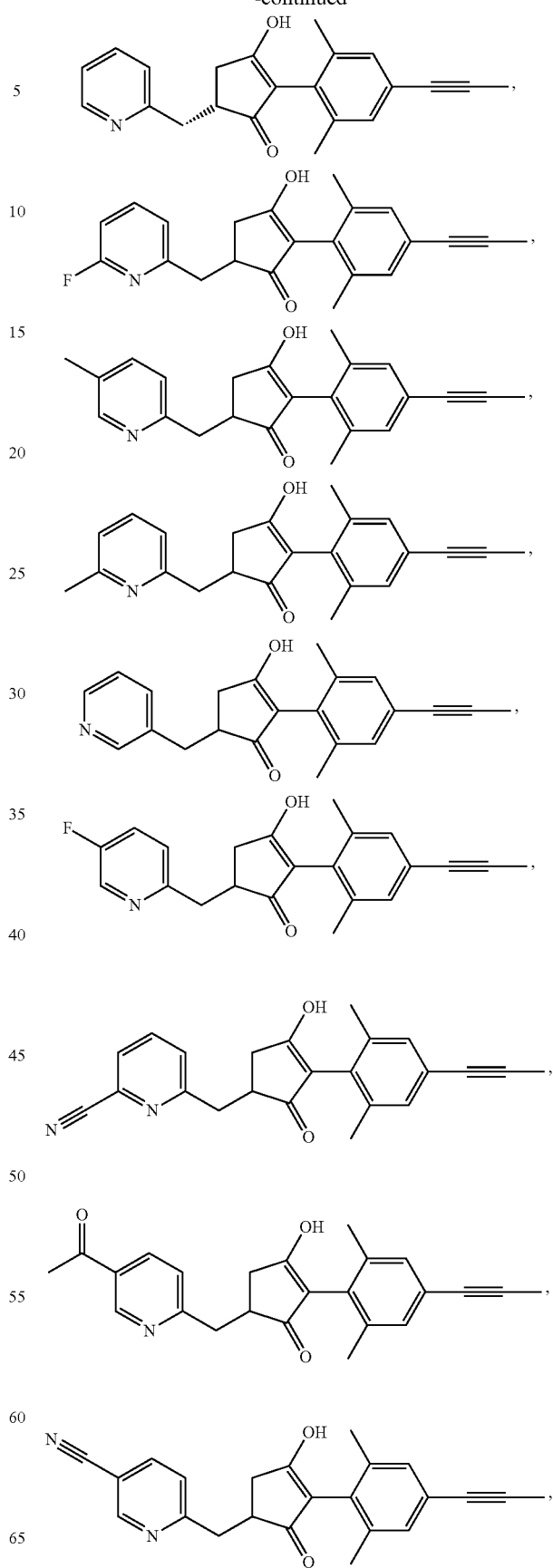

187
-continued
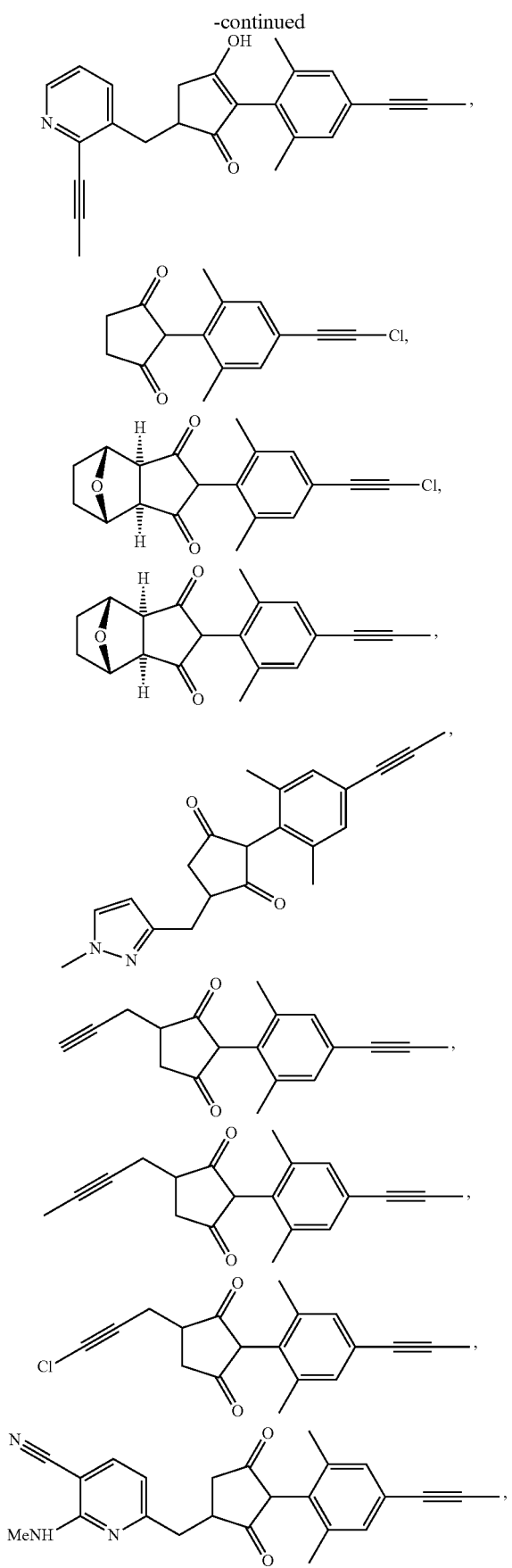
188
-continued
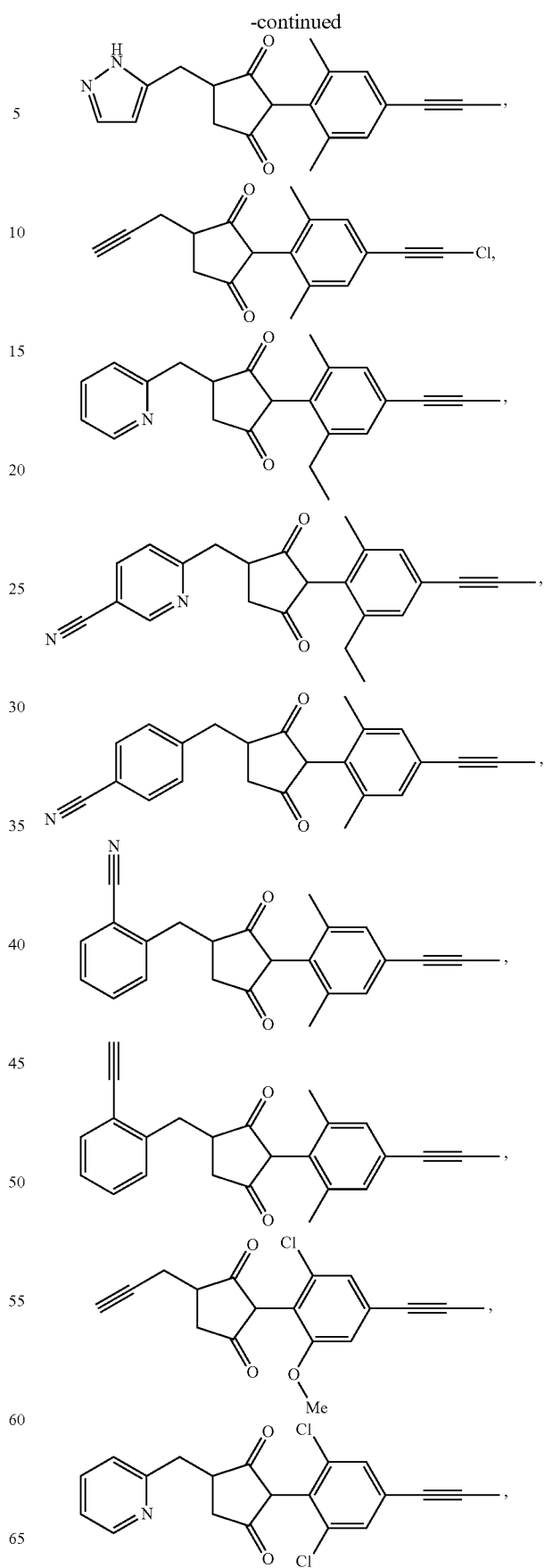

189
-continued
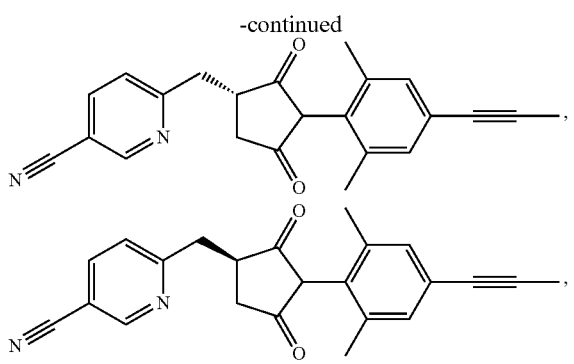
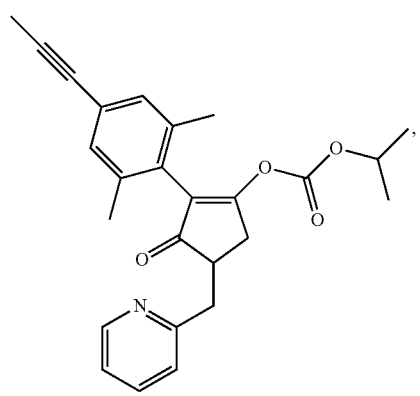
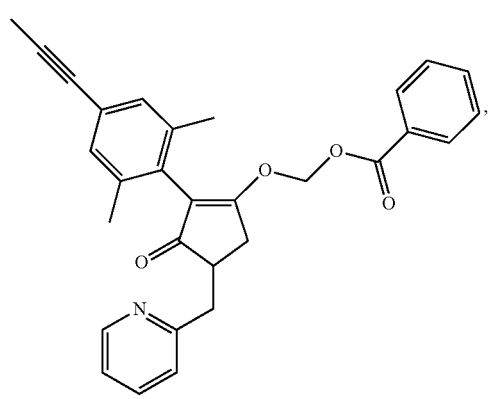
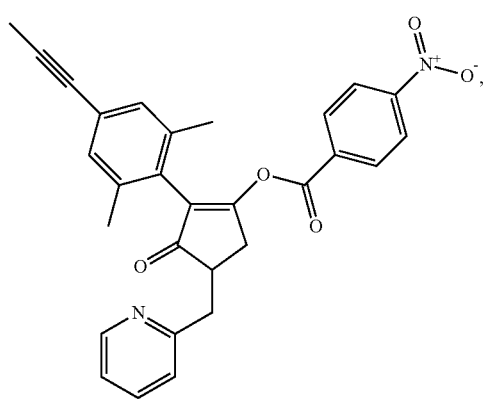
190
-continued
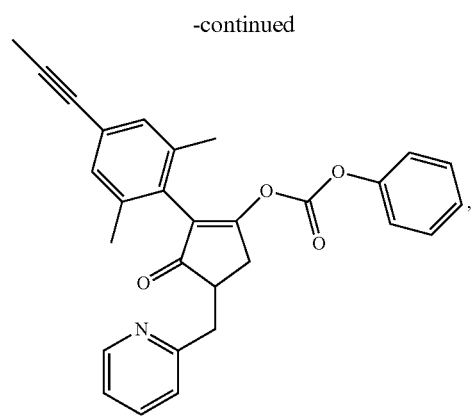
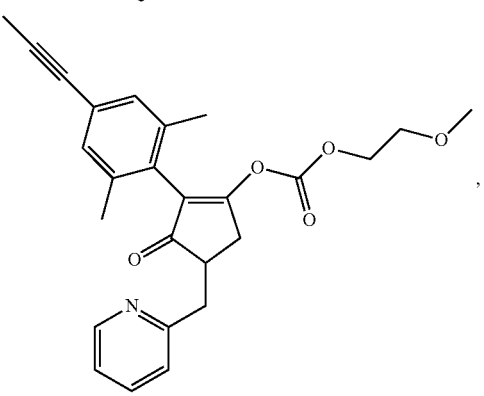
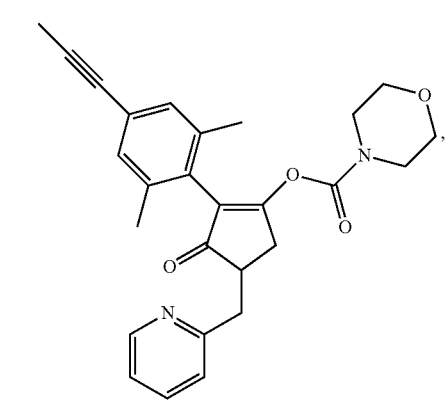
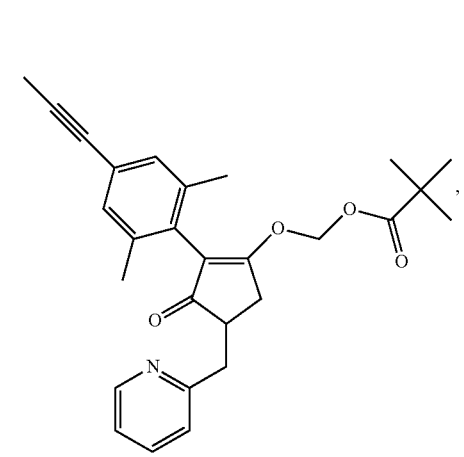

191
-continued
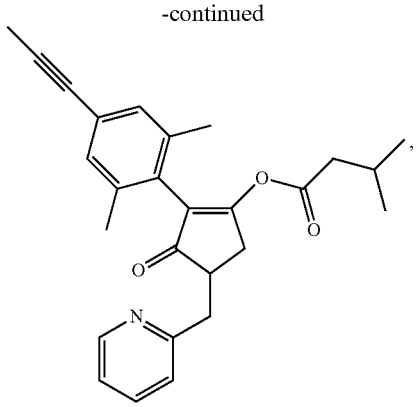
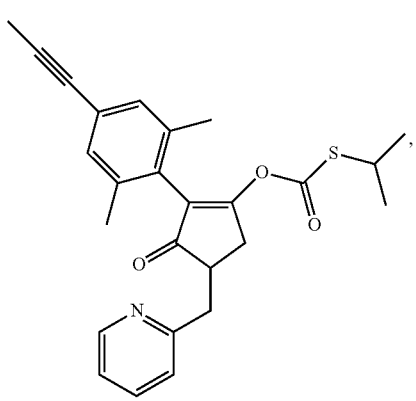
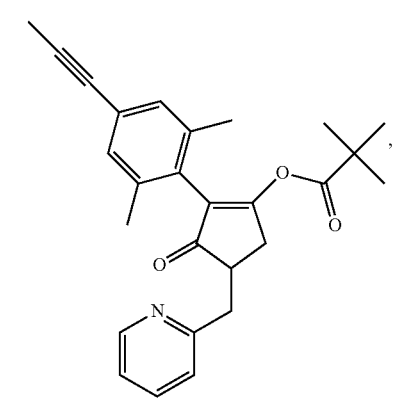
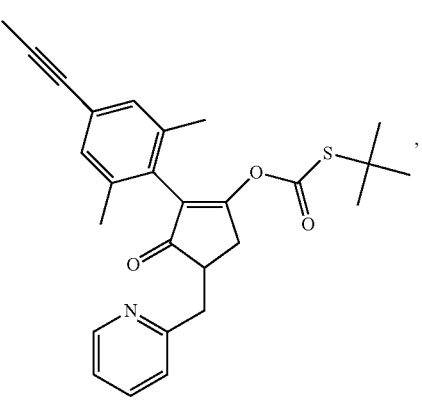
192
-continued
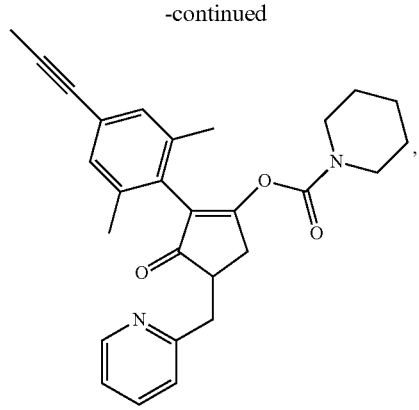
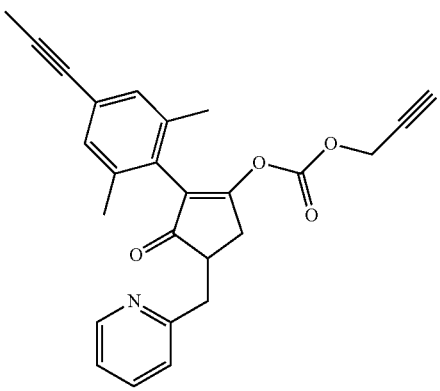
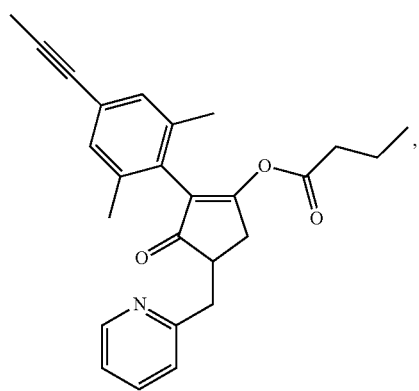
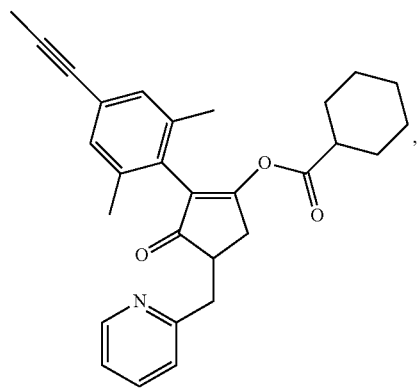

193
-continued
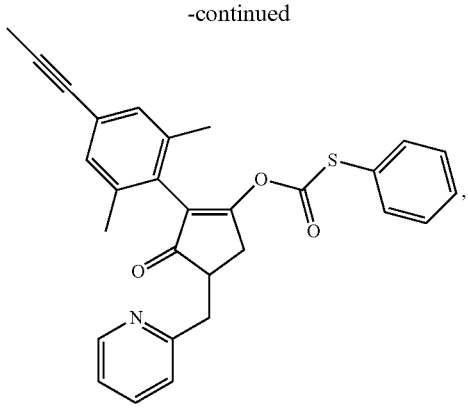
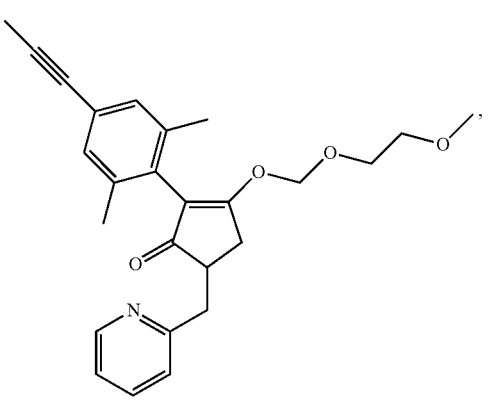
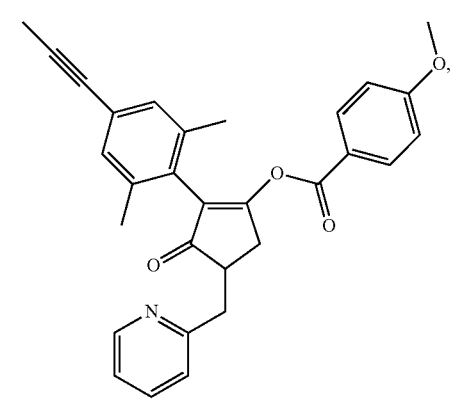
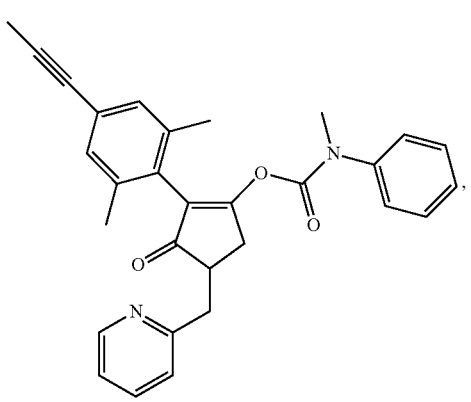
194
-continued
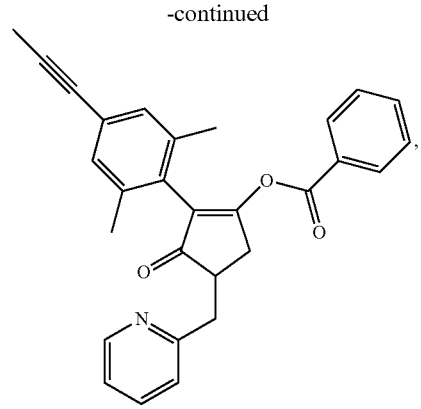
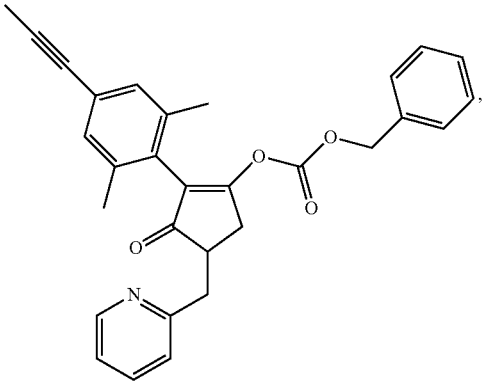
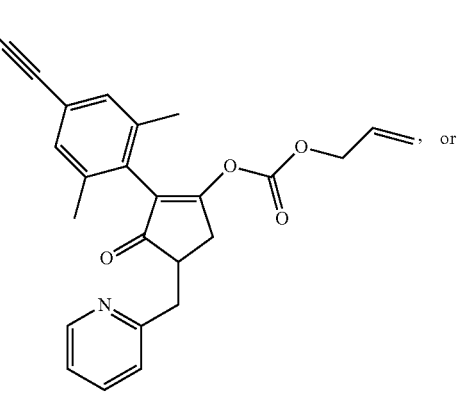
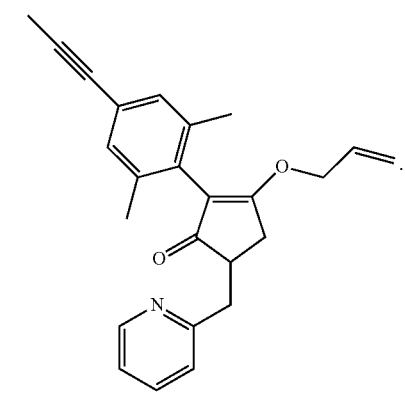

23. A compound as claimed in claim 1, which is a compound of formula (IC):

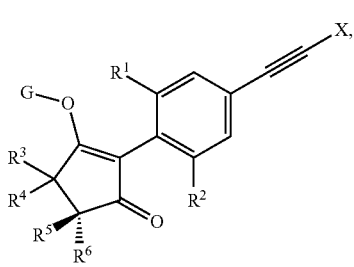

wherein X, $R^1$, $R^2$, $R^3$, $R^4$, $R^5$, $R^6$ and G are as defined in claim 1,
and wherein more than 50% by molarity of the compound of formula (IC) has the indicated stereochemistry at the ring-carbon atom bonded to $R^5$ and $R^6$.

24. A herbicidal composition which comprises:
  a compound of formula (I), as defined in claim 1; and
  an agrochemically acceptable carrier, diluent and/or solvent; and
  optionally, one or more further herbicides; and
  optionally, a safener.

25. A herbicidal composition according to claim 24, comprising a safener, wherein the safener comprises benoxacor, cloquintocet-mexyl, cloquintocet acid or an agrochemically acceptable salt thereof, cyprosulfamide, mefenpyr-diethyl and/or N-(2methoxybenzoy1)-4-[(methylaminocarbonyl)amino]benzenesulfonamide.

26. A method of controlling grassy monocotyledonous weeds in crops of useful plants, comprising applying a compound of formula (I), as defined in claim 1 to the plants or to the locus thereof.

* * * * *